United States Patent
West et al.

(10) Patent No.: US 10,920,191 B2
(45) Date of Patent: Feb. 16, 2021

(54) METHODS OF SCREENING EMBRYONIC PROGENITOR CELL LINES

(71) Applicant: LINEAGE CELL THERAPEUTICS, INC., Carlsbad, CA (US)

(72) Inventors: Michael West, Mill Valley, CA (US); Hal Sternberg, Berkeley, CA (US); Karen Chapman, Mill Valley, CA (US)

(73) Assignee: LINEAGE CELL THERAPEUTICS, INC., Carlsbad, CA (US)

( * ) Notice: Subject to any disclaimer, the term of this patent is extended or adjusted under 35 U.S.C. 154(b) by 0 days.

(21) Appl. No.: 15/846,181

(22) Filed: Dec. 18, 2017

(65) Prior Publication Data

US 2019/0241867 A1 Aug. 8, 2019

Related U.S. Application Data

(63) Continuation of application No. 13/683,241, filed on Nov. 21, 2012, now abandoned, which is a continuation-in-part of application No. PCT/US2011/037969, filed on May 25, 2011, and a continuation-in-part of application No. 13/384,289, filed as application No. PCT/US2010/042369 on Jul. 16, 2010, now Pat. No. 8,685,386, said application No. 13/683,241 is a continuation-in-part of application No. 12/504,630, filed on Jul. 16, 2009, now abandoned.

(60) Provisional application No. 61/349,081, filed on May 27, 2010, provisional application No. 61/415,321, filed on Nov. 18, 2010, provisional application No. 61/383,679, filed on Sep. 16, 2010, provisional application No. 61/379,321, filed on Sep. 1, 2010, provisional application No. 61/426,301, filed on Dec. 22, 2010, provisional application No. 61/226,237, filed on Jul. 16, 2009, provisional application No. 61/243,939, filed on Sep. 18, 2009, provisional application No. 61/349,088, filed on May 27, 2010, provisional application No. 61/365,308, filed on Jul. 16, 2010, provisional application No. 61/081,325, filed on Jul. 16, 2008, provisional application No. 61/178,457, filed on May 14, 2009.

(51) Int. Cl.
*C12N 5/00* (2006.01)
*C12N 5/02* (2006.01)
*C12N 5/0735* (2010.01)
*C12N 5/077* (2010.01)

(52) U.S. Cl.
CPC ......... *C12N 5/0606* (2013.01); *C12N 5/0653* (2013.01)

(58) Field of Classification Search
CPC ... C12N 5/0696; C12N 5/0606; C12N 5/0653
See application file for complete search history.

(56) References Cited

U.S. PATENT DOCUMENTS

| 6,927,285 | B2 | 8/2005 | Cech et al. |
|---|---|---|---|
| 2003/0129745 | A1 | 7/2003 | Robl et al. |
| 2004/0014206 | A1 | 1/2004 | Robl et al. |
| 2005/0153442 | A1 | 7/2005 | Katz et al. |
| 2005/0175595 | A1 | 8/2005 | Kukharchuk et al. |
| 2007/0128727 | A1 | 6/2007 | Kraemer et al. |
| 2008/0057041 | A1 | 3/2008 | Chung et al. |
| 2009/0304654 | A1 | 12/2009 | Lue et al. |
| 2010/0028310 | A1 | 2/2010 | Do et al. |

FOREIGN PATENT DOCUMENTS

| WO | 2007/019398 A1 | 2/2007 |
|---|---|---|
| WO | 2007/047894 A2 | 4/2007 |
| WO | 2007/058671 A1 | 5/2007 |
| WO | 2011/009106 A2 | 1/2011 |

OTHER PUBLICATIONS

West et al. Regenerative Med., 2008, vol. 3, pp. 287-308 and Supplementary Table iii.*
Patel et al. Tissue Engineering, 2005, vol. 11, pp. 1498-1505.*
Hemmrich et al. Biomaterials, 2005, vol. 26, pp. 7025-7037.*
Patrick et al. Tissue Engineering, 1999, vol. 5, pp. 139-151.*
Rhie et al. Key Engineering Materials, 2007, pp. 349-352.*
Wu (2008, Am J Physiol Endocrinol Metab, 295:E205-E215, sup_table, 2008, pp. 1-7).*
csmas, sup_table, http://ajpendo.physiology.org/content/ajpendo/suppl/2008/05/28/90316.2008.DC1/sup_table.xls, 2008, 7 pages.
Human Protein Atlas, EYA4 Expression Across Different Tissues, Retrieved online at: http://www.proteinatlas.orQ/ENSG00000112319-EYA4/tissue, 4 pages.
International Preliminary Report on Patentability received for PCT International Application No. PCT/US2011/037969, dated Feb. 20, 2014, 9 pages.

(Continued)

*Primary Examiner* — Valarie E Bertoglio
(74) *Attorney, Agent, or Firm* — Mintz Levin Cohn Ferris Glovsky and Popeo PC; Marc T. Morley; Melissa J. Brayman

(57) ABSTRACT

Aspects of the present invention include methods and compositions related to the production and use of numerous clonal lineages of embryonic progenitor cell lines derived from differentiating cultures of primordial stem cells with diverse molecular markers and having been cultured for >21 doublings of clonal expansion. The robustness of these clonally-purified lines, their ability to expand for >40 passages while maintaining their pattern of gene expression, lack of tumorigenicity, and their embryonic pattern of gene expression offers novel compositions and methods for modeling numerous differentiation pathways for the first time in vitro, and for the manufacture of purified product not existing in such a purified state in nature or using other manufacturing modalities. Representative progenitor cell lines described herein are capable of development into cutaneous adipocytes, blood-brain barrier cells, neuronal cells, or smooth muscle cells each with therapeutic potential.

6 Claims, 3 Drawing Sheets

Specification includes a Sequence Listing.

(56) References Cited

OTHER PUBLICATIONS

International Search Report and Written Opinion received for PCT Patent International Application No. PCT/US2011/037969, dated Apr. 6, 2012, 12 pages.

Bhattacharya et al. (Oct. 5, 2005) "Comparison of the Gene Expression Profile of Undifferentiated Human Embryonic Stem Cell Lines and Differentiating Embryoid Bodies", BMC Developmental Biology, 5(22):16 pages.

Borsani et al. (1999) "EYA4, a Novel Vertebrate Gene Related to Drosophila Eyes Absent", Human Molecular Genetics, 8(1):11-23.

Cibelli et al. (Jul. 1998) "Transgenic Bovine Chimeric Offspring Produced from Somatic Cell-derived Stemlike Cells", Nature Biotechnology, 16(7):642-646.

Grohmann et al. (Jan. 2005) "Characterization of Differentiated Subcutaneous and Visceral Adipose Tissue from Children: the Influences of TNF-alpha and IGF-1", Journal of Lipid Research, 46(1):93-103.

Lanza et al. (Sep. 1999) "Human Therapeutic Cloning", Nature Medicine, 5(9):975-977.

Laudes et al. (Mar. 19, 2004) "Role of the POZ Zinc Finger Transcription Factor FBI-1 in Human and Murine Adipogenesis", Journal of Biological Chemistry, 279(12):21 pages.

NCBI (Sep. 4, 2016) "ADH1A Alcohol Dehydrogenase 1A (class I), Alpha Polypeptide [*Homo sapiens* human]", Retrieved online at: www.ncbi.nlm.nih.gov/gene/124, 1 page.

NCBI (Sep. 4, 2016) "ADH1B Alcohol Dehydrogenase 1B (class I), Beta Polypeptide [*Homo sapiens* human]", Retrieved online at: www.ncbi.nlm.nih. ov/ ene/125., 1 page.

NCBI (Jun. 8, 2007) "Geo Profiles", 41285267, 2 pages.

NCBI (Sep. 17, 2013) "Geo Profiles", 111038010, 2 pages.

Patel et al. (Jun. 9, 2000) "Mitotic Clonal Expansion During Preadipocyte Differentiation: Calpain-mediated Turnover of p27", Journal of Biological Chemistry, 275(23):17653-17660.

Seale et al. (Apr. 1, 2009) "Transcriptional Control of Brown Adipocyte Development and Physiological Function of Mice and Men", Genes & Development, 23(7):788-797.

Thomson et al. (Nov. 6, 1998) "Embryonic Stem Cell Lines Derived from Human Blastocysts", Science, 282(5391):1145-1147.

Van Ooij et al. (Jul. 1992) "Temporal Expression of the Human Alcohol Dehydrogenase Gene Family During Liver Development Correlates with Differential Promoter Activation by Hepatocyte Nuclear Factor 1, CCAAT/Enhancer-Binding Protein Alpha, Liver Activator Protein, and D-Element- Binding Protein", Molecular and Cellular Biology, 12 (7):3023-3031.

Wu et al. (May 20, 2008) "Wdnm1-like, a New Adipokine with a Role in MMP-2 Activation", American Journal of physiology. Endocrinology and metabolism, 295(1):E205-E215.

\* cited by examiner

METHODS OF SCREENING EMBRYONIC PROGENITOR CELL LINES

CROSS-REFERENCE TO RELATED APPLICATIONS

This patent application is a continuation of U.S. patent application Ser. No. 13/683,241, filed on Nov. 21, 2012, which is a continuation in part of international patent application No. PCT/US11/37969 filed on May 25, 2011, published as WO2011150105 on Dec. 1, 2011, which claims priority to U.S. Provisional Patent Application No. 61/349,081 filed May 27, 2010, U.S. Provisional Patent Application No. 61/379,321 filed Sep. 1, 2010, U.S. Provisional Patent Application No. 61/383,679 filed Sep. 16, 2010, U.S. Provisional Patent Application No. 61/415,321 filed Nov. 18, 2010, and U.S. Provisional Patent Application No. 61/426,301 filed Dec. 22, 2010. The entire contents of each of the aforementioned patent applications are expressly incorporated herein by reference in their entirety.

U.S. patent application Ser. No. 13/683,241, is also a continuation in part of U.S. patent application Ser. No. 13/384,289 which is a national stage application of international patent application No. PCT/US10/042369 which claims priority to U.S. provisional patent application No. 61/226,237 filed Jul. 16, 2009, U.S. provisional application No. 61/243,939 filed Sep. 18, 2009, U.S. provisional patent application No. 61/349,088 filed May 27, 2010, and U.S. provisional patent application No. 61/365,308 filed Jul. 16, 2010. The entire contents of each of the aforementioned patent applications are expressly incorporated herein by reference in their entirety.

U.S. patent application Ser. No. 13/683,241, is also a continuation in part of U.S. patent application Ser. No. 12/504,630 filed Jul. 16, 2009 which claims priority to U.S. provisional patent application No. 61/081,325 filed Jul. 16, 2008 and U.S. provisional patent application No. 61/178,457 filed May 14, 2009. The entire contents of each of the aforementioned patent applications are expressly incorporated herein by reference in their entirety.

REFERENCE TO SEQUENCE LISTING

The instant application contains a Sequence Listing, which has been submitted electronically in ASCII format as "sequence_list_txt_128614_06302." The Sequence Listing in ASCII text form was created on Aug. 28, 2018, is 17.1 KB in size, and is hereby incorporated by reference in its entirety.

BACKGROUND

Advances in stem cell technology, such as the isolation and propagation in vitro of primordial stem cells, including embryonic stem cells ("ES" cells including human ES cells ("hES" cells)) and related primordial stem cells including but not limited to, iPS, EG, EC, ICM, epiblast, or ED cells (including human iPS, EG, EC, ICM, epiblast, or ED cells), constitute an important new area of medical research. hES cells have a demonstrated potential to be propagated in the undifferentiated state and then to be induced subsequently to differentiate into likely any and all of the cell types in the human body, including complex tissues. In addition, many of these primordial stem cells are naturally telomerase positive in the undifferentiated state, thereby allowing the cells to be expanded indefinitely. This expansion potential allows these primordial cells to be genetically modified followed by clonal expansion, thus permitting the production of numerous homogeneous populations of genetically modified primordial stem cells. Since the telomere length of many of these cells is comparable to that observed in sperm DNA (approximately 10-18 kb TRF length), differentiated cells derived from these immortal lines once they begin differentiation (generally associated with the repression of the expression of the catalytic component of telomerase (TERT)) display a long initial telomere length providing the cells with a long replicative capacity compared to fetal or adult-derived tissue. This has led to the suggestion that many diseases resulting from the dysfunction of cells may be amenable to treatment by the administration of hES-derived cells of various differentiated types (Thomson et al., *Science* 282:1145-1147 (1998)). Nuclear transfer studies have demonstrated that it is possible to transform a somatic differentiated cell back to a primordial stem cell state such as that of embryonic stem ("ES") cells (Cibelli et al., *Nature Biotech* 16:642-646 (1998)) or embryo-derived ("ED") cells. The development of technologies to reprogram somatic cells back to a totipotent ES cell state, such as by the transfer of the genome of the somatic cell to an enucleated oocyte and the subsequent culture of the reconstructed embryo to yield ES cells, often referred to as somatic cell nuclear transfer ("SCNT") or through analytical reprogramming technology, offers methods to transplant ES-derived somatic cells with a nuclear genotype of the patient (Lanza et al., *Nature Medicine* 5:975-977 (1999)).

In addition to SCNT, other techniques exist to address the problem of transplant rejection, including the use of gynogenesis and androgenesis (see U.S. application Nos. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US00/29551, filed Oct. 27, 2000; the disclosures of which are incorporated by reference in their entirety). In the case of a type of gynogenesis designated parthenogenesis, pluripotent stem cells may be manufactured without antigens foreign to the gamete donor and therefore useful in manufacturing cells that can be transplanted without rejection. In addition, parthenogenic stem cell lines can be assembled into a bank of cell lines homozygous in the HLA region (or corresponding MHC region of nonhuman animals) to reduce the complexity of a stem cell bank in regard to HLA haplotypes.

In addition, cell lines or a bank of said cell lines can be produced that are hemizygous in the HLA region (or corresponding MHC region of nonhuman animals; see PCT application Ser. No. PCT/US2006/040985 filed Oct. 20, 2006 entitled "Totipotent, Nearly Totipotent or Pluripotent Mammalian Cells Homozygous or Hemizygous for One or More Histocompatibility Antigen Genes", incorporated herein by reference). A bank of hemizygous cell lines provides the advantage of not only reducing the complexity inherent in the normal mammalian MHC gene pool, but it also reduces the gene dosage of the antigens to reduce the expression of said antigens without eliminating their expression entirely, thereby not stimulating a natural killer response.

In addition to SCNT, parthenogenesis, and the construction of banks of cells with homozygous or hemizygous HLA alleles, other techniques exist to address the problem of transplant rejection, including the use of technologies to reprogram somatic cells using transcriptional regulators (see PCT application Ser. No. PCT/US2006/030632 filed on Aug. 3, 2006 and titled "Improved Methods of Reprogramming Animal Somatic Cells", incorporated herein by reference).

In regard to differentiating primordial stem cells into desired cell types, the potential to clonally isolate lines of human embryonic progenitor (hEP) cell lines provides a means to propagate novel highly purified cell lineages useful in the production of diverse secreted factors, for research, and for the manufacture of cell-based therapies (see PCT application Ser. No. PCT/US2006/013519 filed on Apr. 11, 2006 and titled "Novel Uses of Cells With Prenatal Patterns of Gene Expression"; U.S. patent application Ser. No. 11/604,047 filed on Nov. 21, 2006 and titled "Methods to Accelerate the Isolation of Novel Cell Strains from Pluripotent Stem Cells and Cells Obtained Thereby"; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", each incorporated herein by reference).

Nevertheless, there remains a need for improved methods to discover the differentiation potential of said hEP cell lines when exposed to diverse differentiation-inducing factors or other differentiation conditions that induce such differentiation under conditions which are compatible in either a general laboratory setting or in a good manufacturing processes ("GMP") cell manufacturing facility where there is adequate documentation as to the purity and genetic normality of the cells at advanced passages (>18-21 doublings of clonal expansion).

SUMMARY OF THE INVENTION

We have previously demonstrated that the long initial telomere length of hES cells, together with the unexpected robust proliferative capacity of primitive hES-derived progenitor cell types, facilitates the industrial expansion and characterization of >140 diverse and scalable clonal lineages with diverse defined homeobox gene expression as well as diverse transcriptional regulators (West et al., 2008, Regenerative Medicine vol. 3(3) pp. 287-308, incorporated herein by reference, including supplemental information; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety). The robustness of these clonally-purified lines, their ability to expand for >40 passages while maintaining their pattern of gene expression, lack of tumorigenicity, and their embryonic pattern of gene expression offers novel compositions and methods for modeling numerous differentiation pathways for the first time in vitro, and for the manufacture of purified product not existing in such a purified state in nature or using other manufacturing modalities. We disclose novel compositions and methods related to these cells, including novel screening methods and conditions that differentiate human embryonic progenitors into numerous terminally-differentiated cell types of use in medical research and therapy.

DETAILED DESCRIPTION OF THE INVENTION

Figure 1:
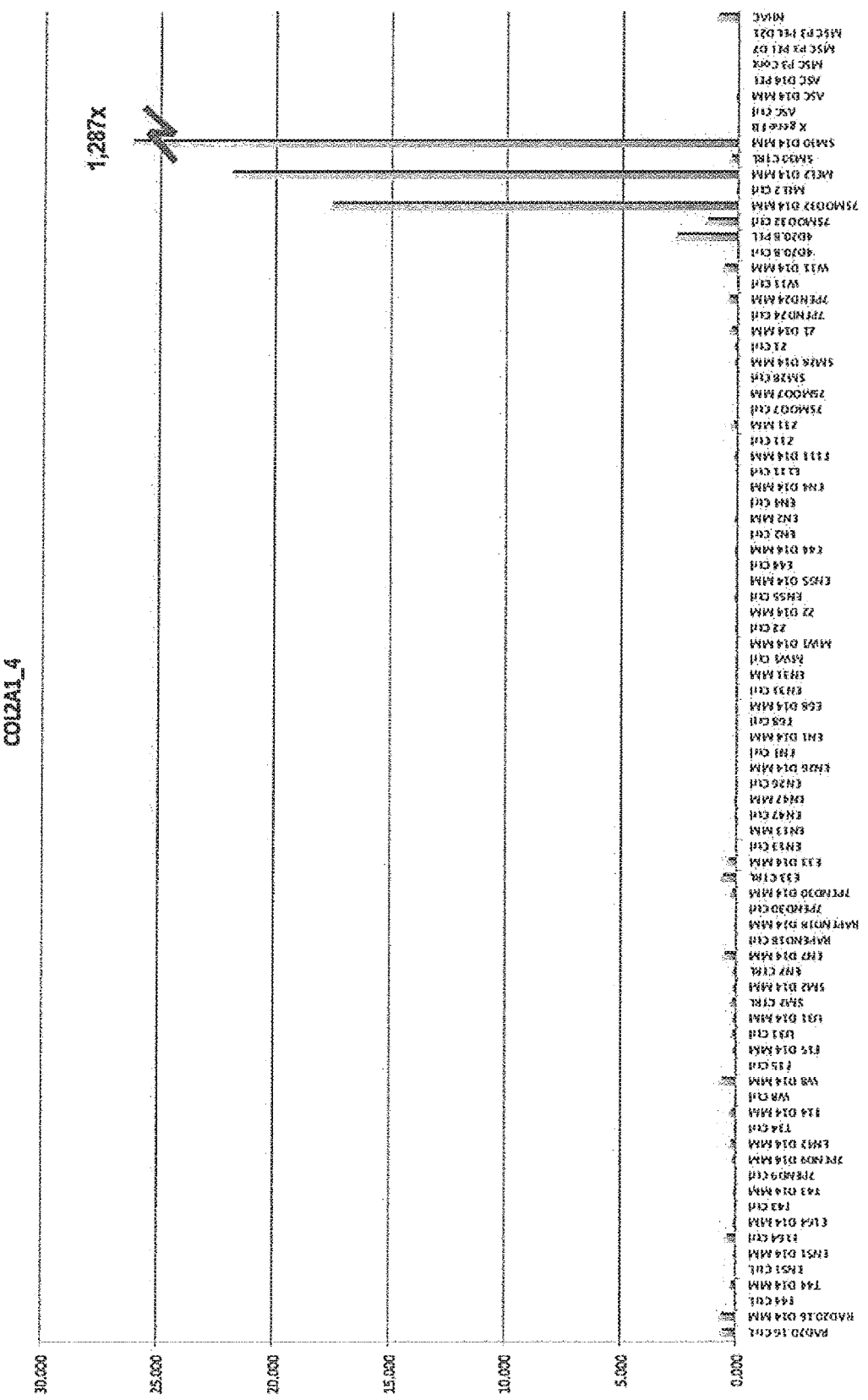
FIG. 1: Levels of induction of COL2A1 in assayed lines before and after 14 days of chondrogenic micromass conditions.

Abbreviations
AFP—Alpha fetoprotein
BMP—Bone Morphogenic Protein
BRL—Buffalo rat liver
BSA—Bovine serum albumin
CD—Cluster Designation
cGMP—Current Good Manufacturing Processes
CNS—Central Nervous System
DMEM—Dulbecco's modified Eagle's medium
DMSO—Dimethyl sulphoxide
DPBS—Dulbecco's Phosphate Buffered Saline
EC—Embryonal carcinoma
EC Cells—Embryonal carcinoma cells; hEC cells are human embryonal carcinoma cells
ECAPCs—Embryonic cutaneous adipocyte progenitor cells
ECM—Extracellular Matrix
ED Cells—Embryo-derived cells; hED cells are human ED cells
EDTA—Ethylenediamine tetraacetic acid
EG Cells—Embryonic germ cells; hEG cells are human EG cells
EP Cells—Embryonic progenitor cells are cells derived from primordial stem cells that are more differentiated than primordial stem cells, in that they no longer display markers such as SSEA4, TRA1-60 or TRA-1-81 seropositivity in the case of the human species, but have not fully differentiated. Embryonic progenitor cells correspond to the embryonic stages as opposed to the postnatal stage of development.
ES Cells—Embryonic stem cells; hES cells are human ES cells
FACS—Fluorescence activated cell sorting
FBS—Fetal bovine serum
GFP—Green Fluorescent Protein
GMP—Good Manufacturing Practices
hED—Cells Human embryo-derived cells
hEG—Cells Human embryonic germ cells are stem cells derived from the primordial germ cells of fetal tissue.
hEP Cells—Human embryonic progenitor cells are embryonic progenitor cells from the human species.
hiPS Cells—Human induced pluripotent stem cells are cells with properties similar to hES cells obtained from somatic cells after exposure to hES-specific transcription factors such as SOX2, KLF4, OCT4, MYC, or NANOG, LIN28, OCT4, and SOX2,
HSE—Human skin equivalents are mixtures of cells and biological or synthetic matrices manufactured for testing purposes or for therapeutic application in promoting wound repair.
HUVEC—Human umbilical vein endothelial cell
ICM—Inner cell mass of the mammalian blastocyst-stage embryo.
iPS Cells—Induced pluripotent stem cells are cells with properties similar to hES cells obtained from somatic cells after exposure to ES-specific transcription factors such as SOX2, KLF4, OCT4, MYC, or NANOG, LIN28, OCT4, and SOX2.
LOH—Loss of Heterozygosity
MEM—Minimal essential medium
miRNA—Micro RNA NT—Nuclear Transfer
PBS—Phosphate buffered saline
PS fibroblasts—Pre-scarring fibroblasts are fibroblasts derived from the skin of early gestational skin or derived from ED cells that display a prenatal pattern of gene expression in that they promote the rapid healing of dermal wounds without scar formation.
RA—Retinoic acid
RFU—Relative Fluorescence Units
SCNT—Somatic Cell Nuclear Transfer
SFM—Serum-Free Medium
SPF—Specific Pathogen-Free
SV40—Simian Virus 40
Tag—Large T-antigen
T-EDTA—Trypsin EDTA Definitions The term "analytical reprogramming technology" refers to a variety of methods to reprogram the pattern of gene expression of a somatic cell to that of a more pluripotent state, such as that of an iPS, ES, ED, EC or EG cell, wherein the reprogramming occurs in multiple and discrete steps and does not rely simply on the transfer of a somatic cell into an oocyte and the activation of that oocyte (see U.S. application Nos. 60/332,510, filed Nov. 26, 2001; Ser. No. 10/304,020, filed Nov. 26, 2002; PCT application no. PCT/US02/37899, filed Nov. 26, 2003; U.S. application No. 60/705,625, filed Aug. 3, 2005; U.S. application No. 60/729,173, filed Aug. 20, 2005; U.S. application No. 60/818,813, filed Jul. 5, 2006, PCT/US06/30632, filed Aug. 3, 2006, the disclosure of each of which is incorporated by reference herein).

The term "blastomere/morula cells" refers to blastomere or morula cells in a mammalian embryo or blastomere or morula cells cultured in vitro with or without additional cells including differentiated derivatives of those cells.

The term "cell expressing gene X", "gene X is expressed in a cell" (or cell population), or equivalents thereof, means that analysis of the cell using a specific assay platform provided a positive result. The converse is also true (i.e., by a cell not expressing gene X, or equivalents, is meant that analysis of the cell using a specific assay platform provided a negative result). Thus, any gene expression result described herein is tied to the specific probe or probes employed in the assay platform (or platforms) for the gene indicated.

The term "cell line" refers to a mortal or immortal population of cells that is capable of propagation and expansion in vitro.

The term "cellular reconstitution" refers to the transfer of a nucleus of chromatin to cellular cytoplasm so as to obtain a functional cell.

The term "clonal" refers to a population of cells obtained the expansion of a single cell into a population of cells all derived from that original single cells and not containing other cells.

The term "colony in situ differentiation" refers to the differentiation of colonies of cells (e.g., hES, hEG, hiPS, hEC or hED) in situ without removing or disaggregating the colonies from the culture vessel in which the colonies were propagated as undifferentiated stem cell lines. Colony in situ differentiation does not utilize the intermediate step of forming embryoid bodies, though embryoid body formation or other aggregation techniques such as the use of spinner culture may nevertheless follow a period of colony in situ differentiation.

The term "cytoplasmic bleb" refers to the cytoplasm of a cell bound by an intact or permeabilized but otherwise intact plasma membrane, but lacking a nucleus.

The term "differentiated cells" when used in reference to cells made by methods of this invention from pluripotent stem cells refer to cells having reduced potential to differentiate when compared to the parent pluripotent stem cells. The differentiated cells of this invention comprise cells that could differentiate further (i.e., they may not be terminally differentiated).

The term "direct differentiation" refers to process of differentiating: blastomere cells, morula cells, ICM cells, ED cells, or somatic cells reprogrammed to an undifferentiated state (such as in the process of making iPS cells but before such cells have been purified in an undifferentiated state) directly without the intermediate state of propagating isolated undifferentiated stem cells such as hES cells as undifferentiated cell lines. A nonlimiting example of direct differentiation would be the culture of an intact human blastocyst into culture and the derivation of ED cells without the generation of a human ES cell line as was described (Bongso et al, 1994. Human Reproduction 9:2110).

The term "embryonic stem cells" (ES cells) refers to cells derived from the inner cell mass of blastocysts, blastomeres, or morulae that have been serially passaged as cell lines while maintaining an undifferentiated state (e.g. expressing TERT, OCT4, and SSEA and TRA antigens specific for ES cells of the species). The ES cells may be derived from fertilization of an egg cell with sperm or DNA, nuclear transfer, parthenogenesis, or by means to generate hES cells with hemizygosity or homozygosity in the MHC region. While ES cells have historically been defined as cells capable of differentiating into all of the somatic cell types as well as germ line when transplanted into a preimplantation embryo, candidate ES cultures from many species, including human, have a more flattened appearance in culture and typically do not contribute to germ line differentiation, and are therefore called "ES-like cells." It is commonly believed that human ES cells are in reality "ES-like", however, in this application we will use the term ES cells to refer to both ES and ES-like cell lines.

The term "histotypic culture" refers to cultured cells that are aggregated to create a three-dimensional structure with tissue-like cell density such as occurs in the culture of some cells over a layer of agar or such as occurs when cells are cultured in three dimensions in a collagen gel, sponge, or other polymers such as are commonly used in tissue engineering.

The term "human embryo-derived" ("hED") cells refers to blastomere-derived cells, morula-derived cells, blastocyst-derived cells including those of the inner cell mass, embryonic shield, or epiblast, or other totipotent or pluripotent stem cells of the early embryo, including primitive endoderm, ectoderm, mesoderm, and neural crest and their derivatives up to a state of differentiation correlating to the equivalent of the first eight weeks of normal human development, but excluding cells derived from hES cells that have been passaged as cell lines (see, e.g., U.S. Pat. Nos. 7,582,479; 7,217,569; 6,887,706; 6,602,711; 6,280,718; and 5,843,780 to Thomson, incorporated herein by reference). The hED cells may be derived from preimplantation embryos produced by fertilization of an egg cell with sperm or DNA, nuclear transfer, or chromatin transfer, an egg cell induced to form a parthenote through parthenogenesis, analytical reprogramming technology, or by means to generate hES cells with hemizygosity or homozygosity in the HLA region.

The term "human embryonic germ cells" (hEG cells) refer to pluripotent stem cells derived from the primordial germ cells of fetal tissue or maturing or mature germ cells such as oocytes and spermatogonial cells, that can differentiate into various tissues in the body. The hEG cells may also be derived from pluripotent stem cells produced by gynogenetic or androgenetic means, i.e., methods wherein the pluripotent cells are derived from oocytes containing only DNA of male or female origin and therefore will comprise all female-derived or male-derived DNA (see U.S. application Nos. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US/00/29551, filed Oct. 27, 2000; the disclosures of which are incorporated herein in their entirety).

The term "human embryonic stem cells" (hES cells) refers to human ES cells.

The term "human iPS cells" refers to cells with properties similar to hES cells, including the ability to form all three germ layers when transplanted into immunocompromised mice wherein said iPS cells are derived from cells of varied somatic cell lineages following exposure to de-differentiation factors, for example hES cell-specific transcription factor combinations: KLF4, SOX2, MYC, and OCT4 or SOX2, OCT4, NANOG, and LIN28. Any convenient combination of de-differentiation factors may be used to produce iPS cells. Said iPS cells may be produced by the expression of these genes through vectors such as retroviral, lentiviral or adenoviral vectors as is known in the art, or through the introduction of the factors as proteins, e.g., by permeabilization or other technologies. For descriptions of such exemplary methods see: PCT application number PCT/US2006/030632, filed on Aug. 3, 2006; U.S. application Ser. No. 11/989,988; PCT Application PCT/US2000/018063, filed on Jun. 30, 2000; U.S. application Ser. No. 09/736,268 filed on Dec. 15, 2000; U.S. application Ser. No. 10/831,599, filed Apr. 23, 2004; and U.S. Patent Publication 20020142397 (application Ser. No. 10/015,824, entitled "Methods for Altering Cell Fate"); U.S. Patent Publication 20050014258 (application Ser. No. 10/910,156, entitled "Methods for Altering Cell Fate"); U.S. Patent Publication 20030046722 (application Ser. No. 10/032,191, entitled "Methods for cloning mammals using reprogrammed donor chromatin or donor cells"); and U.S. Patent Publication 20060212952 (application Ser. No. 11/439,788, entitled "Methods for cloning mammals using reprogrammed donor chromatin or donor cells") all of which are incorporated herein by reference in their entirety.

The term "ICM cells" refers to the cells of the inner cell mass of a mammalian embryo or the cells of the inner cell mass cultured in vitro with or without the surrounding trophectodermal cells.

The term "oligoclonal" refers to a population of cells that originated from a small population of cells, typically 2-1000 cells, that appear to share similar characteristics such as morphology or the presence or absence of markers of differentiation that differ from those of other cells in the same culture. Oligoclonal cells are isolated from cells that do not share these common characteristics, and are allowed to proliferate, generating a population of cells that are essentially entirely derived from the original population of similar cells.

The term "organotypic culture" refers to cultured cells that are aggregated to create a three-dimensional structure with tissue-like cell density such as occurs in the culture of some cells over a layer of agar, cultured as teratomas in an animal, otherwise grown in a three dimensional culture system but wherein said aggregated cells contain cells of different cell lineages, such as, by way of nonlimiting examples, the combination of epidermal keratinocytes and dermal fibroblasts, or the combination of parenchymal cells with their corresponding tissue stroma, or epithelial cells with mesenchymal cells.

The term "pluripotent stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "pooled clonal" refers to a population of cells obtained by combining two or more clonal populations to generate a population of cells with a uniformity of markers such as markers of gene expression, similar to a clonal population, but not a population wherein all the cells were derived from the same original clone. Said pooled clonal lines may include cells of a single or mixed genotypes. Pooled clonal lines are especially useful in the cases where clonal lines differentiate relatively early or alter in an undesirable way early in their proliferative lifespan.

The term "primordial stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Primordial stem cells may be genetically modified or not genetically modified. Genetically modified cells may include markers such as fluorescent proteins to facilitate their identification in vitro or in vivo.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

In addition to the methods described below, methods that find use in the production and use of the cell lines described herein can be found in the following: U.S. Patent Publication 20080070303, entitled "Methods to accelerate the isolation of novel cell strains from pluripotent stem cells and cells obtained thereby"; U.S. patent application Ser. No. 12/504, 630 filed on Jul. 16, 2009 and titled "Methods to Accelerate the Isolation of Novel Cell Strains from Pluripotent Stem Cells and Cells Obtained Thereby"; U.S. provisional application Ser. No. 61/226,237 filed on Jul. 16, 2009 and titled "Methods and Compositions Useful for In Vitro and In Vivo Chondrogenesis Using Embryonic Progenitor Cell Lines"; and PCT Application PCT/US2006/013519, filed on Apr. 11, 2006, entitled "NOVEL USES OF CELLS WITH PRENATAL PATTERNS OF GENE EXPRESSION", each of which is incorporated by reference herein in its entirety.

hES Cell Culture and Generation of Candidate Cultures.

The hES cell lines used were previously described H9 (National Institutes of Health-registered as WA09) and the line (MA03) derived at Advanced Cell Technology (West et al., 2008, *Regenerative Medicine* vol. 3(3) pp. 287-308). hES cells were routinely cultured in hES medium (KO-DMEM (Invitrogen, Carlsbad, Calif.), 1× nonessential amino acids (Invitrogen, Carlsbad, Calif.), 1× Glutamax-1 (Invitrogen, Carlsbad, Calif.), 55 uM beta-mercaptoethanol (Invitrogen, Carlsbad, Calif.), 8% Knock-Out Serum Replacement (Invitrogen, Carlsbad, Calif.), 8% Plasmanate, 10 ng/ml LIF (Millipore, Billerica, Mass.), 4 ng/ml bFGF (Millipore, Billerica, Mass.), 50 unit/ml Penicillin—50 units/ml Streptomycin (Invitrogen, Carlsbad, Calif.). The hES cell lines were maintained at 37 deg C. in an atmosphere of 10% CO2 and 5% O2 on Mitomycin-C treated mouse embryonic fibroblasts (MEFs) and passaged by trypsinization or periodic manual selection of colonies. For the production of clonal embryonic progenitors, hES cells were plated at 500-10,000 cells per 15 cm dish and then differentiated under a two-step protocol, the first step being the differentiation of hES cells under an array of conditions to yield diverse heterogeneous cultures of cells called "candidate cultures." The generation of candidate cultures was performed with either adherent hES cells grown on MEFs (colony in situ differentiation) or with hES-derived embryoid bodies (EB). For colony in situ differentiation experiments, hES cells were allowed to grow to confluence and differentiated by a variety of methods (as described in Supplementary Table I from West et al., 2008, *Regenerative Medicine* vol. 3(3) pp. 287-308, which is incorporated by reference herein in its entirety). By way of nonlimiting example, in the case of colony in situ differentiation in DMEM with 10% FCS, culture medium was aspirated from cultures of hES cell colonies on mouse feeders, and the media was replaced with DMEM medium containing 10% FBS for differentiation and after various time periods (1, 2, 3, 4, 5, 7, and 9 days in differentiation medium). The cells were then dissociated with 0.25% trypsin (Invitrogen, Carlsbad, Calif.) and plated in 150 $cm^2$ flasks for expansion. The candidate cells from each time point in the 150 $cm^2$ flasks were plated out for cloning and expansion as described below. For EB differentiation experiments, confluent hES cultures were treated for 15 minutes at 37 deg C. with 1 mg/ml Collagenase IV (in DMEM, Invitrogen, Carlsbad, Calif.) to release the colonies. The detached, intact colonies were scraped and collected by centrifugation (150×g for 5 minutes), resuspended in differentiation medium described in Supplementary Table I (from West et al., 2008, *Regenerative Medicine* vol. 3(3) pp. 287-308, which is incorporated by reference herein in its entirety) and transferred to a single well of a 6-well Ultra-Low Binding plate (Corning, distributed by Fisher Scientific, Pittsburgh, Pa.) containing the same differentiation medium. The Ebs were allowed to differentiate, depending on the experiment, from 4-7 days and the differentiated Ebs dissociated with 0.25% trypsin, plated in 6-well plates containing various expansion medium. The candidate cultures in the 6 well plates are allowed to grow to confluence and plated out for cloning and expansion as described below.

Isolation and Expansion of Clonal Cell Lines.

The partially differentiated candidate cell cultures described above were dissociated with 0.25% trypsin to single cells and plated onto duplicate 15 cm gelatin coated plates at cloning densities of approximately 500 and/or 1,000 and/or 2,000 and/or 5,000 cells per plate for further differentiation and expansion in a variety of growth media shown in Supplementary Table I (from West et al., 2008, *Regenerative Medicine* vol. 3(3) pp. 287-308, which is incorporated by reference herein in its entirety). The clonal density cells were allowed to grow, undisturbed, for 10-14 days and colonies that develop were identified and collected with cloning cylinders and trypsin using standard techniques. The cloned colonies were transferred onto gelatin-coated 24 well plates for expansion. As the clones become confluent in the 24 well plates (but without letting the cells remain confluent for more than 2 days), they were sequentially expanded to 12 well, 6 well, T-25 flask, T-75 flask, T-150 or T-225 flasks and, finally, roller bottles. Clonal cell lines that expand to the roller bottle stage are assigned a unique ACTC identification number, photographed and cryopreserved in aliquots for later use. Once cells reached a confluent 6 well dish, they were passaged to a T-25 flask and a fraction of the cells ($5\times10^5$) were removed for plating in a gelatinized 6 cm dish for gene expression profile analysis. Alternatively, some cells were first passaged to T-225 flasks, then a fraction of the cells ($5\times10^5$) were removed for plating in a gelatinized 6 cm dish for gene expression profile analysis. The population doublings that the cells had undergone were therefore determined to be 18-21 PDs. Following removal of the cell clones from the cloning plates, remaining colonies were visualized by Crystal violet staining (Sigma HT9132-1L) in 100% ethanol per manufacturer's instructions. Cell Culture media utilized in experiments and described in text and Table III: Smooth muscle cell basal medium (Cat #C-22062B) and growth supplement (Cat #C-39267), Skeletal muscle basal medium (Cat #C-22060B) and growth supplement (Cat #C-39365), Endothelial cell basal medium (Cat #C-22221) and growth supplement (Cat #C-39221), Melanocyte cell basal medium (Cat #C-24010B) and growth supplement (Cat #C-39415) were obtained from PromoCell GmbH (Heidelberg, Germany). Epi-Life, calcium free/phenol red free medium (Cat #M-EPIcf/PRF-500) and low serum growth supplement (Cat #S-003-10) were purchased from Cascade Biologics (Portland, Oreg.). Mesencult basal medium (Cat #05041) and supplement (Cat #5402) were obtained from Stem Cell Technologies (Vancouver, BC). Dulbecco's modified Eagle's medium (Cat #11960-069) and Fetal bovine serum (Cat #SH30070-03) were purchased from Invitrogen (Carlsbad, Calif.) and Hyclone (Logan, Utah) respectively. Medium and supplements were combined according to manufacturer's instructions.

Clonal Embryonic Progenitor Line Nomenclature:

The cell lines of the present invention along with their alternative designations are listed in Table VI along with synonyms that represent minor modifications that result from the manipulation of the names resulting from bioinformatics analysis, including the substitution of "-" for "." and vice versa, the inclusion of an "x" before cell line names beginning with an arabic number, and suffixes such as "bio1" or "bio2" that indicate biological replicates of the same line which are examples of cases where a frozen ampule of the same line was thawed, propagated, and used in a parallel analysis and "Rep1" or "Rep2" which indicate technical replicates wherein RNA isolated from a given cell line is utilized a second time for a repeat analysis without thawing or otherwise beginning with a new culture of cells. Passage number (which is the number of times the cells have been trypsinized and replated) for the cell lines is usually designated by the letter "P" followed by an arabic number, and in contrast, the population doubling number (which refers to the number of estimated doublings the cell lines have undergone in clonal expansion from one cell) is designated by the letters "PD" followed by an arabic number. The number of PDs in a passage varied from experiment to experiment but generally each trypsinization and replating was at a 1:3 to 1:4 ratio (corresponding to an increase of PDs of 1.5 and 2 respectively). In the expansion of clones, the original colonies were removed from tissue culture plates with cloning cylinders, and transferred to 24-well plates, then 12-well, and 6-well as described above. First confluent 24 well is designated P1, the first confluent 12 well culture is P2, the first 6-well culture is P3, then the six well culture was then split into a second 6 well plate (P4) and a T25 (P4). The second 6 well at P4 is utilized for RNA extraction (see U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety) and represents about 18-21 PD of clonal expansion. Typical estimated subsequent passages and PDs are the following split to a T75 flask (19.5-22.5 PD), the P6 passage of the cells to a T225 flask (21-24 PD), then P7 being the transfer of the cells to a roller bottle (850 $cm^2$, 23-26 PD), and P8 the split into 4 rollers (25-28 PD). The ranges shown above in parenthesis represent estimated ranges in cell counts due to cell sizes, attachment efficiency, and counting error.

Propagation of Clonal, Pooled Clonal, Oligoclonal, and Pooled Oligoclonal Cell Lines.

Aspects of the invention provide methods for identifying and differentiating embryonic progenitor cell lines that are derived from a single cell (clonal) or cell lines that are "pooled clonal" meaning that cell lines cloned have indistinguishable markers, such as gene expression markers, and are combined to produce a single cell culture often for the purpose of increasing the number of cells in a culture, or are oligoclonal wherein a line is produced from a small number, typically 2-1,000 similar cells and expanded as a cell line, or "pooled oligoclonal" lines which are lines produced by combining two or more oligoclonal cell lines that have indistinguishable markers such as patterns of gene expression. Said clonal, pooled clonal, oligoclonal, or pooled oligoclonal cell lines are then propagated in vitro through removal of the cells from the substrate to which they are affixed, and the re-plating of the cells at a reduced density of typically ⅓ to ¼ of the original number of cells, to facilitate further proliferation. Examples of said cell lines and their associated cell culture media is disclosed in U.S. patent application Ser. No. 12/504,630 filed on Jul. 16, 2009 and titled "Methods to Accelerate the Isolation of Novel Cell Strains from Pluripotent Stem Cells and Cells Obtained Thereby"; and West et al., 2008, Regenerative Medicine vol. 3(3) pp. 287-308, both of which are incorporated herein by reference, including supplemental information. The compositions and methods of the present invention relate to said cell lines cultured as described but for greater than 21 doublings of clonal expansion.

Gene Expression Analysis

To reduce variations in gene expression due to cell cycle artifacts, and to capture an early gene expression profile of the cells, upon being expanded to six well plates, on the day the cells reached confluence, the cells were placed in media with a reduction of serum to 0.5% in the case where the original serum concentration was >5%. In all other cases, serum and/or other growth factors was reduced to 10% of their original values. These quiescence conditions were imposed for five days and all cultures were re-fed two days prior to harvest to reduce feeding difference artifacts. So, by way of example, if the original media was DMEM medium with 10% FCS, then the quiescence synchronization media was DMEM with 0.5% FCS. Total RNA was extracted directly from cells growing in 6-well or 6 cm tissue culture plates using Qiagen Rneasy mini kits according to the manufacturer's instructions. RNA concentrations were measured using a Beckman DU530 or Nanodrop spectrophotometer and RNA quality determined by denaturing agarose gel electrophoresis or an Agilent 2100 bioanalyzer. Whole-genome expression analysis was carried out using Affymetrix Human Genome U133 Plus 2.0 GeneChip® system, Illumina Human-6 v1 and HumanRef-8 v1 Beadchips (Illumina 1), and Illumina Human-6 v2 Beadchips (Illumina 2), and RNA levels for certain genes were confirmed by quantitative PCR. For Illumina BeadArrays, total RNA was linearly amplified and biotin-labeled using Illumina TotalPrep kits (Ambion), and cRNA was quality controlled using an Agilent 2100 Bioanalyzer. cRNA was hybridized to Illumina BeadChips, processed, and read using a BeadStation array reader according to the manufacturer's instructions (Illumina). Relative Fluorescence Unit (RFU) values for all of the cell lines with common probe sets were quantile normalized. In Supplementary Tables II-IV (from West et al., 2008, *Regenerative Medicine* vol. 3(3) pp. 287-308, which are incorporated by reference herein in their entirety) the genes are displayed in rank order (highest-lowest) for the ratio of (highest RFU value observed for the gene in the entire set of cell lines–Average RFU value)/Ave RFU value. In Supplementary Table V (from West et al., 2008, *Regenerative Medicine* vol. 3(3) pp. 287-308, which is incorporated by reference herein in its entirety) the top 45 differentially expressed genes rank ordered (highest-lowest) for the ratio of (highest RFU value observed for the gene in the individual cell line/Ave RFU value for all cell lines. In Supplementary Table VI (from West et al., 2008, *Regenerative Medicine* vol. 3(3) pp. 287-308, which is incorporated by reference herein in its entirety) the genes corresponding to recognized CD antigens are displayed in rank order (highest-lowest) and also (lowest to highest) for the ratio of highest RFU value observed for the gene in the entire set of cell lines/Ave RFU value and lowest RFU value observed for the gene in the entire set of cell lines/Ave RFU value respectively. In Supplementary Table VII (from West et al., 2008, *Regenerative Medicine* vol. 3(3) pp. 287-308, which is incorporated by reference herein in its entirety) the genes corresponding to secreted proteins are displayed in rank order (highest-lowest) for the ratio of highest RFU value observed for the gene in the entire set of cell lines/Ave RFU value.

Low Throughput Screening and qPCR

The clonal, oligoclonal, or pooled clonal or pooled oligoclonal embryonic progenitor cell lines of the present invention at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion (since before 29 doublings of clonal expansion the cells are available only in limited quantities, and beyond 70 doublings the cells normally approach senescence) are screened simultaneously in 1, 2, 3, 4, 5, or preferably 10 or more diverse differentiation conditions. Said differentiation conditions may include without limitation, all combinations of the human embryonic progenitor cell lines listed in Table I (showing gene expression markers at 18-21 doublings of clonal expansion), together with culture conditions as listed in Table II, exposed to the culture media listed in Table III, and supplemented factors listed in Table IV. The cells are cultured in said differentiation conditions for 1-6 weeks, most preferably two to four weeks.

The readout of the assay can be mRNA markers of differentiation such as those listed in Table V and measured by hybridization to arrayed target sequences, including but not limited to microarrays or by PCR. Detection can also be at the level of peptides or proteins that may be detected through the use of specific antibodies, through the use of enzyme assays, mass spectroscopy, or other similar means well known in the art.

In the case of qPCR, protocols may vary and are well-known in the art. By way of nonlimiting example, samples for testing are prepared in standard Optical 96-well reaction plates (Applied Biosystems Carlsbad, Calif., PN 4306737) consisting of 30 ng of RNA equivalent of cDNA, 0.4 uM per primer, Ultra-Pure distilled water (Invitrogen), diluted 1:1 with 12.5 ul of Power SYBR Green PCR Master Mix (Applied Biosystems Carlsbad, Calif., Cat #4367659) incorporating AmpliTaq Gold DNA polymerase in a total reaction volume of 25 ul. Real-Time qPCR is run using Applied Biosystems 7500 Real-Time PCR System employing SDSv1.2 software. Amplification conditions are set at 50° C. for 2 min. (stage 1), 95° C. for 10 min. (stage 2), 40 cycles of 95° C. for 15 sec then 60° C. for 1 min (stage 3), with a dissociation stage at 95° C. for 15 sec, 60° C. for 1 min, and 95° C. for 15 sec (stage 4). Ct values for amplification products of genes of interest are normalized to the average Ct value of 3 housekeeping genes (GAPD, RPS10, and GUSB).

Medium Throughput Screen of the Fate Space of Clonal or Oligoclonal Embryonic Progenitors.

The clonal, oligoclonal, or pooled clonal or pooled oligoclonal embryonic progenitor cell lines of the present invention at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion (since before 29 doublings of clonal expansion the cells are available only in limited quantities, and beyond 70 doublings the cells normally approach senescence) are screened simultaneously in 10, 20, 30, 40, 50, or preferably 100 or more diverse differentiation conditions. Said differentiation conditions may include without limitation, all combinations of the human embryonic progenitor cell lines listed in Table I (showing gene expression markers at 18-21 doublings of clonal expansion), together with culture conditions as listed in Table II, exposed to the culture media listed in Table III, and supplemented factors listed in Table IV. The cells are cultured in said differentiation conditions for 1-6 weeks, most preferably four weeks.

The readout of the assay can be mRNA markers of differentiation such as those listed in Table V and measured by hybridization to arrayed target sequences, including but not limited to microarrays or PCR. Detection can also be at the level of peptides or proteins that may be detected through the use of specific antibodies, through the use of enzyme assays, mass spectroscopy, or other similar means well known in the art.

Medium Throughput qPCR Screen of hEP Cell Differentiation

The clonal, oligoclonal, or pooled clonal or pooled oligoclonal embryonic progenitor cell lines of the present invention, including but not limited to those shown in Table I, at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion are plated in 6 well culture plates with each well having 10 micromasses of 250,000 cells (i.e. 2.5 million cells per well). Alternatively the cells are treated with other culture conditions as listed in Table II using the same number of cells, exposed to any combination of the culture media listed in Table III, and supplemented factors listed in Table IV or detailed protocols listed in Table VIII. The cells are cultured in said differentiation conditions for 1-6 weeks, most preferably four weeks.

RNA is prepared from cell lysates using the Rneasy mini kits (Qiagen) according to the manufacturer's instructions. Briefly, cell cultures (micromasses) are rinsed in PBS, then lysed in a minimal volume of the RLT lysis buffer. After incubation on ice, the cell debris is removed by centrifugation and the lysate is mixed with RLT buffer, after which ethanol is added to the mixture. The combined mixture is then loaded onto the Rneasy spin column and centrifuged; the loaded column is then washed and the purified RNA is released from the column with a minimal volume of DEPC-treated water (typically 30 ul or less). The concentration of RNA in the final eluate is determined by absorbance at 260 nm.

cDNA synthesis is performed using the SuperScript First Strand cDNA kit (InVitrogen; Carlsbad, Calif.). Briefly, 2.5 ug of purified RNA is heat denatured in the presence of random hexamers. After cooling, the first strand reaction is completed using SuperSript reverse transcriptase enzyme and associated reagents from the kit. The resulting product is further purified using QIAquick PCR Purification kits (Qiagen) according to the manufacturer's instructions. Briefly, PB buffer is added to the first strand cDNA reaction products, then the mixture is loaded onto the QIAquick spin column and centrifuged. The column is washed with PE buffer and the purified cDNA is eluted from the column using a minimal volume of water (20 ul).

qPCR primer pairs are synthesized for each target gene. Briefly, primer pairs for a target gene are designed to amplify only the target mRNA sequence and optimally have annealing temperatures for their target sequences that lie in the range of 65–80° C. and unique amplification products in the size range of 100-500 bp. Primer pairs are supplied at working concentrations (10 uM) to BioTrove, Inc. (Woburn, Mass.) for production of a custom qPCR Open Array plate. OpenArray plates are designed to accommodate 56-336 primer pairs and the final manufactured plate with dried down primer pairs is provided to the service provider. Purified cDNA reaction products (2.) and Syber green master mix are loaded into individual wells of the OpenArray plate using OpenArray autoloader device (BioTrove). The plate is sealed and the qPCR and loaded into the NT Imager/Cycler device (BioTrove) for amplification. Ct values for each sample are calculated using the OpenArray application software.

Markers of differentiation are not those present in embryonic progenitor cell lines, but are present in later stages of differentiation. It is not obvious to what an effective array of such markers would be. For example, COL2A1 is not expressed in the clonal embryonic progenitor cell lines, but is markedly induced >100-fold in a subset of the cell lines of the present invention. Previous attempts to invent an array of differentiation markers were not useful in the context of the present invention because they included a majority of markers that were expressed in both embryonic progenitor cell types and in terminally-differentiated cell types (Luo, Y., Cai, J., Ginis, I., Sun, Y., Lee, S., Yu, S. X., Hoke, A., and Rao, M. 2003. Designing, testing, and validating a focused stem cell microarray for characterization of neural stem cells and progenitor cells. Stem Cells, 21:575-587). An example of a list of said markers useful in determining that a particular differentiation condition induced terminal differentiation in embryonic progenitor cell lines a majority of which are not expressed in embryonic progenitor cell lines are shown in Table VI.

Isolation of Secreted or Extracellular Matrix Proteins
Secreted Protein Isolation Protocol 1—Conditioned Medium Cells were grown in either their normal propagation medium (West et al., 2008, *Regen Med* vol. 3(3) pp. 287-308) or the differentiation conditions described herein. To obtain conditioned medium on a smaller scale (typically 1-2 L or less), the cells were grown in monolayer cultures in T150, T175 or T225 flasks (Corning or BD Falcon) in a 37° C. incubator with 10% $CO_2$ atmosphere. For larger volume medium collections, the cells were typically grown either in 2 L roller bottles, on microcarrier suspensions (porous such as Cytodex varieties from Sigma-Aldrich, St. Louis, Mo., or non-porous such as from SoloHill Engineering, Ann Arbor, Mich.) in spinner flasks or other bioreactors, or in hollow fiber cartridge bioreactors (GE Healthcare, Piscataway, N.J.). Prior to conditioned medium collection, the cultures were rinsed twice with PBS and then incubated for 2 hours at 37° C. in the presence of serum-free medium wherein the medium is the same basal medium as described herein for the propagation or differentiation of the cells, in order to remove fetal serum proteins. The serum-free medium was then removed and replaced with fresh medium, followed by continued as described herein at 37° C. for 24-48 hours.

The culture-conditioned medium was then collected by separation from the cell-bound vessel surface or matrix (e.g., by pouring off directly or after sedimentation) and processed further for secreted protein concentration, enrichment or purification. As deemed appropriate for the collection volume, the culture medium was first centrifuged at 500 to 10,000×g to remove residual cells and cellular debris in 15 or 50 ml centrifuge tubes or 250 ml bottles. It was then passaged through successive 1 µm or 0.45 µm and 0.2 µm filter units (Corning) to remove additional debris, and then concentrated using 10,000 MW cutoff ultrafiltration in a stirred cell or Centricon centrifuge filter (Amicon-Millipore) for smaller volumes, or using a tangential flow ultrafiltration unit (Amicon-Millipore) for larger volumes. The retained protein concentrate was then dialyzed into an appropriate buffer for subsequent purification of specific proteins, and further purified using a combination of isoelectric focusing, size exclusion chromatography, ion exchange chromatography, hydrophobic or reverse phase chromatography, antibody affinity chromatography or other well-known methods appropriate for the specific proteins. During the various steps in the purification process, collection fractions were tested for the presence and quantity of the specific secreted protein by ELISA (e.g., using BMP-2 or BMP-7 ELISA kits from R&D Systems, Minneapolis, Minn.). The purified proteins were then kept in solution or lyophilized and then stored at 4 or minus 20-80° C.

Secreted Protein Isolation Protocol 2—Urea-Mediated Protein Extraction

In the case of some secreted proteins, interactions with the cell or ECM components may reduce the simple diffusion of factors into the medium as described above in Secreted Protein Isolation Protocol 1. A simple comparison of the yield in the two protocols will suffice to determine which protocol provides the highest yield of the desired factors. In the case of Secreted Protein Isolation Protocol 2, a low concentration of urea is added to facilitate the removal of factors. In the case of the examples provided, all urea extractions were performed two days subsequent to feeding. On the second day, cell monolayers in T-150 cell culture flasks were rinsed twice with CMF-PBS and then incubated for two hours at 37° C. in the presence of serum-free medium. The rinse with CMF-PBS and the incubation in serum-free medium together aid in the removal of fetal serum proteins from the surface of the cells. The serum-free medium was then removed and 10 ml/T150 of freshly made 200 mM urea in CMF-PBS was added. The flasks were then placed on a rocker at 37° C. for 6.0 hours. The urea solution was then removed and immediately frozen at −70° C.

Extracellular Matrix Isolation Protocol 1—DOC-Mediated Preparation

Extracellular matrix proteins can be extracted using the method of Hedman et al, 1979 (Isolation of the pericellular matrix of human fibroblast cultures. J. Cell Biol. 81: 83-91). Cell layers are rinsed three times with CMF-PBS buffer at ambient temperature and then washed with 30 mL of 0.5% sodium deoxycholate (DOC), 1 mM phenylmethylsulfonylflfuride (PMSF, from 0.4M solution in EtOH), CMF-PBS buffer 3×10 min. on ice while on a rocking platform. The flasks were then washed in the same manner with 2 mM Tris-HCl, pH 8.0 and 1 mM PMSF 3×5 mM. The protein remaining attached to the flask was then removed in 2 mL of gel loading buffer with a rubber policeman.

Screening of Secreted or Extracellular Matrix Proteins for Biological Activity

The cell lines of the present invention are also useful as a means of screening diverse embryonic secretomes for varied biological activities. The cell lines of the present invention cultured at 18-21 doublings of clonal expansion express a wide array of secreted soluble and extracellular matrix genes (see US Patent Application Publication 2010/0184033 entitled "METHODS TO ACCELERATE THE ISOLATION OF NOVEL CELL STRAINS FROM PLURIPOTENT STEM CELLS AND CELLS OBTAINED THEREBY" filed on Jul. 16, 2009, incorporated herein by reference). At 21 or more doublings of clonal expansion, the cells of the present invention differentially express secreted soluble and extracellular matrix genes shown in Table IX. These proteins, proteoglycans, cytokines, and growth factors may be harvested from the cell lines of the present invention by various techniques known in the art including but not limited to Secreted Protein Isolation Protocol 1 or 2. These pools of secreted and extracellular matrix proteins may be further purified or used as mixtures of factors and used in varied in vitro or in vivo assays of biological activity as is known in the art.

Applications

The disclosed methods for the culture of animal cells and tissues are useful in generating cells or progeny thereof in mammalian and human cell therapy, such as, but not limited to, generating human cells useful in treating dermatological, retinal, cardiac, neurological, endocrinological, muscular, skeletal, articular, hepatic, neurological, renal, gastrointestinal, pulmonary, and blood and vascular cell disorders in humans and nonhuman animals.

In certain embodiments of the invention, single cell-derived and oligoclonal cell-derived cells derived by methods of this invention, are utilized in research and treatment of disorders relating to cell biology, cell-based drug discovery and in cell therapy. The single cell-derived cell populations derived using the methods of the present invention may already have received the requisite signals to be directed down a differentiation pathway. For example, some paraxial or somatopleuric single cell-derived populations of cells may express genes consistent with dermal fibroblast gene expression, in particular, a prenatal pattern of gene expression useful in promoting scarless wound repair and in promoting elastogenesis. Such cells include, for example, including but not limited to: cells of the heart; cells of the musculo-skeletal system; cells of the nervous tissue; cells of the respiratory system; cells of the endocrine system including preadipocytes or adipocytes including but not limited to cutaneous white and brown preadipocytes or adipocytes capable of causing weight loss, increasing insulin sensitivity, lowering blood glucose, and thereby reducing the risk of vascular disease a other symptoms of Type II diabetes, in a human or nonhuman mammal; cells of the vascular system; cells of the hematopoietic system; cells of the integumentary system; cells of the urinary system; cells of the joint such as articular chondrocytes, tendons, synovial membrane, and meniscus; or cells of the gastrointestinal system. Such cells may be stably grafted in a histocompatible host when the cells are grafted into the tissue into which the cells would normally differentiate. Such tissues include, but are not limited to: endoderm-embryonic tissues; mesoderm-embryonic tissues; ectoderm-embryonic tissues; or extraembryonic cells.

In certain embodiments of the invention, single cell-derived and oligoclonal cell-derived cells are introduced into the tissues in which they normally reside in order to exhibit therapeutic utility. In certain embodiments of the invention, single cell-derived and oligoclonal cell-derived cells, derived by methods of this invention, are utilized in inducing the differentiation of other pluripotent stem cells. The generation of single cell-derived populations of cells capable of being propagated in vitro while maintaining an embryonic pattern of gene expression is useful in inducing the differentiation of other pluripotent stem cells. Cell-cell induction is a common means of directing differentiation in the early embryo. Many potentially medically-useful cell types are influenced by inductive signals during normal embryonic development, including spinal cord neurons, cardiac cells, pancreatic beta cells, and definitive hematopoietic cells. Single cell-derived populations of cells capable of being propagated in vitro while maintaining an embryonic pattern of gene expression can be cultured in a variety of in vitro, in ovo, or in vivo culture conditions to induce the differentiation of other pluripotent stem cells to become desired cell or tissue types. Induction may be carried out in a variety of methods that juxtapose the inducer cell with the target cell. By way of nonlimiting examples, the inducer cells may be plated in tissue culture and treated with mitomycin C or radiation to prevent the cells from replicating further. The target cells are then plated on top of the mitotically-inactivated inducer cells. Alternatively, single cell-derived inducer cells may be cultured on a removable membrane from a larger culture of cells or from an original single cell-derived colony and the target cells may be plated on top of the inducer cells or a separate membrane covered with target cells may be juxtaposed so as to sandwich the two cell layers in direct contact. The resulting bilayer of cells may be cultured in vitro, transplanted into a SPF avian egg, or cultured in conditions to allow growth in three dimensions while being provided vascular support (see, for example, international patent publication number WO/2005/068610, published Jul. 28, 2005, the disclosure of which is hereby incorporated by reference). The inducer cells may also be from a source of pluripotent stem cells, including hES or hED cells, in which a suicide construct has been introduced such that the inducer cells can be removed at will. Cell types useful in single cell-derived and oligoclonal cell-derived induction may include cases of induction well known in the art to occur naturally in normal embryonic development. In certain embodiments of the invention, single cell-derived cells and oligoclonal cell-derived cells, derived by methods of this invention, are used as "feeder cells" to support the growth of other cell types, including pluripotent stem cells.

The use of single cell-derived cells and oligoclonal cell-derived cells of the present invention as feeder cells alleviates the potential risk of transmitting pathogens from feeder cells derived from other mammalian sources to the target cells. The feeder cells may be inactivated, for example, by gamma ray irradiation or by treatment with mitomycin C, to limit replication and then co-cultured with the pluripotent stem cells.

In certain embodiments of the invention, the extracellular matrix (ECM) of single cell-derived and oligoclonal cell-derived cells, derived by methods of this invention, may be used to support less differentiated cells (see Stojkovic et al., Stem Cells (2005) 23(3):306-14). Certain cell types that normally require a feeder layer can be supported in feeder-free culture on a matrix (Roster et al., Dev Dyn. (2004) 229(2):259-74). The matrix can be deposited by preculturing and lysing a matrix-forming cell line (see WO 99/20741), such as the STO mouse fibroblast line (ATCC Accession No. CRL-1503), or human placental fibroblasts.

In certain embodiments of the invention, the conditioned media of single cell-derived and oligoclonal cell-derived cell cultures may be collected, pooled, filtered and stored as conditioned medium. This conditioned medium may be formulated and used for research and therapy. Such conditioned medium may contribute to maintaining a less differentiated state and allow propagation of cells such as pluripotent stem cells. In certain embodiments of the invention, conditioned medium of single cell-derived and oligoclonal cell-derived cell cultures derived by the methods of this invention can be used to induce differentiation of other cell types, including pluripotent stem cells. The use of conditioned medium of single cell-derived and oligoclonal cell-derived cell cultures may be advantageous in reducing the potential risk of exposing cultured cells to non-human animal pathogens derived from other mammalian sources (i.e. xenogeneic free).

In another embodiment of the invention, single cell-derived and oligoclonal cell-derived paraxial mesoderm, neural crest mesenchyme, or somatopleuric mesoderm, derived by methods of this invention, can be used to induce embryonic ectoderm or single cell-derived embryonic ectoderm into keratinocytes for use in skin research and grafting for burns, wound repair, and drug discovery. In another embodiment of the invention, the use of single cell-derived and oligoclonal cell-derived prechordal plate mesoderm, derived by methods of this invention, to induce embryonic ectoderm or single cell-derived or oligoclonal cell-derived embryonic ectoderm into neuroectodermal cells capable of generating CNS cells, may be useful in neuron research and grafting for neurodegenerative diseases, as well as drug discovery. The single cell-derived and oligoclonal cell-derived prechordal plate mesoderm can be identified by transcript analysis as described herein through the expression of, for example, lim-1. In another embodiment of the invention, the single cell-derived and oligoclonal cell-derived notochord mesodermal cells, derived by methods of this invention, are identified by their expression of brachyury. In normal development, notochordal cells induce the floor of the neural plate mesoderm (which induces the spinal chord) to make sonic hedgehog ("SHH"), a ventralizing signal, that induces the floor of the neural tube to express SHH as well, which induces the expression of FP1, FP2, and SC1 by the floor plate of the neural tube. Therefore, notochordal mesodermal cells can be used to induce neural plate ectodermal cells or neural tube neuroepithelial cells to differentiate into spinal cord neurons. Such neurons may be identified and confirmed by assaying the gene expression assays described herein for cells expressing FP1, FP2, or SC1. These cells expressing one or more of these markers could be useful in spinal cord regeneration.

Our discovery that various single cell-derived and oligoclonal cell-derived cells in early embryonic lineages may be propagated without the loss of their embryonic phenotype allows numerous types of mesodermal inducer cells to induce differentiation in embryonic ectoderm or endoderm. However, single cell-derived and oligoclonal cell-derived cells from endoderm and ectodermal lineages, derived by methods of this invention, may be useful in induction as well. For example, surface ectoderm and notochord express Shh and thereby induce somites to become sclerotome mesodermal cells that express M-twist and Pax-1 and surface ectoderm. Also, as another example, notochord expresses extracellular proteins of the Wnt family and thereby induces other somite mesodermal cells to become dermatome mesodermal cells that express gMHox, and dermo-1. The juxtaposition of the inducer and target cells provides a useful in vitro model of differentiation that can be used for research into early embryonic differentiation, for drug screening, and for studies of teratology. The target cells differentiated by the single cell-derived inducer cells may also be used for research, drug discovery, and cell-based therapy.

In certain embodiments of the invention, the single cell-derived and oligoclonal cell-derived cells, derived by methods of this invention, may be used to generate skin equivalents, as well as to reconstitute full-thickness human skin, according to the methods described in U.S. application Ser. No. 09/037,191, filed Mar. 9, 1998 (U.S. publication no. 2001/0048917, published Dec. 6, 2001); Ser. No. 10/013,124, filed Dec. 7, 2001 (U.S. publication no. 2002/0120950, published Aug. 29, 2002); Ser. No. 10/982,186, filed Nov. 5, 2004 (U.S. publication no. 2005/0118146, published Jun. 2, 2005); the disclosure of each of which is incorporated herein by reference. For example, the single cell-derived and oligoclonal cell-derived cells may be incorporated into a layered cell sorted tissue that includes a discrete first cell layer and a discrete second cell layer that are formed in vitro by the spontaneous sorting of cells from a homogenous cell mixture. The first cell layer may include any cell type, but preferably includes epithelial cells, in particular, keratinocytes. Other cell types that may be used in the first cell layer are CaCo2 cells, A431 cells, and HUC18 cells. The second cell layer may also include cells of any type, but preferably includes mesenchymal cells, in particular, fibroblasts. The layered cell sorted tissue possesses an epidermal-dermal junction that is substantially similar in structure and function to its native counterpart. That is, the tissue expresses the necessary integral proteins such as hemidesmosomes and collagen I, collagen IV, and collagen VII, to attach the epidermal and dermal layers with the proper basement membrane morphology. The single cell-derived and oligoclonal cell-derived cells may then sort to form an epidermal layer that contacts the connective tissue component. The layered cell sorted tissues comprising the single cell-derived and oligoclonal cell-derived cells may be used as a skin graft that could be used on graft sites such as traumatic wounds and burn injury.

In another embodiment of the invention, single cell-derived and oligoclonal cell-derived cells of this invention may be used as a means to identify and characterize genes that are transcriptionally activated or repressed as the cells undergo differentiation. For example, libraries of gene trap single cell-derived or oligoclonal cell-derived cells may be made by methods of this invention, and assayed to detect changes in the level of expression of the gene trap markers as the cells differentiate in vitro and in vivo. The methods for making gene trap cells and for detecting changes in the expression of the gene trap markers as the cells differentiate are reviewed in Durick et al. (Genome Res. (1999) 9:1019-25), the disclosure of which is incorporated herein by reference). The vectors and methods useful for making gene trap cells and for detecting changes in the expression of the gene trap markers as the cells differentiate are also described in U.S. Pat. No. 5,922,601 (Baetscher et al.), U.S. Pat. No. 6,248,934 (Tessier-Lavigne) and in U.S. patent publication No. 2004/0219563 (West et al.), the disclosures of which are also incorporated herein by reference. Methods for genetically modifying cells, inducing their differentiation in vitro, and using them to generate chimeric or nuclear-transfer cloned embryos and cloned mice are developed and known in the art. To facilitate the identification of genes and the characterization of their physiological activities, large libraries of gene trap cells having gene trap DNA markers randomly inserted in their genomes may be prepared. Efficient methods have been developed to screen and detect changes in the level of expression of the gene trap markers as the cells differentiate in vitro or in vivo. In vivo methods for inducing single cell-derived or oligoclonal cell-derived cells to differentiate further include injecting one or more cells into a blastocyst to form a chimeric embryo that is allowed to develop; fusing a stem cell with an enucleated oocyte to form a nuclear transfer unit (NTU), and culturing the NTU under conditions that result in generation of an embryo that is allowed to develop; and implanting one or more clonogenic differentiated cells into an immune-compromised or a histocompatible host animal (e.g., a SCID mouse, or a syngeneic nuclear donor) and allowing teratomas comprising differentiated cells to form. hi vitro methods for inducing single cell-derived or oligoclonal cell-derived cells to differentiate further include culturing the cells in a monolayer, in suspension, or in three-dimensional matrices, alone or in co-culture with cells of a different type, and exposing them to one of many combinations of chemical, biological, and physical agents, including co-culture with one or more different types of cells, that are known to capable of induce or allow differentiation.

In another embodiment of the invention, cell types that do not proliferate well under any known cell culture conditions may be induced to proliferate such that they can be isolated clonally or oligoclonally according to the methods of this invention through the regulated expression of factors that overcome inhibition of the cell cycle, such as regulated expression of SV40 virus large T-antigen (Tag), or regulated E1a and/or E1b, or papillomavirus E6 and/or E7, or CDK4 (see, e.g., U.S. patent application Ser. No. 11/604,047 filed on Nov. 21, 2006 and titled "Methods to Accelerate the Isolation of Novel Cell Strains from Pluripotent Stem Cells and Cells Obtained Thereby", incorporated herein by reference).

In another embodiment of the invention, the factors that override cell cycle arrest may be fused with additional proteins or protein domains and delivered to the cells. For example, factors that override cell cycle arrest may be joined to a protein transduction domain (PTD). Protein transduction domains, covalently or non-covalently linked to factors that override cell cycle arrest, allow the translocation of said factors across the cell membranes so the protein may ultimately reach the nuclear compartments of the cells. PTDs that may be fused with factors that override cell cycle arrest include the PTD of the HIV transactivating protein (TAT) (Tat 47-57) (Schwarze and Dowdy 2000 *Trends Pharmacol.* *Sci.* 21: 45-48; Krosl et al. 2003 *Nature Medicine* (9): 1428-1432). For the HIV TAT protein, the amino acid sequence conferring membrane translocation activity corresponds to residues 47-57 (Ho et al., 2001, *Cancer Research* 61: 473-477; Vives et al., 1997, *J. Biol. Chem.* 272: 16010-16017). These residues alone can confer protein translocation activity.

In another embodiment of the invention, the PTD and the cycle arrest factor may be conjugated via a linker. The exact length and sequence of the linker and its orientation relative to the linked sequences may vary. The linker may comprise, for example, 2, 10, 20, 30, or more amino acids and may be selected based on desired properties such as solubility, length, steric separation, etc. hi particular embodiments, the linker may comprise a functional sequence useful for the purification, detection, or modification, for example, of the fusion protein.

In another embodiment of the invention, single cell-derived or oligoclonal cell-derived cells of this invention may be reprogrammed to an undifferentiated state through novel reprogramming technique, as described in U.S. application No. 60/705,625, filed Aug. 3, 2005, U.S. application No. 60/729,173, filed Oct. 20, 2005; U.S. application No. 60/818,813, filed Jul. 5, 2006, the disclosures of which are incorporated herein by reference. Briefly, the cells may reprogrammed to an undifferentiated state using at least a two, preferably three-step process involving a first nuclear remodeling step, a second cellular reconstitution step, and finally, a third step in which the resulting colonies of cells arising from step two are characterized for the extent of reprogramming and for the normality of the karyotype and quality. In certain embodiments, the single cell-derived or oligoclonal cell-derived cells of this invention may be reprogrammed in the first nuclear remodeling step of the reprogramming process by remodeling the nuclear envelope and the chromatin of a differentiated cell to more closely resemble the molecular composition of an undifferentiated or a germ-line cell. In the second cellular reconstitution step of the reprogramming process, the nucleus, containing the remodeled nuclear envelope of step one, is then fused with a cytoplasmic bleb containing requisite mitotic apparatus which is capable, together with the transferred nucleus, of producing a population of undifferentiated stem cells such as ES or ED-like cells capable of proliferation. In the third step of the reprogramming process, colonies of cells arising from one or a number of cells resulting from step two are characterized for the extent of reprogramming and for the normality of the karyotype and colonies of a high quality are selected. While this third step is not required to successfully reprogram cells and is not necessary in some applications, the inclusion of the third quality control step is preferred when reprogrammed cells are used in certain applications such as human transplantation. Finally, colonies of reprogrammed cells that have a normal karyotype but not sufficient degree of programming may be recycled by repeating steps one and two or steps one through three.

In another embodiment of the invention, the single cell-derived and oligoclonal cell-derived cells may be used to generate ligands using phage display technology (see U.S. application No. 60/685,758, filed May 27, 2005, and PCT US2006/020552, filed May 26, 2006, the disclosures of which are hereby incorporated by reference).

In another embodiment of the invention, the single cell-derived or oligoclonal cell-derived cells of this invention may exhibit unique patterns of gene expression such as high levels of factors, e.g. secreted factors, that promote the development or formation of specific tissue types either in vitro or in vivo (e.g., angiogenic factors, neurotrophic factors, etc). Such cells may be useful for the delivery of these factors to tissues to promote the formation of specific cell/tissue types where those cells/tissues are therapeutic. For example, in the case of the angiogenic factors, cell lines that express high levels of such factors including VEGFA, B, C, or D or angiopoietin-1 or -2 can be transplanted using delivery technologies appropriate to the target tissue to deliver cells that express said angiogenic factor(s) to induce angiogenesis for therapeutic effect. In another embodiment of the invention, cells may produce large quantities of PTN (Accession number NM_002825.5), MDK (Accession number NM_002391.2), or ANGPT2 (Accession number NM_001147.1), or other angiogenesis factors and therefore may be useful in inducing angiogenesis when injected in vivo as cell therapy, when mitotically inactivated and then injected in vivo, or when combined with a matrix in either a mitotically-inactivated or native state for use in inducing angiogenesis. PTN-producing cells described in the present invention are also useful when implanted in vivo in either a native or mitotically-inactivated state for delivering neuroactive factors, such as in preventing the apoptosis of neurons following injury to said neurons.

As another example, a cell produced by the methods of this invention could produce large amounts of BMP2, BMP7, BMP3b or other members of the BMP family, and this cell could therefore be useful in inducing bone formation (as described below).

The expression of genes of the cells of this invention may be determined. Measurement of the gene expression levels may be performed by any known methods in the art, including but not limited to, microarray gene expression analysis, bead array gene expression analysis and Northern analysis. The gene expression levels may be represented as relative expression normalized to the ADPRT (Accession number NM_001618.2), GAPD (Accession number NM_002046.2), or other housekeeping genes known in the art. The gene expression data may also be normalized by a median of medians method. In this method, each array gives a different total intensity. Using the median value is a robust way of comparing cell lines (arrays) in an experiment. As an example, the median was found for each cell line and then the median of those medians became the value for normalization. The signal from the each cell line was made relative to each of the other cell lines. Based on the gene expression levels, one would expect the expression of the corresponding proteins by the cells of the invention. For example, in the case of cell clone ACTC60 (or B-28) of Series 1, relatively high levels of DKK1, VEGFC and IL1R1 were observed. Therefore, the ability to measure the bioactive or growth factors produced by said cells may be useful in research and in the treatment of disease.

In the case of neutrophic factors, the cells made by the methods of this invention may be used to induce the innervation of tissue such as to improve the sensory innervation of the skin in wound repair or regeneration, or other sensory or motor innervation. For example, the cell clone number 1 (ACTC61/B30) displays a high level of expression of pleiotrophin (PTN) and may therefore be formulated for this use using delivery and formulation technologies well known in the art including by way of nonlimiting example, humans and veterinary animal applications where the dosage will be between $10^2$-$10^6$ cells and the formulation can be, by way of nonlimiting example, a cell suspension in isosmotic buffer or a monolayer of cells attached to a layer of extracellular matrix such as contracted gelatin. Such use of cells that promote angiogenesis or neurite outgrowth may further be combined with an adjunct therapy that includes young hemangioblasts or angioblasts in the case of angiogenesis or neuronal precursors of various kinds in the case of neurite outgrowth. Such combined therapy may have particular utility where the mere administration of angiogenic factors or neurite outgrowth promoting factors by themselves are not sufficient to generate a response due to the fact that there is a paucity of cells capable of responding to the stimulus.

In the case of angiogenesis, the senescence of the vascular endothelium or circulating endothelial precursor cells such as hemangioblasts may blunt the response to angiogenic stimulus. The co-administration of young hemangioblasts by various modalities known in the art based on the size of the animal and the target tissue along with cells capable of delivering an angiogenic stimulus will provide an improved angiogenic response. Such an induction of angiogenesis can be useful in promoting wound healing, the vascularization of tissues prone to ischemia such as aged myocardium, skeletal, or smooth muscle, skin (as in the case of nonhealing skin ulcers such as decubitus or stasis ulcers), intestine, kidney, liver, bone, or brain. Measurement of the gene expression levels may be performed by any known methods in the art, including but not limited to, microarray gene expression analysis, bead array gene expression analysis and Northern analysis. The gene expression levels may be represented as relative expression normalized to the ADPRT (Accession number NM_001618.2), GAPD (Accession number NM_002046.2), or other housekeeping genes known in the art. The gene expression data may also be normalized by a median of medians method. In this method, each array gives a different total intensity. Using the median value is a robust way of comparing cell lines (arrays) in an experiment. As an example, the median was found for each cell line and then the median of those medians became the value for normalization. The signal from the each cell line was made relative to each of the other cell lines.

In another embodiment of the invention, the single cell-derived or oligoclonal cell-derived cells of this invention may express unique patterns of CD antigen gene expression, which are cell surface antigens. The differential expression of CD antigens on the cell surface may be useful as a tool, for example, for sorting cells using commerically available antibodies, based upon which CD antigens are expressed by the cells. The expression profiles of CD antigens of some cells of this invention are shown in West et al., 2008, *Regene Med* vol. 3(3) pp. 287-308, incorporated herein by reference, including supplemental information. For example, there are CD antigens that are expressed in ES cells and not (or in some cases, at reduced levels) in the relatively more differentiated cell lines of this invention. This could be a very useful tool for selecting, sorting, purifying and/or characterizing ES cells. Since the CD antigens are expressed on the cell surface and antibodies to them are, generally speaking, commercially available, antibodies (or specific combinations of them) can be used to purify pure populations of ES cells or cells of this invention out of a heterogeneous mixture of cells. This could be useful in various strategies to grow ES cells or cells of this invention, or prepare these cells for various commercial purposes. There are several CD antigens that are robustly expressed in the relative more differentiated cells of this invention, but are not expressed in ES cells (or in some cases at markedly reduced levels). The antigens that fall into this category include: CD73, CD97, CD140B, CD151, CD172A, CD230, CD280, CDw210b. These antigens may be useful in a negative selection strategy to grow ES cells.

In another embodiment of the invention, the single cell-derived and oligoclonal cell-derived cells, derived by methods of this invention, may be injected into mice to raise antibodies to differentiation antigens. Antibodies to differentiation antigens would be useful for both identifying the cells to document the purity of populations for cell therapies, for research in cell differentiation, as well as for documenting the presence and fate of the cells following transplantation. In general, the techniques for raising antibodies are well known in the art.

In another embodiment of the invention, the single cell-derived and oligoclonal cell-derived cells may be used for the purpose of generating increased quantities of diverse cell types with less pluripotentiality than the original stem cell type, but not yet fully differentiated cells. mRNA or miRNA can then be prepared from these cell lines and microarrays of their relative gene expression can be performed as described herein. In another embodiment of the invention, the single cell-derived and oligoclonal cell-derived cells may be used in animal transplant models, e.g. transplanting escalating doses of the cells with or without other molecules, such as ECM components, to determine whether the cells proliferate after transplantation, where they migrate to, and their long-term differentiated fate in safety studies.

In another embodiment of the invention, the single cell-derived and oligoclonal cell-derived cells generated according to the methods of the present invention are useful for harvesting mRNA, microRNA, and cDNA from either single cells or a small number of cells (i.e., clones) to generate a database of gene expression information. This database allows researchers to identify the identity of cell types by searching for which cell types in the database express or do not express genes at comparable levels of the cell type or cell types under investigation. For example, the relative expression of mRNA may be determined using microarray analysis as is well known in the art. The relative values may be imported into a software such as Microsoft Excel and gene expression values from the different cell lines normalized using various techniques well known in the art such as mean, mode, median, and quantile normalization. Hierarchical clustering with the single linkage method may be performed with the software such as The R Project for Statistical Computing as is well known in the art. An example of such documentation may be found at http(colon)//sekhon(dot)berkeley(dot)edu/stats/html/hclust.html. A hierarchical clustering analysis can then be performed as is well known in the art. These software programs perform a hierarchical cluster analysis using a group of dissimilarities for the number of objects being clustered. At first, each object is put in its own cluster, then iteratively, each similar cluster is joined until there is one cluster. Distances between clusters are computed by Lance-Williams dissimilarity update formula (Becker, R. A., Chambers, J. M. and Wilks, A. R. (1988) The New S Language. Wadsworth & Brooks/Cole. (S version.); Everitt, B. (1974). Cluster Analysis. London: Heinemann Educ. Books). Typically the vertical axis of the dendograms displays the extent of similarity of the gene expression profiles of the cell clones. That is, the farther down they branch apart, the more similar they are. The verticle axis is a set of n−1 non-decreasing real values. The clustering height is the value of the criterion associated with the clustering method for the particular agglomeration. In order to determine if a new cell line is identical to existing cell lines, two types of replicates are performed: biological and technical replicates. Biological replicates require that new cell lines be grown, mRNA harvested, and then the analysis compared. Technical replicates, on the other hand, analyze the same RNA twice. A line cutoff is then drawn just above where the replicates branch such that cells branching below the cutoff line are considered the same cell type. Another source of data for the database described above may be microRNA profiles of the single cell-derived and oligoclonal cell-derived cells generated according to the methods of the present invention. MicroRNAs (miRNA) are endogenous RNAs of −22 nucleotides that play important regulatory roles in animals & plants by targeting mRNAs for cleavage or translational repression. More than 700 miRNAs have been identified across species. Their expression levels vary among species and tissues. Low abundant miRNAs have been difficult to detect based on current technologies such as cloning, Northern hybridization, and the modified Invader® assay. In the present invention, an alternative approach using a new real-time quantitation method termed looped-primer RT-PCR was used for accurate and sensitive detection of miRNAs as well as other non-coding RNA (ncRNA) molecules present in human embryonic stem cells and in cell lines differentiated from human embryonic stem cells.

In another embodiment of the invention, gene expression analysis may be used to identify the developmental pathways and cell types for in vitro differentiated hES cells. Gene expression analysis of single cells or a small number of cells from human or nonhuman embryonic or fetal tissues provides another means to generate a database of unique gene expression profiles for distinct populations of cells at different stages of differentiation. Gene expression analysis on single cells isolated from specific tissues may be performed as previously described by Kurimoto et al., Nucleic Acids Research (2006) Vol. 34, No. 5, e42. Thus, cellular miRNA profiles on their own or in conjunction with gene expression profiles, immunocytochemistry, and proteomics provide molecular signatures that can be used to identify the tissue and developmental stage of differentiating cell lines. This technique illustrates that the database may be used to accurately identify cell types and distinguish them from other cell types.

The cells of the present invention are also useful in providing a subset of gene expression markers that are expressed at relatively high levels in some cell lines while not be expressed at all in other cell lines as opposed to genes expressed in all cell lines but at different levels of expression. This subset of "all-or none" markers can be easily identified by comparing the levels of expression as measured for instance through the use of oligonucleotide probes or other means know in the art, and comparing the level of a gene's expression in one line compared to all the other lines of the present invention. Those genes that are expressed at relatively high levels in a subset of lines, and not at all in other lines, are used to generate a short list of gene expression markers. When applied to the cells and gene expression data described herein, where negative expression in Illumina 1 is <170 RFU and positive expression is >500 RFU, negative expression in Illumina 2 is <160 RFU and positive expression is >300 RFU, and negative expression in Affy is <50 RFU and positive expression is >250 RFU, a nonlimiting example of such genes is ACTC, AGC1, AKR1C1, ALDH1A1, ANXA8, APCDD1, AQP1, AREG, ATP8B4, BEX1, CFB, BMP4, C3, C6, C7, PRSS35, C20orf103, CCDC3, CD24, CDH3, CDH6, CLDN11, CNTNAP2, COL15A1, COL21A1, COMP, COP1, CRIP1, CRLF1, CRYAB, CXADR, DIO2, METTL7A, DKK2, DLK1, DPT, EGR2, EMID1, FGFR3, TMEM100, FMO1, FMO3, FOXF1, FOXF2, FST, GABRB1, GAP43, GDF5, GDF10, GJB2, GSC, HOXA5, HSD11B2, HSD17B2, HSPA6, HSPB3, HTRA3, ICAM5, ID4, IFI27, IFIT3, IGF2, IGFBP5, IL1R1, INA, KCNMB1, KIAA0644, KRT14, KRT17, KRT19, KRT34, LAMC2, TMEM119, IGFL3, LOC92196, MFAP5, MASP1, MEOX1, MEOX2, MGP, MMP1, MSX1, MSX2, MX1, MYBPH, MYH3, MYH11, MYL4, IL32, NLGN4X, TAGLN3, NPAS1, NPPB, OGN, OLR1, OSR2, PAX2, PAX9, PDE1A, PENK, PITX2, PODN, POSTN, PRELP, PRG4, PROM1, PRRX1, PRRX2, PTGS2, PTN, PTPRN, RARRES1, RASD1, RELN, RGMA, RGS1, RPS4Y2, S100A4, SERPINA3, SFRP2, SLITRK6, SMOC1, SMOC2, SNAP25, SOD3, SOX11, SRCRB4D, STMN2, SYT12, TAC1, TFPI2, RSPO3, THY1, TNFSF7, TNNT2, TRH, TSLP, TUBB4, UGT2B7, WISP2, ZD52F10, ZIC1, and ZIC2.

Neural Differentiation Medium 2

The cell line to be tested is plated in six well plates at two different densities 5×10$^5$ cells/well. The cells are grown under standard growth conditions until they reach confluence. The media is then replaced with 50% DMEM 50% F12 media supplemented with N2 containing and MEM-NEAA, 2 mg/ml heparin, 1 mM cAMP, 200 ng/ml ascorbic acid, 50 ng/ml IGF-1, 10 ng/ml GDNF, 10 ng/ml BDNF).

Safranin O Staining Assay

The well-known techniques of staining of formalin-fixed, paraffin-embedded tissue sections with Safranin O are commonly used in the detection of cartilage-related proteoglycans, however, the assay is not absolutely specific to cartilage since it also stains mucin, mast cell granules, and likely other substances in other cell types. A nonlimiting example of the protocol where cartilage and mucin will be stained orange to red, and the nuclei will be stained black and the background stained green uses formalin-fixed micromasses, pellets, or similar aggregations of cells. Reagents used include Weigert's Iron Hematoxylin Solution: in which Stock Solution A composed of 1 gram of Hematoxylin in 100 ml of 95% Alcohol; Stock Solution B composed of 4 ml of 29% Ferric chloride in water diluted in 95 ml of Distilled water and 1.0 ml of concentrated Hydrochloric acid; Weigert's Iron Hematoxylin Working Solution composed of equal parts of stock solution A and B and used within four weeks; 0.001% Fast Green (FCF) Solution composed of 0.01 gram of Fast green, FCF, C.I. 42053 in 1000 ml Distilled water; 1% Acetic Acid Solution composed of 1.0 ml glacial acetic acid in 99 ml Distilled water; and 0.1% Safranin 0 Solution composed of 0.1 gram Safranin O, C.I. 50240 in 100 ml Distilled water. Samples are Deparaffinized and hydrated with distilled water. They are stained with Weigert's iron hematoxylin working solution for 10 minutes, then washed in running tap water for 10 minutes, stained with fast green (FCF) solution for 5 minutes, rinsed quickly with 1% acetic acid solution for no more than 10-15 seconds, stained in 0.1% safranin O solution for 5 minutes, dehydrated and cleared with 95% ethyl alcohol, absolute ethyl alcohol, and xylene, using 2 changes each, 2 minutes each, mounted using resinous medium, and imaged and analyzed for stains as described above. Cartilage-related proteoglycan stains dark red-orange.

Human Embryonic Chondrogenic Progenitor Line Markers

The gene expression markers of the human embryonic progenitor cell lines capable of differentiating into chondroblasts and then chondrocytes expressing higher levels of COL2A1 than normal early passage cultured human articular chondrocytes when said human embryonic progenitor cell lines have undergone 18-21 doublings of clonal expansion following isolation from human ES or similar human primordial stem cell-derived cells are:

The cell line SM30 is positive for the markers: COL15A1, CRYAB, DYSF, FST, GDF5, HTRA3, TMEM119, MMP1, MSX1, MSX2, MYL4, POSTN, SERPINA3, SRCRB4D and ZIC2 and is negative for the markers: ACTC, AGC1, AKR1C1, ALDH1A1, ANXA8, APCDD1, AQP1, ATP8B4, CFB, C3, C6, C7, C20orf103, CD24, CDH3, CLDN11, CNTNAP2, COMP, DIO2, METTL7A, DKK2, DLK1, DPT, FGFR3, TMEM100, FMO1, FMO3, FOXF2, GABRB1, GJB2, GSC, HOXA5, HSD11B2, HSPA6, ID4, IFI27, IL1R1, KCNMB1, KIAA0644, KRT14, KRT17, KRT34, IGFL3, LOC92196, MEOX1, MEOX2, MGP, MYBPH, MYH3, MYH11, NLGN4X, NPPB, OGN, OLR1, OSR2, PAX2, PAX9, PDE1A, PENK, PRG4, PROM1, PRRX1, PTN, RARRES1, RASD1, RELN, RGS1, SLITRK6, SMOC1, SMOC2, SNAP25, STMN2, TAC1, RSPO3, TNFSF7, TNNT2, TRH, TUBB4, UGT2B7 and WISP2.

The cell line X4D20.8 is positive for the markers: BEX1, CDH6, CNTNAP2, COL21A1, CRIP1, CRYAB, DIO2, DKK2, GAP43, ID4, LAMC2, LHX8, MMP1, MSX2, S100A4, SOX11 and THY1 and is negative for the markers: AGC1, ALDH1A1, AREG, ATP8B4, CFB, C3, C7, C20orf103, CDH3, CLDN11, COP1, CRLF1, DLK1, DPT, FMO1, FMO3, GDF10, GJB2, GSC, HOXA5, HSD11B2, HSD17B2, HSPA6, HSPB3, ICAM5, IFI27, IGF2, KRT14, KRT17, KRT34, MASP1, MEOX2, MSX1, MX1, MYBPH, MYH3, MYH11, TAGLN3, NPAS1, NPPB, OGN, OLR1, PAX2, PDE1A, PRG4, PROM1, PTN, PTPRN, RARRES1, RGS1, SNAP25, STMN2, TAC1, TNNT2, TRH, TUBB4, WISP2, ZIC1 and ZIC2.

The group of cell lines SK11, SK44, SK50 and SK52 are positive for the markers: BEX1, COL21A1, FST, ICAM5, IL1R1, TMEM119, PTPRN, SERPINA3, SFRP2 and ZIC1 and are negative for the markers: ACTC, AGC1, ALDH1A1, AQP1, ATP8B4, C6, C20orf103, CCDC3, CDH3, CLDN11, CNTNAP2, DIO2, DKK2, EMID1, GABRB1, GSC, HOXA5, HSPA6, IFI27, INA, KRT14, KRT34, IGFL3, LOC92196, MEOX1, MEOX2, MMP1, MX1, MYH3, MYH11, IL32, NLGN4X, NPPB, OLR1, PAX2, PAX9, PDE1A, PENK, PROM1, PTN, RARRES1, RASD1, RELN, RGS1, SMOC1, SMOC2, STMN2, TAC1, TFPI2, RSPO3, TNFSF7, TNNT2, TRH and TUBB4.

The cell line MEL2 is positive for the markers: AKR1C1, AQP1, COL21A1, CRYAB, CXADR, DIO2, METTL7A, DKK2, DLK1, DLX5, HAND2, HSD17B2, HSPB3, MGP, MMP1, MSX2, PENK, PRRX1, PRRX2, S100A4, SERPINA3, SFRP2, SNAP25, SOX11, TFPI2 and THY1 and is negative for the markers: ACTC, ALDH1A1, AREG, CFB, C3, C20orf103, CD24, CDH3, CDH6, CNTNAP2, COL15A1, COMP, COP1, CRLF1, FGFR3, FMO1, FMO3, FOXF2, FST, GABRB1, GAP43, GDF5, GDF10, GJB2, GSC, HOXA5, HSD11B2, HSPA6, ICAM5, KCNMB1, KRT14, KRT17, KRT19, KRT34, MASP1, MEOX1, MEOX2, MYBPH, MYH3, MYH11, TAGLN3, NPAS1, NPPB, OLR1, PAX2, PDE1A, PITX2, PRG4, PTN, PTPRN, RASD1, RELN, RGS1, SMOC1, STMN2, TAC1, TNFSF7, TRH, TUBB4, WISP2, ZIC1 and ZIC2.

The cell line X7SM0032 is positive for the markers: ACTC, BEX1, CDH6, COL21A1, CRIP1, CRLF1, DIO2, DLK1, EGR2, FGFR3, FOXF1, FOXF2, FST, GABRB1, IGFBP5, KIAA0644, KRT19, LAMC2, TMEM119, MGP, MMP1, MSX1, MSX2, PODN, POSTN, PRG4, PRRX2, PTN, RGMA, S100A4, SERPINA3, SOX11 and SRCRB4D and is negative for the markers: AGC1, AKR1C1, ALDH1A1, ANXA8, APCDD1, AREG, ATP8B4, BMP4, C3, C6, C7, PRSS35, C20orf103, CCDC3, CD24, CLDN11, CNTNAP2, COL15A1, COP1, CXADR, METTL7A, DKK2, DPT, EMID1, TMEM100, FMO1, FMO3, GDF5, GDF10, GJB2, GSC, HOXA5, HSD11B2, HSD17B2, HSPA6, HSPB3, HTRA3, ICAM5, ID4, IFI27, IL1R1, INA, KCNMB1, KRT14, KRT17, KRT34, IGFL3, LOC92196, MFAP5, MASP1, MEOX1, MEOX2, MYBPH, MYH3, MYH11, MYL4, IL32, NLGN4X, NPPB, OGN, OLR1, OSR2, PAX2, PAX9, PDE1A, PITX2, PRELP, PROM1, PTPRN, RASD1, RGS1, SFRP2, SMOC1, SMOC2, SOD3, STMN2, SYT12, TAC1, RSPO3, TNFSF7, TNNT2, TRH, TSLP, TUBB4, UGT2B7, WISP2, ZD52F10, ZIC1 and ZIC2.

The cell line E15 is positive for the markers: ACTC, BEX1, PRSS35, CRIP1, CRYAB, GAP43, GDF5, HTRA3, KRT19, MGP, MMP1, POSTN, PRRX1, S100A4, SOX11, SRCRB4D and THY1 and are negative for the markers: AGC1, AKR1C1, ALDH1A1, ANXA8, APCDD1, AQP1, AREG, ATP8B4, CFB, C3, C6, C7, C20orf103, CDH3, CNTNAP2, COP1, CXADR, METTL7A, DLK1, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IFI27, IFIT3, IGF2, INA, KRT14, TMEM119, IGFL3, LOC92196, MFAP5, MASP1, MEOX1, MEOX2, MSX1, MX1, MYBPH, MYH3, MYL4, NLGN4X, TAGLN3, NPAS1, NPPB, OGN, OLR1, PAX2, PAX9, PDE1A, PENK, PITX2, PRG4, PROM1, PTPRN, RARRES1, RASD1, RELN, RGS1, SLITRK6, SMOC1, SMOC2, SNAP25, STMN2, TAC1, TFPI2, RSPO3, TNFSF7, TNNT2, TRH, TSLP, TUBB4, UGT2B7, WISP2, ZD52F10 and ZIC1.

Tissue Engineered Constructs

In certain embodiments, cells of the present invention are employed in therapeutic applications to repair, replace, or enhance tissue function in a subject (e.g., a mammal, e.g., a human patient). A number of therapies that employ cells incorporated in engineered matrices have been described, a few of which are summarized below. The cells of the present invention may be embedded in such matrices to provide form and function as is well-known in the art.

In certain embodiments, synthetic matrices or biological resorbable immobilization vehicles (sometimes referred to as "scaffolds") may be impregnated with cells of the present invention. A variety of synthetic carrier matrices have been used to date and include: three-dimensional collagen gels (U.S. Pat. No. 4,846,835; Nishimoto (1990) Med. J. Kinki University 15; 75-86; Nixon et al. (1993) Am. J. Vet. Res. 54:349-356; Wakitani et al. (1989) J. Bone Joint Surg. 71B:74-80; Yasui (1989) J. Jpn. Ortho. Assoc. 63:529-538); reconstituted fibrin-thrombin gels (U.S. Pat. Nos. 4,642,120; 5,053,050 and 4,904,259); synthetic polymer matrices containing polyanhydride, polyorthoester, polyglycolic acid and copolymers thereof (U.S. Pat. No. 5,041,138); and hyaluronic acid-based polymers (Robinson et al. (1990) Calcif. Tissue Int. 46:246-253).

For example, the cells of the present invention may be employed in tissue reconstruction as described in Methods of Tissue Engineering (2002), edited by Anthony Atala and Robert P. Lanza and published by Academic Press (London), incorporated by reference herein for its description of tissue reconstruction (see, e.g, pages 1027 to 1039). As described therein, cells may be placed into a molded structure (e.g., by injection molding) and transplanted into an animal. Over time, tissue produced by the cells of the present invention will replace the molded structure, thereby producing a formed structure (i.e., in the shape of the initial molded structure). Exemplary mold materials for the molded structure include hydrogels (e.g., alginate, agarose, polaxomers (Pluronics)) and natural materials (e.g., type I collagen, type II collagen, and fibrin).

In certain embodiments, cells of the present invention may be cultured in vitro to form a synthetic tissue-like material. The resulting tissue may be implanted subsequently into a subject at the site of the defect. This type of approach has the advantage that the development of the synthetic tissue may be monitored prior to implantation. In addition, the resulting tissue may be characterized biochemically and morphologically prior to implantation. Numerous different procedures have been developed for growing synthetic tissue in vitro, including growing cells in an anchorage-dependent or an anchorage-independent manner.

In the anchorage-independent manner, cells may be cultured as colonies within an agarose gel. See for example: Benya et al. (1982) Cell 30:215-224; Aydlotte et al. (1990) in Methods and Cartilage Research Chapter 23:pp. 90-92; Aulthouse et al. (1989) In Vitro Cellular and Developmental Biology 25:659-668; Delbruck et al. (1986) Connective Tissue Res. 15:1550-172; and Bohme et al. (1992) J. Cell Biol. 116:1035-1042. Alternatively, in another anchorage-independent method, cells may be cultured as colonies in suspension culture. See for example, Franchimont et al. (1989) J. Rheumatol. 16:5-9; and Bassleer et al. (1990) in "Methods and Cartilage Research", Academic Press Ltd., Chapter 24.

In the anchorage-dependent method, primary cultures of cells may be grown as monolayers attached to the surface of a cell culture flask. See for example: Yoshihashi (1983) J. Jpn. Ortho. Assoc. 58:629-641; and U.S. Pat. No. 4,356,261, incorporated by reference herein in its entirety.

In certain embodiments, a cartilage therapy of the invention includes those described in U.S. Pat. Nos. 5,723,331 and 5,786,217 (entitled "Methods and compositions for the repair of articular cartilage defects in mammals", both of which are incorporated by reference herein in their entirety). These patents describe methods for preparing in vitro a synthetic cartilage patch for the repair of a cartilage defect. When the cartilage-producing cells of the present invention are employed, the methods include the steps of: (1) seeding cartilage-producing cells of the present invention into a pre-shaped well having a cell contacting, cell adhesive surface; and (2) culturing the cartilage-producing cells of the present invention in the well for a time sufficient to permit the cells to secrete an extracellular matrix, thereby to form a three-dimensional, multi cell-layered patch of synthetic cartilage. The resulting synthetic cartilage (e.g., synthetic articular cartilage), contains cartilage-producing cells of the present invention dispersed within an endogenously produced and secreted extracellular matrix. The resulting synthetic cartilage patch may be used subsequently for the repair (or replacement) of a cartilage defect in a subject (e.g., a mammal).

The cells of the present invention thus find use in numerous therapeutic applications for treating diseases or conditions characterized by tissue damage or degeneration as well as for complete replacement of those tissues. Diseases and conditions include, but are not limited to: osteoarthritis, chondromalacia, chondromalacia patella, hallux rigidus, hip labral tear, torn meniscus, cartilage replacement (ear, nose), nervous disorders, endocrine disorders, muscle disease, injuries to tendons and ligaments, etc.

Direct Injection of Cells to Impart Tissue Regeneration

Direct injection of cells, such as the cell lines of the present invention are also of therapeutic utility. Doses and formulation will vary depending on the route of administration, tissue type, and nature of the pathology to be treated as is known in the art, but in the case of humans and most veterinary animals species, the dosage will be between $10^2$-$10^6$ cells and the formulation can be, by way of non-limiting example, a cell suspension in isosmotic buffer or a monolayer of cells attached to an layer of extracellular matrix such as contracted gelatin. Cellular compositions of the present invention may further comprise an acceptable carrier, such as a hydrophilic, e.g., pharmaceutically acceptable, carrier.

Systems and Kits

Also provided by the subject invention are systems and kits that include the cells of the invention for use in various applications, as described herein. The systems and kits may further include reagents and materials for the propagation and use of the cells for research and/or therapeutic applications as described herein.

Biological Deposits

Cell lines described in this application have been deposited with the American Type Culture Collection ("ATCC"; P.O. Box 1549, Manassas, Va. 20108, USA) under the Budapest Treaty. The cell line 4D20.8 (also known as ACTC84) was deposited at the ATCC at passage 11 on Jul. 23, 2009 and has ATCC Accession No. PTA-10231. The cell line SM30 (also known as ACTC256) was deposited at the ATCC on Jul. 23, 2009 at passage 12 and has ATCC Accession No. PTA-10232. The cell line 7SM0032 (also known as ACTC278) was deposited at the ATCC at passage 12 on Jul. 23, 2009 and has ATCC Accession No. PTA-10233. The cell line E15 (also known as ACTC98) was deposited at the ATCC at passage number 20 on Sep. 15, 2009 and has ATCC Accession No. PTA-10341. The cell line MEL2 (also known as ACTC268) was deposited at the ATCC at passage number 22 on Jul. 1, 2010 and has ATCC Accession No. PTA-11150. The cell line SK11 (also known as ACTC250) was deposited at the ATCC at passage number 13 on Jul. 1, 2010 and has ATCC Accession No. PTA-11152. The cell line 7PEND24 (also known as ACTC283) was deposited at the ATCC at passage number 11 on Jul. 1, 2010 and has ATCC Accession No. PTA-11149.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

As described in U.S. patent application Ser. No. 12/504,630 filed on Jul. 16, 2009 and titled "Methods to Accelerate the Isolation of Novel Cell Strains from Pluripotent Stem Cells and Cells Obtained Thereby" (incorporated herein by reference in its entirety), the gene expression markers of cell lines cultured as described show evidence of marked diversity. Also described in U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety, is the observation that said gene expression markers vary with cell culture passage. Therefore the markers were described as useful in identifying said cell lines at the point in clonal or oligoclonal passage described, specifically, the markers shown in Table I herein were taught as useful markers when the cell lines were at 18-21 population doublings of clonal expansion (i.e. the first cell being doubling zero, the first doubling being two cells, the second doubling being four cells, the twentieth doubling being approximately one million cells).

The cell line Z11 (also known as ACTC194) described in U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety, and whose gene expression markers are disclosed in Table 1 as being positive for ATP8B4, CD24, DLK1, FOXF1, FST (NM_013409.1), HTRA3, IGF2 (Illumina probe ID 2413956), IGFBP5, IL1R1, MSX1, NLGN4X (NM_181332.1), OSR2 (NM_053001.1), PODN, PROM1, PRRX2, PTN, SOD3, SOX11, SRCRB4D, STMN2 and TFPI2 and negative for the markers: ACTC, AGC1, AKR1C1, ALDH1A1, ANXA8, APCDD1, AREG, CFB, C6, C7, PRSS35, CCDC3, CDH3, CLDN11, CNTNAP2, COMP, CRIP1, CRLF1, DIO2 (NM_000793.2), DKK2, DPT, EMID1, FMO1, FMO3 (NM_006894.3), GAP43, GDF10, GJB2, GSC, HOXA5, HSD11B2, HSPA6, HSPB3, IFI27, INA, KCNMB1, KIAA0644, KRT14, KRT17, KRT34, LAMC2 (NM_005562.1), IGFL3, LOC92196, MFAP5, MEOX1, MEOX2, MX1, MYBPH, MYH3, MYH11, MYL4 (NM_002476.2), IL32, NPPB, OLR1, PAX2, PITX2, RARRES1, RASD1, RGS1, SMOC1, SMOC2, SNAP25, TAC1, TNFSF7, TNNT2, TRH, TUBB4, UGT2B7, WISP2, ZIC1 and ZIC2 at 18-21 doublings of clonal expansion was passaged in Promocell Smooth Muscle medium (Cat #C-22062B) with supplements as per manufacturer's instructions. At passage 18 (corresponding to a total of approximately 45 doublings of clonal expansion) the cells were plated in conditions to synchronize in quiescence as described herein, and microarray analysis of gene expression was performed as described herein. At this number of doublings, the line expressed similar markers, being positive for ATP8B4, CD24, DLK1, FOXF1, FST (NM_013409.1), IGF2 (Illumina probe ID 2413956), IGFBP5, IL1R1, MSX1, PODN, PROM1, PRRX2, PTN, SOD3, SOX11, STMN2 and TFPI2 and negative for the markers: ACTC, AGC1, AKR1C1, ALDH1A1, ANXA8, APCDD1, AREG, CFB, C6, C7, PRSS35, CCDC3, CLDN11, CNTNAP2, COMP, CRIP1, CRLF1, DIO2, DKK2, EMID1, GAP43, GDF10, GJB2, GSC, HOXA5, HSD11B2, HSPB3, IFI27, INA, KCNMB1, KIAA0644, KRT14, KRT17, KRT34, LAMC2 (NM_005562.1), IGFL3, LOC92196, MFAP5, MEOX1, MEOX2, MX1, MYBPH, MYH3, MYH11, IL32, NPPB, PAX2, PITX2, RARRES1, RASD1, RGS1, SMOC1, SMOC2, SNAP25, TAC1, TRH, TUBB4, UGT2B7, WISP2, ZIC1, ZIC2, and little to no expression of PRSS35, but unlike the cells at 18-21 doublings, the cells at P18 (45-50 doublings of clonal expansion) lost expression of HTRA3, NLGN4X (NM_181332.1) and little to no detectable OSR2 (NM_053001.1) and SRCRB4D and were positive for the expression of CDH3, DPT, OLR1, TNNT2, they were positive for FMO3 accession numbers NM_001002294.1 and NM_006894.4 and showed a low but positive expression of FMO1 and MYL4 (NM_002476.2). The cells were FST positive for NM_013409.1 but low or negative for NM_006350.2, not inconsistent with earlier findings.

Example 2. The Discovery of Muscle Progenitors

The cell line Z11 (also known as ACTC194) described in U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety, and whose gene expression markers at 18-21 doublings of clonal expansion are disclosed in Table 1 and in Example 3 (where markers at both 18-21 and 45-50 doublings of clonal expansion are disclosed), was passaged in Promocell Smooth Muscle medium (Cat #C-22062B) with supplements as per manufacturer's instructions. At passage 18 (corresponding to a total of approximately 45-50 doublings of clonal expansion) the cells were plated as micromasses of approximately 250,000 cells for 14 days under conditions described as In vitro conditions to induce chondrogenenesis—Micromass Culture in Table VIII, that are expected to cause chondrogenic differentiation in cells capable of such differentiation. Despite the expression of markers such as DLX5 and MSX1 (markers of mandibular mesenchyme), Z11 did not differentiate into chondrocytes, instead, surprisingly, such conditions induced the cell line Z11 to differentiate into cells with markers of muscle cells, including the up-regulation of MYH11 (106 RFUs (background levels and consistent with them being negative for this marker at 18-21 doublings of clonal expansion) in control cultures to 9067 RFUs at day 14), (DES from RFU value of 104 (background level) to RFU of 824), and (ACTA1 from 103 (background level) to 202).

Example 3. Low Throughput Screen for Chondrogenic Progenitors Scoring by qPCR

The cell lines of the present invention designated 7SMOO32, W10, 7PEND24, 7SMOO7, 4D20.8, SM28, EN2, Z11,EN13, EN31, EN47, EN55, MW1, W11, E44, E68, E111, MEL2, EN1, EN26, Z1, Z2, EN4, RAPEND18, 7PEND30, E33, SM2, SM30, EN7, EN42, T14, U31, F15, W8, E164, T43, 7PEND9, RAD20.16, T44, EN51, RAPEND15, EN16, B16, 7SMOO25, RAD20.6, E69, SM33, SK11, EN18, SK25, SM35, 7PEND12, SK47, CMO2, SK17, 7SKEL4, SK49, SK46, RASKEL18, E15, RASMO19, T7, SM8, SM22, SK18, SK31, Z3, T42, 75M009, 10RPE8, RAD20.24, 7SMOO7, RASMO12, T36, RAD20.5, T20, E120, 4D20.9, E85, C4ELSR10, C4ELSR5.1, C4ELS5.6, RAD20.19, and 4.4 were expanded in vitro >21 doublings of clonal expansion since they were isolated from hES-derived cells, synchronized in quiescence by growing to confluence and replacing the media with media supplemented with a 10-fold reduction in serum or other mitogens as described herein. RNA was extracted from these cells as a control. In a low throughput screen for cells capable of chondogenesis in vitro, cells were cultured in micromass conditions to induce chondrogenesis as described herein for 14 days. RNA from each of these two conditions was converted to cDNA and then examined for expression of genes commonly associated with chondrogenesis (i.e. COL2A1, COMP, CILP, SCX, CRTL1, SOX9, BARX2). Gene-specific primer pair probes were obtained from Invitrogen. Samples for testing were prepared in standard Optical 96-well reaction plates (Applied Biosystems Carlsbad, Calif., PN 4306737) consisting of 30 ng of RNA equivalent of cDNA, 0.4 uM per primer, Ultra-Pure distilled water (Invitrogen), diluted 1:1 with 12.5 ul of Power SYBR Green PCR Master Mix (Applied Biosystems Carlsbad, Calif., Cat #4367659) incorporating AmpliTaq Gold DNA polymerase in a total reaction volume of 25 ul. Real-Time qPCR was run using Applied Biosystems 7500 Real-Time PCR System employing SDSv1.2 software. Amplification conditions were set at 50° C. for 2 min. (stage 1), 95° C. for 10 min. (stage 2), 40 cycles of 95° C. for 15 sec then 60° C. for 1 min (stage 3), with a dissociation stage at 95° C. for 15 sec, 60° C. for 1 min, and 95° C. for 15 sec (stage 4). Ct values for amplification products of genes of interest were normalized to the average Ct value of 3 housekeeping genes (GAPD, RPS10, and GUSB), and gene expression analyzed relative to that of early passage knee-Normal Human Articular Chondrocytes (Lonza) and cultured human bone marrow mesenchymal stem cells.

The primer sets used to detect chondrogenic genes were ("f" is forward primer; "r" is reverse primer):

| Gene symbol | | Sequence 5' → 3' | SEQ ID NO |
|---|---|---|---|
| COMP | f2 | CCGACAGCAACGTGGTCTT | 1 |
| COMP | r2 | CAGGTTGGCCCAGATGATG | 2 |
| CRTL1 | f1 | TGCTCAGATTGCAAAAGTGG | 3 |
| CRTL1 | r1 | TATCTGGGAAACCCACGAAG | 4 |
| CILP | f1 | CCTGGTCCTGGAAGTCACAT | 5 |
| CILP | r1 | CCATGTTGTCCACTCACCAG | 6 |
| CEP68 | f1 | ATCCGTAGAGAGCACGGAGA | 7 |
| CEP68 | r1 | GGACTCTCCATGGGACAAGA | 8 |
| COL2A1 | f3 | GGCAATAGCAGGTTCACGTACA | 9 |
| COL2A1 | r3 | CGATAACAGTCTTGCCCCACTT | 10 |
| COL2A1 | f4 | TGGCCTGAGACAGCATGA | 11 |
| COL2A1 | r4 | AGTGTTGGGAGCCAGATTG | 12 |
| CEP68 | f1 | ATCCGTAGAGAGCACGGAGA | 13 |
| CEP68 | r1 | GGACTCTCCATGGGACAAGA | 14 |
| SOX9 | f1 | TACGACTACACCGACCACCA | 15 |
| SOX9 | r1 | TCAAGGTCGAGTGAGCTGTG | 16 |
| SCXA | f1 | TCCAGCTACATCTCGCACCT | 17 |
| SCXA | r1 | CGGTCCTTGCTCAACTTTCT | 18 |
| BARX2 | f1 | GGACTTGGCTCAGTCTCTGG | 19 |
| BARX2 | r1 | TGGGGATGGAGTTCTTCTTG | 20 |
| GAPDH | f2 | GGCCTCCAAGGAGTAAGACC | 21 |
| GAPDH | r2 | AGGGGTCTACATGGCAACTG | 22 |
| RPS10 | f1 | ATTTGGTCGTGGACGTGGT | 23 |
| RPS10 | r1 | TTTGGCTGTAAGTTTATTCAATGC | 24 |
| GUSB | f1 | AAACGATTGCAGGGTTTCAC | 25 |
| GUSB | r1 | CTCTCGTCGGTGACTGTTCA | 26 |
| COL2A1 | f1 | TCTACCCCAATCCAGCAAAC | 27 |
| COL2A1 | r1 | GTTGGGAGCCAGATTGTCAT | 28 |
| COL2A1 | f2 | CACACTGGTAAGTGGGGCAAGACCG | 29 |
| COL2A1 | r2 | ACGAGGTCCTCACTGGTGAA | 30 |
| ACAN | f1 | TGAGTCCTCAAGCCTCCTGT | 31 |
| ACAN | r1 | TGGTCTGCAGCAGTTGATTC | 32 |

-continued

| Gene symbol | | Sequence 5' → 3' | SEQ ID NO |
|---|---|---|---|
| ACAN | f2 | ACAGCTGGGGACATTAGTGG | 33 |
| ACAN | r2 | GTGGAATGCAGAGGTGGTTT | 34 |
| COL10A1 | f1 | GCTAAGGGTGAAAGGGGTTC | 35 |
| COL10A1 | r1 | CTCCAGGATCACCTTTTGGA | 36 |
| BGN | f1 | GGACTCTGTCACACCCACCT | 37 |
| BGN | r1 | AGCTCGGAGATGTCGTTGTT | 38 |
| COL9A2 | f1 | AGCATCATTCGGCTGTTACC | 39 |
| COL9A2 | r1 | CTGAGGGGTGGAACTGTAGC | 40 |
| CDMP1 | f1 | CCCATCAGCATCCTCTTCAT | 41 |
| CDMP1 | r1 | TGTAGATGCTCCTGCCACAG | 42 |
| VERSICAN | f1 | ACCACGCTTCCTATGTGACC | 43 |
| VERSICAN | r1 | TGTTGTAACTGGGTGGCAAA | 44 |
| COL11A1 | f1 | TCGAGGGTTTGATGGACTTC | 45 |
| COL11A1 | r1 | CATCTTCTCCCCTCATTCCA | 46 |
| DCN | f1 | TGGCAACAAAATCAGCAGAG | 47 |
| DCN | r1 | GCCATTGTCAACAGCAGAGA | 48 |
| FMOD | f1 | CCTCCAAGGCAATAGGATCA | 49 |
| FMOD | r1 | GCTGCGCTTGATCTCGTTC | 50 |
| LUM | f1 | TGATCTGCAGTGGCTCATTC | 51 |
| LUM | r1 | AAAAGAGCCCAGCTTTGTGA | 52 |
| COL1A1 | f1 | GTGCTAAAGGTGCCAATGGT | 53 |
| COL1A1 | r1 | ACCAGGTTCACCGCTGTTAC | 54 |
| COL1A1 | f2 | GTGCTAAAGGTGCCAATGGT | 55 |
| COL1A1 | r2 | CTCCTCGCTTTCCTTCCTCT | 56 |
| PRELP | f1 | TCCCAATCTTGCCTTCATTC | 57 |
| PRELP | r1 | GTCATGGAACGCCACTAGGT | 58 |
| ACAN | f3 | TCGAGGACAGCGAGGCC | 59 |
| ACAN | r3 | TCGAGGGTGTAGCGTGTAGAGA | 60 |
| COL10A1 | f2 | CAAGGCACCATCTCCAGGAA | 61 |
| COL10A1 | r2 | AAAGGGTATTTGTGGCAGCATATT | 62 |
| CRTL1 | f2 | TTCCACAAGCACAAACTTTACACAT | 63 |
| CRTL1 | r2 | GTGAAACTGAGTTTTGTATAACCTCTCAGT | 64 |
| LUM | f2 | ACCAGATTGACCATATTGATGA | 65 |
| LUM | r2 | GGACAGATCCAGCTCAACC | 66 |
| SOX9 | f2 | AGGCAAGCAAAGGAGATGAA | 67 |
| SOX9 | r2 | TGGTGTTCTGAGAGGCACAG | 68 |
| SOX9 | f3 | ACTGAGTCATTTGCAGTGTTTCTGCC | 69 |
| SOX9 | r3 | GTGGGCTGATCCCCTCCAGGT | 70 |
| SOX5 | f1 | TGGCACTGCACTGGGTAGGA | 71 |
| SOX5 | r1 | AAGGCTGGGAGCCCGTCACT | 72 |
| AGC1/ACAN | f4 | TGAGTCCTCAAGCCTCCTGT | 73 |
| AGC1/ACAN | r4 | CCTCTGTCTCCTTGCAGGTC | 74 |
| IHH | f1 | GGCCGGGAGACCGTGTGTTG | 75 |
| IHH | r1 | TGGGGCTCGCGGTCCAGTAA | 76 |
| IHH | f2 | TACGCCTGGGAGAGTGGGGCG | 77 |
| IHH | r2 | TGGGGCTCGCGGTCCAGTAA | 78 |
| COL2A1 | f5 | TCGTGGGTCCCAGGGGTGAA | 79 |
| COL2A1 | r5 | GACCTGGAGGGCCCTGTGCG | 80 |
| COL2A1 | f6 | TGCTGCCCCATCTGCCCAAC | 81 |
| COL2A1 | r6 | CCTGCAGGTCCCTGAGGCCC | 82 |
| COL2A1 | f7 | AGGGCCAGGATGTCCGGCAA | 83 |
| COL2A1 | r7 | TCTGCCACGAGGTCCAGGGG | 84 |
| CRTAC1 (CEP-68) | f2 | CGGGGCGATGGCACCTTTGT | 85 |
| CRTAC1 (CEP-68) | r2 | GATAGAGGCGGTGGGGGCCA | 86 |
| COMP | f1 | ACAATGACGGAGTCCCTGAC | 87 |
| COMP | r1 | TCTGCATCAAAGTCGTCCTG | 88 |
| BARX2 | f2 | GAGTCAGAGACGGAACAGCC | 89 |
| BARX2 | r2 | AGTCCCAGAGACTGAGCCAA | 90 |
| CHM1 (LECT1) | f1 | GCGCAAGTGAAGGCTCGTAT | 91 |
| CHM1 (LECT1) | r1 | GTTTGGAGGAGATGCTCTGTTTG | 92 |

Col2A1 expression expressed as fold-expression compared to cultured early passage normal human articular chondrocytes for the lines screened is shown in FIG. 1. Early passage normal human articular chondrocytes (NHAC) set as 1.0 in value. The expression level of COL2A1, quantified as fold-induction compared to NHACs, was not markedly elevated in the majority of the cell lines but strikingly elevated in a small subset of the lines, namely, 7SM0032 technical replicate 2 (154× NHAC expression), 7SM0032 biological replicate 2 (137×NHAC expression), 4D20.8 biological replicate 2 (130×NHAC expression), SM30 (1287× NHAC expression), SM30 biological replicate 2 (13,494× NHAC expression), SM30 technical replicate 2 (1168× NHAC expression), E15 (10,809×NHAC expression), E15 technical replicate 2 (9810x NHAC expression), MEL2 (22x NHAC expression), and SK11 (4×NHAC expression).

Surprisingly, there was little if any correlation of COL2A1 induction with commonly-used markers for chondrogenic mesenchyme such as SOX9. Similarly, markers such as AQP1 speculated to be a marker of chondrogenic mesenchymal cells was present at an RFU value of foreskin dermal fibroblasts that did not induce COL2A1 in micromass chondrogenic conditions and was absent in the cell lines of the present invention prior to and after differentiation. For instance, prior to differentiation, AQP1 expression was absent (RFU 135 which is background) in the line SM30, absent (RFU of 126) in SK11, and absent (RFU 139) in the line E15, at 18-21 doublings of clonal expansion (West et al., 2008, Regenerative Medicine vol. 3(3) pp. 287-308, supplementary Table II). Neither was the level of expression of SOX9 in the undifferentiated cell lines of the present invention of predictive value in forecasting whether a cell line of the present invention was capable of chondrogenesis. Indeed, no genes could be found in the undifferentiated lines prior to differentiation that correlated sufficiently with the potential of these lines to become chondrocytes to predict such an outcome. The diversity of gene expression markers within the group of SK11, 7SMOO32, 4D20.8, MEL2, SM30, and E15 including site-specific homeobox gene expression, suggest that each line represents a unique and distinguishable type of chondrogenic progenitor. Also surprising was that many of the genes commonly used as markers of in vitro chondrogenesis such as COMP and CILP were induced in the culture conditions in a nonspecific manner in virtually any cell type including cultured dermal fibroblasts, regardless of whether said dermal fibroblast, for instance, was capable of undergoing true chondrogenesis under the same conditions as evidenced by the expression of COL2A1 and showing histological evidence of cartilage formation. In addition, the cell lines SK11, 7SMOO32, 4D20.8, MEL2, SM30, and E15 were clearly distinguishable from cultured bone marrow MSCs in regard to gene expression markers both before and after differentiation. While the bone marrow MSC is commonly described as ALCAM (CD166) positive, the cell lines of the present invention in the undifferentiated state such as SK11, 7SMOO32, 4D20.8, MEL2, SM30, and E15 showed CD166 expression was absent (RFU 125 which is background) in the line SM30, absent (RFU of 164) in SK11 (West et al., 2008, Regenerative Medicine vol. 3(3) pp. 287-308, supplementary Table II). Additional differences of the cell lines of the present invention when compared to MSCs, by way of nonlimiting example, is the expression of CD74 that has been demonstrated to be a more precise marker of MSCs than many of the commonly-used markers that are actually not specific (Ishii et al, 2005 BBRC 332:297-303). As shown in Table VII, undifferentiated MSCs indeed expressed very high levels of CD74 transcript, adipocyte stem cells expressed CD74 as well at lower levels, dental pulp stem cells expressed CD74 at the limits of detection, but the transcript was not detected at all in undifferentiated cells of the present invention capable of inducing COL2A1 including SK11, 7SMOO32, 4D20.8, MEL2, SM30, and E15, nor in cultured dermal fibroblasts or in the nonchondrogenic embryonic progenitor line 7SMOO7. An additional nonlimiting example demonstrating the diversity of the lines and the striking differences with the adult stem cell types studied herein, is the expression of the developmental gene NNAT (NM_181689.1) expressed at high levels in the cell line E15, but not in adult stem cells such as MSCs, adipocyte stem cells, dental pulp stem cells, or dermal fibroblasts. Yet another nonlimiting example of the salient differences of the cell lines of the present invention capable of inducing COL2A1 expression from stem cell types in the art, can be seen by measuring the expression of the gene KCNK2 (NM_001017425.2) known to be a marker of MSCs. As shown in Table VII, KCNK2 is expressed at high levels in MSCs, adipocyte stem cells, and dental pulp stem cells, but was not detectible in several of the lines of the present invention capable of inducing the expression of COL2A1 such as SM30, E15, 4D20.8, MEL2, and SK11. A striking difference of the cell lines of the present invention and bone marrow-derived MSCs is also seen in genes that indicate important therapeutic differences in the cell types. MSCs suffer from undergoing transformation into hypertrophic chondrocytes when they differentiate in vitro. Hypertrophic chondrocytes express genes useful in inducing angiogenesis and provide a temporary matrix that is later invaded by osteoblasts to make bone. Therefore, MSCs do not perform well when injected into the joint, or otherwise transplanted into articular cartilage, in an effort to regenerate that tissue for the treatment of joint cartilage trauma, arthritis, or related uses. The cell lines of the present invention when induced by the chondrogenic conditions herein, induced very little if any expression of IHH, a marker of hypertrophic chondrocytes, while MSCs expressed very high levels of IHH transcript. Similarly, the line 4D20.8 did not express detectable levels of COL10A1, another marker of hypertrophic chondrocytes, while MSCs expressed very high levels of the transcript. Therefore, the cell lines of the present invention such as 7SMOO32, 4D20.8, SM30, and E15 show markers that they are superior to MSCs in their ability to differentiate into permanent cartilage for the repair of joint cartilage pathology. Further nonlimiting examples of the differences in the lines SK11, 7SMOO32, 4D20.8, MEL2, SM30, and E15 compared with cultured human bone marrow MSCs, adipocyte stem cells, adult dental pulp stem cells is, is shown in Table VII or can be seen by comparing the gene expression markers of the cells with those described herein such as in Table I. Therefore, these results suggest that the cell lines identified in this screen are novel, that the markers commonly used to identify MSCs are not predictive of chondrogenic capacity in human embryonic progenitor cell lines, and that there currently exists no markers that would have predicted that said cell lines would have been the small subset of lines that would respond to chrondrogenic stimuli in expressing true markers of chondrogenesis. Evidence is provided in Example 7 of histological evidence of cartilage formation.

Example 4. Histological and Immunochemical Confirmation of Cartilage Formation

Figure 2:
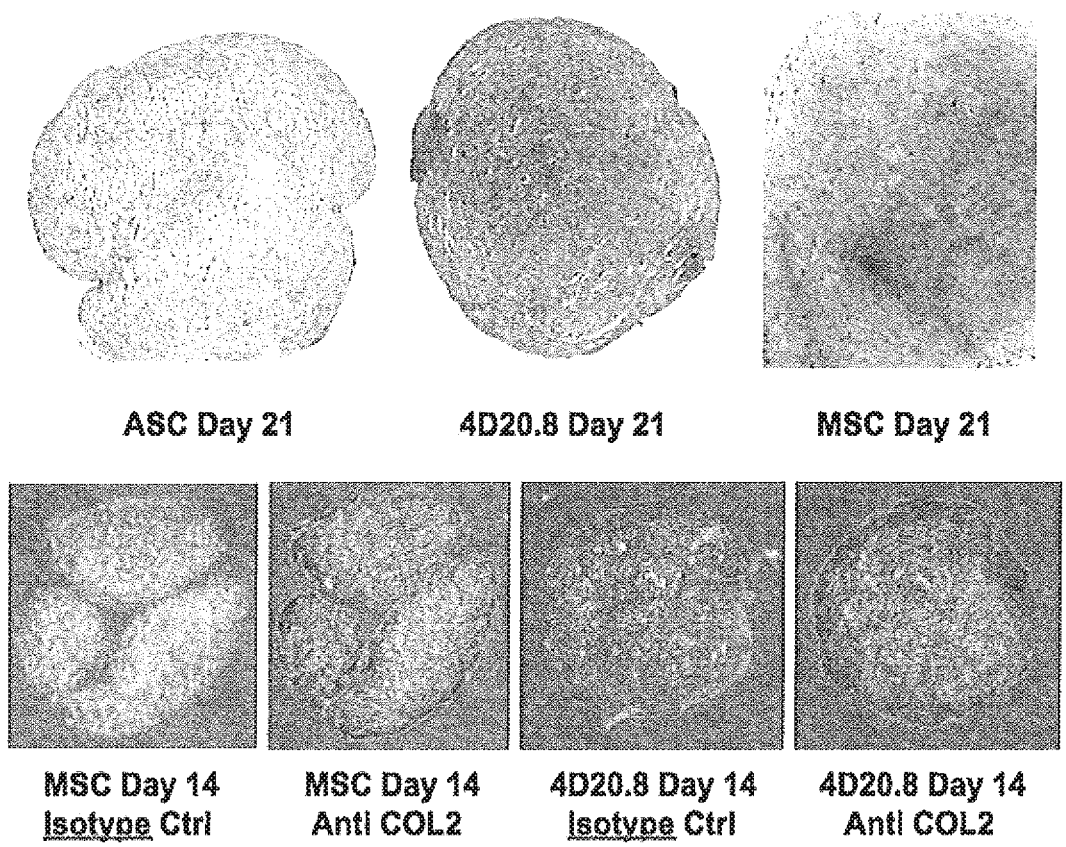
FIG. 2: An example of the Safranin O staining of adipose tissue stem cells compared to the lines 4D20.8 at passage 14 compared to MSCs at passage 6 all at day 21 of differentiation as a pellet and immunostaining with isotype controls in day 14 pellets of the line 4D20.8 and MSCs.

Cell lines of the present invention, such as those discovered in the low throughput screen in Example 6 above as showing moderate to robust induction of COL2A1 such as 7PEND24, 7SMOO32, MEL2, SM30, E15, SK11, and 4D20.8 as well as controls such as MSCs, adipocyte stem cells, and other cell lines such as foreskin dermal fibroblasts, Z11, dental pulp stem cells, 7SMOO7, E44 and others were exposed to micromass and pellet chondrogenic conditions as described herein for varying times including 1,8,14, and 21 days, and a subset of said pellets when transferred into the kidney capsule of SCID mice to promote extended differentiation. Said micromasses and pellets were fixed in formalin and analyzed histologically with H&E stains, Safranin O staining of proteoglycans as described herein, and for immunoreactive COL2A1 using specific antibody and non-specific antibody as a control. Strong reactivity to Safranin O and/or COL2A1 immunoreactivity was observed in day 14 and 21 pellets of the line 4D20.8 and strong Safranin O staining in day 14 micromasses of the line E15. Surprisingly, the cell line RAD20.6 showed immunoreactivity to COL2A1 and Safranin O staining in a day 14 pellet. FIG. 2 shows an example of the Safranin O staining of adipose tissue stem cells compared to the lines 4D20.8 at passage 14 compared to MSCs at passage 6 all at day 21 of differentiation as a pellet and immunostaining with isotype controls in day 14 pellets of the line 4D20.8 and MSCs.

Example 5

Cell lines of the present invention capable of chondrogenesis are tested for capacity to repair articular cartilage as follows: donated human articular tissue is explanted. 5×10$^5$ cells of the lines 7PEND24, 7SMOO32, MEL2, SM30, E15, SK11, and 4D20.8 were spun down in 15 ml conical tube at 400×g for 5 min in 10% FBS/DMEM/F12, and incubated overnight to generate cell aggregates. Six mm diameter cylindrical plugs were cored out from the articular explants with Arthrex Single Use OATS System (Naples, Fl). A surgical curette was used to make partial thickness defects approximately 2 mm in size in the articular surface. The defects were filled with cell aggregates of 7PEND24, 7SMOO32, MEL2, SM30, E15, SK11, and 4D20.8. The cartilage explants were incubated in 10% FBS/DMEM/F12, in the presence or absence of TGFβ3. After 4 weeks, explants were fixed, paraffin-embedded, sectioned, and stained with Safranin O for scoring.

Example 6. The Discovery of Neural Crest Cells Capable of Differentiation into Dopaminergic Cells The regulator of G-protein signaling 5 (RGS5) accession number NM_003617.2, UDP-N-acetyl-alpha-D-galactosamine-polypeptide N-acetylgalactosaminyltransferase 14 (GALNT14) accession number NM_024572.2, hairy/enhancer-of-split related with YRPW motif 2 (HEY2) accession number NM_012259.1, EPH receptor A5 (EPHA5) accession number NM_004439.4, ankyrin 1, erythrocytic (ANK1) accession number NM_020478.3, cAMP-regulated phosphoprotein, 21 kDa (ARPP21) accession number NM_016300.4, and neurotrophic tyrosine kinase, receptor, type 2 (NTRK2) accession number NM_001007097.1 positive cell line U31 (also known as ACTC236), which is described in U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety, and whose additional gene expression markers at 18-21 doublings of clonal expansion are disclosed in Table 1. The line is distinguishable from fetal neuronal stem cells in that fetal neuronal stem cells did not express GALNT14, RGS5, EPHA5, or NTRK2. To determine the differentiation potential of the line U31, the line was passaged to P17 and P18. The cells were plated as micromasses of approximately 250,000 cells for 14 days in the presence of the conditions described as In vitro conditions to induce chondrogenenesis—Micromass Culture in Table VIII. Surprisingly, the line U31 did not differentiate into chondrocytes under these culture conditions but instead differentiated into cells with markers of dopaminergic cells with GABA transporters. Said dopaminergic markers include the markers protein phosphatase 1, regulatory (inhibitor) subunit 1B (PPP1R1B aka DARPP-32 accession number NM_181505.1, cAMP-regulated phosphoprotein, 21 kDa (ARPP21) accession number NM_016300.4, and tyrosine hydroxylase (TH) accession numnber NM_199293.2, as well as other markers of the nervous system such as the neuropeptide galanin (GAL) accession number NM_015973.3. Said GABA transporters include: solute carrier family 6 (neurotransmitter transporter, GABA), member 1 (SLC6A1) also known as GAT-1 accession number NM_003042.2, solute carrier family 6 (neurotransmitter transporter, GABA), member 13 (SLC6A13) also known as GAT-2 accession number NM_016615.2, solute carrier family 6 (neurotransmitter transporter, betaine/GABA), member 12 (SLC6A12) also known as BGT-1 accession number NM_003044.2. Clonal, oligoclonal, or polyclonal embryonic progenitors with a pattern of gene expression of the cell line of the present invention U31 are useful in screening for pharmaceutically-active agents targeting transporters such as SLC6A1 useful in the treatment of anxiety (Thoeringer C K, et al, 2009 The GABA transporter 1 (SLC6A1): a novel candidate gene for affective disorders including anxiety (J Neural Transm. June; 116(6): 649-57. Epub 2008 Jul. 8), neuropathic pain (Gosselin R D et al, 2010. Upregulation of the GABA transporter GAT-1 in the *gracile* nucleus in the spared nerve injury model of neuropathic pain, Neurosci. Lett. 480:132), and SLC6A13, and SLC6A12 for agents useful in the treatment of epilepsy, stroke, schizophrenia, Huntington's disease Parkinson's disease (Madsen K K et al, 2009 Synaptic and extrasynaptic GABA transporters as targets for anti-epileptic drugs. J Neurochem. 109: Suppl 1: 139-144; Clarkson A N et al, 2010 Reducing excessive GABA-mediated tonic inhibition promotes functional recovery after stroke. Nature 468:305; Kleppner, S R and Tobin, A J 2001 GABA signalling: therapeutic targets for epilepsy, Parkinson's disease and Huntington's disease Expert Opinion on Therapeutic Targets April 2001, Vol. 5, No. 2: Pages 219-239). Said hES or hiPS-derived clonal, oligoclonal, or polyclonal cultured embryonic progenitor cells where the culture is assayed positive for a pattern of gene expression of: NTRK2, RGS5, ANK1, GALNT14, HEY2, EPHA5, and ARPP21 can be formulated for therapeutic use such as by injection into the brain, peripheral nervous system, or spinal cord as cells in an saline, or other solutions well known in the art. In the case of ischemic disease such as stroke, the cells may be injected directly into the stroke cavity where the cells and the trophic effects of the cells can be used to improve neuroplasticity and clinical outcome in peri-infarct tissue. Specifically, the cells may by combined with biopolymer hydrogels designed to increased stability and survival during transport and engraftment, thereby reducing the need for multiple injections, and reduce the distribution of the cells to peripheral organs. Hyaluronan gels have mechanical properties similar to brain tissue and do not promote local scarring or tissue reaction. Including but not limited to Zhong J, et al, 2010 Hydrogel matrix to support stem cell survival after brain transplantation in stroke (Neurorehabil Neural Repair. 24(7):636-44. Epub 2010 Apr. 27) incorporated herein by reference. In brief, A hyaluronan-heparin-collagen hydrogel (HyStem-HP, Glycosan, Salt Lake City, Utah) is polymerized with thiol-modified sodium hyaluronate, heparin sulfate, and gelatin that is cross-linked with polyethylene glycol diacrylate. Therapeutically-useful doses of cells with a pattern of gene expression of the cell line of the present invention U31 such as 100,000, 500,000, 1 million, 5 million, 10 million, 50 million, 100 million, or 500 million cells are mixed in 1, 5, 10, 20, 30, 40, or 50 mL volume respectively of hyaluronan/heparin sulfate, gelatin, and cross-linker to form a stem-cell-hydrogel formulation.

Example 7. The Discovery of Additional Cells Capable of Differentiation into Smooth Muscle Cells The HAND2 and SCARA5 positive cell line W10 (also known as ACTC196) whose most distal HOX gene expression was HOXA4, B7, which is described in U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety, and whose gene expression markers at 18-21 doublings of clonal expansion are disclosed in Table 1, was passaged to P14. The cells were plated as micromasses of approximately 250,000 cells for 14 days under conditions described as In vitro conditions to induce chondrogenenesis—Micromass Culture in Table VIII, that are expected to cause chondrogenic differentiation in cells capable of such differentiation. Surprisingly, the line W10 did not differentiate into chondrocytes under these conditions but instead differentiated into cells with markers of smooth muscle cells, including the markers MYH11 and GNA14. The presence of MYH11 was confirmed by immunocytochemistry. A comparison of alternative differentiation conditions including two weeks of culture in the presence of 1.0 uM all trans retinoic acid also showed an induction of MYH11 in the W10 cell line.

Example 8. The Discovery of Cells Capable of Differentiation into Derivatives of Intermediate Mesoderm The WT1 and NPNT positive cell line RASMO12 (also known as ACTC154), which displayed distal HOX gene expression of HOXA4, HOXB8, and HOXC8 as a result of differentiation in the presence of retinoic acid as described in U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety, and whose gene expression markers at 18-21 doublings of clonal expansion are disclosed in Table 1, was passaged to P14. The cells were plated as micromasses of approximately 250,000 cells for 14 days under conditions described as In vitro conditions to induce chondrogenenesis—Micromass Culture in Table VIII, expected to cause chondrogenic differentiation in cells capable of such differentiation. Surprisingly, the line RASMO12 did not differentiate into chondrocytes under these conditions but instead differentiated into cells with markers of nephrogenic mesenchyme, including an induction of MSX/and SALL1.

Example 9. The Discovery of Cells Capable of Expressing EGFL6

The secreted protein encoded by the gene EGF-like-domain, multiple 6 (EGFL6) also known as MAEG, is a member of the epidermal growth factor (EGF) repeat superfamily. It is expressed in fetal tissues and numerous tumors including those of the lung and meninges. It has also been shown to promote adipogenesis and hair follicle growth in normal tissues. The ability of Egfl6 to promote mitogenesis in meningeal and epidermal cell types and to promote adipogenesis makes a source of the factor useful as a means to promote epithelial tissue growth, e.g., skin keratinocyte regeneration and hair follicle growth stimulation, repair of meninges resulting from trauma or CNS surgery, and to promote adipogenesis such as in the case of age-related atrophy of subcutaneous fat, such as commonly occurs on the dorsal aspect of the hands and if the tissue surrounding the globe of the eye. Cell lines naturally producing the factor can be used to manufacture the protein in vitro wherein the protein is extracted by means known in the art such as Secreted Protein Extraction Method 1 or Extracellular Matrix Extraction Methods 1 and 2 and purified for research or therapeutic use or the cells could be transplanted at the site of injury or disease to produce the factor in vivo. Such in vivo use may utilize cells in a variety of formulations described herein including engineered matrices combined with the cells that are viable or cells that have been mitotically inactivated in order to allow the cells to produce the factor for a limited duration.

Research uses of the factor include the use of the factor to enhance proliferation of varied cells in vitro including epithelial and meningeal cells, and to promote adipocyte differentiation in vitro. The protein can be purified by Secreted Protein Extraction Methodx 1 or 2 or Extracellular Matrix Extraction Method 1 (as described hereinabove) or left as an intact ECM on tissue culture plastic for use in cell culture.

To identify cells of the present invention useful in producing EGFL6, the lines of the present invention were exposed to diverse differentiation conditions as described herein and the levels of EGFL6 expression by microarray analysis was scored. The clonal human embryonic progenitor cell line 7SM0032 which was observed to expresses the metabotropic glutamate receptor GRM1, the nicotinic cholinergic receptor CHRNA3, the transcription factors LHX1 and MSX2, and the genes BBOX1, DLK1, and BMP5, expressed EGFL6 in both the undifferentiated state as well as most differentiation conditions, such as Micromass 1.

Example 10. In Vitro Model of Stabilization Using Mural Cells of the Present Invention Cell lines expressing RGS5 are detected by microarray, PCR, immunocytochemistry, or other means known in the art (see, e.g., Uemura A K, Kusuhara S et al (2006) Angiogenesis in the mouse retina: a model system for experimental manipulation. Exp Cell Res 312(5):676-683). For example, the cell lines CM02, E33, E111 (which express the gene expression markers MAL, EYA4, RGS5, MEOX1, CLDN2, UGT2B7, ELF3, ANKRD34B, and ZBED2), E164, SM28, and U31 express RGS5 (relative fluorescence values of >150 being considered positive). Additional markers for these cell lines can be found in Table I.

Example 11. Embryonic Progenitors to the Blood Brain Barrier

Aspects of the present invention include embryonic progenitors of blood brain barrier cells. These cells find use in numerous therapeutic applications, e.g., repair of blood brain barrier cells, as well as in drug screening assays.

The blood-brain barrier is formed by the brain capillary endothelium and excludes from the brain ~100% of large-molecule neurotherapeutics and more than 98% of all small-molecule drugs, thus making it a bottleneck in brain drug development that limits the growth of neurotherapeutics (see, e.g., Pardridge, NeuroRx. 2005 January; 2(1): 3-14 entitled "The Blood-Brain Barrier: Bottleneck in Brain Drug Development"; incorporated herein by reference in its entirety). In view of this bottle-neck, the development of in vitro assays for screening therapeutic agents that can cross the blood brain barrier, or agents that can facilitate the crossing of other thereapeutic agents that cannot themselves cross the blood brain barrier, is needed.

A number of different genes have been identified that play a role in transport of molecules, including therapeutic agents, across cells, including cells of the blood brain barrier. These genes include those that encode so called transporters, e.g., efflux and uptake (or influx) transporters. Exemplary transporter genes include efflux transporters ABCB1, ABCG2 and ABCC2, as well as uptake (or influx) transporters SLCO1B1, SLCO2B1 and SLC22A1 (the organic anion transporting polypeptides (OATP) family of influx transporters). (For further description of transporters, see the following exemplary references, which are incorporated herein by reference: Rodrigues et al., *Acta Pharmacol Sin.* 2009 July; 30(7):956-64 "The expression of efflux and uptake transporters are regulated by statins in Caco-2 and HepG2 cells."; Luo et al., *Amino Acids.* 2010 Apr. 11. "Design and recombinant expression of insulin-like peptide 5 precursors and the preparation of mature human INSL5."; and Kalliokoski, et al., *Br J Pharmacol.* 2009 October; 158(3):693-705 "Impact of OATP transporters on pharmacokinetics.")

Example 12. Preadipocytes and their Uses

At least three distinct types of adipocytes are known in mammals; namely, visceral white adipocytes, and subcutaneous white and brown adipocytes. While an increased mass of visceral white adipocytes is thought to play a role in type 2 diabetes mellitus, dyslipidemia, cholesterol gallstones, hypertension, atherosclerosis, and hepatic steatosis, an increased number of subcutaneous white and brown adipocytes is thought to lead to improved glucose metabolism and energy consumption potentially leading to overall loss of body fat. Brown fat is a source of heat through uncoupling reactions. It has recently been speculated that the transplantation of certain non-visceral white or brown adipocytes, preadipocytes, or similar adipocyte progenitor cells could be useful in improving insulin sensitivity, and decreasing body fat with numerous potential health benefits (Tran and Kahn, 2010. *Nat. Rev. Endocrinol.* 6(4): 195-213). However, said cell-based therapies require a robust source of purified and specific cells useful in supplying such activity. Markers known in the art as useful in identifying adipocyte progenitors include PPARG. MYF5 has been reported to be a marker of brown adipocyte progenitors with PRDM16 and CEBPB being critical transcription factors in brown adipocyte differentiation (Seale P, et al. PRDM16 controls a brown fat/skeletal muscle switch. *Nature* 2008; 454:961-8). However, many cell types express these factors and therefore one skilled in the art would not be able to identify primordial stem cell-derived clonal embryonic progenitors capable of differentiating into visceral white, cutaneous white, or brown adipocyte based on markers known in the art.

To obtain hES-derived clonal progenitor lines of the present invention capable of differentiating into cutaneous white and brown adipocytes, designated herein as clonal embryonic cutaneous adipocyte progenitor cells (ECAPCs), progenitor lines expressing EYA4 were identified. Among other differentiated cell types, EYA4 is expressed in primitive dermatome progenitors.

The cell lines of the present invention designated C4ELSR2, C4ELS5.1, E111, E120, J16 (expressing ADH1A, ADH1B, EYA4, FABP4, CD36, PPARG, ANGPT2, EBF2, and DBC1), and RAD20.5 are differentiated according to adipogenesis protocols 1 and 2 (Table VIII), RNA is harvested after 3, 5, 7, and 14 days, and gene expression is analyzed as described herein to detect EYA4 positive embryonic progenitors capable of undergoing differentiation into cutaneous adipocytes and useful for the study of adipocyte differentiation, in transplantation for cosmetic surgery, for imparting weight loss, and for alleviating the symptoms of Type II diabetes as described herein.

Preadipocytes (ECAPC) and their differentiated progeny (e.g., cutaneous adipocytes) are useful in numerous autologous and allogeneic transplantation into an animal for both cosmetic and therapeutic purposes. For ECAPCs, differentiation takes place in vivo by means of factors either naturally in the environment and/or introduced factors. In certain embodiments, the site of transplantation is a diseased organ or tissue in need of cosmesis. In other embodiments, the site of transplantation is subcutaneous, intraperitoneal, topical, intrasynovial, vaginal, rectal, or intrathecal. Preferably, the subject is mammalian, more preferably, the subject is human. The cell of the invention can be induced to differentiate in vitro or after implantation into a patient.

In certain aspects of the invention, the ECAPCs are introduced along with support cells that provide an environment suitable for the in vivo differentiation of the ECAPCs. The support cells can be derived from any source, e.g., from primary cultures and/or cell lines. In some embodiments, the support cells are obtained autologously. In other embodiments, the support cells are obtained allogeneically.

In certain embodiments, an ECAPC is provided to a subject in combination with a pharmaceutically acceptable carrier for a therapeutic application to an animal, including but not limited to imparting weight loss, for alleviating the symptoms of Type II diabetes, tissue repair, regeneration, reconstruction or enhancement, and the like. The ECAPC can, in an alternative embodiment, be administered to a host in a two- or three-dimensional matrix for a desired therapeutic purpose.

In certain embodiments, the ECAPCs are encapsulated in a biomaterial compatible with transplantation into a mammal, preferably a human and then transplanting the encapsulated cells into an animal. The encapsulation material should be selected not hinder the release of desired proteins secreted by the cells. The materials used include but are not limited to collagen derivatives, hydrogels, calcium alginate, agarose, hyaluronic acid, poly-lactic acid/poly-glycolic acid derivatives and fibrin.

In certain embodiments, transplanted cells and/or their progeny are evaluated histologically for evidence of rejection, teratoma formation, and efficacy.

Example 13. Discovery of Embryonic Progenitor Cell Lines Expressing BMP2 and BMP7

Loss of bone mass such as occurs in age-related osteoporosis or osteonecrosis is a large and growing health care problem despite the availability of recombinant growth factors such as BMP2 and BMP7 (also known as osteogenic protein-1 (OP-1)) that are capable of inducing new bone formation. Cell lines of the present invention capable of expressing relatively high levels of these factors could provide novel therapies wherein these and other useful osteogenic factors are administered through cell transplantation where the cell lines of the present invention continuously secrete osteogenic factors over an extended period of time. The cell line Z2 (P12) was differentiated for 14 days in the presence of recombinant human EGF (100 ng/ml). The expression of BMP2 by microarray showed a RFU value of 1015, and BMP an RFU value of 1084 where an RFU value >150 was considered positive.

The cell lines of the present invention 7SMOO7 (also designated ACTC298 and used at P18), C4.4 (also designated ACTC87 and used at P14), E44 (also designated ACTC170 and used at P18), E69 (also designated ACTC101 and used at P15), SK17 (also designated ACTC162 and used at P14), SK31 (also designated ACTC164 used at P15), SM35 (also designated ACTC260 used at P12), T36 (also designated ACTC198 used at P19), T43 (also designated ACTC120 used at P17), W11 (also designated ACTC197 used at P12), and Z2 (also designated ACTC255 used at P12), are cultured to five day quiescence as described herein or alternatively exposed to differentiation conditions of Differentiation Factor Protocol I in Table VIII. Individual differentiation factors from Table III tested in this example included 1.0 uM all-trans retinoic acid (Sigma R2625), 10 ng/mL SCF, 10 ng/mL bFGF, 100 ng/mL Activin, 100 ng/mL Noggin, 20 ng/mL HGF, 100 ng/mL EGF, or 100 ng/mL NGF for 7 days in the case of 7SMOO7, E44, and T43, and 14 days in the case of C4.4SK17 E69, SK17, SK31, SM35, T36, W11, and Z2. RNA was isolated as described herein and analyzed by Illumina microarrays.

At five days of quiescence, the line Z2 differentially expressed gene expression markers such as UGT2B17 (Illumina probe ID 6860392, accession number NM_001077.2), copy-number variation of which is associated with susceptibility to osteoporosis, UGT2B10, MASP1, Amelotin (AMTN) which is specifically expressed in maturation-stage ameloblasts, and FOXQ1. The most distal HOX gene expression is HOXC6, these markers being rarely observed in the other cell clonal embryonic progenitor cell lines of the present invention. Surprisingly, in the case of the cell line Z2 (P12) differentiation for 14 days in the presence of recombinant human EGF (100 ng/ml) led to marked expression of both BMP2 and BMP7 transcripts where BMP2 by microarray showed a RFU value of 1015, and BMP7 an RFU value of 1084 where an RFU value >150 was considered positive. Still significant, though lower amounts of BMP7 expression were observed with cells treated for 14 days in 1.0 uM retinoic acid (271 RFU) and 10 ng/mL of bFGF (196 RFU). While BMP2 transcript was seen in several lines, BMP7 was not previously observed in the cell lines of the present invention, not even in numerous adult-derived cells such as osteoblasts, bone marrow mesenchymal stem cells, dermal fibroblasts, or articular chondrocytes. This is also surprising since there is no knowledge in the art that cells hES-derived clonal progenitors with the gene expression markers of the line Z2 would be capable of expressing these two genes at such relatively high levels.

Such cells can be useful in the treatment of disorders associated with poor bone formation, poor repair of fractures, osteonecrosis, or spinal trauma wherein fusion of vertebrae would stabilize the spinal cord. Treatments include the use of the cells of the present invention as transplant therapy into the site requiring osteogenesis, or the use of the cells in vitro as a means of manufacturing the factors, such as the use of Secreted Protein Isolation Protocol 1 or Secreted Protein Isolation Protocol 2 described herein.

Example 14. Renin-Expressing Cell Lines

Renin is a regulatory component of the renin-angiotensin system. It plays an important role in the regulation of blood pressure and fluid balance. Renin is expressed in the juxtaglomerular cells (JG cells, also known as granular cells) of the kidney which synthesize, store, and secrete the enzyme. It is also occasionally expressed in interlobular and perinrenal arteries. When released, renin cleaves angioteninogen to produce angiotensin I which may be further processed by angiotensin converting enzyme (ACE) to produce angiotensin II that has multiple activities that ultimately elevate systemic blood pressure and electrolyte retention by the kidney. Juxtaglomerular cells are specialized smooth muscle cells in the wall of afferent renal arterioles that deliver blood to the glomerulus. The cell lines of the present invention 7SMOO7 (also designated ACTC298 and used at P18), C4.4 (also designated ACTC87 and used at P14), E44 (also designated ACTC170 and used at P18), E69 (also designated ACTC101 and used at P15), SK17 (also designated ACTC162 and used at P14), SK31 (also designated ACTC164 used at P15), SM35 (also designated ACTC260 used at P12), T36 (also designated ACTC198 used at P19), T43 (also designated ACTC120 used at P17), W11 (also designated ACTC197 used at P12), and Z2 (also designated ACTC255 used at P12), and cultured to five day quiescence as described herein or alternatively exposed to differentiation conditions of Differentiation Factor Protocol I in Table VIII. Individual differentiation factors from Table III tested in this example included 1.0 uM all-trans retinoic acid (Sigma R2625), 10 ng/mL SCF, 10 ng/mL bFGF, 100 ng/mL Activin, 100 ng/mL Noggin, 20 ng/mL HGF, 100 ng/mL EGF, or 100 ng/mL NGF for 7 days in the case of 7SMOO7, E44, and T43, and 14 days in the case of C4.4SK17 E69, SK17, SK31, SM35, T36, W11, and Z2. RNA was isolated as described herein and analyzed by Illumina microarrays.

At five days of quiescence, the line SK17 differentially expressed skeletal muscle markers such as MYOD1 (Illumina probe ID 5570307, accession number NM_002478.4), MYOG (Illumina probe ID 4200224, accession number NM_002479.4), CDH15 (Illumina probe ID 5090195, accession number NM_004933.2), MYLPF (Illumina probe ID 6840092, accession number NM_013292.3), ART3 (Illumina probe ID 7040497, accession number NM_001179.3), SHD (Illumina probe ID 730093, accession number NM_020209.2), JPH1 (Illumina probe ID 5490025, accession number NM_020647.2), and MYH3 (Illumina probe ID 1070541, accession number NM_002470.2) rarely observed in the other cell clonal embryonic progenitor cell lines of the present invention. Surprisingly, after day 14 the addition of retinoic acid to SK17 markedly upregulated the smooth muscle marker MYH11 (Illumina probe ID6280133, accession number NM_002474.2) to 1715 RFUs as well as renin (REN; Illumina probe ID 780768, accession number NM_000537.2) not previously observed in the cell lines of the present invention. This is also surprising since while the embryological origins of renin-expressing cells is a matter of dispute, it is generally believed that they arise from metanephric blastema (Maria Luisa S. et al, 2001. Embryonic origin and lineage of juxtaglomerular cells *Am J Physiol Renal Physiol* 281: F345-F356), and therefore would not be expected to differentiate from a clonal embryonic progenitor cell line expressing skeletal muscle progenitor markers.

Such cells can be useful in the treatment of disorders associated with low or dysfunction renin expression including but not limited to renal tubular dysgenesis. Treatments include the use of the cells of the present invention as transplant therapy into dysfunctional kidney or elsewhere in the body to replace lost or dysfunctional renin-secreting cells, or the use of the cells in vitro as a means of manufacturing renin.

Example 15—Unique Fate Space of W11

The clonal human embryonic progenitor cell line W11 was derived from the registered parental hES cell line H9 (WA09) as described (West et al., 2008, *Regenerative Medicine* vol. 3(3) pp. 287-308). It expresses killer cell lectin-like receptor subfamily C, member 2 and 3 (KLRC2, KLRC3), and Sulfotransferase 1C2 (SULT1C4) that Catalyzes the sulfate conjugation of many drugs and therefore useful in drug discovery. It also expresses BMP5. The most distal HOX gene expression is HOXB2, C6. Upon differentiation under conditions described as In vitro conditions to induce chondrogenenesis—Micromass Culture in Table VIII, the line up-regulates smooth muscle markers such as MYH11.

Example 16—Unique Fate Space of SK31

The clonal human embryonic progenitor cell line SK31 was derived from the registered parental hES cell line H9 (WA09) as described (West et al., 2008, *Regenerative Medicine* vol. 3(3) pp. 287-308). It expresses ART3, CSAG3A, CSAG3B and oculocutaneous albinism II (OCA2). The most distal HOX gene expression is HOXA5, HOXB8, HOXD13. Upon differentiation under conditions described as In vitro conditions to induce chondrogenenesis—Micromass Culture in Table VIII, the line up-regulates tyrosinase-related protein 1 (TYRP1).

Example 17—Unique Fate Space of SM35

The clonal human embryonic progenitor cell line SM35 was derived from the registered parental hES cell line H9 (WA09) as described (West et al., 2008, Regenerative Medicine vol. 3(3) pp. 287-308). It expresses KLF5, CCDC3, NCAM1, and AMTN. The most distal HOX gene expression is HOXC6. Upon differentiation under conditions described as In vitro conditions to induce chondrogenenesis—Micromass Culture in Table VIII. The line up-regulates LAIR2 implicated in the modulation of mucosal tolerance.

Example 18—The Discovery of Novel Endothelial Progenitors

Figure 3:
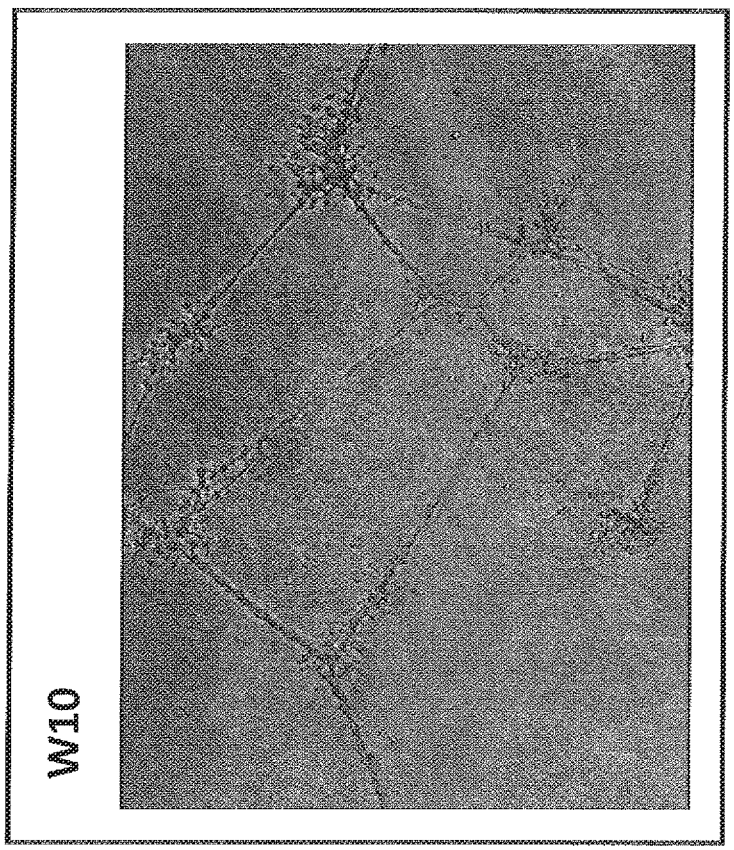
FIG. 3: Comparison of endothelial tubes formed by HUVECs and the line W10.
Figure 3:
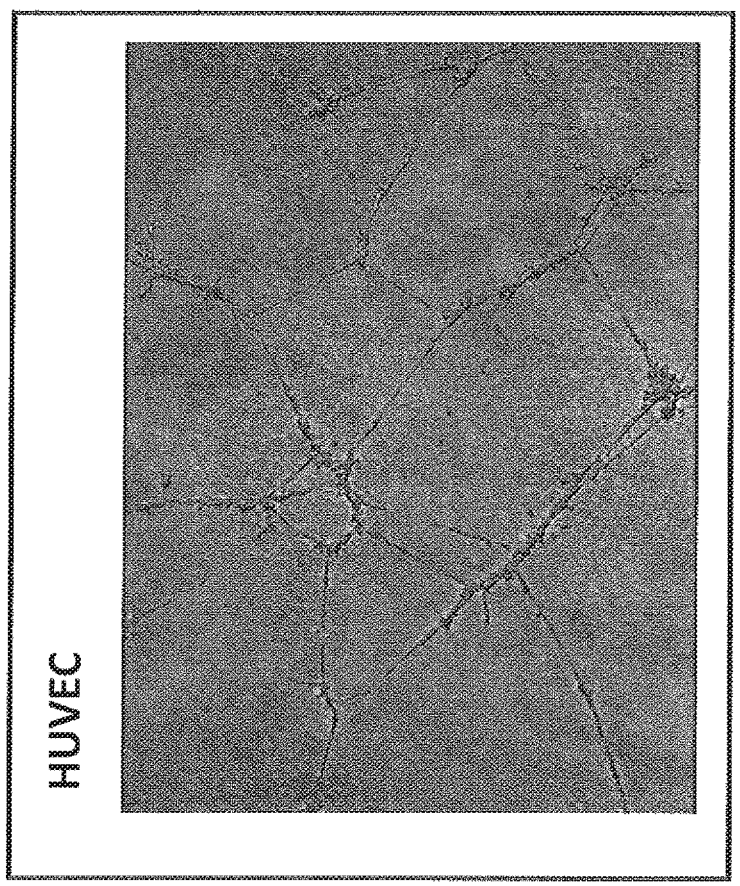

There is a widespread interest in understanding the biology of angiogenesis and the invention of means to induce vasculogenesis, neoangiogenesis, and vascular repair in vivo for therapeutic effect. To discover which of the cell lines of the present invention are capable of differentiation into vascular endothelium, As described in Example 10, the cell line W10 (also known as ACTC196) which when cultured >21 doublings of clonal expansion since derivation expresses the differential markers: HAND2 (Illumina probe ID 4640563, accession number NM_021973.2), GPR44 (Illumina probe ID 940519, accession number NM_004778.2), SLC7A14 (Illumina probe ID 6100717, accession number NM_020949.1), ACTN3 (Illumina probe ID 830348, accession number NM_001104.1), SULT1 C4 (Illumina probe ID 4610593, accession number NM_006588.2), AMOT (Illumina probe ID 3290646, accession number NM_133265.2), FOXF1 (Illumina probe ID 3800554, accession number NM_001451.2), NOVA1 (Illumina probe ID 3780402, accession number NM_006491.2), and SCARA5 (Illumina probe ID 1030477, accession number NM_173833.4), positive cell line W10 whose most distal HOX gene expression was HOXA4, B7, which is described in U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety, and whose gene expression markers at 18-21 doublings of clonal expansion are disclosed in Table 1, and which is capable of differentiation into smooth muscle cells expressing MYH11, was assayed for capacity to differentiate into endothelial cells using the Endothelial Formation Protocol (Tube Formation) described in Table VIII, using HUVECs as a positive control. In brief, W10 and HUVEC cells were cultured in 12 wells (24 well plate) coated with 250 ml of matrigel for each cell line. $1 \times 10^5$ cells were plated per well (12 wells per cell line). The cells were cultured in EGM2 medium (containing VEGF, IGF and EGF as growth factors), as well as in their corresponding growth media lacking endothelial growth factors. The cell lines W10 and were routinely grown in endothelial medium with no VWF or CHD5 expression while in the undifferentiated state. One of the differential markers of this cell line is HAND2 generally thought to be a marker of neural crest lineages that are believed to be incapable of endothelial differentiation. The cell W10 also did not express KDR as judged by microarray expression using Illumina probe ID 5270452 (accession number NM_002253.1) which is known in the art as one of the earliest markers of endothelial cell fate. However, surprisingly, when incubated 16 hours at 37° C. using the Endothelial Formation Protocol (Tube Formation), W10 cells formed endothelial tubes similar to that of HUVECs (see FIG. 3).

Cell lines with markers of cell line W10 allow a direct scalability of vascular progenitors and are therefore useful in the scale up of cells for research and therapy. They are also useful as cells delivered intraveneously to induce angiogenesis in tissues such as ischemic myocatdial or other tissues as occurs in aging or peripheral artery disease, or non healing cutaneous ulcers. The cells can be enhanced to target particular tissues when administered intraveneously through the addition of cell surface associated antibodies or peptides such as peptides designed to target diseased or ischemic tissue such as those described in U.S. Pat. Nos. 6,180,084 and 6,491,894; both to Rouslahti Erkki, et al. and titled "NGR receptor and methods of identifying tumor homing molecules that home to angiogenic vasculature using same" and U.S. Pat. No. 6,576,239, to Rouslahti Erkki, et al. and titled "Angiogenic homing molecules and conjugates derived therefrom" each of which is incorporated herein by reference. In addition, the cells are useful in targeting tumor vasculaure to deliver suicide constructs to destroy tumors as described in WO2003/061591 to West entitled "Stem Cell-Derived Endothelial Cells Modified to Disrupt Tumor Angiogenesis" and incorporated herein by reference. Cell lines with the differential markers of the line W10 as described herein are also useful for research in angiogenesis including the study of alterations in gene expression, miRNA expression, and protein composition in cells during the differentiation of cells into varied types of endothelial cells. One skilled in the art would also understand that such cells may be transfected with promoter constructs including CDH5 or other endothelial-specific genes driving the expression of a marker gene or constitutively expressing a marker genes including but not limited to GFP, luciferase, beta galactosidase, or other similar markers in order to track the integration of said cells into the tissues or vascularization of animals, including humans for basic research and for the diagnosis of vascular disorders and cancer wherein cancers display an enhanced vascular turnover. One skilled in the art would also understand that said cells expressing the molecular markers of the cell line W10 capable of undergoing endothelial differentiation can also be generated from pluripotent stem cells such as hES, hiPS, and other primordial stem cells including but not limited to cell banks made under GMP conditions or cells engineered to excape immune surveillance such as by the modification of placental HLA genes such as HLAG or HLAH as described in WO2008/121894 to Hantash entitled "Endogenous expression of HLA-G and/or HLA-E by Mesenchymal Cells" incorporate herein by reference for the purpose of making said cells more suitable of transplant therapy in humans.

Example 19—The Discovery of Novel Bioactive Secreted Protein Formulations

The cell lines 7SM0032, W10, 7PEND24, 7SMOO7, 4D20.8, SM28, EN2, Z11, EN13, EN31, EN47, EN55, MW1, W11, E44, E68, E111, MEL2, EN1, EN26, Z1, Z2, EN4, RAPEND18, 7PEND30, E33, SM2, SM30, EN7, EN42, T14, U31, F15, W8, E164, T43, 7PEND9, RAD20.16, T44, EN51, RAPEND15, EN16, B16, 7SM0025, RAD20.6, E69, SM33, SK11, EN18, SK25, SM35, 7PEND12, SK47, CMO2, SK17, 7SKEL4, SK49, SK46, RASKEL18, E15, RASMO19, T7, SM8, SM22, SK18, SK31, Z3, T42, 7SM009, 10RPE8, RAD20.24, 7SMOO7, RASMO12, T36, RAD20.5, T20, E120, 4D20.9, E85, C4ELSR10, C4ELSR5.1, C4ELS5.6, RAD20.19, and 4.4 are expanded in vitro >21 doublings of clonal expansion since they were isolated from hES-derived cells, synchronized in quiescence by growing to confluence and replacing the media with media supplemented with a 10-fold reduction in serum or other mitogens as described herein. Secreted and extracellular matrix pooled proteins from the cell lines are prepared and screened as described in the method titled Screening of secreted or extracellular matrix proteins for biological activity above. Pooled proteins are mixed with HyStem matrix as described herein and screened for the ability of reducing scarring and improving healing in murine models of wound repair.

Example 20. Screening for Cells with Osteogenic Potential

The cells of the present invention are screened for osteogenic potential by means known in the art, or means simulating conditions leading to bone in normal embryogenesis. By way of nonlimiting example, tissue culture plates were exposed to 12 ug/mL of Type I collagen (gelatin) and 12 ug/mL of vitronectin for 24 hours. This gelatin/vitronectin solution was then aspirated and the cell lines of the present invention: CM02, E15, E33, E68, SK11, 4SKEL20, 4D20.8, SM30, J16, and mesenchymal stem cells were plated to confluence and exposed to osteogenic media as described in Table VIII Osteogenic Protocol 1 for 15-21 days. Osteogenesis was scored based on the intensity of calcium deposit staining by Alizarin Red and visualized by phase contrast as described in Table VIII. The cell lines E15, SK11, 4D20.8, showed strong staining, providing evidence that they are capable of producing bone. Such bone-forming cells are useful in research in the embryological origins of diverse types of bone and for therapy, such as in the repair of fractured or otherwise injured bone resulting from trauma or surgery, or from bone forming disorders including age-related osteoporosis.

Example 21. Discovery of the Differentiation Potential of Cells with the Pattern of Gene Expression of the Cell Line B16

The cell line of the present invention designated B16 (ACTC59) that expresses the unique pattern of markers MKX (accession number NM_173576.1), CDH10 (accession number NM_006727.2), MEG3 (accession number NR_002766.1), SCUBE3 (accession number NM_152753.2), and distal HOX genes HOXA11 (accession number NM_000522.3), and HOXD11 (accession number NM_021192.2) when synchronized at quiescence as described herein by culturing 5 days at confluence in DMEM medium with 0.5% serum at passage 16-19 was differentiated in micromass conditions and in a hydrogel containing crosslinked hyaluronic acid and gelatin with supplemented growth factors from Table III as described in Table VIII under the headings "In vitro conditions to induce chondrogenenesis—Micromass Culture" and "Differentiation in gels containing crosslinked hyaluronic acid and gelatin" in the presence of TGFβ3 and retinoic acid as also described in Table VIII under the subheadings "Differentiation in Hydrogels Containing Crosslinked Hyaluronic Acid and Gelatin to Induce Chondrogenesis" and "Retinoic acid and EGF-Containing HyStem-CSS" respectively. Differentiation under conditions described in Table VIII under the headings "In vitro conditions to induce chondrogenenesis—Micromass Culture" led to a profound upregulation of ANGPTL7 (accession number NM_021146.2), INSL5 (accession number NM_005478.3), the tendon marker TNMD (accession number NM_022144.1), and the tendon marker THBS4 (accession number NM_003248.3). The resulting cells are therefore useful in the treatment of tendon injuries and tendonitis, or inhibit angiogenesis in a given tissue, such as to prevent neovascularization in the cornea, retina, and to inhibit angiogenesis and thereby the growth of malignant tumors. In the differentiation conditions described in Table VIII as "Differentiation in gels containing crosslinked hyaluronic acid and gelatin" in the presence of TGFβ3 led to a similar upregulation of ANGPTL7 (accession number NM_021146.2), INSL5 (accession number NM_005478.3), and the tendon marker TNMD (accession number NM_022144.1). In the differentiation conditions described in Table VIII as "Differentiation in gels containing crosslinked hyaluronic acid and gelatin" in the presence of retinoic acid led to a marked upregulation of natriuretic peptide precursor B (NPPB, accession number NM_002521.2) to 11,851 RFUs of expression. The natriuretic protein encoded by NPPB would be useful in the treatment of heart failure in a manner similar to the exogenous, often intravenous administration of the recombinant protein Nesiritide (Scios) encoded by NPPB is useful for the treatment of heart failure by causing vasodilation and reducing blood pressure and the load on the heart. Unlike the intravenous administration of the natriuretic protein encoded by NPPB, stable engraftment of cells expressing the protein can be utilized to provide a more stable level of expression of the protein over time.

TABLE I

Exemplary progenitor cell lines and associated gene expression markers at 18-21 doublings of clonal expansion The group of cell lines X2.1 (also known as 2.1 and ACTC63), X2.2 (also known as X2.2Rep1 and X2.2Rep2 and 2.2 and ACTC62) are positive for the markers: CFB, CLDN11, COMP, CRLF1, EGR2, FST, KRT14, KRT19, KRT34, MFAP5, MGP, PENK, PITX2, POSTN, PTGS2, RARRES1, S100A4, SOD3, TFPI2, THY1 and ZIC1 and are negative for the markers: AGC1, ALDH1A1, APCDD1, AREG, ATP8B4, C6, C7, C20orf103, CCDC3, CDH3, CDH6, CNTNAP2, COP1, CXADR, DIO2, METTL7A, DKK2, DLK1, EMID1,

TABLE I-continued

Exemplary progenitor cell lines and associated gene expression markers at 18-21 doublings of clonal expansion FGFR3, FMO3, FOXF1, FOXF2, GABRB1, GDF10, GSC, HSD11B2, HSD17B2, HSPA6, HSPB3, ID4, IGF2, IGFBP5, INA, KCNMB1, IGFL3, LOC92196, MEOX1, MSX2, MX1, MYBPH, MYH11, MYL4, NLGN4X, NPPB, PAX2, PAX9, PDE1A, PRELP, PROM1, RASD1, RELN, RGS1, RPS4Y2, SFRP2, SMOC1, SMOC2, SNAP25, SYT12, TAC1, RSPO3, TUBB4, UGT2B7, WISP2, ZD52F10 and ZIC2.

The cell line B1 is positive for the markers: CD24, CDH6, HTRA3, INA, KRT17, KRT19, LAMC2, MMP1, IL32, TAGLN3, PAX2, RELN, UGT2B7 and ZIC2 and is negative for the markers: ACTC, AGC1, ALDH1A1, APCDD1, ATP8B4, BEX1, CFB, C3, C6, C7, PRSS35, C20orf103, CCDC3, CDH3, CNTNAP2, COL15A1, COL21A1, COP1, CRLF1, DIO2, METTL7A, DKK2, DLK1, DPT, EGR2, EMID1, FGFR3, TMEM100, FMO1, FMO3, FOXF1, FOXF2, FST, GABRB1, GAP43, GDF10, GSC, HOXA5, HSD11B2, HSD17B2, HSPA6, ID4, IF127, IGF2, KCNMB1, KIAA0644, KRT14, TMEM119, IGFL3, LOC92196, MFAP5, MASP1, MEOX2, MGP, MYBPH, MYH3, MYH11, MYL4, NPAS1, OGN, OLR1, OSR2, PAX9, PDE1A, PENK, POSTN, PRELP, PRG4, PROM1, PRRX1, PRRX2, PTN, PTPRN, RARRES1, RASD1, RGMA, RGS1, SERPINA3, SLITRK6, SMOC1, SMOC2, SNAP25, SOD3, STMN2, TAC1, RSPO3, TNNT2, TRH, TSLP, TUBB4, WISP2 and ZIC1.

The group of cell lines X4.1, X4.3 and B10 are positive for the markers: MMP1, AQP1, CDH6, HTRA3, INA, KRT19, LAMC2, IL32, TAGLN3, NPPB and UGT2B7 and are negative for the markers: AGC1, ALDH1A1, APCDD1, AREG, ATP8B4, CFB, C3, C6, C7, C20orf103, CNTNAP2, COL21A1, COMP, COP1, CRLF1, DIO2, METTL7A, DKK2, DLK1, DPT, EMID1, TMEM100, FMO1, FMO3, FOXF1, FOXF2, GABRB1, GAP43, GSC, HOXA5, HSD11B2, HSD17B2, HSPA6, ID4, IF127, IFIT3, IGF2, KRT14, TMEM119, LOC92196, MASP1, MEOX2, MGP, MYBPH, MYH3, MYL4, OGN, OSR2, PAX9, PDE1A, PENK, PRELP, PRRX2, PTN, RARRES1, RGMA, RGS1, RPS4Y2, SERPINA3, SLITRK6, SMOC1, SMOC2, TAC1, RSPO3, TNNT2, TRH, TUBB4 and WISP2.

The group of cell lines B11, B25, B26 and B3 are positive for the markers: AKR1C1, CFB, BMP4, CLDN11, FST, GDF5, HTRA3, IL1R1, KRT14, KRT19, KRT34, MGP, MMP1, PODN, POSTN, PRG4, RARRES1, S100A4, THY1 and ZIC1 and are negative for the markers: ACTC, ALDH1A1, APCDD1, C6, C7, C20orf103, CCDC3, CD24, CXADR, DIO2, DKK2, DLK1, EMID1, FGFR3, FMO1, FMO3, FOXF1, FOXF2, GABRB1, GDF10, HSD11B2, HSD17B2, HSPA6, HSPB3, ID4, IGF2, INA, KCNMB1, IGFL3, LOC92196, MEOX1, MSX1, MYBPH, MYH3, MYH11, MYL4, NLGN4X, TAGLN3, NPPB, OLR1, PAX2, PAX9, PROM1, RASD1, RGS1, RPS4Y2, SLITRK6, SMOC1, SMOC2, SNAP25, TAC1, RSPO3, TUBB4, UGT2B7, ZD52F10 and ZIC2.

The group of cell lines B12 and B4 are positive for the markers: CLDN11, FST, GDF5, HTRA3, KRT19, KRT34, MFAP5, MGP, MMP1, POSTN, PTGS2, S100A4, THY1 and ZIC1 and are negative for the markers: AGC1, ALDH1A1, APCDD1, AREG, ATP8B4, C3, C6, C7, C20orf103, CCDC3, CDH3, CNTNAP2, COP1, CXADR, DIO2, DKK2, DLK1, DPT, EMID1, FMO1, FMO3, FOXF1, FOXF2, GABRB1, GDF10, HOXA5, HSD11B2, HSD17B2, HSPA6, HSPB3, IGFBP5, IGFL3, LOC92196, MEOX1, MYBPH, MYH3, MYH11, MYL4, NPAS1, NPPB, OLR1, PAX2, PAX9, PITX2, PROM1, RGS1, SLITRK6, SMOC1, SMOC2, SNAP25, TAC1, RSPO3, TNNT2, TRH, TUBB4, ZD52F10 and ZIC2.

The group of cell lines B20 and B15 are positive for the markers: BMP4, CD24, CRIP1, HTRA3, KRT19, LAMC2, MGP, MMP1, POSTN, RELN, S100A4, THY1 and UGT2B7 and are negative for the markers: AGC1, ALDH1A1, ANXA8, AREG, ATP8B4, CFB, C6, C7, C20orf103, CNTNAP2, DIO2, METTL7A, DLK1, DPT, EMID1, TMEM100, FMO1, FMO3, FOXF2, GABRB1, GSC, HOXA5, HSD11B2, HSD17B2, HSPA6, ID4, IF127, KRT14, KRT34, IGFL3, MASP1, MEOX1, MEOX2, MYBPH, MYH3, MYL4, NPAS1, NPPB, OGN, OLR1, OSR2, PAX9, PDE1A, PENK, PROM1, PRRX2, RGS1, SLITRK6, SMOC1, SMOC2, STMN2, TAC1, TNNT2, TRH, TUBB4, WISP2 and ZIC1.

The group of cell lines B16Bio1b, B16Bio2b, E72 and E75 are positive for the markers: AKR1C1, BMP4, CLDN11, FST, GDF5, HTRA3, IL1R1, KRT19, KRT34, MFAP5, MGP, MMP1, OSR2, PODN, POSTN, PRG4, PRRX1, RARRES1, S100A4, SOD3, THY1 and ZIC1 and are negative for the markers: ACTC, AGC1, ALDH1A1, AREG, C6, C7, C20orf103, CCDC3, CDH3, CNTNAP2, DKK2, EMID1, FGFR3, FMO3, FOXF1, FOXF2, GABRB1, GDF10, HSD11B2, HSD17B2, HSPA6, ID4, IGF2, INA, LAMC2, IGFL3, LOC92196, MEOX1, MSX1, MYBPH, MYH11, MYL4, NLGN4X, NPAS1, NPPB, OLR1, PAX2, PAX9, PROM1, PTPRN, RASD1, RGS1, SLITRK6, SMOC1, SMOC2, SNAP25, TAC1, RSPO3, TNNT2, TUBB4, ZD52F10 and ZIC2.

The group of cell lines B17Bio1b, B17Bio2c and B17Bio3c are positive for the markers: BEX1, COL15A1, CRIP1, CRYAB, HTRA3, KCNMB1, KRT19, MGP, POSTN, S100A4, SFRP2, THY1 and TNFSF7 and are negative for the markers: , AGC1, ALDH1A1, APCDD1, AREG, ATP8B4, C6, C7, CNTNAP2, METTL7A, DLK1, DPT, EMID1, FMO1, FMO3, FOXF1, GABRB1, GSC, HOXA5, HSD11B2, HSD17B2, HSPA6, IF127, KRT14, KRT34, IGFL3, MASP1, MEOX1, MEOX2, MYBPH, MYH3, MYL4, NPPB, OGN, PAX9, PDE1A, PENK, PROM1, RASD1, RGS1, SLITRK6, SMOC1, SMOC2, STMN2, TAC1, TRH, TSLP, TUBB4 and ZIC1.

The group of cell lines B2, B7 and X6.1 are positive for the markers: AKR1C1, CFB, BMP4, C3, CLDN11, COL21A1, FST, GDF5, HTRA3, ICAM5, IL1R1, KRT19, MGP, MMP1, PENK, PODN, POSTN, PRG4, RARRES1, RGMA, S100A4, SERPINA3, SOD3, STMN2, THY1 and WISP2 and are negative for the markers: ACTC, AGC1, ALDH1A1, C6, C7, C20orf103, CCDC3, CD24, CDH3, CXADR, DIO2, DLK1, EMID1, FGFR3, FMO3, FOXF1, FOXF2, GABRB1, GDF10, HSD11B2, HSD17B2, HSPA6, HSPB3, ID4, IGF2, INA, IGFL3, LOC92196, MEOX1, MYH11, MYL4, NLGN4X, TAGLN3, NPAS1, NPPB, OLR1, PAX2, PAX9, PITX2, PROM1, PTPRN, RASD1, RGS1, RPS4Y2, SLITRK6, SMOC1, SMOC2, SNAP25, SOX11, TAC1, RSPO3, TUBB4, UGT2B7, ZD52F10 and ZIC2.

The group of cell lines B22, CM30.2 and X6 are positive for the markers: BMP4, CLDN11, CRIP1, CRYAB, HTRA3, KRT19, S100A4, SFRP2, SRCRB4D, THY1 and UGT2B7 and are negative for the markers: AGC1, ALDH1A1, APCDD1, AREG, ATP8B4, C3, C6, C7, C20orf103, CDH3, CNTNAP2, COL21A1, COP1, DIO2, METTL7A, DKK2, DLK1, DPT, FMO1, FMO3, FOXF1, FOXF2, GABRB1, GSC, HOXA5, HSD11B2, HSPA6, IF127, IFIT3, IGF2, KRT14, MASP1, MEOX2, MYBPH, MYH3, MYH11, NPPB, OGN, OLR1, OSR2, PAX9, PDE1A, PENK, PROM1, RGS1, SMOC1, SNAP25, STMN2, TAC1, TRH, TSLP, TUBB4 and WISP2.

The group of cell lines B27, B9, CM10.1, X2, X4.2 and X4.4 are positive for the markers: HTRA3, KRT19, LAMC2, IL32, TAGLN3, PAX2, RELN and UGT2B7 and are negative for the markers: AGC1, ALDH1A1, APCDD1, AREG, ATP8B4, CFB, C3, C6, C7, C20orf103, CCDC3, CDH3, CNTNAP2, COL21A1, COP1, CRLF1, DIO2, METTL7A, DLK1, DPT, EMID1, TMEM100, FMO1, FMO3, FOXF1, FOXF2, GABRB1, TABLE I-continued Exemplary progenitor cell lines and associated gene expression markers at 18-21 doublings of clonal expansion GAP43, GSC, HOXA5, HSD11B2, HSD17B2, HSPA6, IF127, IGF2, KIAA0644, KRT14, IGFL3, LOC92196, MASP1, MEOX2, MGP, MYH3, MYH11, MYL4, NPAS1, OGN, OLR1, OSR2, PAX9, PDE1A, PENK, PRELP, PTN, RARRES1, RGMA, RGS1, SERPINA3, SLITRK6, SMOC1, SMOC2, SNAP25, SOD3, STMN2, TAC1, RSPO3, TNNT2, TRH, TUBB4 and WISP2.

The cell line B28 is positive for the markers: CFB, BMP4, COL15A1, CRIP1, CRYAB, FST, GAP43, IL1R1, KCNMB1, KRT14, KRT19, KRT34, MFAP5, MGP, MMP1, IL32, PODN, POSTN, S100A4, THY1 and ZIC1 and are negative for the markers: ACTC, ALDH1A1, ANXA8, AREG, ATP8B4, BEX1, C3, C6, C7, C20orf103, CCDC3, CNTNAP2, CXADR, DIO2, METTL7A, DKK2, DLK1, EMID1, FGFR3, FMO1, FMO3, FOXF1, FOXF2, GABRB1, GDF10, HOXA5, HSD11B2, HSD17B2, HSPA6, ID4, IF127, IGF2, IGFBP5, INA, IGFL3, LOC92196, MASP1, MEOX1, MYBPH, MYH3, MYL4, NLGN4X, NPAS1, NPPB, OLR1, PAX9, PDE1A, PITX2, PROM1, PTPRN, RASD1, RGS1, RPS4Y2, SLITRK6, SMOC1, SMOC2, SNAP25, STMN2, TAC1, TRH, TSLP, TUBB4, ZD52F10 and ZIC2.

The cell line B29 is positive for the markers: ANXA8, AQP1, CD24, CDH6, CRIP1, GJB2, HTRA3, KRT17, KRT19, LAMC2, IL32, TAGLN3, PAX2, RELN, S100A4, SFRP2, SRCRB4D, THY1, TNFSF7, UGT2B7, ZD52F10 and ZIC2 and are negative for the markers: AGC1, ALDH1A1, APCDD1, AREG, ATP8B4, BEX1, C3, C6, C7, C20orf103, CCDC3, CLDN11, CNTNAP2, COL21A1, COP1, CRLF1, DIO2, METTL7A, DLK1, DPT, EMID1, TMEM100, FMO1, FMO3, FOXF1, FOXF2, GABRB1, GAP43, GDF10, GSC, HOXA5, HSD11B2, HSD17B2, HSPA6, HSPB3, IF127, IFIT3, IGF2, KRT14, KRT34, IGFL3, MFAP5, MASP1, MEOX2, MMP1, MSX1, MYBPH, MYH3, MYL4, NPAS1, NPPB, OGN, OLR1, OSR2, PAX9, PDE1A, PENK, PITX2, POSTN, PRG4, PROM1, PRRX2, PTPRN, RARRES1, RASD1, RGS1, RPS4Y2, SERPINA3, SLITRK6, SMOC1, SMOC2, SNAP25, SOD3, STMN2, TAC1, RSPO3, TRH, TSLP, TUBB4, WISP2 and ZIC1.

The cell line B30 is positive for the markers: PRSS35, CDH6, COL21A1, CRIP1, CRYAB, DKK2, GAP43, KCNMB1, KRT17, KRT19, PRRX1, PTN, RGMA, S100A4, SOX11 and ZIC2 and are negative for the markers: ACTC, AGC1, AKR1C1, ALDH1A1, ANXA8, APCDD1, AQP1, AREG, ATP8B4, CFB, C3, C6, C7, C20orf103, CD24, CDH3, CLDN11, CNTNAP2, COL15A1, COMP, COP1, CRLF1, METTL7A, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IF127, IFIT3, IGF2, KRT34, LAMC2, IGFL3, LOC92196, MFAP5, MASP1, MEOX1, MEOX2, MSX1, MYBPH, MYH3, MYL4, NLGN4X, NPPB, OGN, OLR1, PAX2, PAX9, PDE1A, PENK, PITX2, PRG4, PROM1, PTPRN, RARRES1, RASD1, RELN, RGS1, RPS4Y2, SFRP2, SLITRK6, SMOC1, SNAP25, STMN2, TAC1, TFPI2, TNFSF7, TNNT2, TRH, TSLP, TUBB4, UGT2B7, WISP2, ZD52F10 and ZIC1.

The cell line B6 is positive for the markers: CCDC3, CDH6, COL15A1, CRIP1, DKK2, FST, GDF10, HTRA3, KRT19, LOC92196, MYL4, NLGN4X, S100A4, SOX11, SRCRB4D, THY1, ZIC1 and ZIC2 and are negative for the markers: AGC1, AKR1C1, ALDH1A1, AREG, ATP8B4, BEX1, CFB, C3, C6, C7, CNTNAP2, COMP, COP1, DIO2, METTL7A, DLK1, DPT, EMID1, TMEM100, FMO3, FOXF1, FOXF2, GABRB1, GSC, HOXA5, HSD11B2, HSPA6, HSPB3, ID4, IF127, IFIT3, KRT14, TMEM119, MFAP5, MASP1, MEOX1, MEOX2, MGP, MMP1, MSX2, MYBPH, MYH3, NPAS1, NPPB, OGN, OLR1, OSR2, PAX2, PAX9, PDE1A, PENK, PRG4, PROM1, PTPRN, RASD1, RGS1, RPS4Y2, SLITRK6, SMOC1, SNAP25, STMN2, TAC1, TRH, TSLP, TUBB4, UGT2B7, WISP2 and ZD52F10.

The cell line C4ELS5.1 is positive for the markers: AKR1C1, C7, CDH6, COL15A1, DIO2, FMO1, FMO3, FOXF2, IGF2, IL1R1, KRT19, LAMC2, TMEM119, PODN, PRRX1, PRRX2, RGMA, SFRP2, TAC1, TFPI2 and RSPO3 and are negative for the markers: ACTC, AGC1, ALDH1A1, ANXA8, APCDD1, AQP1, AREG, ATP8B4, BEX1, CFB, BMP4, C3, C20orf103, CCDC3, CDH3, CLDN11, CNTNAP2, COMP, COP1, CRLF1, CRYAB, CXADR, DKK2, DLK1, EGR2, EMID1, FGFR3, FOXF1, GABRB1, GAP43, GDF10, GJB2, HOXA5, HSD17B2, HSPA6, HSPB3, ICAM5, ID4, IF127, KRT14, KRT17, KRT34, IGFL3, LOC92196, MFAP5, MEOX1, MEOX2, MGP, MMP1, MSX1, MSX2, MX1, MYBPH, MYH3, MYH11, MYL4, IL32, NLGN4X, TAGLN3, NPAS1, NPPB, OLR1, PAX2, PAX9, PENK, PRELP, PROM1, PTPRN, RARRES1, RELN, RGS1, RPS4Y2, SMOC1, SMOC2, STMN2, THY1, TNFSF7, TNNT2, TRH, TUBB4, UGT2B7, ZD52F10, ZIC1 and ZIC2.

The cell line C4ELS5.5 is positive for the markers: BEX1, BMP4, C7, PRSS35, CDH6, DKK2, FMO3, FOXF2, FST, GDF10, HSD17B2, IGF2, TMEM119, PITX2, PODN, PRRX1, SERPINA3, SFRP2, TFPI2 and ZIC2 and are negative for the markers: AGC1, ALDH1A1, APCDD1, AQP1, AREG, ATP8B4, C3, C6, C20orf103, CD24, CDH3, CNTNAP2, COMP, COP1, CRLF1, CXADR, DLK1, DPT, EMID1, FGFR3, TMEM100, FOXF1, GJB2, HOXA5, HSD11B2, HSPA6, HSPB3, ID4, IF127, KCNMB1, KRT14, KRT17, KRT34, IGFL3, MFAP5, MEOX1, MEOX2, MGP, MMP1, MSX2, MX1, MYBPH, MYH3, MYH11, IL32, NLGN4X, TAGLN3, NPPB, OGN, OLR1, OSR2, PAX2, PAX9, PDE1A, PENK, PRELP, PRG4, PTPRN, RARRES1, RASD1, RELN, RGS1, SMOC2, STMN2, TAC1, THY1, TNFSF7, TNNT2, TRH, TSLP, TUBB4, WISP2, ZD52F10 and ZIC1.

The cell line C4ELSR.12 is positive for the markers: C7, CDH6, COL21A1, DIO2, FMO1, FMO3, FOXF2, FST, IGF2, IL1R1, TMEM119, PRRX1, PRRX2, PTN, RGMA, SFRP2, SRCRB4D, TAC1, TFPI2, RSPO3, UGT2B7 and ZIC2 and are negative for the markers: ACTC, AGC1, ALDH1A1, ANXA8, APCDD1, AQP1, ATP8B4, C3, C20orf103, CD24, CDH3, CNTNAP2, COMP, COP1, CRLF1, CXADR, DPT, EMID1, FGFR3, TMEM100, FOXF1, GABRB1, GAP43, GJB2, HOXA5, HSPA6, HSPB3, ICAM5, IF127, INA, KRT14, KRT17, KRT34, IGFL3, MFAP5, MEOX1, MEOX2, MGP, MMP1, MX1, MYBPH, MYH11, MYL4, IL32, NLGN4X, NPAS1, NPPB, OLR1, OSR2, PAX2, PAX9, PENK, POSTN, PRELP, PROM1, PTPRN, RARRES1, RASD1, RELN, RGS1, SLITRK6, SMOC2, STMN2, SYT12, THY1, TNFSF7, TNNT2, TRH, TSLP, TUBB4, WISP2, ZD52F10 and ZIC1.

The group of cell lines C4ELSR2, C4ELSR2Bio2 and C4ELSR2Bio2.1 are positive for the markers: C7, CDH6, COL21A1, DKK2, FMO3, FST, GSC, IGF2, TMEM119, PITX2, SFRP2, TFPI2 and ZIC2 and are negative for the markers: ACTC, AGC1, ALDH1A1, APCDD1, AQP1, ATP8B4, CFB, C3, C6, CCDC3, CD24, CDH3, CLDN11, CNTNAP2, COMP, COP1, CRLF1, CRYAB, DLK1, DPT, EMID1, FGFR3, TMEM100, FOXF1, GABRB1, GJB2, HOXA5, HSD11B2, HSD17B2, HSPA6, HSPB3, ID4, IF127, KIAA0644, KRT14, KRT17, KRT34, IGFL3, MFAP5, MEOX1, MGP, MSX2, MX1, MYBPH, MYH3, MYH11, IL32, NLGN4X, NPAS1, NPPB, OLR1, PAX2, PAX9, PDE1A, PENK, POSTN, PRELP, PROM1, PTPRN, RARRES1, RASD1, RELN, RGS1, SMOC1, SMOC2, STMN2, THY1, TNFSF7, TRH, TSLP, TUBB4, ZD52F10 and ZIC1.

TABLE I-continued

Exemplary progenitor cell lines and associated gene expression markers at 18-21 doublings of clonal expansion The group of cell lines CM0.2 and E31 are positive for the markers: AQP1, CD24, CDH6, HTRA3, KRT19, KRT34, TAGLN3, RELN, S100A4, SFRP2, SRCRB4D and UGT2B7 and are negative for the markers: AGC1, ALDH1A1, APCDD1, AREG, ATP8B4, CFB, C3, C6, C7, C20orf103, CDH3, CNTNAP2, COMP, COP1, CRLF1, DIO2, METTL7A, DLK1, DPT, EMID1, TMEM100, FMO1, FMO3, FOXF1, FOXF2, GABRB1, GAP43, GSC, HOXA5, HSD11B2, HSPA6, HSPB3, IF127, IFIT3, IGF2, KRT14, MFAP5, MASP1, MEOX2, MYH3, NPAS1, OGN, OLR1, OSR2, PAX9, PDE1A, PENK, PRG4, PROM1, PTPRN, RARRES1, RASD1, RGS1, SERPINA3, SLITRK6, SMOC1, SMOC2, SNAP25, SOD3, STMN2, TAC1, TRH, TSLP, TUBB4 and WISP2.

The group of cell lines CM0.2, CM0.5 and CM50.5 are positive for the markers: PRSS35, CLDN11, CRIP1, CRYAB, FST, KRT19, KRT34, MFAP5, MEOX2, MGP, MMP1, PODN, POSTN, PRRX1, S100A4, THY1 and ZIC1 and are negative for the markers: ACTC, ALDH1A1, APCDD1, AREG, ATP8B4, BEX1, C3, C6, C7, C20orf103, CCDC3, CDH3, CNTNAP2, CXADR, DIO2, DKK2, DLK1, EMID1, TMEM100, FMO1, FMO3, FOXF1, FOXF2, GABRB1, GDF10, GJB2, GSC, HSD11B2, HSD17B2, HSPA6, IGF2, IGFBP5, INA, LAMC2, IGFL3, LOC92196, MEOX1, MX1, MYBPH, MYL4, NLGN4X, TAGLN3, NPAS1, NPPB, PAX2, PAX9, PDE1A, PENK, PITX2, PROM1, PTPRN, RASD1, RGS1, SLITRK6, SMOC1, SMOC2, SNAP25, STMN2, TAC1, RSPO3, TRH, TSLP, TUBB4, ZD52F10 and ZIC2.

The group of cell lines CM10.4, CM20.4, CM30.5 and X2.3 are positive for the markers: CLDN11, COMP, CRIP1, FST, KRT19, KRT34, MFAP5, MGP, PITX2, POSTN, S100A4 and THY1 and are negative for the markers: ACTC, ALDH1A1, AQP1, ATP8B4, C6, C7, C20orf103, CDH3, CNTNAP2, COP1, CXADR, METTL7A, DLK1, DPT, EMID1, FGFR3, TMEM100, FMO1, FMO3, FOXF1, FOXF2, GABRB1, GDF10, HSD11B2, HSD17B2, HSPA6, HSPB3, IGF2, IGFL3, LOC92196, MEOX1, MX1, MYBPH, MYH3, MYH11, MYL4, NLGN4X, TAGLN3, NPPB, PAX2, PAX9, PDE1A, PRELP, PROM1, PTPRN, RASD1, RELN, RGS1, SLITRK6, SMOC2, SNAP25, STMN2, TAC1, RSPO3, TUBB4, UGT2B7, WISP2, ZD52F10 and ZIC2.

The group of cell lines E111 and E111Bio2 are positive for the markers: CD24, CDH6, CRIP1, HTRA3, INA, TAGLN3, SFRP2, SRCRB4D, UGT2B7 and ZIC2 and are negative for the markers: AGC1, AKR1C1, ALDH1A1, APCDD1, AREG, ATP8B4, CFB, C3, C6, C7, C20orf103, CDH3, CNTNAP2, COP1, CRLF1, DIO2, METTL7A, DLK1, DPT, EMID1, TMEM100, FMO1, FMO3, FOXF1, FOXF2, GABRB1, GAP43, GSC, HOXA5, HSD11B2, HSD17B2, HSPA6, HSPB3, ID4, IF127, IFIT3, IGF2, KRT14, LAMC2, MASP1, MEOX2, MX1, MYBPH, MYH3, MYH11, NPAS1, OGN, OLR1, PAX9, PDE1A, PENK, PRG4, PROM1, PRRX2, PTPRN, RARRES1, RASD1, RGMA, RGS1, SLITRK6, SMOC1, SMOC2, SNAP25, STMN2, TAC1, TNNT2, TRH, TUBB4 and WISP2.

The cell line E120 is positive for the markers: ACTC, BEX1, CLDN11, COL15A1, CRIP1, CRYAB, FST, GDF10, GJB2, HTRA3, IGFL3, MGP, MX1, IL32, POSTN, S100A4, SFRP2, THY1, TNFSF7, ZD52F10 and ZIC2 and are negative for the markers: AGC1, AKR1C1, ALDH1A1, APCDD1, AQP1, AREG, ATP8B4, BMP4, C3, C6, C7, PRSS35, C20orf103, CD24, CDH3, CNTNAP2, COL21A1, COMP, COP1, CRLF1, CXADR, DIO2, METTL7A, DKK2, DLK1, EMID1, FGFR3, FMO1, FMO3, FOXF1, FOXF2, GABRB1, GAP43, GDF5, GSC, HOXA5, HSD11B2, HSD17B2, HSPA6, HSPB3, IF127, IGF2, INA, KRT14, LAMC2, TMEM119, MASP1, MEOX2, MMP1, MSX2, MYBPH, MYH3, MYH11, NLGN4X, TAGLN3, NPAS1, NPPB, OGN, OLR1, OSR2, PAX2, PAX9, PDE1A, PENK, PITX2, PODN, PRG4, PROM1, RASD1, RELN, RGMA, RGS1, SLITRK6, SMOC1, SMOC2, SNAP25, SYT12, TAC1, RSPO3, TNNT2, TRH, TUBB4, UGT2B7 and WISP2.

The cell line E15 is positive for the markers: ACTC, BEX1, PRSS35, CRIP1, CRYAB, GAP43, GDF5, HTRA3, KRT19, MGP, MMP1, POSTN, PRRX1, S100A4, SOX11, SRCRB4D and THY1 and are negative for the markers: AGC1, AKR1C1, ALDH1A1, ANXA8, APCDD1, AQP1, AREG, ATP8B4, CFB, C3, C6, C7, C20orf103, CDH3, CNTNAP2, COP1, CXADR, METTL7A, DLK1, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IF127, IFIT3, IGF2, INA, KRT14, TMEM119, IGFL3, LOC92196, MFAP5, MASP1, MEOX1, MEOX2, MSX1, MX1, MYBPH, MYH3, MYL4, NLGN4X, TAGLN3, NPAS1, NPPB, OGN, OLR1, PAX2, PAX9, PDE1A, PENK, PITX2, PRG4, PROM1, PTPRN, RARRES1, RASD1, RELN, RGS1, SLITRK6, SMOC1, SMOC2, SNAP25, STMN2, TAC1, TFPI2, RSPO3, TNFSF7, TNNT2, TRH, TSLP, TUBB4, UGT2B7, WISP2, ZD52F10 and ZIC1.

The cell line E164 is positive for the markers: AQP1, CD24, CDH6, CRIP1, HTRA3, KRT17, KRT19, IL32, TAGLN3, PAX2, RELN, S100A4, SFRP2, SRCRB4D, THY1, TNFSF7, UGT2B7, ZD52F10 and ZIC2 and are negative for the markers: ACTC, AGC1, ALDH1A1, ANXA8, APCDD1, AREG, ATP8B4, C3, C6, C7, C20orf103, CCDC3, CDH3, CLDN11, CNTNAP2, COL15A1, COL21A1, COMP, COP1, CRLF1, DIO2, METTL7A, DKK2, DLK1, DPT, EGR2, EMID1, TMEM100, FMO1, FMO3, FOXF1, FOXF2, GABRB1, GAP43, GDF5, GSC, HOXA5, HSD11B2, HSD17B2, HSPA6, HSPB3, ID4, IF127, KCNMB1, KRT14, KRT34, TMEM119, MFAP5, MASP1, MEOX2, MGP, MSX2, MYBPH, MYH3, MYH11, MYL4, NPAS1, NPPB, OGN, OLR1, PAX9, PDE1A, PENK, PITX2, POSTN, PRELP, PRG4, PRRX1, PRRX2, PTGS2, PTPRN, RARRES1, RASD1, RGMA, RGS1, SERPINA3, SLITRK6, SMOC1, SMOC2, SNAP25, SOD3, STMN2, TAC1, TNNT2, TRH, TUBB4 and WISP2.

The group of cell lines E69 and E169 are positive for the markers: BEX1, CDH6, CRIP1, FST, GDF5, HTRA3, MMP1, POSTN, PTN, S100A4 and ZIC2 and are negative for the markers: AGC1, ALDH1A1, APCDD1, AQP1, AREG, ATP8B4, BMP4, C3, C6, C7, C20orf103, CDH3, CNTNAP2, COMP, CRLF1, CXADR, DLK1, DPT, EGR2, EMID1, FMO1, FMO3, FOXF1, FOXF2, GABRB1, GJB2, GSC, HOXA5, HSD11B2, HSD17B2, HSPA6, HSPB3, IF127, IGF2, INA, KRT14, IGFL3, LOC92196, MASP1, MEOX1, MEOX2, MYBPH, MYH3, MYH11, MYL4, NLGN4X, TAGLN3, NPAS1, NPPB, OGN, OLR1, PAX2, PAX9, PDE1A, PENK, PITX2, PROM1, RARRES1, RASD1, RELN, RGS1, SLITRK6, SMOC1, SMOC2, SNAP25, STMN2, SYT12, TAC1, RSPO3, TNNT2, TRH, TUBB4, UGT2B7 and ZD52F10.

The cell line E19 is positive for the markers: ACTC, BEX1, PRSS35, CLDN11, CRIP1, CRYAB, DKK2, HTRA3, ICAM5, KRT17, KRT19, KRT34, MX1, POSTN, THY1, ZIC1 and ZIC2 and are negative for the markers: AGC1, AKR1C1, ALDH1A1, APCDD1, AQP1, AREG, ATP8B4, CFB, BMP4, C3, C6, C7, C20orf103, CDH3, CNTNAP2, COL21A1, COP1, CXADR, METTL7A, DLK1, DPT, EGR2, EMID1, TMEM100, FMO1, FMO3, FOXF1, FOXF2, GABRB1, GAP43, GDF10, GJB2, GSC, HOXA5, HSD11B2, HSD17B2, HSPA6, IGF2, IL1R1, KIAA0644, TMEM119, IGFL3, LOC92196, MASP1, MEOX1, MEOX2, MGP, MYBPH, MYH3, NLGN4X, TAGLN3, OGN, PAX2, PAX9, PDE1A, PENK, PRG4, PROM1, PRRX2, RARRES1, RASD1, RELN, RGMA, RGS1, SFRP2, SLITRK6, SMOC1, SMOC2, SNAP25, SOD3, STMN2, TABLE I-continued Exemplary progenitor cell lines and associated gene expression markers at 18-21 doublings of clonal expansion SYT12, TAC1, TFPI2, RSPO3, TNFSF7, TNNT2, TRH, TSLP, TUBB4, UGT2B7, WISP2 and ZD52F10.
The group of cell lines E3, E30, E20Bio2, E67, E73, E57 and E84 are positive for the markers: KRT19, KRT34, MFAP5, MGP, MMP1, S100A4, THY1 and ZIC1 and are negative for the markers: ALDH1A1, AREG, ATP8B4, C7, C20orf103, CDH3, CNTNAP2, DKK2, DLK1, DPT, FMO1, FMO3, FOXF1, FOXF2, GDF10, GSC, HOXA5, HSD17B2, IGF2, MEOX1, NPPB, PAX9, PROM1, PTPRN, RGS1, SMOC1, SNAP25, STMN2, TAC1, TUBB4 and ZIC2.
The cell line E33 is positive for the markers: AQP1, PRSS35, CD24, CDH6, CLDN11, CRIP1, CRYAB, DKK2, HTRA3, KRT17, KRT19, KRT34, LOC92196, MFAP5, MGP, MYH11, TAGLN3, POSTN, S100A4, SRCRB4D, UGT2B7, ZIC1 and ZIC2 and are negative for the markers: AGC1, AKR1C1, ALDH1A1, APCDD1, AREG, ATP8B4, CFB, C3, C6, C7, C20orf103, CDH3, CNTNAP2, COMP, COP1, CRLF1, DIO2, METTL7A, DLK1, DPT, EMID1, TMEM100, FMO1, FMO3, FOXF1, FOXF2, GABRB1, GDF5, GJB2, GSC, HOXA5, HSD11B2, HSPA6, HSPB3, IF127, IFIT3, IGF2, TMEM119, IGFL3, MASP1, MX1, MYBPH, NPAS1, NPPB, OGN, OLR1, OSR2, PAX9, PDE1A, PENK, PITX2, PRG4, PROM1, PTPRN, RARRES1, RASD1, RGMA, RGS1, SERPINA3, SFRP2, SLITRK6, SMOC1, SMOC2, SNAP25, STMN2, TAC1, RSPO3, TRH, TSLP, TUBB4, WISP2 and ZD52F10.
The cell line E40 is positive for the markers: BEX1, CDH6, CLDN11, CRIP1, CRYAB, DKK2, FST, HTRA3, KRT17, KRT19, MMP1, POSTN, S100A4, SRCRB4D and ZIC2 and are negative for the markers: AGC1, AKR1C1, ALDH1A1, APCDD1, AQP1, AREG, ATP8B4, CFB, BMP4, C3, C6, C7, C20orf103, CDH3, CNTNAP2, COMP, COP1, CRLF1, CXADR, METTL7A, DLK1, DPT, EGR2, EMID1, TMEM100, FMO1, FMO3, FOXF1, FOXF2, GABRB1, GJB2, GSC, HOXA5, HSD11B2, HSD17B2, HSPA6, HSPB3, IF127, IFIT3, IGF2, KIAA0644, KRT14, IGFL3, LOC92196, MASP1, MEOX1, MEOX2, MGP, MX1, MYBPH, MYH3, NLGN4X, TAGLN3, NPAS1, NPPB, OGN, OLR1, OSR2, PAX2, PAX9, PDE1A, PENK, PITX2, PRG4, PROM1, PRRX2, PTPRN, RARRES1, RASD1, RELN, RGS1, SLITRK6, SMOC1, SMOC2, SNAP25, STMN2, SYT12, TAC1, TFPI2, RSPO3, TNFSF7, TNNT2, TRH, TSLP, TUBB4, WISP2, ZD52F10 and ZIC1.
The cell line E44 is positive for the markers: BEX1, CLDN11, CRIP1, FST, GDF5, HTRA3, IF127, IFIT3, MGP, MMP1, MSX1, MX1, IL32, PRRX2, PTN, S100A4, SOD3 and ZIC2 and are negative for the markers: ACTC, AGC1, ALDH1A1, AQP1, AREG, ATP8B4, BMP4, C6, C7, C20orf103, CDH3, CDH6, CNTNAP2, COL21A1, COMP, CRLF1, DKK2, DPT, EGR2, EMID1, FGFR3, FMO1, FMO3, FOXF2, GABRB1, GDF10, GSC, HOXA5, HSD11B2, HSD17B2, HSPA6, HSPB3, IGF2, INA, KCNMB1, KRT14, KRT34, TMEM119, IGFL3, LOC92196, MFAP5, MEOX1, MEOX2, MYBPH, MYH3, MYH11, MYL4, NLGN4X, NPAS1, NPPB, OGN, OLR1, PAX2, PAX9, PDE1A, PENK, PITX2, POSTN, PRELP, PRG4, PROM1, RASD1, RELN, RGMA, RGS1, RPS4Y2, SFRP2, SLITRK6, SMOC1, SMOC2, SNAP25, SRCRB4D, STMN2, SYT12, TAC1, RSPO3, TNNT2, TRH, TUBB4, UGT2B7, ZD52F10 and ZIC1.
The cell line E45 is positive for the markers: AQP1, CD24, CDH6, COL21A1, CRIP1, DKK2, HTRA3, KRT17, KRT19, MGP, TAGLN3, PRRX1, S100A4, SOX11, UGT2B7, ZIC1 and ZIC2 and are negative for the markers: AGC1, ALDH1A1, ANXA8, APCDD1, AREG, ATP8B4, BEX1, BMP4, C3, C6, C7, C20orf103, CDH3, CNTNAP2, COL15A1, COMP, COP1, CRLF1, METTL7A, DLK1, DPT, EMID1, TMEM100, FMO1, FMO3, FOXF1, FOXF2, GABRB1, GAP43, GJB2, GSC, HOXA5, HSD11B2, HSPA6, HSPB3, ID4, IF127, KRT14, LAMC2, IGFL3, MFAP5, MASP1, MEOX1, MEOX2, MYBPH, MYH3, MYH11, NPAS1, NPPB, OGN, OLR1, OSR2, PAX9, PDE1A, PENK, PITX2, PRG4, PROM1, PTPRN, RARRES1, RASD1, RELN, RGS1, SERPINA3, SFRP2, SLITRK6, SMOC1, SMOC2, SNAP25, STMN2, TAC1, RSPO3, TRH, TSLP, TUBB4, WISP2 and ZD52F10.
The cell line E50 is positive for the markers: ACTC, BEX1, CD24, CDH6, COL21A1, CRIP1, CRYAB, DKK2, FST, KRT17, KRT19, LOC92196, POSTN, PTN, S100A4, SFRP2, SRCRB4D, ZIC1 and ZIC2 and are negative for the markers: AGC1, AKR1C1, ALDH1A1, APCDD1, AQP1, AREG, ATP8B4, CFB, BMP4, C6, C7, CDH3, CLDN11, CNTNAP2, COMP, COP1, CRLF1, METTL7A, DLK1, DPT, EMID1, TMEM100, FMO3, FOXF1, FOXF2, GABRB1, GSC, HOXA5, HSD11B2, HSD17B2, HSPA6, HSPB3, IF127, IFIT3, KRT14, KRT34, LAMC2, TMEM119, IGFL3, MFAP5, MASP1, MEOX1, MEOX2, MMP1, MYH3, NLGN4X, NPAS1, NPPB, OGN, OLR1, PAX2, PAX9, PENK, PRG4, PROM1, PTGS2, PTPRN, RARRES1, RASD1, RELN, RGS1, SERPINA3, SLITRK6, SMOC1, SMOC2, STMN2, SYT12, TAC1, TFPI2, RSPO3, TRH, TSLP, TUBB4, UGT2B7, WISP2 and ZD52F10.
The cell line E51 is positive for the markers: PRSS35, CCDC3, CDH6, CRIP1, CRYAB, DIO2, DKK2, HTRA3, ID4, KCNMB1, KRT17, KRT19, KRT34, MGP, MYH11, POSTN, PRRX1, S100A4, SOX11 and ZIC2 and are negative for the markers: AGC1, AKR1C1, ALDH1A1, APCDD1, AREG, ATP8B4, BMP4, C3, C6, C7, C20orf103, CDH3, CNTNAP2, COP1, CRLF1, CXADR, METTL7A, DLK1, DPT, EMID1, FMO1, FMO3, FOXF1, FOXF2, GABRB1, GSC, HOXA5, HSD17B2, HSPA6, HSPB3, IF127, IFIT3, IGF2, IGFBP5, TMEM119, IGFL3, LOC92196, MASP1, MEOX1, MEOX2, MX1, MYBPH, MYH3, MYL4, NLGN4X, TAGLN3, NPAS1, NPPB, OGN, OLR1, PAX2, PAX9, PDE1A, PENK, PRG4, PROM1, PTPRN, RARRES1, RASD1, RELN, RGS1, SFRP2, SMOC1, SMOC2, SNAP25, STMN2, SYT12, TAC1, TFPI2, TNFSF7, TNNT2, TRH, TUBB4, UGT2B7, WISP2 and ZD52F10.
The group of cell lines E68 and E68Bio2 are positive for the markers: CD24, CRIP1, CRYAB, HTRA3, KRT17, KRT19, TAGLN3, UGT2B7, ZIC1 and ZIC2 and are negative for the markers: AGC1, AREG, ATP8B4, C6, C7, CDH3, COP1, CRLF1, DLK1, DPT, TMEM100, FMO1, FMO3, FOXF1, FOXF2, GSC, HOXA5, HSD11B2, HSPA6, HSPB3, IGF2, LAMC2, IGFL3, MEOX1, MEOX2, MMP1, MYBPH, MYH3, NPAS1, OGN, PAX9, PITX2, PRG4, PROM1, RARRES1, RGS1, SMOC2, TAC1, RSPO3, TRH, TSLP and WISP2.
The group of cell lines C4ELS5.6 and C4ELS5.6Bio2 are positive for the markers: BMP4, COP1, METTL7A, TMEM100, FOXF1, HSD17B2, HTRA3, IGF2, IGFBP5, IL1R1, KRT19, MASP1, OLR1, PITX2, PODN and TSLP and are negative for the markers: ACTC, AGC1, ALDH1A1, AQP1, CFB, C6, C7, C20orf103, CDH3, CDH6, CLDN11, CNTNAP2, COL21A1, COMP, CRLF1, DKK2, DPT, EGR2, EMID1, FMO3, FOXF2, GABRB1, GAP43, GDF10, GSC, HOXA5, HSPA6, HSPB3, ID4, IF127, INA, KRT17, KRT34, LAMC2, TMEM119, IGFL3, LOC92196, MFAP5, MEOX1, MEOX2, MGP, MSX1, MYH3, MYH11, IL32, NLGN4X, TAGLN3, NPAS1, NPPB, OGN, PAX2, PAX9, PDE1A, PENK, PRG4, PROM1, PRRX1, PRRX2, PTPRN, RARRES1, RASD1, RELN, RGMA, RGS1, SFRP2, SMOC1, SMOC2, SNAP25, SOD3, SYT12, TAC1, RSPO3, THY1, TNFSF7, TNNT2, TRH, TUBB4, UGT2B7, WISP2, ZD52F10, ZIC1 and ZIC2.
The cell line C4ELS5.8 is positive for the markers: AKR1C1, ALDH1A1, BMP4, C3, COP1, METTL7A, TMEM100, FOXF1, HSD17B2, HTRA3, ICAM5, IFIT3, IGF2, IGFBP5, IL1R1, KRT19, MASP1, MX1, TABLE I-continued Exemplary progenitor cell lines and associated gene expression markers at 18-21 doublings of clonal expansion OLR1, PODN, STMN2, TFPI2 and THY1 and are negative for the markers: ACTC, AGC1, APCDD1, BEX1, C6, C7, PRSS35, C20orf103, CCDC3, CD24, CDH3, CLDN11, CNTNAP2, COL21A1, COMP, CRIP1, CRLF1, DKK2, DLK1, DPT, EMID1, FGFR3, FMO3, FOXF2, GABRB1, GAP43, GDF10, GSC, HOXA5, HSD11B2, HSPA6, HSPB3, ID4, INA, KCNMB1, KRT14, KRT17, TMEM119, IGFL3, LOC92196, MFAP5, MEOX1, MEOX2, MGP, MSX2, MYH3, MYH11, MYL4, IL32, NLGN4X, TAGLN3, NPPB, OGN, PAX2, PAX9, PDE1A, PENK, POSTN, PRRX1, PRRX2, PTPRN, RARRES1, RASD1, RELN, RGMA, RGS1, SLITRK6, SMOC1, SMOC2, SOD3, SOX11, SYT12, TAC1, RSPO3, TNFSF7, TNNT2, TRH, TUBB4, UGT2B7, WISP2, ZD52F10, ZIC1 and ZIC2.

The cell line C4ELSR13 is positive for the markers: AKR1C1, ANXA8, AREG, BMP4, C3, COP1, METTL7A, FMO3, FOXF1, HTRA3, IFI27, IFIT3, IGF2, IL1R1, KRT19, MASP1, MX1, MYBPH, OLR1, PITX2, PODN, S100A4 and TFPI2 and are negative for the markers: AGC1, APCDD1, AQP1, ATP8B4, C6, C20orf103, CD24, CDH3, CDH6, CLDN11, CNTNAP2, COL15A1, COL21A1, COMP, CRIP1, CRLF1, CRYAB, DKK2, DLK1, DPT, EGR2, EMID1, FGFR3, TMEM100, FMO1, FOXF2, GABRB1, GAP43, GDF10, GSC, HOXA5, HSD11B2, HSD17B2, HSPA6, HSPB3, ID4, INA, KIAA0644, KRT14, KRT17, IGFL3, LOC92196, MFAP5, MEOX1, MEOX2, MGP, MSX1, MSX2, MYH3, MYH11, MYL4, IL32, NLGN4X, TAGLN3, NPAS1, NPPB, OGN, OSR2, PAX2, PAX9, PDE1A, PENK, POSTN, PROM1, PRRX1, PTPRN, RARRES1, RASD1, RELN, RGMA, RGS1, RPS4Y2, SERPINA3, SLITRK6, SMOC2, SNAP25, SOD3, SOX11, STMN2, SYT12, TAC1, RSPO3, THY1, TNNT2, TRH, TUBB4, UGT2B7, ZD52F10, ZIC1 and ZIC2.

The cell line C4ELSR18 is positive for the markers: AQP1, BEX1, BMP4, C20orf103, CDH6, FST, HOXA5, IGF2, IGFBP5, OLR1, OSR2, PDE1A, PRRX2, S100A4, SFRP2, SLITRK6, TFPI2 and ZIC2 and are negative for the markers: AGC1, ALDH1A1, ANXA8, APCDD1, ATP8B4, CFB, C6, CCDC3, CD24, CDH3, CLDN11, CNTNAP2, COL15A1, COMP, COP1, CRLF1, CRYAB, DLK1, DPT, EGR2, EMID1, TMEM100, FOXF1, GABRB1, GAP43, GDF10, GSC, HSD11B2, HSD17B2, HSPA6, HSPB3, ID4, IFI27, IFIT3, KCNMB1, KRT14, KRT17, KRT34, TMEM119, IGFL3, LOC92196, MFAP5, MASP1, MEOX1, MEOX2, MSX1, MSX2, MX1, MYH3, MYH11, MYL4, IL32, NPAS1, NPPB, OGN, PAX2, PAX9, PENK, PITX2, PODN, PRG4, PTPRN, RARRES1, RASD1, RELN, RGS1, SERPINA3, SMOC1, SMOC2, SOD3, SOX11, STMN2, SYT12, TAC1, THY1, TNFSF7, TNNT2, TRH, TUBB4, UGT2B7, ZD52F10 and ZIC1.

The group of cell lines EN11 and W10 are positive for the markers: DLK1, FOXF1, FST, GABRB1, GDF5, HTRA3, IGF2, IGFBP5, IL1R1, POSTN, PTN, SOX11, SRCRB4D and TFPI2 and are negative for the markers: ACTC, AGC1, ALDH1A1, ANXA8, APCDD1, AQP1, AREG, CFB, BMP4, C3, C6, C7, CCDC3, CD24, CDH6, CLDN11, CNTNAP2, COL15A1, COMP, COP1, CRYAB, DKK2, DPT, EGR2, EMID1, FGFR3, FMO1, FMO3, FOXF2, GAP43, GDF10, GSC, HSD11B2, HSD17B2, HSPA6, HSPB3, ID4, IFI27, INA, KCNMB1, KRT14, KRT17, KRT34, IGFL3, LOC92196, MEOX1, MEOX2, MX1, MYBPH, MYH3, MYH11, MYL4, IL32, NLGN4X, NPAS1, NPPB, OLR1, PAX2, PAX9, PENK, PITX2, PRELP, PROM1, RARRES1, RASD1, RELN, RGS1, SMOC1, SMOC2, STMN2, SYT12, TAC1, THY1, TNFSF7, TNNT2, TRH, TUBB4, UGT2B7, WISP2, ZIC1 and ZIC2.

The group of cell lines EN7, EN13Bio1b, EN13Bio2c and EN13Bio3c are positive for the markers: CDH6, DLK1, FOXF1, FST, HTRA3, IGF2, IL1R1, MSX1, POSTN, SOD3, ZIC1 and ZIC2 and are negative for the markers: ACTC, ALDH1A1, ANXA8, ATP8B4, BMP4, C3, C20orf103, CCDC3, CD24, CDH3, CLDN11, CNTNAP2, COMP, CRYAB, DIO2, DKK2, GSC, HOXA5, HSD11B2, HSD17B2, HSPA6, HSPB3, IFI27, INA, KRT14, KRT17, KRT34, IGFL3, LOC92196, MFAP5, MEOX1, MEOX2, MGP, MMP1, MX1, MYH3, MYH11, MYL4, IL32, NPAS1, NPPB, OLR1, PAX2, PAX9, PDE1A, PENK, PITX2, PROM1, RELN, SFRP2, SMOC2, STMN2, TAC1, RSPO3, THY1, TNFSF7, TNNT2, TRH, TUBB4 and ZD52F10.

The cell line EN16 is positive for the markers: COL15A1, DIO2, DPT, FMO3, FOXF1, FOXF2, FST, HSPB3, HTRA3, IGF2, IL1R1, TMEM119, MGP, MMP1, PODN and PRRX2 and are negative for the markers: ACTC, AGC1, AKR1C1, ALDH1A1, ANXA8, AQP1?+0 AREG, ATP8B4, BEX1, CFB, C3, C6, C7, C20orf103, CCDC3, CD24, CDH3, CLDN11, CNTNAP2, COMP, CRIP1, CRLF1, DKK2, FGFR3, TMEM100, GABRB1, GAP43, GDF5, GDF10, GJB2, GSC, HOXA5, HSD11B2, HSD17B2, HSPA6, ID4, IFI27, KCNMB1, KRT14, KRT17, KRT34, LAMC2, IGFL3, LOC92196, MFAP5, MEOX1, MEOX2, MYBPH, MYH3, MYH11, MYL4, IL32, NLGN4X, TAGLN3, NPAS1, NPPB, PAX2, PAX9, PENK, PITX2, POSTN, PTGS2, PTPRN, RARRES1, RASD1, RGS1, SMOC1, SMOC2, SNAP25, STMN2, TAC1, RSPO3, THY1, TNFSF7, TNNT2, TRH, TUBB4, UGT2B7, ZD52F10, ZIC1 and ZIC2.

The group of cell lines EN1, EN1Bio2 and EN18 are positive for the markers: DIO2, DLK1, FOXF1, GDF5, HTRA3, IGF2, IL1R1, MGP, POSTN, PRRX2 and SRCRB4D and are negative for the markers: ACTC, AGC1, ALDH1A1, ANXA8, AQP1, CFB, C20orf103, CCDC3, CD24, CLDN11, CNTNAP2, CRYAB, CXADR, DKK2, GABRB1, GAP43, GDF10, GSC, HSD11B2, HSD17B2, HSPA6, IFI27, INA, KCNMB1, KRT14, KRT17, KRT34, IGFL3, LOC92196, MFAP5, MEOX1, MEOX2, MX1, MYH3, MYH11, MYL4, NPAS1, NPPB, PAX2, PAX9, PENK, PITX2, PROM1, RASD1, RGS1, SMOC1, SMOC2, STMN2, TAC1, RSPO3, THY1, TNFSF7, TNNT2, TRH, TUBB4, UGT2B7, ZD52F10, ZIC1 and ZIC2.

The cell line EN19 is positive for the markers: CDH6, COL15A1, COL21A1, DLK1, FOXF1, FST, GDF5, IGF2, TMEM119, MSX1, RGMA, SERPINA3, SOD3, ZIC1 and ZIC2 and are negative for the markers: ACTC, AGC1, ANXA8, AQP1, ATP8B4, C3, C6, C7, C20orf103, CD24, CDH3, CLDN11, CNTNAP2, CRIP1, CXADR, DIO2, DKK2, EMID1, TMEM100, GABRB1, GAP43, GJB2, GSC, HOXA5, HSD11B2, HSD17B2, HSPA6, HSPB3, IFI27, INA, KCNMB1, KRT14, KRT17, KRT19, KRT34, IGFL3, LOC92196, MFAP5, MEOX1, MEOX2, MGP, MX1, MYH3, MYH11, MYL4, IL32, NLGN4X, NPPB, OLR1, OSR2, PAX2, PAX9, PDE1A, PENK, PROM1, RARRES1, RASD1, RELN, RGS1, SLITRK6, SMOC1, SMOC2, SNAP25, STMN2, SYT12, TAC1, RSPO3, THY1, TNFSF7, TNNT2, TRH, TUBB4, UGT2B7 and ZD52F10.

The cell line EN2 is positive for the markers: FST, GDF5, HTRA3, IGF2, IGFBP5, IL1R1, PRRX2, PTN, SFRP2, SOX11, SRCRB4D, TFPI2 and RSPO3 and are negative for the markers: ACTC, AGC1, AKR1C1, ALDH1A1, ANXA8, APCDD1, AREG, ATP8B4, CFB, C3, C6, C7, PRSS35, C20orf103, CCDC3, CD24, CDH6, CLDN11, COMP, COP1, CRLF1, CXADR, DKK2, DPT, EGR2, EMID1, TMEM100, FMO1, FOXF2, GAP43, GDF10, GJB2, GSC, HOXA5, HSD11B2, HSD17B2, HSPA6, HSPB3, ICAM5, IFI27, INA, KRT14, KRT17, KRT19, KRT34, TMEM119, IGFL3, LOC92196, MFAP5, MEOX1, MEOX2, MX1, MYBPH, MYH3, MYH11, MYL4, NLGN4X, TAGLN3, NPAS1, NPPB, OGN, OLR1, PAX2, PAX9, PDE1A, PENK, PITX2, POSTN, PRELP, PRG4, PTGS2, RARRES1, RASD1, RELN, RGS1, SMOC1, SMOC2, SNAP25, STMN2, SYT12, TAC1, THY1, TNFSF7, TNNT2, TRH, TSLP, TUBB4, UGT2B7, ZD52F10, ZIC1 and ZIC2.

TABLE I-continued

Exemplary progenitor cell lines and associated gene expression markers at 18-21 doublings of clonal expansion The cell line EN25 is positive for the markers: CDH6, CNTNAP2, COL15A1, COL21A1, DLK1, FOXF1, FST, HTRA3, IGF2, SERPINA3, SRCRB4D, TFPI2, ZIC1 and ZIC2 and are negative for the markers: ACTC, AGC1, AKR1C1, ALDH1A1, AQP1, ATP8B4, C3, C6, C7, C20orf103, CCDC3, CD24, CDH3, CLDN11, CRIP1, DIO2, DKK2, EMID1, FOXF2, GSC, HOXA5, HSD11B2, HSD17B2, HSPA6, HSPB3, IF127, IFIT3, INA, KCNMB1, KRT14, KRT17, KRT34, IGFL3, LOC92196, MFAP5, MEOX1, MEOX2, MGP, MMP1, MX1, MYBPH, MYH3, MYH11, MYL4, IL32, NLGN4X, NPPB, OLR1, PAX2, PAX9, PENK, PITX2, PRELP, PROM1, PRRX1, PTN, RARRES1, RASD1, RELN, SFRP2, SLITRK6, SMOC2, STMN2, TAC1, RSPO3, THY1, TNFSF7, TNNT2, TRH, TUBB4, UGT2B7 and ZD52F10.

The cell line EN26 is positive for the markers: DIO2, DPT, FMO3, FOXF1, FOXF2, FST, GDF5, HTRA3, IGF2, IL1R1, TMEM119, PODN, PRRX1, PRRX2, SFRP2, SOD3 and SRCRB4D and are negative for the markers: ACTC, AGC1, AKR1C1, ALDH1A1, ANXA8, AQP1, ATP8B4, BEX1, C3, C6, C7, C20orf103, CCDC3, CD24, CLDN11, CNTNAP2, COL21A1, COMP, CRIP1, CXADR, DKK2, GABRB1, GAP43, GDF10, GJB2, GSC, HOXA5, HSD11B2, HSD17B2, HSPA6, ID4, IF127, INA, KCNMB1, KRT14, KRT17, KRT19, KRT34, LAMC2, IGFL3, LOC92196, MFAP5, MEOX1, MEOX2, MMP1, MX1, MYBPH, MYH3, MYH11, MYL4, NLGN4X, NPAS1, NPPB, PAX2, PAX9, PENK, PITX2, PROM1, PTGS2, PTPRN, RARRES1, RASD1, RELN, RGS1, SLITRK6, SMOC1, SMOC2, STMN2, TAC1, RSPO3, THY1, TNFSF7, TNNT2, TRH, TUBB4, UGT2B7, ZD52F10, ZIC1 and ZIC2.

The cell line EN27 is positive for the markers: DIO2, FMO3, FOXF1, FOXF2, FST, HSPB3, HTRA3, IGF2, IL1R1, TMEM119, MSX2, OGN, PODN, PRELP, PRRX2, SERPINA3 and SLITRK6 and are negative for the markers: , ACTC, AGC1, ALDH1A1, ANXA8, AQP1, AREG, ATP8B4, CFB, C3, C6, C7, C20orf103, CCDC3, CD24, CDH3, CDH6, CLDN11, CNTNAP2, CRIP1, CRLF1, DKK2, EMID1, FGFR3, TMEM100, GABRB1, GAP43, GDF10, GJB2, GSC, HOXA5, HSD11B2, HSD17B2, HSPA6, ICAM5, ID4, IF127, IFIT3, IGFBP5, INA, KCNMB1, KRT14, KRT17, KRT19, KRT34, LAMC2, IGFL3, LOC92196, MFAP5, MASP1, MEOX1, MEOX2, MMP1, MX1, MYBPH, MYH3, MYH11, MYL4, IL32, NLGN4X, NPAS1, NPPB, OLR1, PAX2, PAX9, PENK, PITX2, PROM1, RARRES1, RASD1, RELN, RGS1, SFRP2, SMOC1, SMOC2, STMN2, TAC1, RSPO3, THY1, TNFSF7, TNNT2, TRH, TUBB4, UGT2B7, ZD52F10, ZIC1 and ZIC2.

The cell line EN28 is positive for the markers: COL15A1, COL21A1, DIO2, FOXF1, FOXF2, FST, HSPB3, HTRA3, IGF2, IGFBP5, IL1R1, TMEM119, PODN, PRRX1, PTN, SFRP2 and SOX11 and are negative for the markers: ACTC, AGC1, AKR1C1, ALDH1A1, ANXA8, AQP1, AREG, ATP8B4, CFB, BMP4, C3, C6, C7, C20orf103, CCDC3, CD24, CDH3, CDH6, CLDN11, CNTNAP2, COP1, CRIP1, DKK2, EMID1, TMEM100, GAP43, GDF10, GJB2, GSC, HOXA5, HSD11B2, HSD17B2, HSPA6, ID4, IF127, INA, KCNMB1, KIAA0644, KRT14, KRT17, KRT34, IGFL3, LOC92196, MFAP5, MEOX1, MEOX2, MGP, MMP1, MX1, MYBPH, MYH3, MYH11, MYL4, IL32, NLGN4X, NPPB, OLR1, OSR2, PAX2, PAX9, PDE1A, PENK, PITX2, POSTN, PRELP, PRG4, PROM1, PTGS2, RARRES1, RELN, RGS1, SLITRK6, SMOC1, SMOC2, STMN2, SYT12, TAC1, RSPO3, TNFSF7, TNNT2, TRH, TSLP, TUBB4, UGT2B7, ZD52F10, ZIC1 and ZIC2.

The cell line EN31 is positive for the markers: CDH6, COL21A1, DLK1, FMO3, FOXF1, FST, GDF5, HTRA3, IGF2, IL1R1, MSX1, MSX2, OGN, OSR2, PRRX2, SERPINA3, SLITRK6, SOD3, TSLP, ZIC1 and ZIC2 and are negative for the markers: ACTC, AGC1, ALDH1A1, ANXA8, AQP1, ATP8B4, BEX1, BMP4, C3, C6, C7, PRSS35, C20orf103, CCDC3, CD24, CLDN11, CNTNAP2, COMP, CRIP1, CRLF1, CRYAB, CXADR, DIO2, DKK2, EMID1, TMEM100, GAP43, GDF10, GJB2, GSC, HOXA5, HSD11B2, HSD17B2, HSPA6, HSPB3, ICAM5, ID4, IFI27, INA, KRT14, KRT17, KRT19, KRT34, LAMC2, IGFL3, LOC92196, MFAP5, MEOX1, MEOX2, MGP, MMP1, MX1, MYBPH, MYH3, MYH11, MYL4, IL32, NLGN4X, TAGLN3, NPAS1, NPPB, OLR1, PAX2, PAX9, PENK, PITX2, PROM1, PTGS2, RARRES1, RASD1, RELN, SFRP2, SMOC2, SNAP25, STMN2, SYT12, TAC1, RSPO3, TNFSF7, TNNT2, TRH, TUBB4, UGT2B7 and ZD52F10.

The cell line EN38 is positive for the markers: BEX1, CDH6, COL21A1, DLK1, FOXF1, FST, GDF5, HTRA3, IGF2, IL1R1, TMEM119, MGP, MSX1, OGN, PODN, PRRX1, PRRX2, RGMA, SERPINA3, SOD3 and TSLP and are negative for the markers: ACTC, AGC1, AKR1C1, ALDH1A1, ANXA8, AQP1, AREG, ATP8B4, BMP4, C3, C6, C7, C20orf103, CCDC3, CD24, CDH3, CLDN11, CNTNAP2, CRIP1, DIO2, DKK2, DPT, GABRB1, GAP43, GDF10, GJB2, GSC, HOXA5, HSD11B2, HSD17B2, HSPA6, HSPB3, ID4, IFI27, INA, KCNMB1, KRT14, KRT17, KRT34, IGFL3, LOC92196, MFAP5, MEOX1, MEOX2, MX1, MYBPH, MYH3, MYH11, MYL4, IL32, NLGN4X, NPPB, OLR1, PAX2, PAX9, PDE1A, PENK, PITX2, PRELP, PRG4, PROM1, RASD1, RELN, RGS1, SFRP2, SLITRK6, SMOC1, SMOC2, SNAP25, STMN2, SYT12, TAC1, RSPO3, THY1, TNFSF7, TNNT2, TRH, TUBB4, ZD52F10, ZIC1 and ZIC2.

The cell line EN4 is positive for the markers: COL21A1, DLK1, FMO1, FMO3, FOXF1, FOXF2, FST, GDF5, HTRA3, IGF2, IGFBP5, IL1R1, TMEM119, MGP, MSX1, OGN, PODN, PRRX1, PRRX2, PTN, RGMA, SOD3 and TSLP and are negative for the markers: ACTC, AGC1, AKR1C1, ALDH1A1, ANXA8, AQP1, AREG, CFB, BMP4, C3, C6, C7, C20orf103, CCDC3, CD24, CDH3, CLDN11, CNTNAP2, CRIP1, DIO2, DKK2, DPT, EMID1, FGFR3, TMEM100, GABRB1, GAP43, GDF10, GJB2, GSC, HOXA5, HSD11B2, HSD17B2, HSPA6, HSPB3, ID4, IFI27, INA, KCNMB1, KRT14, KRT17, KRT34, LAMC2, IGFL3, LOC92196, MFAP5, MASP1, MEOX1, MEOX2, MX1, MYBPH, MYH3, MYH11, MYL4, IL32, NLGN4X, NPAS1, NPPB, OLR1, PAX2, PAX9, PENK, PROM1, PTGS2, RARRES1, RASD1, RGS1, SFRP2, SMOC1, SMOC2, SNAP25, STMN2, TAC1, RSPO3, THY1, TNFSF7, TNNT2, TRH, TUBB4, UGT2B7 and ZD52F10.

The cell line EN42 is positive for the markers: COL15A1, COL21A1, FMO3, FOXF1, FST, GDF5, HTRA3, IGF2, IL1R1, TMEM119, MGP, OGN, PODN, PRRX1, PRRX2, PTN, RGMA, SERPINA3, SNAP25 and SOD3 and are negative for the markers: ACTC, AGC1, AKR1C1, ALDH1A1, ANXA8, AQP1, ATP8B4, BMP4, C3, C6, C7, C20orf103, CCDC3, CD24, CDH3, CLDN11, CNTNAP2, COMP, CXADR, DIO2, DKK2, DPT, EMID1, FGFR3, TMEM100, GAP43, GDF10, GSC, HOXA5, HSD11B2, HSD17B2, HSPA6, HSPB3, ID4, IFI27, INA, KCNMB1, KRT14, KRT17, KRT19, KRT34, LAMC2, IGFL3, LOC92196, MFAP5, MASP1, MEOX1, MEOX2, MMP1, MX1, MYBPH, MYH3, MYH11, MYL4, IL32, NLGN4X, NPAS1, NPPB, OLR1, PAX9, PENK, PITX2, PRG4, PROM1, RARRES1, RASD1, RELN, RGS1, SMOC1, SMOC2, STMN2, RSPO3, THY1, TNFSF7, TNNT2, TRH, TUBB4, UGT2B7, ZD52F10, ZIC1 and ZIC2.

The cell line EN47 is positive for the markers: CDH6, COP1, DLK1, FMO3, FOXF1, FST, HTRA3, IGF2, IL1R1, MSX1, POSTN, PTPRN, RGS1, SOD3, TFPI2, TSLP, ZIC1 and ZIC2 and are negative for the markers: AGC1, ALDH1A1, APCDD1, BMP4, C3, C20orf103, CCDC3, CD24, CDH3, DIO2, DKK2, TABLE I-continued Exemplary progenitor cell lines and associated gene expression markers at 18-21 doublings of clonal expansion FOXF2, GSC, HOXA5, HSD11B2, HSD17B2, HSPA6, HSPB3, IFI27, INA, KCNMB1, KRT14, KRT17, KRT34, LAMC2, TMEM119, IGFL3, LOC92196, MFAP5, MEOX1, MEOX2, MX1, MYH3, MYH11, MYL4, IL32, NLGN4X, NPAS1, NPPB, OLR1, PAX2, PAX9, PENK, PITX2, PRELP, PROM1, RARRES1, SFRP2, SMOC2, STMN2, TAC1, RSPO3, THY1, TNFSF7, TNNT2, TRH, TUBB4, UGT2B7 and ZD52F10.

The cell line EN5 is positive for the markers: COL21A1, DLK1, FMO3, FOXF1, FOXF2, FST, HTRA3, IGF2, IL1R1, KIAA0644, TMEM119, MGP, MSX1, MSX2, OGN, PRRX1 and PRRX2 and are negative for the markers: ACTC, AGC1, AKR1C1, ALDH1A1, ANXA8, AQP1, AREG, BMP4, C3, C6, C7, C20orf103, CCDC3, CD24, CDH3, CLDN11, CNTNAP2, COMP, CRIP1, CRLF1, CRYAB, CXADR, DKK2, GABRB1, GAP43, GDF10, GJB2, GSC, HOXA5, HSD11B2, HSD17B2, HSPA6, HSPB3, ID4, IFI27, INA, KCNMB1, KRT14, KRT17, KRT34, LAMC2, IGFL3, LOC92196, MFAP5, MEOX1, MEOX2, MMP1, MX1, MYH3, MYH11, MYL4, IL32, NLGN4X, NPAS1, NPPB, PAX2, PAX9, PENK, PITX2, PRELP, PRG4, PROM1, RASD1, RELN, RGS1, SMOC1, SMOC2, STMN2, SYT12, TAC1, TFPI2, RSPO3, THY1, TNFSF7, TNNT2, TRH, TUBB4, UGT2B7, ZD52F10 and ZIC1.

The cell line EN50 is positive for the markers: BEX1, CDH6, COL21A1, DIO2, FMO1, FOXF1, FOXF2, FST, GDF5, HTRA3, IGF2, IGFBP5, IL1R1, KRT19, TMEM119, MASP1, MGP, MSX1, PODN, PRRX2, PTPRN, SERPINA3, SOD3, WISP2, ZIC1 and ZIC2 and are negative for the markers: ACTC, AGC1, ALDH1A1, APCDD1, AQP1, BMP4, C3, C6, C20orf103, CDH3, CLDN11, CNTNAP2, COMP, DKK2, DPT, EGR2, EMID1, TMEM100, GABRB1, GAP43, GDF10, GSC, HOXA5, HSD11B2, HSPA6, HSPB3, IFI27, KIAA0644, KRT17, KRT34, IGFL3, LOC92196, MFAP5, MEOX1, MEOX2, MX1, MYBPH, MYH3, MYH11, NLGN4X, NPPB, OGN, OSR2, PAX2, PAX9, PDE1A, PENK, PITX2, PRELP, PROM1, PRRX1, RARRES1, RASD1, RGS1, SMOC2, SNAP25, STMN2, SYT12, TAC1, RSPO3, TNFSF7, TNNT2, TRH, TUBB4, UGT2B7 and ZD52F10.

The cell line EN51 is positive for the markers: CDH6, DLK1, FMO1, FMO3, FOXF1, FST, HTRA3, IGF2, IL1R1, MSX1, MSX2, OGN, SERPINA3, SOD3, TSLP, ZIC1 and ZIC2 and are negative for the markers: ACTC, AGC1, AKR1C1, ALDH1A1, ANXA8, APCDD1, AQP1, ATP8B4, CFB, C3, C6, C20orf103, CCDC3, CD24, CDH3, CLDN11, CRIP1, CRYAB, CXADR, DIO2, DKK2, DPT, EMID1, TMEM100, FOXF2, GABRB1, GSC, HOXA5, HSD11B2, HSD17B2, HSPA6, HSPB3, ID4, IFI27, INA, KCNMB1, KRT14, KRT17, KRT19, KRT34, LAMC2, IGFL3, LOC92196, MFAP5, MEOX1, MEOX2, MGP, MMP1, MX1, MYH3, MYH11, MYL4, IL32, NLGN4X, NPAS1, NPPB, OLR1, PAX2, PAX9, PDE1A, PENK, PITX2, PRELP, PROM1, PTGS2, RARRES1, RASD1, RELN, RGS1, SFRP2, SMOC2, STMN2, TAC1, RSPO3, THY1, TNFSF7, TNNT2, TRH, TUBB4, UGT2B7 and ZD52F10.

The cell line EN53 is positive for the markers: BEX1, COL21A1, FST, GDF5, HTRA3, ICAM5, KRT19, TMEM119, PTPRN, SERPINA3, SOD3 and ZIC2 and are negative for the markers: ACTC, AGC1, ALDH1A1, APCDD1, AQP1, ATP8B4, BMP4, C3, C6, C7, C20orf103, CCDC3, CDH3, CLDN11, CNTNAP2, COP1, CRYAB, DIO2, DKK2, DPT, EMID1, FGFR3, TMEM100, FMO3, FOXF2, GABRB1, GAP43, GJB2, GSC, HOXA5, HSPA6, HSPB3, ID4, IFI27, INA, KCNMB1, KIAA0644, KRT14, KRT17, KRT34, IGFL3, LOC92196, MFAP5, MEOX1, MEOX2, MGP, MMP1, MX1, MYBPH, MYH3, MYH11, MYL4, IL32, NLGN4X, NPPB, OGN, OLR1, OSR2, PAX2, PAX9, PDE1A, PENK, PITX2, POSTN, PRELP, PROM1, PTN, RASD1, RELN, RGS1, SLITRK6, SMOC2, STMN2, SYT12, TAC1, RSPO3, THY1, TNFSF7, TNNT2, TRH, TUBB4, UGT2B7 and ZIC1.

The cell line EN55 is positive for the markers: DIO2, FOXF1, FOXF2, FST, GDF5, HTRA3, IGF2, IL1R1, KIAA0644, MGP, MSX2, PODN, PRRX2, PTN, SLITRK6 and SRCRB4D and are negative for the markers: ACTC, AGC1, AKR1C1, ALDH1A1, ANXA8, AQP1, ATP8B4, CFB, BMP4, C6, C7, C20orf103, CCDC3, CD24, CDH3, CLDN11, CNTNAP2, CRIP1, CRYAB, DKK2, FGFR3, FMO1, GABRB1, GAP43, GDF10, GSC, HOXA5, HSD11B2, HSD17B2, HSPA6, HSPB3, ICAM5, ID4, IFI27, INA, KCNMB1, KRT14, KRT17, KRT34, LAMC2, IGFL3, LOC92196, MFAP5, MEOX1, MEOX2, MX1, MYBPH, MYH3, MYH11, MYL4, IL32, NLGN4X, NPAS1, NPPB, OLR1, PAX2, PAX9, PENK, PITX2, POSTN, PROM1, PRRX1, PTGS2, RARRES1, RASD1, RELN, RGS1, SFRP2, SMOC1, SMOC2, SOD3, STMN2, SYT12, TAC1, RSPO3, THY1, TNFSF7, TNNT2, TRH, TUBB4, UGT2B7, ZD52F10, ZIC1 and ZIC2.

The group of cell lines H9.Bio1 and H9.Bio2 are positive for the markers: ACTC, BEX1, CD24, CDH3, CNTNAP2, CXADR, METTL7A, FGFR3, FST, GAP43, INA, KRT19, NLGN4X, PROM1, PTN, PTPRN, RGMA, SFRP2, SOX11, SRCRB4D, ZD52F10 and ZIC2 and are negative for the markers: AGC1, ALDH1A1, ANXA8, APCDD1, AQP1, AREG, ATP8B4, CFB, C6, C7, PRSS35, C20orf103, CDH6, CLDN11, COL15A1, COL21A1, COP1, DIO2, DKK2, DPT, EGR2, TMEM100, FMO1, FMO3, FOXF1, FOXF2, GABRB1, GDF10, GJB2, HSD17B2, HSPA6, HSPB3, IFI27, IFIT3, IGF2, IL1R1, KRT14, KRT17, KRT34, TMEM119, IGFL3, LOC92196, MEOX1, MEOX2, MGP, MMP1, MSX1, MSX2, MX1, MYBPH, MYH3, MYH11, OGN, OLR1, OSR2, PAX2, PAX9, PDE1A, PENK, POSTN, PRELP, PRG4, PRRX1, PTGS2, RARRES1, RELN, RGS1, SERPINA3, SLITRK6, SMOC1, SNAP25, RSPO3, TNFSF7, TNNT2, TRH, TUBB4, UGT2B7 and WISP2.

The cell line J13 is positive for the markers: CDH6, CLDN11, FST, GDF5, IGF2, MMP1, PRRX1, PRRX2, RGMA, SLITRK6, TFPI2 and ZIC2 and are negative for the markers: ACTC, AGC1, ALDH1A1, ANXA8, AQP1, AREG, ATP8B4, CFB, C3, C6, PRSS35, C20orf103, CCDC3, CD24, CDH3, CNTNAP2, COL15A1, COMP, COP1, CRLF1, CRYAB, DIO2, METTL7A, DKK2, DLK1, DPT, EGR2, EMID1, FGFR3, TMEM100, FMO1, FOXF1, GABRB1, GAP43, GDF10, GSC, HOXA5, HSD11B2, HSD17B2, HSPA6, HSPB3, ID4, IFI27, IGFBP5, KCNMB1, KIAA0644, KRT14, KRT17, KRT34, LAMC2, IGFL3, LOC92196, MFAP5, MEOX1, MEOX2, MGP, MYBPH, MYH3, MYH11, MYL4, IL32, NPAS1, NPPB, OGN, OLR1, PAX2, PAX9, PENK, PITX2, POSTN, PRELP, PRG4, PROM1, PTGS2, PTPRN, RARRES1, RASD1, RELN, RGS1, RPS4Y2, SFRP2, SMOC1, SMOC2, SRCRB4D, STMN2, TAC1, RSPO3, THY1, TNFSF7, TNNT2, TRH, TUBB4, UGT2B7 and ZIC1.

The cell line J16Bio2 is positive for the markers: BEX1, BMP4, CCDC3, CDH6, CLDN11, COL21A1, CRYAB, FMO3, FST, ICAM5, IGF2, KRT17, TMEM119, POSTN, SERPINA3, SFRP2, SYT12, TFPI2, UGT2B7 and ZIC2 and are negative for the markers: AGC1, ALDH1A1, APCDD1, AQP1, AREG, ATP8B4, C3, C6, C20orf103, CD24, CDH3, CNTNAP2, COMP, CRLF1, DLK1, DPT, EMID1, FGFR3, TMEM100, FMO1, FOXF1, FOXF2, GABRB1, GAP43, GDF10, GJB2, GSC, HOXA5, HSD11B2, HSPA6, HSPB3, HTRA3, ID4, IFI27, KIAA0644, KRT14, KRT34, IGFL3, LOC92196, MEOX1, MEOX2, MSX1, MYBPH, MYH3, NLGN4X, NPPB, OGN, PAX2, PAX9, PDE1A, PENK, PITX2, PRELP, PRG4, PROM1, PTPRN, RARRES1, RASD1, RELN, RGS1, SMOC1, SMOC2, STMN2, TAC1, THY1, TNFSF7, TRH, TUBB4, WISP2 and ZD52F10.

TABLE I-continued

Exemplary progenitor cell lines and associated gene expression markers at 18-21 doublings of clonal expansion The cell line J8 is positive for the markers: BEX1, BMP4, CLDN11, CRYAB, IGF2, INA, KRT19, MX1, IL32, TAGLN3, SFRP2, TSLP and UGT2B7 and is negative for the markers: AGC1, ALDH1A1, ANXA8, APCDD1, ATP8B4, CFB, C3, C6, C7, C20orf103, CCDC3, CDH3, CNTNAP2, COL15A1, COL21A1, COMP, COP1, CRLF1, DIO2, METTL7A, DKK2, DLK1, DPT, EGR2, EMID1, FGFR3, TMEM100, FMO1, FMO3, FOXF1, FOXF2, GABRB1, GAP43, GSC, HOXA5, HSD11B2, HSPA6, HSPB3, ID4, IF127, IGFBP5, KCNMB1, KIAA0644, KRT14, KRT34, IGFL3, LOC92196, MFAP5, MASP1, MEOX1, MEOX2, MGP, MMP1, MSX1, MYH3, MYH11, MYL4, NPAS1, NPPB, OGN, OLR1, OSR2, PAX2, PAX9, PENK, PITX2, PRELP, PROM1, PRRX1, PTGS2, PTN, PTPRN, RARRES1, RGMA, RGS1, SLITRK6, SMOC1, SMOC2, SNAP25, STMN2, TAC1, TNNT2, TRH, TUBB4, WISP2 and ZD52F10.

The cell line MW1 is positive for the markers: APCDD1, BEX1, BMP4, C3, CD24, CDH3, CRLF1, CRYAB, DIO2, METTL7A, TMEM100, FOXF1, FST, GJB2, IGF2, IGFBP5, IL1R1, KIAA0644, KRT19, TMEM119, OLR1, PODN, PROM1, SERPINA3, SNAP25, SRCRB4D, STMN2, TFPI2 and THY1 and are negative for the markers: ACTC, AGC1, AKR1C1, ALDH1A1, AQP1, AREG, ATP8B4, C6, C7, PRSS35, C20orf103, CCDC3, CDH6, CLDN11, CNTNAP2, COL15A1, COL21A1, COMP, COP1, CXADR, DKK2, DLK1, DPT, EGR2, EMID1, FGFR3, FMO1, FMO3, FOXF2, GABRB1, GAP43, GDF5, GDF10, GSC, HOXA5, HSD11B2, HSD17B2, HSPA6, HSPB3, HTRA3, ICAM5, ID4, IF127, INA, KCNMB1, KRT14, KRT17, KRT34, IGFL3, LOC92196, MFAP5, MASP1, MEOX1, MEOX2, MGP, MMP1, MSX2, MYBPH, MYH3, MYH11, MYL4, IL32, NLGN4X, TAGLN3, NPAS1, NPPB, OGN, OSR2, PAX2, PAX9, PENK, POSTN, PRELP, PRG4, PRRX1, PRRX2, PTGS2, PTPRN, RARRES1, RELN, RGS1, SFRP2, SLITRK6, SMOC1, SMOC2, SOD3, SYT12, TAC1, RSPO3, TNFSF7, TNNT2, TRH, TSLP, TUBB4, UGT2B7, WISP2, ZD52F10, ZIC1 and ZIC2.

The cell line MW2 is positive for the markers: C6, C7, CRLF1, DIO2, METTL7A, FMO1, FMO3, FOXF1, FOXF2, HTRA3, IGF2, IL1R1, TMEM119, MGP, OGN, PRRX2, RGMA, SFRP2, SYT12 and TFPI2 and are negative for the markers: ACTC, AGC1, AKR1C1, ALDH1A1, ANXA8, AQP1, AREG, CFB, C3, C20orf103, CCDC3, CD24, CDH3, CNTNAP2, COMP, COP1, CRYAB, CXADR, DKK2, DLK1, EMID1, FGFR3, GABRB1, GAP43, GDF5, GDF10, GSC, HOXA5, HSD17B2, HSPA6, HSPB3, ICAM5, ID4, IF127, INA, KCNMB1, KRT14, KRT17, KRT34, LAMC2, IGFL3, LOC92196, MFAP5, MEOX1, MEOX2, MMP1, MSX1, MX1, MYBPH, MYH3, MYH11, MYL4, IL32, NPAS1, NPPB, OLR1, OSR2, PAX2, PAX9, PENK, PITX2, POSTN, PROM1, PRRX1, PTPRN, RASD1, RELN, RGS1, SMOC1, SMOC2, STMN2, THY1, TNFSF7, TNNT2, TRH, TUBB4, UGT2B7, ZD52F10, ZIC1 and ZIC2.

The cell line MW6 is positive for the markers: BEX1, C6, C7, DIO2, DPT, FOXF1, FST, HTRA3, IGF2, IL1R1, TMEM119, PITX2, POSTN, PRRX2, SERPINA3, SFRP2, SRCRB4D and SYT12 and are negative for the markers: AGC1, ALDH1A1, ANXA8, AQP1, ATP8B4, CFB, BMP4, C20orf103, CCDC3, CDH3, CNTNAP2, COP1, CXADR, DKK2, DLK1, EMID1, FGFR3, TMEM100, GABRB1, GDF10, GSC, HSD11B2, HSD17B2, HSPA6, HSPB3, ID4, IF127, IFIT3, INA, KCNMB1, KRT14, KRT17, KRT34, IGFL3, LOC92196, MFAP5, MEOX1, MEOX2, MMP1, MSX1, MX1, MYH3, MYH11, MYL4, IL32, NLGN4X, NPPB, OLR1, PAX2, PAX9, PENK, PRELP, PROM1, PRRX1, RARRES1, RASD1, RELN, RGS1, SLITRK6, SMOC1, SMOC2, SNAP25, TAC1, TFPI2, THY1, TNFSF7, TNNT2, TRH, TSLP, TUBB4, UGT2B7, ZIC1 and ZIC2.

The cell line Q4 is positive for the markers: AREG, BEX1, CRYAB, FMO1, FST, HTRA3, ICAM5, IGF2, IL1R1, KRT19, TMEM119, PTPRN, SERPINA3, SOD3, SRCRB4D, ZD52F10 and ZIC2 and are negative for the markers: ACTC, AGC1, ALDH1A1, ANXA8, APCDD1, ATP8B4, CFB, BMP4, C20orf103, CCDC3, CDH3, CDH6, CLDN11, CNTNAP2, COL15A1, COMP, COP1, DIO2, DKK2, DPT, EGR2, EMID1, FMO3, GAP43, GDF10, GJB2, GSC, HOXA5, HSD17B2, HSPA6, HSPB3, ID4, IFIT3, INA, KCNMB1, KIAA0644, KRT17, KRT34, IGFL3, LOC92196, MEOX1, MEOX2, MGP, MMP1, MSX2, MX1, MYBPH, MYH3, MYH11, NLGN4X, NPPB, OGN, OLR1, OSR2, PAX2, PAX9, PENK, PROM1, PRRX2, PTGS2, RARRES1, RELN, RGMA, RGS1, SLITRK6, SMOC1, SMOC2, STMN2, SYT12, TAC1, RSPO3, THY1, TNFSF7, TNNT2, TRH, TSLP, TUBB4 and UGT2B7.

The cell line Q6 is positive for the markers: AREG, BEX1, COL21A1, DLK1, FMO1, FST, GDF10, ICAM5, IL1R1, TMEM119, MYL4, OGN, POSTN, SERPINA3, SFRP2, SOD3, SRCRB4D, ZIC1 and ZIC2 and are negative for the markers: AGC1, ALDH1A1, ANXA8, AQP1, ATP8B4, CFB, C3, C6, C20orf103, CD24, CDH3, CDH6, CLDN11, CNTNAP2, COMP, COP1, CXADR, DIO2, DKK2, DPT, EMID1, FGFR3, FMO3, FOXF1, FOXF2, GABRB1, GJB2, GSC, HOXA5, HSD11B2, HSD17B2, HSPA6, IF127, INA, KCNMB1, KIAA0644, KRT17, KRT19, KRT34, IGFL3, LOC92196, MFAP5, MASP1, MEOX1, MEOX2, MMP1, MX1, MYBPH, MYH3, MYH11, IL32, NLGN4X, NPPB, OLR1, OSR2, PAX2, PAX9, PENK, PITX2, PRELP, PROM1, PTN, PTPRN, RARRES1, RASD1, RELN, RGS1, SMOC1, SMOC2, SYT12, TAC1, TFPI2, RSPO3, THY1, TNFSF7, TNNT2, TRH, TUBB4 and WISP2.

The cell line Q7 is positive for the markers: AREG, BEX1, COL15A1, COL21A1, COMP, EGR2, FST, GDF10, HSD17B2, IGF2, SERPINA3, ZIC1 and ZIC2 and is negative for the markers: ACTC, AGC1, AKR1C1, ALDH1A1, AQP1, ATP8B4, CFB, C3, C6, C7, PRSS35, C20orf103, CCDC3, CD24, CDH3, CLDN11, CNTNAP2, DIO2, DKK2, DLK1, EMID1, FGFR3, TMEM100, FMO1, FMO3, GABRB1, GDF5, GJB2, GSC, HOXA5, HSD11B2, HSPA6, HSPB3, ID4, IF127, KCNMB1, KIAA0644, KRT14, KRT17, KRT34, IGFL3, LOC92196, MFAP5, MASP1, MEOX1, MEOX2, MGP, MMP1, MSX2, MX1, MYBPH, MYH3, MYH11, IL32, NLGN4X, NPAS1, NPPB, OGN, OLR1, OSR2, PAX2, PAX9, PDE1A, PENK, PITX2, PODN, POSTN, PRELP, PROM1, PRRX2, PTGS2, PTN, RARRES1, RASD1, RELN, RGMA, RGS1, SLITRK6, SMOC2, SNAP25, STMN2, TAC1, RSPO3, THY1, TNFSF7, TNNT2, TRH, TUBB4, UGT2B7 and WISP2.

The cell line RAD20.16 is positive for the markers: ACTC, CD24, CRIP1, CRYAB, FST, HOXA5, HTRA3, KRT19, LAMC2, MFAP5, MASP1, MGP, MMP1, MSX1, POSTN, S100A4, SRCRB4D and THY1 and is negative for the markers: AGC1, ALDH1A1, AQP1, AREG, ATP8B4, CFB, C6, C7, C20orf103, CCDC3, CDH3, CLDN11, CNTNAP2, COL15A1, COL21A1, CRLF1, DLK1, DPT, TMEM100, FMO1, FMO3, FOXF2, GABRB1, GDF10, GJB2, GSC, HSD11B2, HSD17B2, HSPA6, HSPB3, IF127, IGF2, KCNMB1, KRT14, TMEM119, IGFL3, LOC92196, MEOX1, MEOX2, MSX2, MX1, MYH3, MYH11, NLGN4X, NPPB, OGN, OSR2, PAX2, PAX9, PDE1A, PENK, PRG4, PROM1, PRRX1, RARRES1, RASD1, RGS1, SFRP2, SMOC1, SMOC2, SOD3, STMN2, TAC1, TFPI2, RSPO3, TRH, TSLP, TUBB4, UGT2B7, WISP2, ZIC1 and ZIC2.

The cell line RAD20.19 is positive for the markers: ACTC, BEX1, CD24, CRIP1, CRYAB, FST, HOXA5, INA, KRT19, KRT34, LAMC2, MFAP5, MASP1, MMP1, MSX1, NPPB, PTPRN and THY1 and is negative TABLE I-continued Exemplary progenitor cell lines and associated gene expression markers at 18-21 doublings of clonal expansion for the markers: AGC1, ALDH1A1, APCDD1, AQP1, AREG, ATP8B4, CFB, C6, C7, C20orf103, CDH3, CNTNAP2, COL15A1, COL21A1, COP1, CRLF1, DIO2, METTL7A, DKK2, DLK1, DPT, EGR2, EMID1, TMEM100, FMO1, FMO3, FOXF2, GABRB1, GDF10, GJB2, GSC, HSD11B2, HSD17B2, HSPA6, HSPB3, ID4, IF127, IGF2, KIAA0644, KRT14, KRT17, IGFL3, LOC92196, MEOX1, MEOX2, MGP, MX1, MYBPH, MYH3, NLGN4X, OGN, OSR2, PAX2, PAX9, PDE1A, PENK, PROM1, PRRX1, PTN, RARRES1, RASD1, RGMA, RGS1, SFRP2, SLITRK6, SMOC1, SMOC2, SNAP25, STMN2, SYT12, TAC1, RSPO3, TNFSF7, TRH, TSLP, TUBB4, WISP2, ZIC1 and ZIC2.

The cell line RAD20.5 is positive for the markers: AKR1C1, CRIP1, METTL7A, FOXF1, HOXA5, HTRA3, KIAA0644, KRT19, MASP1, MMP1, MSX1, POSTN, PTPRN, S100A4, SRCRB4D and THY1 and is negative for the markers: AGC1, ALDH1A1, ANXA8, APCDD1, AQP1, AREG, ATP8B4, BEX1, CFB, C6, C7, PRSS35, C20orf103, CCDC3, CDH3, CLDN11, CNTNAP2, COL15A1, COL21A1, COMP, CRLF1, CNTNAP2, DKK2, DLK1, DPT, EGR2, EMID1, TMEM100, FMO1, FMO3, FOXF2, GAP43, GDF10, GSC, HSD11B2, HSD17B2, HSPA6, HSPB3, ID4, IGF2, KCNMB1, KRT14, KRT34, IGFL3, LOC92196, MEOX1, MEOX2, MGP, MSX2, MYBPH, MYH3, MYH11, MYL4, IL32, NLGN4X, NPAS1, NPPB, OGN, PAX2, PAX9, PDE1A, PENK, PRELP, PRG4, PROM1, RARRES1, RGMA, RGS1, SFRP2, SLITRK6, SMOC1, SMOC2, SOD3, STMN2, SYT12, TAC1, TRH, TSLP, TUBB4, UGT2B7, WISP2, ZIC1 and ZIC2.

The cell line RAPEND17 is positive for the markers: ANXA8, BEX1, C3, CD24, CRIP1, CRYAB, METTL7A, FST, HOXA5, HTRA3, ICAM5, IFIT3, IGF2, IL1R1, KRT19, LAMC2, MFAP5, MASP1, OLR1, POSTN, PTN, PTPRN and TFPI2 and is negative for the markers: ACTC, AGC1, APCDD1, AQP1, ATP8B4, CFB, C6, C7, PRSS35, C20orf103, CCDC3, CDH3, CDH6, CLDN11, CNTNAP2, COL15A1, COL21A1, DKK2, DLK1, DPT, EGR2, EMID1, TMEM100, FMO1, FMO3, FOXF2, GABRB1, GAP43, GDF10, GSC, HSD11B2, HSD17B2, HSPA6, HSPB3, ID4, KCNMB1, KRT14, KRT17, IGFL3, LOC92196, MEOX1, MEOX2, MGP, MSX2, MYH3, MYH11, NLGN4X, OGN, OSR2, PAX2, PAX9, PDE1A, PENK, PRELP, PROM1, PRRX1, PRRX2, RARRES1, RELN, RGMA, RGS1, SFRP2, SLITRK6, SMOC1, SMOC2, SOD3, SYT12, TAC1, RSPO3, THY1, TNFSF7, TNNT2, TRH, TSLP, TUBB4, UGT2B7, WISP2, ZD52F10, ZIC1 and ZIC2.

The cell line RASKEL18 is positive for the markers: AREG, CD24, CRYAB, METTL7A, DPT, FST, GJB2, HTRA3, IGF2, IGFBP5, IL1R1, PTN, PTPRN, SERPINA3, SOX11, SRCRB4D and RSPO3 and is negative for the markers: ACTC, AKR1C1, ALDH1A1, ANXA8, AQP1, CFB, C7, PRSS35, C20orf103, CDH6, CLDN11, CNTNAP2, COMP, COP1, DIO2, DKK2, DLK1, EGR2, EMID1, FGFR3, FMO1, FMO3, GAP43, GDF10, GSC, HSD11B2, HSD17B2, HSPA6, HSPB3, IF127, INA, KCNMB1, KRT14, KRT17, KRT19, TMEM119, IGFL3, LOC92196, MFAP5, MASP1, MEOX1, MEOX2, MMP1, MSX2, MYBPH, MYH3, MYH11, MYL4, IL32, NLGN4X, TAGLN3, NPAS1, NPPB, OGN, OLR1, PAX2, PAX9, PENK, PRELP, PRG4, PROM1, PRRX1, PRRX2, PTGS2, RARRES1, RASD1, RELN, RGMA, RGS1, SLITRK6, SMOC1, SMOC2, STMN2, SYT12, TAC1, TFPI2, THY1, TNFSF7, TNNT2, TRH, TSLP, TUBB4, WISP2, ZIC1 and ZIC2.

The cell line RASKEL6 is positive for the markers: AREG, BEX1, C3, CRLF1, CRYAB, METTL7A, FST, HTRA3, IGF2, IL1R1, TMEM119, PITX2, SERPINA3 and TFPI2 and is negative for the markers: ACTC, AKR1C1, ALDH1A1, ANXA8, AQP1, CFB, BMP4, C6, CCDC3, CDH3, CDH6, CLDN11, CNTNAP2, COL15A1, COMP, COP1, CXADR, DKK2, DLK1, EGR2, EMID1, FMO1, FMO3, FOXF2, GAP43, GDF10, GSC, HSD17B2, HSPA6, ID4, IF127, IFIT3, IGFBP5, INA, KIAA0644, KRT17, KRT34, LAMC2, IGFL3, LOC92196, MFAP5, MASP1, MEOX1, MEOX2, MMP1, MSX2, MYBPH, MYH3, MYH11, IL32, NLGN4X, TAGLN3, NPAS1, NPPB, OGN, OLR1, OSR2, PAX2, PAX9, PENK, POSTN, PRELP, PROM1, PRRX1, PRRX2, RARRES1, RELN, RGMA, RGS1, SLITRK6, SMOC1, SMOC2, STMN2, SYT12, TAC1, RSPO3, THY1, TNFSF7, TRH, TUBB4, UGT2B7, WISP2, ZIC1 and ZIC2.

The cell line RASKEL8 is positive for the markers: AREG, BEX1, C7, CRIP1, CRLF1, CRYAB, FST, HOXA5, HTRA3, ICAM5, IGF2, IL1R1, KRT19, LAMC2, PITX2, POSTN, PTPRN, SERPINA3 and TFPI2 and is negative for the markers: ACTC, AGC1, ALDH1A1, AQP1, ATP8B4, CFB, C6, PRSS35, C20orf103, CCDC3, CDH3, CDH6, CLDN11, CNTNAP2, COMP, COP1, DKK2, DLK1, DPT, EMID1, FMO1, FMO3, FOXF2, GABRB1, GAP43, GDF10, GSC, HSD11B2, HSD17B2, HSPA6, HSPB3, IF127, IGFBP5, KCNMB1, KIAA0644, KRT14, KRT17, KRT34, IGFL3, LOC92196, MEOX1, MEOX2, MGP, MMP1, MSX2, MX1, MYH3, MYH11, NLGN4X, TAGLN3, NPPB, OGN, OSR2, PAX2, PAX9, PDE1A, PENK, PRELP, PRG4, PROM1, PRRX1, PRRX2, PTN, RARRES1, RELN, RGMA, RGS1, SFRP2, SLITRK6, SMOC1, SMOC2, SNAP25, STMN2, SYT12, TAC1, RSPO3, TNFSF7, TNNT2, TRH, TSLP, TUBB4, WISP2, ZIC1 and ZIC2.

The cell line SK1 is positive for the markers: AKR1C1, BEX1, C6, C7, COL21A1, CRIP1, METTL7A, DLK1, TMEM100, FMO1, FMO3, FOXF2, FST, HSD11B2, HTRA3, ICAM5, IGF2, IL1R1, TMEM119, MGP, MSX1, PRG4, PTN, PTPRN, S100A4, SERPINA3, SFRP2, SOD3, SOX11, WISP2 and ZIC1 and is negative for the markers: AGC1, ALDH1A1, ANXA8, AQP1, ATP8B4, BMP4, C20orf103, CD24, CDH3, CDH6, CLDN11, CNTNAP2, COMP, COP1, CRLF1, DKK2, EGR2, EMID1, FGFR3, GABRB1, GAP43, GDF10, GJB2, GSC, HOXA5, HSD17B2, HSPA6, ID4, IF127, IFIT3, INA, KCNMB1, KRT14, KRT17, KRT19, KRT34, LAMC2, IGFL3, LOC92196, MFAP5, MASP1, MEOX1, MEOX2, MMP1, MSX2, MX1, MYBPH, MYH11, IL32, NLGN4X, NPAS1, NPPB, OLR1, PAX2, PAX9, PENK, PITX2, POSTN, PRELP, PROM1, RARRES1, RGS1, SMOC2, SYT12, TFPI2, RSPO3, THY1, TNNT2, TRH, TSLP, TUBB4 and ZIC2.

The group of cell lines SK10Bio1 and SK10Bio2 are positive for the markers: BEX1, COL21A1, FST, ICAM5, IL1R1, TMEM119, SERPINA3 and ZIC2 and are negative for the markers: ACTC, AGC1, ALDH1A1, AQP1, CFB, BMP4, C3, C6, C20orf103, CDH3, CLDN11, CNTNAP2, DKK2, DPT, EMID1, TMEM100, FMO3, GABRB1, GAP43, GSC, HOXA5, HSPA6, ID4, IF127, KIAA0644, KRT14, KRT34, IGFL3, LOC92196, MFAP5, MEOX1, MEOX2, MX1, MYBPH, MYH3, MYH11, NLGN4X, NPPB, OLR1, PAX2, PAX9, PDE1A, PENK, PROM1, RARRES1, RASD1, RELN, RGS1, SLITRK6, SMOC1, SMOC2, STMN2, SYT12, TAC1, RSPO3, THY1, TNNT2 and TUBB4.

The group of cell lines SK11, SK44, SK50 and SK52 are positive for the markers: BEX1, COL21A1, FST, ICAM5, IL1R1, TMEM119, PTPRN, SERPINA3, SFRP2 and ZIC1 and are negative for the markers: ACTC, AGC1, ALDH1A1, AQP1, ATP8B4, C6, C20orf103, CCDC3, CDH3, CLDN11, CNTNAP2, DIO2, DKK2, EMID1, GABRB1, GSC, HOXA5, HSPA6, IF127, INA, KRT14, KRT34, IGFL3, LOC92196, MEOX1, MEOX2, MMP1, MX1, MYH3, MYH11, IL32, NLGN4X, NPPB, OLR1, PAX2, PAX9, PDE1A, PENK, PROM1, PTN, RARRES1, RASD1, RELN, RGS1, SMOC1, SMOC2, STMN2, TAC1, TFPI2, RSPO3, TNFSF7, TNNT2, TRH and TUBB4.

TABLE I-continued

Exemplary progenitor cell lines and associated gene expression markers at 18-21 doublings of clonal expansion The group of cell lines SK14, SK53, SK60 and SK61 are positive for the markers: C7, COL21A1, CRYAB, HTRA3, IL1R1, MGP, PTPRN, RGMA, SERPINA3 and SFRP2 and are negative for the markers: ACTC, AGC1, ALDH1A1, ANXA8, AQP1, ATP8B4, CFB, BMP4, CCDC3, CDH3, CNTNAP2, COP1, CXADR, DKK2, GABRB1, GAP43, GDF10, GJB2, GSC, HOXA5, HSD17B2, IFI27, IFIT3, KRT14, KRT17, KRT34, IGFL3, LOC92196, MFAP5, MEOX1, MEOX2, MMP1, MX1, MYBPH, MYH3, MYH11, IL32, NLGN4X, NPPB, OLR1, PAX2, PAX9, PENK, PROM1, RASD1, RELN, RGS1, SLITRK6, SMOC1, SMOC2, STMN2, TAC1, RSPO3, TNNT2, TRH, TUBB4, UGT2B7, ZIC1 and ZIC2.

The cell line SK17 is positive for the markers: ACTC, APCDD1, BEX1, COL21A1, METTL7A, DLK1, FST, HOXA5, HSPB3, HTRA3, IGF2, IL1R1, KIAA0644, MASP1, MGP, MYBPH, MYH3, NLGN4X, PDE1A, PTN, RGMA, SRCRB4D, STMN2, RSPO3 and TNNT2 and is negative for the markers: AGC1, AKR1C1, ALDH1A1, ANXA8, AQP1, CFB, C6, C20orf103, CCDC3, CDH3, CDH6, CLDN11, CNTNAP2, COL15A1, COMP, COP1, CRLF1, DKK2, DPT, TMEM100, FMO1, FMO3, FOXF2, GABRB1, GDF10, GSC, HSD17B2, HSPA6, ID4, IFI27, INA, KCNMB1, KRT14, KRT34, LAMC2, TMEM119, IGFL3, LOC92196, MFAP5, MEOX1, MEOX2, MMP1, MX1, MYH11, IL32, NPAS1, NPPB, OLR1, PAX2, PAX9, PENK, PITX2, PRELP, RASD1, RELN, RGS1, S100A4, SLITRK6, SMOC1, SMOC2, TAC1, THY1, TNFSF7, TRH, TSLP, TUBB4, UGT2B7, WISP2, ZIC1 and ZIC2.

The cell line SK18 is positive for the markers: APCDD1, COL21A1, METTL7A, FMO1, FOXF1, FST, HTRA3, IGF2, IL1R1, TMEM119, OGN, PITX2, PRRX1, RGMA, SERPINA3, SFRP2, SOD3 and TSLP and is negative for the markers: ACTC, AGC1, AKR1C1, ALDH1A1, ANXA8, AQP1, AREG, ATP8B4, CFB, BMP4, C3, C6, C7, C20orf103, CCDC3, CD24, CDH3, CNTNAP2, COP1, CXADR, DIO2, DKK2, DLK1, DPT, EMID1, TMEM100, GABRB1, GAP43, GDF5, GDF10, GJB2, GSC, HOXA5, HSD17B2, HSPA6, HSPB3, ID4, IFI27, INA, KIAA0644, KRT14, KRT17, KRT19, KRT34, LAMC2, IGFL3, LOC92196, MFAP5, MEOX1, MEOX2, MMP1, MSX1, MX1, MYBPH, MYH3, MYH11, MYL4, IL32, NLGN4X, NPPB, OLR1, OSR2, PAX2, PAX9, PDE1A, PENK, PRELP, PROM1, RARRES1, RASD1, RELN, RGS1, SLITRK6, SMOC1, SMOC2, STMN2, TAC1, TFPI2, RSPO3, THY1, TNFSF7, TNNT2, TRH, TUBB4, UGT2B7, ZIC1 and ZIC2.

The cell line SK26 is positive for the markers: APCDD1, BEX1, COL21A1, CRYAB, FMO1, FOXF2, FST, HTRA3, ICAM5, IL1R1, TMEM119, PRRX1, PTPRN, SERPINA3 and SFRP2 and is negative for the markers: ACTC, AGC1, ALDH1A1, ANXA8, AQP1, AREG, ATP8B4, CFB, BMP4, C3, C6, C7, C20orf103, CCDC3, CD24, CDH3, CLDN11, CNTNAP2, COP1, CXADR, DKK2, DLK1, DPT, EGR2, EMID1, FGFR3, GABRB1, GAP43, GDF10, GJB2, GSC, HOXA5, HSD17B2, HSPA6, IFI27, IFIT3, KIAA0644, KRT14, KRT17, KRT34, IGFL3, LOC92196, MFAP5, MEOX1, MEOX2, MMP1, MX1, MYBPH, MYH3, MYH11, MYL4, IL32, NLGN4X, NPPB, OLR1, OSR2, PAX2, PAX9, PDE1A, PENK, PITX2, POSTN, PROM1, PTN, RARRES1, RASD1, RELN, RGS1, SLITRK6, SMOC1, SMOC2, SNAP25, STMN2, TAC1, TFPI2, RSPO3, THY1, TNFSF7, TNNT2, TRH, TUBB4, UGT2B7 and ZIC1.

The group of cell lines SK27 and T7 are positive for the markers: BEX1, PRSS35, CCDC3, CDH6, COL21A1, CRIP1, CRYAB, GAP43, IGF2, KRT19, LAMC2, POSTN, S100A4, SFRP2, SOX11 and ZIC2 and are negative for the markers: AGC1, ALDH1A1, APCDD1, AREG, ATP8B4, CFB, C3, C7, C20orf103, CDH3, CLDN11, CNTNAP2, COP1, CXADR, DLK1, DPT, EGR2, EMID1, GDF10, GJB2, GSC, HOXA5, HSD11B2, HSD17B2, HSPA6, HSPB3, IFI27, INA, KRT14, IGFL3, LOC92196, MFAP5, MEOX1, MEOX2, MMP1, MYBPH, MYH3, MYL4, NLGN4X, NPPB, OLR1, PAX2, PAX9, PDE1A, PENK, PRG4, PROM1, RARRES1, RASD1, RELN, RGS1, SLITRK6, SMOC1, SMOC2, SNAP25, STMN2, TAC1, TFPI2, RSPO3, TNNT2, TRH, TUBB4 and ZIC1.

The group of cell lines SK28 and SK57 are positive for the markers: BEX1, COL21A1, CRYAB, HTRA3, ICAM5, IGF2, IL1R1, PTPRN and SERPINA3 and are negative for the markers: AGC1, ALDH1A1, AQP1, ATP8B4, CFB, BMP4, C20orf103, CCDC3, CDH3, CDH6, CLDN11, CNTNAP2, COP1, CXADR, DIO2, DKK2, EMID1, GABRB1, GAP43, GDF10, GSC, HOXA5, HSD17B2, HSPA6, HSPB3, ID4, IFI27, KCNMB1, KIAA0644, KRT14, KRT17, KRT34, IGFL3, LOC92196, MFAP5, MEOX1, MEOX2, MMP1, MSX2, MX1, MYH3, MYH11, MYL4, IL32, NLGN4X, NPPB, OLR1, OSR2, PAX2, PAX9, PENK, PROM1, PTN, RARRES1, RASD1, RELN, RGS1, SLITRK6, SMOC1, SMOC2, STMN2, TAC1, TFPI2, RSPO3, TNFSF7, TNNT2, TRH, TUBB4 and UGT2B7.

The group of cell lines SK30 and W4 are positive for the markers: BEX1, FST, HTRA3, IGF2, TMEM119, POSTN, SOX11, SRCRB4D, ZIC1 and ZIC2 and are negative for the markers: AGC1, ALDH1A1, ANXA8, AQP1, ATP8B4, C3, C6, C7, C20orf103, CCDC3, CDH3, CLDN11, CRYAB, DIO2, METTL7A, EGR2, EMID1, FMO3, FOXF2, GABRB1, GSC, HOXA5, HSD11B2, HSPA6, HSPB3, ID4, IF127, INA, KRT14, KRT17, KRT34, IGFL3, LOC92196, MFAP5, MASP1, MEOX1, MEOX2, MMP1, MX1, MYH3, MYH11, NPPB, OLR1, OSR2, PAX2, PAX9, PDE1A, PENK, PRELP, PROM1, RARRES1, RASD1, RELN, SMOC2, STMN2, SYT12, TAC1, RSPO3, TNFSF7, TNNT2 and TUBB4.

The group of cell lines SK31 and SK54 are positive for the markers: BEX1, COL21A1, CRIP1, CRYAB, TMEM100, FMO1, FMO3, FOXF1, FOXF2, IGF2, IGFBP5, IL1R1, KRT19, LAMC2, TMEM119, NPAS1, PDE1A, PRRX2, S100A4, SERPINA3, SNAP25, SOX11, SRCRB4D and WISP2 and are negative for the markers: ACTC, AGC1, AKR1C1, ALDH1A1, ANXA8, AQP1, AREG, ATP8B4, CFB, BMP4, C3, CCDC3, CD24, CDH3, CLDN11, CNTNAP2, COMP, COP1, CXADR, DKK2, DLK1, DPT, EMID1, FGFR3, GABRB1, GAP43, GDF10, GSC, HSD17B2, HSPA6, HTRA3, ID4, IF127, INA, KCNMB1, KRT14, KRT17, KRT34, IGFL3, LOC92196, MFAP5, MASP1, MEOX1, MEOX2, MMP1, MYH3, MYH11, MYL4, IL32, NLGN4X, NPPB, OGN, OLR1, OSR2, PAX2, PAX9, PENK, PITX2, PRELP, PROM1, PRRX1, RELN, RGS1, SLITRK6, SMOC1, SMOC2, SOD3, STMN2, SYT12, TAC1, TFPI2, RSPO3, TNFSF7, TNNT2, TRH, TSLP, TUBB4, ZIC1 and ZIC2.

The cell line SK32 is positive for the markers: AKR1C1, BEX1, C6, C7, C20orf103, COL21A1, CRYAB, METTL7A, DPT, GDF5, HTRA3, ICAM5, IL1R1, TMEM119, MGP, OGN, POSTN, PTPRN, RGMA, SERPINA3, SFRP2, SOD3, WISP2 and ZIC1 and is negative for the markers: ACTC, AGC1, ALDH1A1, ANXA8, AQP1, AREG, ATP8B4, CFB, BMP4, C3, CCDC3, CD24, CDH3, CDH6, CLDN11, CNTNAP2, COL15A1, COMP, COP1, CXADR, DIO2, DKK2, EGR2, EMID1, FGFR3, FMO3, FOXF1, FOXF2, GABRB1, GAP43, GDF10, GSC, HOXA5, HSD17B2, HSPA6, HSPB3, ID4, IF127, IFIT3, INA, KIAA0644, KRT14, KRT17, KRT19, KRT34, IGFL3, LOC92196, MFAP5, MASP1, MEOX1, MEOX2, MMP1, MX1, MYBPH, MYH3, MYH11, MYL4, IL32, NLGN4X, NPPB, OLR1, OSR2, PAX2, PAX9, PENK, PITX2, PRELP, PROM1, PTGS2, RASD1, RELN, RGS1, SLITRK6, SMOC1, SMOC2, STMN2, SYT12, TFPI2, RSPO3, THY1, TNFSF7, TNNT2, TRH, TSLP, TUBB4 and ZIC2.

TABLE I-continued

Exemplary progenitor cell lines and associated gene expression markers at 18-21 doublings of clonal expansion The group of cell lines SK40 and SK40Bio2 are positive for the markers: BEX1, COL21A1, CRYAB, FMO1, FST, ICAM5, IGFBP5, TMEM119, MSX1, MYL4, PTPRN, SERPINA3, SOD3, ZIC1 and ZIC2 and are negative for the markers: AGC1, AKR1C1, ALDH1A1, AQP1, ATP8B4, BMP4, C3, C20orf103, CCDC3, CD24, CDH3, CLDN11, CNTNAP2, COP1, DIO2, DKK2, DPT, TMEM100, FMO3, GABRB1, GAP43, GSC, HOXA5, HSPA6, HSPB3, ID4, IF127, INA, KCNMB1, KIAA0644, KRT14, KRT17, KRT34, IGFL3, LOC92196, MEOX1, MEOX2, MX1, MYBPH, MYH11, NLGN4X, NPPB, OGN, OLR1, PAX2, PAX9, PDE1A, PENK, PITX2, PRELP, PROM1, RARRES1, RASD1, RELN, RGS1, SMOC2, SNAP25, SYT12, TAC1, TFPI2, RSPO3, THY1, TNFSF7, TRH, TSLP and TUBB4

The cell line SK46 is positive for the markers: APCDD1, COL21A1, DIO2, METTL7A, FMO1, FMO3, FOXF1, FOXF2, FST, HTRA3, IGF2, IL1R1, TMEM119, OGN, PRRX1, PRRX2, SERPINA3, SFRP2, SLITRK6, TSLP and ZIC2 and is negative for the markers: ACTC, AGC1, ALDH1A1, ANXA8, AQP1, ATP8B4, CFB, BMP4, C3, C6, C7, C20orf103, CCDC3, CD24, CDH3, CLDN11, CNTNAP2, COP1, CRIP1, CXADR, DKK2, DPT, EMID1, FGFR3, GABRB1, GAP43, GDF5, GDF10, GJB2, GSC, HOXA5, HSD17B2, HSPA6, HSPB3, IF127, INA, KRT14, KRT17, KRT19, KRT34, LAMC2, IGFL3, LOC92196, MFAP5, MEOX1, MEOX2, MMP1, MX1, MYBPH, MYH3, MYH11, MYL4, IL32, NLGN4X, TAGLN3, NPAS1, NPPB, OLR1, OSR2, PAX2, PAX9, PDE1A, PENK, PITX2, POSTN, PRELP, PROM1, RARRES1, RASD1, RELN, RGS1, SMOC1, SMOC2, STMN2, TFPI2, RSPO3, THY1, TNFSF7, TNNT2, TRH, TUBB4, UGT2B7 and ZIC1.

The cell line SK47 is positive for the markers: BEX1, COL21A1, METTL7A, FMO1, FOXF1, FOXF2, FST, HTRA3, ICAM5, IGF2, IL1R1, KRT19, TMEM119, MSX1, PRRX2, PTPRN, SERPINA3, SOD3 and ZIC1 and is negative for the markers: AGC1, ALDH1A1, AQP1, ATP8B4, CFB, BMP4, C3, C6, C7, C20orf103, CCDC3, CD24, CDH3, CLDN11, CNTNAP2, COL15A1, COP1, CRLF1, DKK2, DPT, EGR2, EMID1, FGFR3, GABRB1, GAP43, GDF10, GJB2, GSC, HOXA5, HSD17B2, HSPA6, HSPB3, ID4, IF127, INA, KCNMB1, KRT14, KRT17, KRT34, IGFL3, LOC92196, MFAP5, MEOX1, MEOX2, MGP, MMP1, MX1, MYBPH, MYH3, MYH11, IL32, NLGN4X, NPPB, OLR1, PAX2, PAX9, PDE1A, PENK, PITX2, POSTN, PRELP, PROM1, RARRES1, RASD1, RELN, RGS1, SLITRK6, SMOC1, SMOC2, STMN2, SYT12, TAC1, TFPI2, RSPO3, THY1, TNFSF7, TNNT2, TRH, TUBB4 and ZD52F10.

The group of cell lines SK5.Biol, SK5.Bio2, SK5Bio3 and SK5BioUT are positive for the markers: ACTC, C7, CRLF1, CRYAB, FST, HTRA3, IL1R1, TMEM119, MGP, PTPRN, SERPINA3, SFRP2 and ZIC1 and are negative for the markers: ALDH1A1, ANXA8, CFB, BMP4, C3, C20orf103, CDH3, CLDN11, CNTNAP2, COP1, DKK2, EMID1, FMO3, GABRB1, GDF10, GSC, HSD17B2, HSPB3, IF127, KRT14, KRT17, KRT34, IGFL3, LOC92196, MFAP5, MEOX1, MEOX2, MYH11, IL32, NPPB, OLR1, OSR2, PAX2, PAX9, PENK, PRELP, PROM1, RARRES1, RELN, RGS1, SLITRK6, SMOC1, SMOC2, STMN2, RSPO3, TNFSF7, TNNT2, TRH, TUBB4 and ZIC2.

The cell line SK8 is positive for the markers: APCDD1, BEX1, COL21A1, CRLF1, FMO1, FMO3, FOXF2, FST, HTRA3, ICAM5, IGF2, IL1R1, TMEM119, MASP1, PTPRN, SERPINA3 and SFRP2 and is negative for the markers: ACTC, AGC1, ALDH1A1, ANXA8, AQP1, ATP8B4, CFB, BMP4, C7, PRSS35, C20orf103, CD24, CDH3, CDH6, CLDN11, CNTNAP2, COP1, DKK2, EMID1, GABRB1, GAP43, GDF10, GJB2, GSC, HOXA5, HSD17B2, HSPA6, HSPB3, IF127, IFIT3, INA, KIAA0644, KRT14, KRT17, KRT34, IGFL3, LOC92196, MFAP5, MEOX1, MEOX2, MMP1, MX1, MYBPH, MYH3, MYH11, MYL4, IL32, NLGN4X, NPPB, OLR1, OSR2, PAX2, PAX9, PDE1A, PENK, PRELP, PROM1, PTN, RARRES1, RASD1, RELN, RGS1, SMOC1, SMOC2, STMN2, TAC1, RSPO3, THY1, TNFSF7, TNNT2, TRH, TUBB4, ZIC1 and ZIC2.

The cell line SM17 is positive for the markers: BEX1, CD24, CRYAB, EGR2, FOXF1, FST, GDF5, HTRA3, IGFBP5, KRT19, MMP1, MSX1, MSX2, IL32, PODN, POSTN, PRELP, PRRX2, SRCRB4D, TFPI2, TSLP and ZIC1 and is negative for the markers: AGC1, AKR1C1, ALDH1A1, ANXA8, APCDD1, AQP1, AREG, ATP8B4, CFB, BMP4, C6, C7, C20orf103, CCDC3, CDH3, CLDN11, CNTNAP2, COL15A1, DIO2, METTL7A, DKK2, DLK1, DPT, FGFR3, TMEM100, FMO1, FMO3, GABRB1, GAP43, GDF10, GSC, HOXA5, HSD11B2, HSD17B2, HSPA6, IF127, IGF2, KCNMB1, KRT14, KRT17, KRT34, IGFL3, LOC92196, MFAP5, MEOX1, MEOX2, MYBPH, MYH3, MYH11, NLGN4X, NPPB, OLR1, OSR2, PAX2, PAX9, PDE1A, PENK, PRG4, PROM1, RARRES1, RASD1, RELN, RGS1, SMOC1, SMOC2, SNAP25, STMN2, TAC1, RSPO3, TNFSF7, TNNT2, TRH, TUBB4, UGT2B7, WISP2 and ZIC2.

The cell line SM19 is positive for the markers: BEX1, CNTNAP2, CRYAB, FST, GDF5, MMP1, POSTN, PRRX2, SERPINA3 and SFRP2 and is negative for the markers: ACTC, AGC1, AKR1C1, ALDH1A1, ANXA8, AQP1, AREG, ATP8B4, CFB, BMP4, C3, C6, C7, C20orf103, CDH3, CDH6, CLDN11, COL21A1, COMP, COP1, CRLF1, DIO2, METTL7A, DKK2, DLK1, DPT, EMID1, FGFR3, TMEM100, FMO1, FMO3, FOXF2, GABRB1, GDF10, GSC, HOXA5, HSD11B2, HSD17B2, HSPA6, ID4, IF127, IGF2, IGFBP5, IL1R1, KCNMB1, KIAA0644, KRT14, KRT17, KRT34, IGFL3, LOC92196, MFAP5, MASP1, MEOX1, MEOX2, MGP, MX1, MYBPH, MYH3, MYH11, NLGN4X, NPPB, OGN, OLR1, OSR2, PAX2, PAX9, PDE1A, PENK, PITX2, PRG4, PROM1, RARRES1, RASD1, RGS1, SLITRK6, SMOC1, SMOC2, SNAP25, STMN2, SYT12, TAC1, TFPI2, RSPO3, THY1, TNFSF7, TNNT2, TRH, UGT2B7, WISP2, ZIC1 and ZIC2.

The cell line SM2 is positive for the markers: CDH6, CNTNAP2, COL15A1, COL21A1, FST, GDF5, TMEM119, MMP1, MSX1, POSTN, PRRX1, SOD3, ZIC1 and ZIC2 and is negative for the markers: ACTC, AGC1, AKR1C1, ALDH1A1, ANXA8, APCDD1, AQP1, AREG, ATP8B4, BEX1, BMP4, C3, C6, C7, PRSS35, C20orf103, CCDC3, CD24, CDH3, CLDN11, COMP, CRIP1, CRYAB, DIO2, DPT, EMID1, FGFR3, TMEM100, FMO3, GDF10, GJB2, GSC, HOXA5, HSD11B2, HSD17B2, HSPA6, HSPB3, ID4, IF127, INA, KCNMB1, KIAA0644, KRT14, KRT17, KRT19, KRT34, IGFL3, LOC92196, MFAP5, MASP1, MEOX1, MEOX2, MGP, MX1, MYBPH, MYH3, MYH11, MYL4, IL32, NLGN4X, NPAS1, NPPB, OLR1, OSR2, PAX2, PAX9, PDE1A, PENK, PITX2, PROM1, RARRES1, RASD1, RELN, RGS1, SFRP2, SLITRK6, SMOC1, SMOC2, STMN2, SYT12, TAC1, TFPI2, RSPO3, TNFSF7, TNNT2, TRH, TUBB4 and UGT2B7.

The cell line SM22 is positive for the markers: CDH6, CRLF1, DLK1, FOXF1, FST, GDF5, HTRA3, IGFBP5, IL1R1, MGP, MMP1, MSX1, MSX2, OGN, POSTN, PRRX2, PTN, RGMA, SOD3, SRCRB4D, STMN2, TSLP, ZD52F10 and ZIC1 and is negative for the markers: AGC1, ALDH1A1, ANXA8, APCDD1, AQP1, AREG, BMP4, C3, C6, C7, C20orf103, CCDC3, CDH3, CLDN11, CNTNAP2, COL15A1, CRIP1, CXADR, DIO2, DKK2, DPT, TMEM100, FMO1, FOXF2, GDF10, GJB2, GSC, HOXA5, HSD11B2, HSD17B2, HSPA6, HSPB3, ICAM5, IF127, INA, KRT14, KRT17, KRT34, LAMC2, TMEM119, IGFL3, LOC92196, MFAP5, MASP1, MEOX1, MEOX2, MX1, MYBPH, MYH3, MYH11, MYL4, IL32, NLGN4X, NPAS1, NPPB, OLR1, OSR2, PAX2, PAX9, PENK, PITX2, PRG4, PROM1, PTPRN, RARRES1, RASD1, RELN, TABLE I-continued Exemplary progenitor cell lines and associated gene expression markers at 18-21 doublings of clonal expansion RGS1, SFRP2, SMOC1, SMOC2, SNAP25, TAC1, RSPO3, TNFSF7, TNNT2, TRH, TUBB4, UGT2B7 and ZIC2.
The group of cell lines SM25 and Z8 are positive for the markers: FOXF1, FST, GDF5, HTRA3, MSX1, MSX2, PRRX2 and SRCRB4D and are negative for the markers: ACTC, AGC1, AKR1C1, ALDH1A1, ANXA8, AQP1, AREG, ATP8B4, BMP4, C6, C7, C20orf103, CD24, CDH3, CLDN11, CNTNAP2, METTL7A, DKK2, EMID1, TMEM100, FMO1, GABRB1, GDF10, GSC, HOXA5, HSD11B2, HSD17B2, HSPA6, ID4, IF127, KCNMB1, KRT14, KRT17, KRT34, IGFL3, LOC92196, MFAP5, MEOX1, MEOX2, MYBPH, MYH3, MYH11, MYL4, NLGN4X, NPPB, OLR1, OSR2, PAX2, PAX9, PDE1A, PENK, PITX2, PROM1, RARRES1, RASD1, RGS1, RPS4Y2, SFRP2, SLITRK6, SMOC1, SMOC2, TAC1, RSPO3, TNFSF7, TNNT2, TRH, TUBB4 and UGT2B7.
The cell line SM28 is positive for the markers: COMP, CRLF1, DIO2, EGR2, FOXF1, FOXF2, FST, HSPB3, INA, TMEM119, MGP, MMP1, MSX2, POSTN, PRELP, PRRX2, PTN and SYT12 and is negative for the markers: ACTC, AGC1, AKR1C1, ALDH1A1, ANXA8, APCDD1, AQP1, AREG, ATP8B4, BEX1, CFB, C3, C6, C7, C20orf103, CD24, CDH6, CLDN11, CNTNAP2, COL21A1, CXADR, METTL7A, DKK2, DLK1, FGFR3, TMEM100, FMO1, GABRB1, GAP43, GDF10, GJB2, GSC, HOXA5, HSD11B2, HSD17B2, HSPA6, ID4, IF127, IFIT3, KCNMB1, KRT14, KRT17, KRT19, KRT34, LAMC2, IGFL3, LOC92196, MFAP5, MEOX1, MEOX2, MX1, MYBPH, MYH3, MYH11, IL32, NLGN4X, TAGLN3, NPPB, OGN, OLR1, OSR2, PAX2, PAX9, PDE1A, PENK, PITX2, PRG4, PROM1, PTGS2, PTPRN, RARRES1, RASD1, RGS1, RPS4Y2, SERPINA3, SFRP2, SMOC1, SMOC2, SNAP25, STMN2, TAC1, RSPO3, TNFSF7, TNNT2, TRH, TUBB4, UGT2B7, WISP2, ZD52F10, ZIC1 and ZIC2.
The cell line SM29 is positive for the markers: FOXF1, FOXF2, FST, HTRA3, IGF2, IGFBP5, IL1R1, MASP1, MGP, MMP1, MSX2, OGN, PODN, POSTN, PRELP, PRRX2, PTN, SRCRB4D and TSLP and is negative for the markers: ACTC, AKR1C1, ALDH1A1, ANXA8, APCDD1, AQP1, CFB, C6, C7, CCDC3, CDH3, CLDN11, CNTNAP2, COL15A1, COL21A1, CRIP1, CRLF1, CRYAB, DKK2, DPT, FGFR3, TMEM100, GDF10, GSC, HOXA5, HSD11B2, HSD17B2, HSPA6, ID4, IF127, INA, KCNMB1, KRT14, KRT17, KRT34, LAMC2, IGFL3, LOC92196, MFAP5, MEOX1, MEOX2, MX1, MYBPH, MYH3, MYH11, MYL4, IL32, NLGN4X, NPPB, OLR1, OSR2, PAX9, PDE1A, PENK, PITX2, PROM1, RARRES1, RASD1, RELN, RGS1, S100A4, SMOC1, SMOC2, SNAP25, TAC1, RSPO3, TNFSF7, TNNT2, TRH, TUBB4, UGT2B7, WISP2, ZIC1 and ZIC2.
The cell line SM30 is positive for the markers: COL15A1, CRYAB, DYSF, FST, GDF5, HTRA3, TMEM119, MMP1, MSX1, MSX2, MYL4, POSTN, SERPINA3, SRCRB4D and ZIC2 and is negative for the markers: ACTC, AGC1, AKR1C1, ALDH1A1, ANXA8, APCDD1, AQP1, ATP8B4, CFB, C3, C6, C7, C20orf103, CD24, CDH3, CLDN11, CNTNAP2, COMP, DIO2, METTL7A, DKK2, DLK1, DPT, FGFR3, TMEM100, FMO1, FMO3, FOXF2, GABRB1, GJB2, GSC, HOXA5, HSD11B2, HSPA6, ID4, IF127, IL1R1, KCNMB1, KIAA0644, KRT14, KRT17, KRT34, IGFL3, LOC92196, MEOX1, MEOX2, MGP, MYBPH, MYH3, MYH11, NLGN4X, NPPB, OGN, OLR1, OSR2, PAX2, PAX9, PDE1A, PENK, PRG4, PROM1, PRRX1, PTN, RARRES1, RASD1, RELN, RGS1, SLITRK6, SMOC1, SMOC2, SNAP25, STMN2, TAC1, RSPO3, TNFSF7, TNNT2, TRH, TUBB4, UGT2B7 and WISP2.
The cell line SM33 is positive for the markers: BEX1, CDH6, CRLF1, EGR2, FOXF1, FST, IGFBP5, MSX1, MSX2, PRELP, SERPINA3, SRCRB4D, SYT12, TSLP and ZIC2 and is negative for the markers: ACTC, AGC1, AKR1C1, ALDH1A1, ANXA8, APCDD1, AQP1, AREG, ATP8B4, CFB, BMP4, C3, C6, C7, C20orf103, CD24, CDH3, CLDN11, CNTNAP2, COL21A1, CRIP1, DIO2, METTL7A, DLK1, DPT, EMID1, FGFR3, TMEM100, FMO1, GABRB1, GAP43, GSC, HOXA5, HSD11B2, HSPA6, HSPB3, ID4, IF127, IL1R1, KCNMB1, KRT14, KRT17, KRT34, IGFL3, LOC92196, MEOX1, MEOX2, MX1, MYBPH, MYH3, MYH11, NLGN4X, NPPB, OGN, OSR2, PAX2, PAX9, PDE1A, PENK, PRG4, PROM1, PTGS2, RARRES1, RASD1, RELN, RGS1, RPS4Y2, SFRP2, SMOC1, SMOC2, SNAP25, STMN2, TAC1, RSPO3, THY1, TNFSF7, TRH, TUBB4, UGT2B7, WISP2 and ZIC1.
The cell line SM4 is positive for the markers: BEX1, CCDC3, CDH6, CRLF1, EGR2, FST, GABRB1, GAP43, GDF5, HSPB3, HTRA3, MMP1, MSX1, MSX2, PRELP, PRRX1, PRRX2 and SRCRB4D and is negative for the markers: AGC1, ALDH1A1, ANXA8, APCDD1, AQP1, AREG, ATP8B4, CFB, BMP4, C3, C6, C7, PRSS35, C20orf103, CD24, CDH3, CLDN11, CNTNAP2, COL15A1, COL21A1, COP1, CXADR, METTL7A, DKK2, DLK1, DPT, EMID1, FGFR3, TMEM100, FMO1, FMO3, GDF10, GJB2, GSC, HOXA5, HSD11B2, HSD17B2, HSPA6, ICAM5, ID4, IF127, IGF2, KRT14, KRT17, KRT19, KRT34, IGFL3, LOC92196, MFAP5, MASP1, MEOX1, MEOX2, MX1, MYBPH, MYH3, MYH11, MYL4, IL32, NLGN4X, TAGLN3, NPAS1, NPPB, OLR1, OSR2, PAX2, PAX9, PDE1A, PENK, PITX2, PRG4, PROM1, RARRES1, RASD1, RELN, RGS1, SFRP2, SLITRK6, SMOC1, SMOC2, SNAP25, STMN2, TAC1, RSPO3, TNFSF7, TNNT2, TRH, TSLP, TUBB4, UGT2B7, WISP2, ZD52F10 and ZIC1.
The cell line SM40 is positive for the markers: BEX1, CD24, CRYAB, FST, HSPB3, IGFBP5, KRT19, MMP1, MYL4, POSTN, PRELP, SRCRB4D and ZD52F10 and is negative for the markers: AGC1, AKR1C1, ALDH1A1, ANXA8, APCDD1, AQP1, AREG, CFB, C6, C7, CDH3, CDH6, CLDN11, CNTNAP2, COL15A1, COL21A1, COMP, CRLF1, DIO2, METTL7A, DKK2, DLK1, DPT, EMID1, FGFR3, TMEM100, FMO1, FMO3, GABRB1, GAP43, GDF10, GJB2, GSC, HOXA5, HSD11B2, HSD17B2, HSPA6, ID4, IF127, IGF2, KRT14, KRT17, KRT34, IGFL3, LOC92196, MEOX1, MEOX2, MGP, MX1, MYBPH, MYH3, MYH11, NLGN4X, NPPB, OGN, OSR2, PAX2, PAX9, PDE1A, PENK, PITX2, PROM1, PRRX1, RARRES1, RASD1, RELN, RGMA, RGS1, RPS4Y2, SFRP2, SLITRK6, SMOC1, SMOC2, SOX11, STMN2, TAC1, RSPO3, TNFSF7, TNNT2, TRH, TUBB4, UGT2B7, WISP2, ZIC1 and ZIC2.
The cell line SM42 is positive for the markers: COL15A1, EGR2, FST, GDF5, TMEM119, MMP1, MSX1, MSX2, PRELP, PRRX1, PRRX2, SFRP2, SRCRB4D, ZIC1 and ZIC2 and is negative for the markers: ACTC, AGC1, AKR1C1, ALDH1A1, ANXA8, APCDD1, AQP1, ATP8B4, CFB, BMP4, C3, C6, C7, C20orf103, CCDC3, CD24, CDH3, CLDN11, CNTNAP2, CRIP1, CRYAB, DIO2, METTL7A, DKK2, DLK1, DPT, EMID1, FGFR3, TMEM100, FOXF2, GABRB1, GAP43, GJB2, GSC, HOXA5, HSD11B2, HSPA6, ID4, IF127, KIAA0644, KRT14, KRT17, KRT19, KRT34, IGFL3, LOC92196, MFAP5, MEOX1, MEOX2, MGP, MX1, MYBPH, MYH3, MYH11, NLGN4X, NPPB, OGN, OLR1, PAX2, PAX9, PDE1A, PENK, PITX2, PRG4, PROM1, RARRES1, RASD1, RELN, RGS1, SLITRK6, SMOC1, SMOC2, SNAP25, STMN2, TAC1, RSPO3, TNFSF7, TNNT2, TRH, TUBB4 and UGT2B7.
The cell line SM44 is positive for the markers: CDH6, COMP, CRLF1, CRYAB, EGR2, FOXF1, FST, GDF5, HTRA3, MGP, MMP1, MSX2, POSTN, PRELP, PRRX2, SYT12 and TSLP and is negative for the markers: ACTC, AGC1, AKR1C1, ALDH1A1, ANXA8, APCDD1, AQP1, AREG, ATP8B4, CFB, BMP4, C3, C6, C7,

TABLE I-continued

Exemplary progenitor cell lines and associated gene expression markers at 18-21 doublings of clonal expansion C20orf103, CD24, CDH3, CLDN11, CNTNAP2, COL15A1, COL21A1, COP1, CXADR, METTL7A, DKK2, DLK1, DPT, EMID1, FGFR3, TMEM100, FMO1, FMO3, FOXF2, GABRB1, GDF10, GJB2, GSC, HOXA5, HSD11B2, HSD17B2, HSPA6, ID4, IF127, IFIT3, IGF2, KRT14, KRT17, KRT19, KRT34, IGFL3, LOC92196, MFAP5, MEOX1, MEOX2, MX1, MYBPH, MYH3, MYH11, MYL4, NLGN4X, NPPB, OGN, OLR1, OSR2, PAX2, PAX9, PDE1A, PENK, PRG4, PROM1, PTN, PTPRN, RARRES1, RASD1, RELN, RGS1, SFRP2, SLITRK6, SMOC1, SMOC2, SNAP25, STMN2, TAC1, RSPO3, TNFSF7, TNNT2, TRH, TUBB4, UGT2B7, WISP2, ZD52F10, ZIC1 and ZIC2.

The cell line SM49 is positive for the markers: FOXF1, FOXF2, FST, GAP43, GDF5, HSPB3, HTRA3, IGFBP5, MGP, MMP1, MSX2, POSTN, PRELP, PRRX2, PTN, RGMA, SOD3, SRCRB4D and SYT12 and is negative for the markers: ACTC, AGC1, AKR1C1, ALDH1A1, ANXA8, APCDD1, AQP1, AREG, CFB, BMP4, C6, C7, C20orf103, CD24, CDH3, CLDN11, CNTNAP2, COL15A1, COL21A1, DIO2, METTL7A, DPT, EMID1, FGFR3, TMEM100, FMO1, GABRB1, GDF10, GJB2, GSC, HOXA5, HSD11B2, HSD17B2, HSPA6, ID4, IF127, IFIT3, KIAA0644, KRT14, KRT17, KRT19, KRT34, LAMC2, IGFL3, LOC92196, MFAP5, MEOX1, MEOX2, MYBPH, MYH3, MYH11, MYL4, NLGN4X, TAGLN3, NPAS1, NPPB, OGN, OLR1, OSR2, PAX2, PAX9, PDE1A, PENK, PITX2, PRG4, PROM1, RARRES1, RELN, RGS1, SMOC1, SMOC2, SNAP25, TAC1, RSPO3, THY1, TNFSF7, TNNT2, TRH, TUBB4, UGT2B7, WISP2, ZIC1 and ZIC2

The cell line SM8 is positive for the markers: BEX1, CDH6, FOXF1, FST, GDF5, GDF10, IGF2, IGFBP5, MMP1, MSX1, TFPI2, TSLP and ZIC2 and is negative for the markers: ACTC, AGC1, AKR1C1, ALDH1A1, ANXA8, APCDD1, AQP1, ATP8B4, CFB, BMP4, C3, C6, C7, PRSS35, C20orf103, CCDC3, CDH3, CLDN11, COL21A1, COMP, CRYAB, DIO2, METTL7A, DKK2, DLK1, DPT, EMID1, FGFR3, TMEM100, FMO1, FMO3, FOXF2, GABRB1, GJB2, GSC, HOXA5, HSD11B2, HSD17B2, HSPA6, HSPB3, ICAM5, ID4, IF127, KCNMB1, KIAA0644, KRT14, KRT17, KRT34, TMEM119, IGFL3, LOC92196, MFAP5, MASP1, MEOX1, MEOX2, MGP, MX1, MYBPH, MYH3, MYH11, MYL4, NLGN4X, NPAS1, NPPB, OGN, OLR1, OSR2, PAX2, PAX9, PDE1A, PENK, PITX2, POSTN, PRELP, PRG4, PROM1, PRRX1, PTGS2, RGMA, RGS1, S100A4, SFRP2, SLITRK6, SMOC2, STMN2, TAC1, RSPO3, TNFSF7, TNNT2, TRH, TUBB4, UGT2B7, WISP2 and ZD52F10.

The cell line T14 is positive for the markers: BEX1, PRSS35, CCDC3, COL15A1, CRIP1, CRYAB, FST, HTRA3, IGF2, KCNMB1, KRT17, KRT19, LAMC2, PITX2, POSTN, S100A4, SOX11, THY1 and TNNT2 and is negative for the markers: AGC1, ALDH1A1, AQP1, AREG, ATP8B4, CFB, C3, C6, C7, C20orf103, CDH3, CLDN11, CNTNAP2, COP1, CXADR, METTL7A, DLK1, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IF127, IGFBP5, KIAA0644, KRT14, IGFL3, LOC92196, MASP1, MEOX1, MEOX2, MGP, MX1, MYH3, IL32, NLGN4X, TAGLN3, NPPB, OGN, OLR1, OSR2, PAX2, PAX9, PDE1A, PENK, PRG4, PROM1, PTGS2, PTPRN, RARRES1, RASD1, RELN, RGS1, SLITRK6, SMOC1, SMOC2, SNAP25, SOD3, STMN2, TAC1, TFPI2, RSPO3, TNFSF7, TRH, TUBB4, WISP2, ZD52F10, ZIC1 and ZIC2.

The group of cell lines T4 and T23 are positive for the markers: BEX1, CCDC3, DKK2, KRT19 and LAMC2 and are negative for the markers: ALDH1A1, APCDD1, AQP1, CFB, C3, C6, C20orf103, CDH3, CLDN11, CNTNAP2, COL15A1, COMP, CRLF1, METTL7A, DPT, EMID1, TMEM100, FMO3, FOXF2, GDF10, GJB2, GSC, HOXA5, HSD11B2, HSPA6, IFI27, IL1R1, KRT14, IGFL3, LOC92196, MASP1, MEOX1, MEOX2, MGP, MX1, MYBPH, MYH3, MYH11, NLGN4X, NPAS1, OGN, OLR1, PAX2, PAX9, PDE1A, PENK, PROM1, PRRX2, PTPRN, RARRES1, RASD1, RGMA, RGS1, RPS4Y2, SFRP2, SLITRK6, SMOC1, SMOC2, SNAP25, STMN2, SYT12, TAC1, RSPO3, TNFSF7, TRH, WISP2, ZD52F10 and ZIC1.

The group of cell lines T36 and T42 are positive for the markers: BEX1, CCDC3, CDH6, CRIP1, FST, HTRA3, KRT17, PTN, S100A4, SRCRB4D, THY1 and ZIC2 and are negative for the markers: AGC1, ALDH1A1, APCDD1, AREG, ATP8B4, C3, C6, C7, PRSS35, C20orf103, CDH3, CLDN11, CNTNAP2, CRLF1, METTL7A, DLK1, DPT, EMID1, FMO1, FMO3, FOXF2, GJB2, GSC, HOXA5, HSD11B2, HSD17B2, HSPA6, HSPB3, IFI27, KRT14, IGFL3, LOC92196, MFAP5, MASP1, MEOX1, MEOX2, MGP, MMP1, MYBPH, MYH3, NLGN4X, TAGLN3, NPAS1, NPPB, OGN, OLR1, PAX9, PDE1A, PENK, PRG4, PROM1, PTPRN, RARRES1, RASD1, RELN, RGS1, SLITRK6, SMOC2, SNAP25, STMN2, TAC1, RSPO3, TRH, TUBB4 and WISP2.

The group of cell lines T43 and T44 are positive for the markers: BEX1, PRSS35, CCDC3, CDH6, COL21A1, CRIP1, CRYAB, ICAM5, KRT17, LAMC2, POSTN, S100A4, SFRP2 and THY1 and are negative for the markers:
AGC1, ALDH1A1, APCDD1, AQP1, AREG, ATP8B4, C3, C6, C7, C20orf103, CDH3, CNTNAP2, COP1, METTL7A, DLK1, DPT, EMID1, FMO1, FMO3, FOXF1, FOXF2, GABRB1, GDF10, GJB2, GSC, HOXA5, HSD11B2, HSD17B2, HSPA6, IFI27, IGFBP5, IGFL3, LOC92196, MEOX1, MEOX2, MGP, NLGN4X, TAGLN3, NPPB, OGN, OLR1, OSR2, PAX2, PAX9, PDE1A, PRG4, PROM1, RARRES1, RASD1, RELN, RGS1, SLITRK6, SMOC1, SMOC2, SNAP25, STMN2, TAC1, TRH, TUBB4, UGT2B7, WISP2, ZD52F10 and ZIC2.

The cell line U18 is positive for the markers: ANXA8, BEX1, PRSS35, CCDC3, CDH6, CRYAB, DKK2, KRT19, MYH11, NPPB, TNNT2 and ZIC2 and is negative for the markers: ACTC, AGC1, ALDH1A1, APCDD1, AQP1, AREG, ATP8B4, CFB, C3, C6, C7, C20orf103, CD24, CDH3, CLDN11, CNTNAP2, COL15A1, COP1, CRLF1, DIO2, METTL7A, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IFI27, IGF2, IGFBP5, KIAA0644, KRT14, TMEM119, IGFL3, LOC92196, MEOX1, MEOX2, MGP, MX1, MYBPH, MYH3, NLGN4X, OGN, OLR1, PAX2, PAX9, PDE1A, PENK, PROM1, PTPRN, RARRES1, RASD1, RELN, RGS1, SFRP2, SLITRK6, SMOC1, SMOC2, SNAP25, SOD3, STMN2, TAC1, TFPI2, RSPO3, THY1, TNFSF7, TRH, TUBB4, WISP2 and ZIC1.

The group of cell lines U30, U30 and U31 are positive for the markers: BEX1, CDH6, CRYAB, KCNMB1, KRT17, MYH11, ZIC1 and ZIC2 and are negative for the markers: ALDH1A1, ATP8B4, C3, C7, C20orf103, CD24, CDH3, CLDN11, CNTNAP2, COP1, CRLF1, METTL7A, DPT, FMO1, FMO3, FOXF1, FOXF2, GABRB1, GSC, HOXA5, HSD11B2, HSD17B2, HSPA6, IFI27, KIAA0644, KRT14, MEOX2, MGP, MYH3, OGN, OLR1, PAX2, PAX9, PDE1A, PROM1, PTPRN, RASD1, RGS1, SFRP2, SMOC1, SNAP25, TAC1, TNNT2, TRH, TUBB4 and WISP2.

The cell line W11 is positive for the markers: COL15A1, COL21A1, DIO2, DLK1, FMO1, FOXF1, FOXF2, FST, HTRA3, IGF2, IL1R1, TMEM119, OGN, PRRX2, PTN, SERPINA3, SLITRK6, SOD3, TFPI2 and WISP and is negative for the markers: ACTC, AGC1, AKR1C1, ALDH1A1, ANXA8, APCDD1, AQP1, TABLE I-continued Exemplary progenitor cell lines and associated gene expression markers at 18-21 doublings of clonal expansion ATP8B4, CFB, C3, C6, C7, C20orf103, CCDC3, CD24, CDH3, CLDN11, CNTNAP2, CRIP1, CRYAB,
CXADR, DKK2, EMID1, FGFR3, GAP43, GDF10, GJB2, GSC, HOXA5, HSD11B2, HSD17B2, HSPA6,
HSPB3, ID4, IFI27, INA, KRT14, KRT17, KRT19, KRT34, LAMC2, IGFL3, LOC92196, MFAP5, MEOX1,
MEOX2, MGP, MMP1, MX1, MYBPH, MYH3, MYH11, MYL4, IL32, NLGN4X, NPAS1, NPPB, OLR1,
PAX2, PAX9, PENK, PITX2, POSTN, PRG4, PROM1, RASD1, RELN, RGS1, SMOC1, SMOC2, STMN2,
TAC1, RSPO3, THY1, TNFSF7, TNNT2, TRH, TUBB4, UGT2B7, ZD52F10, ZIC1 and ZIC2.

The cell line W2 is positive for the markers: BEX1, CD24, COL21A1, FST, HTRA3, ICAM5, IGF2, IGFBP5,
IL1R1, KRT19, LAMC2, TMEM119, MSX1, MSX2, PTN, SERPINA3, SFRP2, SOD3, SOX11, SRCRB4D
and ZIC2 and is negative for the markers: AGC1, AKR1C1, ALDH1A1, APCDD1, ATP8B4, BMP4, C6, C7,
C20orf103, CCDC3, CDH3, CLDN11, CNTNAP2, COL15A1, COMP, COP1, CRLF1, DKK2, DLK1, DPT,
EGR2, EMID1, TMEM100, FMO3, FOXF2, GAP43, GDF10, GSC, HOXA5, HSD11B2, HSPA6, ID4, IFI27,
INA, KCNMB1, KIAA0644, KRT14, KRT17, IGFL3, LOC92196, MEOX1, MEOX2, MGP, MYBPH,
MYH3, MYH11, NLGN4X, NPPB, OGN, OLR1, OSR2, PAX2, PAX9, PDE1A, PENK, PITX2, PRG4,
PROM1, PTGS2, RARRES1, RASD1, RELN, RGMA, RGS1, SLITRK6, SMOC1, SMOC2, STMN2, SYT12,
TAC1, TNFSF7, TNNT2, TRH, TSLP, TUBB4 and ZIC1.

The cell line W3 is positive for the markers: BEX1, CRIP1, FOXF1, FST, GDF5, HSPA6, HTRA3, IGF2,
IGFBP5, KRT19, LAMC2, MMP1, MSX1, POSTN, PTPRN and TFPI2 and is negative for the markers:
ACTC, AGC1, ALDH1A1, ANXA8, APCDD1, AQP1, ATP8B4, CFB, BMP4, C6, C7, PRSS35, C20orf103,
CCDC3, CDH3, CLDN11, CNTNAP2, COL15A1, COL21A1, COMP, DIO2, METTL7A, DKK2, DLK1,
DPT, EGR2, EMID1, FGFR3, FMO1, FMO3, FOXF2, GAP43, GDF10, GJB2, GSC, HOXA5, HSD11B2,
HSD17B2, IF127, IFIT3, INA, KIAA0644, KRT14, KRT17, IGFL3, LOC92196, MEOX1, MEOX2, MGP,
MX1, MYBPH, MYH3, MYH11, MYL4, IL32, NLGN4X, NPPB, OGN, OSR2, PAX2, PAX9, PDE1A,
PENK, PRELP, PRG4, PROM1, PRRX1, RARRES1, RELN, RGMA, RGS1, SLITRK6, SMOC1, SMOC2,
SOX11, SYT12, TAC1, RSPO3, THY1, TNFSF7, TNNT2, TRH, TUBB4, UGT2B7, ZIC1 and ZIC2.

The cell line W8 is positive for the markers: AQP1, CDH6, DIO2, DLK1, EMID1, FOXF1, FOXF2, FST,
HTRA3, IL1R1, MSX1, MSX2, PRRX2, PTN, SLITRK6, SRCRB4D, TSLP and ZIC2 and is negative for the
markers: ACTC, AGC1, AKR1C1, ALDH1A1, ANXA8, APCDD1, BMP4, C6, C7, C20orf103, CCDC3,
CD24, CDH3, CLDN11, CNTNAP2, CRLF1, CRYAB, CXADR, DKK2, DPT, EGR2, FGFR3, TMEM100,
GABRB1, GAP43, GDF10, GJB2, GSC, HOXA5, HSD11B2, HSD17B2, HSPA6, HSPB3, ID4, IF127, IFIT3,
INA, KCNMB1, KRT14, KRT17, KRT34, IGFL3, LOC92196, MFAP5, MEOX1, MEOX2, MX1, MYBPH,
MYH3, MYH11, MYL4, NLGN4X, NPPB, OLR1, PAX2, PAX9, PENK, PITX2, POSTN, PRELP, PROM1,
PRRX1, RARRES1, RASD1, RGMA, RGS1, SMOC1, SMOC2, STMN2, SYT12, TAC1, RSPO3, THY1,
TNFSF7, TNNT2, TRH, TUBB4, UGT2B7, WISP2, ZD52F10 and ZIC1.

The cell line X4 is positive for the markers: ACTC, AQP1, BEX1, BMP4, CD24, CDH6, CLDN11
CRYAB, CXADR, HTRA3, INA, KRT17, KRT19, LAMC2, MMP1, IL32, NLGN4X, TAGLN3, NPPB,
PAX2, PROM1, RASD1, RELN and UGT2B7 and is negative for the markers: AGC1, ALDH1A1, APCDD1,
ATP8B4, CFB, C3, C6, C7, C20orf103, CCDC3, CDH3, CNTNAP2, COL15A1, COL21A1, COMP, COP1,
CRLF1, DIO2, METTL7A, DKK2, DLK1, DPT, EGR2, EMID1, TMEM100, FMO1, FMO3, FOXF1, FOXF2,
FST, GABRB1, GAP43, GDF10, GJB2, GSC, HOXA5, HSD11B2, HSD17B2, HSPA6, ID4, IF127, IFIT3,
IGF2, IL1R1, KCNMB1, KIAA0644, TMEM119, IGFL3, LOC92196, MFAP5, MASP1, MEOX1, MEOX2,
MGP, MX1, MYBPH, MYH3, MYL4, OGN, OSR2, PAX9, PDE1A, PENK, PITX2, PRELP, PRRX1,
PRRX2, PTGS2, PTN, RARRES1, RGMA, RGS1, SERPINA3, SLITRK6, SMOC1, SMOC2, SOD3, TAC1,
RSPO3, TNNT2, TRH, TUBB4, WISP2, ZD52F10, ZIC1 and ZIC2.

The cell line X5.4 is positive for the markers: ACTC, CD24, CLDN11, CRIP1, CRYAB, HTRA3, KRT19,
KRT34, LAMC2, MMP1, IL32, NLGN4X, TAGLN3, NPPB, PAX2, POSTN, RELN, S100A4, SFRP2,
SRCRB4D, THY1 and UGT2B7 and is negative for the markers: AGC1, ALDH1A1, APCDD1, AREG,
ATP8B4, CFB, C3, C6, C7, C20orf103, CNTNAP2, COL21A1, COMP, COP1, CRLF1, DIO2, METTL7A,
DKK2, DLK1, DPT, EMID1, TMEM100, FMO1, FMO3, FOXF1, FOXF2, GABRB1, GAP43, GDF10, GJB2,
GSC, HOXA5, HSD11B2, HSD17B2, HSPA6, ID4, IF127, IFIT3, IGF2, KIAA0644, TMEM119, IGFL3,
MASP1, MEOX2, MSX1, MX1, MYBPH, MYH3, MYL4, NPAS1, OGN, OSR2, PAX9, PDE1A, PENK,
PRELP, PRRX1, PRRX2, PTPRN, RARRES1, RGMA, RGS1, SLITRK6, SMOC1, SMOC2, SNAP25, SOD3,
TAC1, RSPO3, TNNT2, TRH, TUBB4, WISP2, ZD52F10, ZIC1 and ZIC2.

The cell line X5 is positive for the markers: ACTC, AKR1C1, BEX1, CLDN11, COMP, CRIP1, CRYAB,
GDF5, HTRA3, KIAA0644, KRT14, KRT19, KRT34, LAMC2, MFAP5, MEOX2, MGP, MMP1, PENK,
PITX2, POSTN, PTGS2, S100A4 and THY1 and is negative for the markers: AGC1, ALDH1A1, ANXA8,
APCDD1, AQP1, AREG, ATP8B4, C6, C7, C20orf103, CCDC3, CDH6, CNTNAP2, COL15A1, COL21A1,
COP1, CXADR, DIO2, DKK2, DLK1, DPT, EMID1, FGFR3, TMEM100, FMO1, FMO3, FOXF1, FOXF2,
GAP43, GDF10, HSD11B2, HSD17B2, HSPA6, IF127, IFIT3, IGF2, IGFL3, LOC92196, MEOX1, MSX1,
MSX2, MYBPH, MYH3, MYH11, MYL4, NLGN4X, NPPB, OGN, OLR1, PAX2, PAX9, PDE1A, PROM1,
PTPRN, RASD1, RELN, RGS1, SERPINA3, SFRP2, SMOC2, SNAP25, STMN2, SYT12, TAC1, RSPO3,
TNNT2, TRH, TUBB4, UGT2B7, WISP2, ZD52F10, ZIC1 and ZIC2.

The group of cell lines X7PEND12 and X7PEND24 are positive for the markers: AQP1, BEX1, CDH3, DIO2,
DLK1, FOXF1, FST, GABRB1, IGF2, IGFBP5, IL1R1, KIAA0644, MSX1, PODN, PRRX2, SERPINA3,
SOX11, SRCRB4D and TFPI2 and are negative for the markers: ACTC, AGC1, AKR1C1, ALDH1A1,
ANXA8, APCDD1, AREG, CFB, C3, C6, C7, PRSS35, CCDC3, CDH11, COMP, COP1, CXADR,
DKK2, EMID1, FGFR3, FMO1, FMO3, GAP43, GDF10, GSC, HOXA5, HSD11B2, HSPA6, HTRA3,
ICAM5, ID4, IF127, IFIT3, INA, KCNMB1, KRT14, KRT17, KRT34, IGFL3, LOC92196, MFAP5, MASP1,
MEOX1, MEOX2, MMP1, MX1, MYBPH, MYH3, MYH11, MYL4, IL32, NLGN4X, NPPB, OGN, OSR2,
PAX2, PAX9, PENK, PITX2, PRELP, PRG4, PRRX1, RARRES1, RELN, RGMA, SFRP2, SMOC1, SMOC2,
SOD3, SYT12, TAC1, TNFSF7, TRH, TSLP, TUBB4, UGT2B7, WISP2, ZD52F10, ZIC1 and ZIC2.

The group of cell lines X7PEND9 and X7PEND16 are positive for the markers: BEX1, CDH6, DLK1,
TMEM100, FOXF1, FOXF2, IGF2, IGFBP5, IL1R1, KIAA0644, TMEM119, MGP, MSX1, MSX2, PDE1A,
PODN, PRRX2, PTN, S100A4, SERPINA3, SNAP25, SOX11 and SRCRB4D and are negative for the
markers: ACTC, AGC1, AKR1C1, ALDH1A1, ANXA8, AREG, ATP8B4, BMP4, C3, C20orf103, CCDC3,
CD24, CDH3, CNTNAP2, COP1, CRYAB, CXADR, METTL7A, DKK2, EMID1, FGFR3, FMO1, GDF10,
GSC, HOXA5, HSD11B2, HSD17B2, HSPA6, HSPB3, ICAM5, ID4, IF127, INA, KCNMB1, KRT14,
KRT17, KRT34, IGFL3, LOC92196, MFAP5, MASP1, MEOX1, MEOX2, MMP1, MYBPH, MYH3,
MYH11, MYL4, IL32, NLGN4X, NPAS1, NPPB, OLR1, OSR2, PAX2, PAX9, PENK, PITX2, PRELP, TABLE I-continued Exemplary progenitor cell lines and associated gene expression markers at 18-21 doublings of clonal expansion PRG4, PROM1, PTPRN, RASD1, RELN, RGS1, SFRP2, SMOC1, SMOC2, SOD3, SYT12, TAC1, RSPO3, THY1, TNFSF7, TNNT2, TRH, TSLP, TUBB4, UGT2B7, ZD52F10, ZIC1 and ZIC2.
The cell line X7PEND30 is positive for the markers: BEX1, PRSS35, CDH6, COL15A1, DIO2, DLK1, DPT, TMEM100, FMO1, FMO3, FOXF1, FOXF2, FST, HSPB3, IGF2, IGFBP5, IL1R1, KIAA0644, KRT19, LAMC2, TMEM119, MGP, MSX1, PDE1A, PODN, PRRX2, S100A4, SERPINA3, SOX11 and SRCRB4D and is negative for the markers: ACTC, AGC1, AKR1C1, ALDH1A1, ANXA8, APCDD1, AQP1, AREG, ATP8B4, C3, C7, C20orf103, CCDC3, CD24, CDH3, CLDN11, CNTNAP2, COP1, CXADR, DKK2, EMID1, FGFR3, GAP43, GDF5, GDF10, GJB2, GSC, HOXA5, HSD11B2, HSD17B2, HSPA6, HTRA3, ICAM5, ID4, IF127, INA, KCNMB1, KRT14, KRT17, KRT34, IGFL3, LOC92196, MFAP5, MASP1, MEOX1, MEOX2, MMP1, MYBPH, MYH3, MYH11, MYL4, IL32, NLGN4X, NPPB, OSR2, PAX2, PAX9, PENK, PITX2, PRELP, PRRX1, PTGS2, PTPRN, RELN, RGS1, SFRP2, SMOC1, SMOC2, SOD3, STMN2, SYT12, TAC1, RSPO3, THY1, TNFSF7, TNNT2, TRH, TSLP, TUBB4, UGT2B7, WISP2, ZD52F10, ZIC1 and ZIC2.
The cell line X7SKEL2 is positive for the markers: APCDD1, BEX1, C6, C7, PRSS35, COL21A1, CRIP1, CRLF1, CRYAB, DLK1, TMEM100, FMO1, FOXF2, GDF5, HSD11B2, IGF2, IGFBP5, KRT19, LAMC2, TMEM119, MGP, NPAS1, PRRX2, PTPRN, RGMA, S100A4, SERPINA3, SNAP25 and SOX11 and is negative for the markers: ACTC, AGC1, AKR1C1, ALDH1A1, ANXA8, AQP1, AREG, ATP8B4, CFB, BMP4, C3, C20orf103, CCDC3, CD24, CDH3, CDH6, CLDN11, CNTNAP2, COMP, COP1, CXADR, DIO2, METTL7A, DKK2, DPT, EGR2, EMID1, FGFR3, FOXF1, GABRB1, GDF10, GJB2, GSC, HOXA5, HSD17B2, HSPA6, HTRA3, ID4, IF127, IFIT3, KCNMB1, KIAA0644, KRT14, KRT17, KRT34, IGFL3, LOC92196, MFAP5, MASP1, MEOX1, MEOX2, MMP1, MSX2, MX1, MYBPH, MYH3, MYH11, MYL4, IL32, NLGN4X, NPPB, OGN, OLR1, OSR2, PAX2, PAX9, PENK, PITX2, POSTN, PRELP, PROM1, PRRX1, PTGS2, PTN, RARRES1, RELN, RGS1, SLITRK6, SMOC1, SMOC2, SOD3, STMN2, SYT12, TAC1, TFPI2, RSPO3, THY1, TNFSF7, TRH, TSLP, TUBB4, UGT2B7, ZIC1 and ZIC2.
The cell line X7SKEL22 is positive for the markers: ACTC, BEX1, C7, PRSS35, COL21A1, CRIP1, CRYAB, DIO2, DPT, EGR2, FMO3, FOXF1, FOXF2, FST, GJB2, HSPB3, IGF2, IGFBP5, IL1R1, KRT19, LAMC2, TMEM119, MGP, NPAS1, PODN, PRRX2, SERPINA3, SOX11 and SRCRB4D and is negative for the markers: AGC1, AKR1C1, ALDH1A1, ANXA8, AQP1, AREG, ATP8B4, CFB, BMP4, C3, C20orf103, CCDC3, CD24, CDH3, CDH6, CLDN11, CNTNAP2, COL15A1, COMP, COP1, CXADR, METTL7A, DKK2, DLK1, EMID1, FGFR3, TMEM100, GABRB1, GAP43, GDF5, GDF10, GSC, HOXA5, HSD17B2, HSPA6, HTRA3, ICAM5, ID4, IF127, IFIT3, KCNMB1, KRT14, KRT17, KRT34, IGFL3, LOC92196, MFAP5, MASP1, MEOX1, MEOX2, MMP1, MSX1, MSX2, MX1, MYBPH, MYH3, MYH11, MYL4, IL32, NLGN4X, NPPB, OGN, OLR1, OSR2, PAX2, PAX9, PENK, PITX2, POSTN, PRELP, PRG4, PROM1, PRRX1, PTN, RARRES1, RASD1, RELN, RGS1, SFRP2, SLITRK6, SMOC1, SMOC2, SOD3, STMN2, SYT12, TAC1, TFPI2, RSPO3, TNFSF7, TNNT2, TRH, TSLP, TUBB4, UGT2B7, ZD52F10, ZIC1 and ZIC2.
The group of cell lines X7SKEL4, X7SKEL6 and X7SKEL7 are positive for the markers: BEX1, COL21A1, CRLF1, DLK1, FMO1, FMO3, FOXF1, FOXF2, HSD11B2, IGF2, IGFBP5, IL1R1, TMEM119, PRRX2, RGMA, SERPINA3, SNAP25, SOX11 and SRCRB4D and are negative for the markers: ACTC, AGC1, AKR1C1, ALDH1A1, ANXA8, AQP1, AREG, ATP8B4, CFB, BMP4, C3, C20orf103, CCDC3, CD24, CDH3, CLDN11, CNTNAP2, COL15A1, COMP, COP1, CXADR, DKK2, EMID1, FGFR3, GDF10, GJB2, GSC, HOXA5, HSD17B2, HSPA6, HTRA3, ID4, IF127, IFIT3, INA, KCNMB1, KRT14, KRT17, KRT34, IGFL3, LOC92196, MFAP5, MASP1, MEOX1, MEOX2, MMP1, MYBPH, MYH3, MYH11, MYL4, IL32, NLGN4X, NPPB, OLR1, OSR2, PAX2, PENK, PITX2, POSTN, PRELP, PROM1, RELN, RGS1, SFRP2, SLITRK6, SMOC1, SMOC2, SOD3, STMN2, SYT12, TAC1, TFPI2, RSPO3, THY1, TNFSF7, TNNT2, TRH, TSLP, TUBB4 and ZIC1.
The cell line X7SMOO12 is positive for the markers: BEX1, CDH6, COL21A1, CRIP1, DIO2, DLK1, EGR2, FOXF1, FOXF2, FST, IGF2, IGFBP5, TMEM119, MSX1, MSX2, MX1, PODN, POSTN, PRRX2, PTN, S100A4, SERPINA3, SOX11, TFPI2, WISP2 and ZIC2 and is negative for the markers: ACTC, AGC1, AKR1C1, ALDH1A1, ANXA8, APCDD1, AQP1, AREG, CFB, C3, C6, C7, C20orf103, CCDC3, CD24, CLDN11, CNTNAP2, COMP, COP1, CRYAB, CXADR, METTL7A, DKK2, EMID1, FGFR3, TMEM100, GABRB1, GAP43, GDF10, GJB2, GSC, HOXA5, HSD11B2, HSD17B2, HSPA6, HSPB3, HTRA3, ICAM5, ID4, IF127, IL1R1, KCNMB1, KRT14, KRT17, KRT34, IGFL3, LOC92196, MFAP5, MASP1, MEOX1, MEOX2, MGP, MMP1, MYBPH, MYH3, MYH11, MYL4, IL32, NLGN4X, NPPB, OGN, OSR2, PAX2, PAX9, PDE1A, PENK, PITX2, PRELP, PRG4, PTGS2, RARRES1, RGS1, SFRP2, SMOC1, SMOC2, SOD3, SYT12, TAC1, RSPO3, TNFSF7, TRH, TSLP, TUBB4, UGT2B7, ZD52F10 and ZIC1.
The cell line X7SMOO19 is positive for the markers: BEX1, CDH6, COL15A1, COL21A1, COMP, CRIP1, DLK1, EGR2, FMO1, FMO3, FOXF1, FOXF2, FST, HSPA6, IGF2, IGFBP5, KIAA0644, KRT19, LAMC2, TMEM119, MSX1, MSX2, OGN, PODN, PRRX2, RGMA, S100A4, SERPINA3, SNAP25, SOX11, SRCRB4D, TNNT2 and ZIC2 and is negative for the markers: ACTC, AGC1, AKR1C1, ALDH1A1, ANXA8, APCDD1, AREG, ATP8B4, C3, C6, C7, C20orf103, CCDC3, CD24, CLDN11, COP1, CXADR, DIO2, METTL7A, DKK2, DPT, EMID1, TMEM100, GABRB1, GJB2, GSC, HOXA5, HSD11B2, HSD17B2, HTRA3, ICAM5, ID4, IF127, IL1R1, INA, KCNMB1, KRT14, KRT17, KRT34, IGFL3, LOC92196, MFAP5, MASP1, MEOX1, MEOX2, MMP1, MYBPH, MYH3, MYH11, MYL4, IL32, NLGN4X, NPPB, OLR1, OSR2, PAX2, PAX9, PENK, PITX2, PRG4, PROM1, PTPRN, RARRES1, RELN, RGS1, SFRP2, SLITRK6, SMOC1, SMOC2, SOD3, STMN2, SYT12, TAC1, RSPO3, TNFSF7, TRH, TSLP, TUBB4, UGT2B7, WISP2, ZD52F10 and ZIC1.
The cell line X7SMOO25 is positive for the markers: AQP1, ATP8B4, BEX1, CDH3, COL21A1, CRIP1, DLK1, FOXF1, FOXF2, FST, GABRB1, HSPB3, IGF2, IGFBP5, IL1R1, KRT19, LAMC2, TMEM119, MSX1, MSX2, PODN, POSTN, PRRX2, PTN, RGMA, S100A4, SERPINA3, SLITRK6, SOX11, SRCRB4D, TFPI2, RSPO3 and THY1 and is negative for the markers: ACTC, AGC1, AKR1C1, ANXA8, APCDD1, AREG, CFB, BMP4, C3, C6, C7, PRSS35, C20orf103, CCDC3, CLDN11, COL15A1, COP1, CXADR, METTL7A, DKK2, EGR2, EMID1, FGFR3, TMEM100, FMO1, FMO3, GDF10, GJB2, GSC, HOXA5, HSD11B2, HSD17B2, HSPA6, HTRA3, ICAM5, ID4, IF127, INA, KCNMB1, KRT14, KRT17, KRT34, IGFL3, LOC92196, MASP1, MEOX1, MEOX2, MGP, MYBPH, MYH3, MYH11, MYL4, IL32, NLGN4X, NPPB, OGN, OLR1, OSR2, PAX2, PAX9, PDE1A, PENK, PITX2, PRELP, PRG4, PROM1, PRRX1, PTPRN, RASD1, RELN, RGS1, SFRP2, SMOC1, SMOC2, SOD3, SYT12, TAC1, TNFSF7, TRH, TSLP, TUBB4, UGT2B7, WISP2, ZD52F10, ZIC1 and ZIC2.
The cell line X7SMOO26 is positive for the markers: BEX1, CCDC3, CDH6, COL15A1, COL21A1, COMP, CRIP1, CRLF1, CRYAB, DIO2, EGR2, FOXF1, FOXF2, FST, GDF10, HSPB3, IGF2, IGFBP5, KRT19,

TABLE I-continued

Exemplary progenitor cell lines and associated gene expression markers at 18-21 doublings of clonal expansion LAMC2, TMEM119, MSX1, MSX2, NPAS1, PODN, POSTN, PRRX2, S100A4, SERPINA3, SOX11, SRCRB4D, TNNT2 and ZIC2 and is negative for the markers: ACTC, AGC1, AKR1C1, ALDH1A1, ANXA8, APCDD1, AREG, ATP8B4, CFB, BMP4, C3, C6, C7, C20orf103, CD24, CDH3, CLDN11, COP1, METTL7A, DLK1, DPT, EMID1, FGFR3, TMEM100, FMO1, FMO3, GJB2, GSC, HOXA5, HSD11B2, HSPA6, HTRA3, ICAM5, ID4, IF127, IL1R1, KCNMB1, KIAA0644, KRT14, KRT34, IGFL3, LOC92196, MFAP5, MASP1, MEOX1, MEOX2, MGP, MMP1, MX1, MYBPH, MYH3, IL32, NLGN4X, OGN, OLR1, OSR2, PAX2, PAX9, PDE1A, PENK, PITX2, PRELP, PRG4, PROM1, PTGS2, PTN, PTPRN, RARRES1, RASD1, RELN, RGS1, SFRP2, SLITRK6, SMOC1, SMOC2, SNAP25, SOD3, STMN2, SYT12, TAC1, TFPI2, RSPO3, THY1, TNFSF7, TRH, TSLP, TUBB4, UGT2B7, WISP2, ZD52F10 and ZIC1.

The group of cell lines X75MOO9 and X75MOO29 are positive for the markers: BEX1, COL21A1, CRIP1, CRLF1, DIO2, DLK1, FOXF1, FOXF2, FST, IGF2, IGFBP5, KIAA0644, TMEM119, MSX1, PODN, POSTN, PRRX2, RGMA, S100A4, SERPINA3, SNAP25, SOX11 and SRCRB4D and are negative for the markers: ACTC, AGC1, AKR1C1, ALDH1A1, ANXA8, APCDD1, AQP1, AREG, ATP8B4, C3, C6, C7, PRSS35, C20orf103, CCDC3, CD24, CDH3, CLDN11, COP1, CXADR, METTL7A, DKK2, EMID1, GDF10, GJB2, GSC, HOXA5, HSD11B2, HSD17B2, HSPA6, HTRA3, ICAM5, ID4, IFI27, IL1R1, INA, KCNMB1, KRT14, KRT17, KRT19, KRT34, IGFL3, LOC92196, MFAP5, MASP1, MEOX1, MEOX2, MYH3, MYH11, MYL4, IL32, NLGN4X, NPPB, OLR1, OSR2, PAX2, PAX9, PENK, PITX2, PRELP, PROM1, PTPRN, RASD1, RELN, RGS1, SMOC1, SMOC2, SYT12, TAC1, TNFSF7, TRH, TSLP, TUBB4, UGT2B7, ZD52F10 and ZIC1.

The cell line X7SMOO32 is positive for the markers: ACTC, BEX1, CDH6, COL21A1, CRIP1, CRLF1, DIO2, DLK1, EGR2, FGFR3, FOXF1, FOXF2, FST, GABRB1, IGFBP5, KIAA0644, KRT19, LAMC2, TMEM119, MGP, MMP1, MSX1, MSX2, PODN, POSTN, PRG4, PRRX2, PTN, RGMA, S100A4, SERPINA3, SOX11 and SRCRB4D and is negative for the markers: AGC1, AKR1C1, ALDH1A1, ANXA8, APCDD1, AREG, ATP8B4, BMP4, C3, C6, C7, PRSS35, C20orf103, CCDC3, CD24, CLDN11, CNTNAP2, COL15A1, COP1, CXADR, METTL7A, DKK2, DPT, EMID1, TMEM100, FMO1, FMO3, GDF5, GDF10, GJB2, GSC, HOXA5, HSD11B2, HSD17B2, HSPA6, HSPB3, HTRA3, ICAM5, ID4, IFI27, IL1R1, INA, KCNMB1, KRT14, KRT17, KRT34, IGFL3, LOC92196, MFAP5, MASP1, MEOX1, MEOX2, MYBPH, MYH3, MYH11, MYL4, IL32, NLGN4X, NPPB, OGN, OLR1, OSR2, PAX2, PAX9, PDE1A, PITX2, PRELP, PROM1, PTPRN, RASD1, RGS1, SFRP2, SMOC1, SMOC2, SOD3, STMN2, SYT12, TAC1, RSPO3, TNFSF7, TNNT2, TRH, TSLP, TUBB4, UGT2B7, WISP2, ZD52F10, ZIC1 and ZIC2.

The cell line X7SMOO6 is positive for the markers: ACTC, BEX1, CNTNAP2, COL15A1, COL21A1, CRIP1, CRLF1, CRYAB, DLK1, EGR2, FMO1, FMO3, FOXF1, FOXF2, FST, HSPB3, IGF2, IGFBP5, KRT19, LAMC2, TMEM119, MGP, MSX1, MSX2, NPAS1, OGN, PODN, POSTN, PRRX2, RGMA, S100A4, SERPINA3, SNAP25, SOX11, SRCRB4D, STMN2 and TNNT2 and is negative for the markers: AGC1, AKR1C1, ALDH1A1, ANXA8, APCDD1, AQP1, AREG, ATP8B4, C3, C6, C7, C20orf103, CCDC3, CD24, CLDN11, COP1, CXADR, DIO2, METTL7A, DKK2, EMID1, TMEM100, GAP43, GDF10, GJB2, GSC, HOXA5, HSD11B2, HSD17B2, HSPA6, HTRA3, ICAM5, ID4, IFI27, IL1R1, INA, KCNMB1, KRT14, KRT17, KRT34, IGFL3, LOC92196, MFAP5, MASP1, MEOX1, MEOX2, MYBPH, MYH3, MYH11, MYL4, IL32, NLGN4X, TAGLN3, NPPB, OSR2, PAX2, PAX9, PDE1A, PENK, PITX2, PRG4, PRRX1, PTGS2, PTPRN, RASD1, RELN, RGS1, SFRP2, SMOC1, SMOC2, SYT12, TAC1, RSPO3, TNFSF7, TRH, TSLP, TUBB4, UGT2B7, ZD52F10, ZIC1 and ZIC2.

The cell line X7SMOO7 is positive for the markers: ACTC, BEX1, CDH6, CRIP1, CRLF1, CRYAB, DLK1, EGR2, FOXF1, FOXF2, FST, HSPA6, IGF2, IGFBP5, INA, LAMC2, MMP1, MSX1, MSX2, TAGLN3, POSTN, PRRX2, PTGS2, PTPRN, RASD1, RELN, S100A4, SNAP25, SOX11, SRCRB4D, TAC1, TFPI2 and RSPO3 and is negative for the markers: AGC1, AKR1C1, ALDH1A1, ANXA8, APCDD1, AQP1, AREG, CFB, BMP4, C3, C6, C7, C20orf103, CCDC3, CDH3, CLDN11, CNTNAP2, COL15A1, COL21A1, COP1, CXADR, METTL7A, DKK2, DPT, EMID1, FMO3, GAP43, GDF5, GDF10, GSC, HOXA5, HSD11B2, HSD17B2, HSPB3, HTRA3, ID4, IFI27, IFIT3, KCNMB1, KIAA0644, KRT14, KRT17, IGFL3, LOC92196, MFAP5, MASP1, MEOX1, MEOX2, MGP, MYBPH, MYH3, MYH11, MYL4, IL32, NLGN4X, NPPB, OGN, OLR1, OSR2, PAX2, PAX9, PDE1A, PENK, PITX2, PRELP, PRG4, PROM1, PRRX1, PTN, RGMA, RGS1, SFRP2, SLITRK6, SMOC2, SOD3, STMN2, SYT12, TNNT2, TRH, TSLP, TUBB4, WISP2 and ZIC1.

The group of cell lines Z1, Z6 and Z7 are positive for the markers: FST, GDF5, MMP1, MSX1, SRCRB4D, ZIC1 and ZIC2 and are negative for the markers: ACTC, AGC1, AKR1C1, ALDH1A1, ANXA8, APCDD1, AQP1, AREG, ATP8B4, CFB, BMP4, C3, C6, C7, C20orf103, CDH3, CLDN11, CNTNAP2, CRLF1, DIO2, METTL7A, DKK2, DLK1, DPT, EMID1, FGFR3, TMEM100, FMO1, FMO3, FOXF2, GABRB1, GJB2, GSC, HOXA5, HSD11B2, HSPA6, HSPB3, ID4, IFI27, IGF2, KCNMB1, KIAA0644, KRT14, IGFL3, LOC92196, MFAP5, MASP1, MEOX1, MEOX2, MGP, MYBPH, MYH3, MYH11, NLGN4X, NPPB, OGN, OLR1, PAX2, PAX9, PDE1A, PENK, PITX2, PRG4, PROM1, RARRES1, RASD1, RELN, RGS1, SFRP2, SMOC1, SMOC2, SNAP25, STMN2, SYT12, TAC1, RSPO3, TNFSF7, TNNT2, TRH, TUBB4 and WISP2.

The cell line Z11 (also known as Z11Rep1 and Z11Rep2 and ACTC194) is positive for the markers: ATP8B4, CD24, DLK1, FOXF1, FST, HTRA3, IGF2, IGFBP5, IL1R1, MSX1, NLGN4X, OSR2, PODN, PROM1, PRRX2, PTN, SOD3, SOX11, SRCRB4D, STMN2 and TFPI2 and are negative for the markers: ACTC, AGC1, AKR1C1, ALDH1A1, ANXA8, APCDD1, AREG, CFB, C6, C7, PRSS35, CCDC3, CDH3, CLDN11, CNTNAP2, COMP, CRIP1, CRLF1, DIO2, DKK2, DPT, EMID1, FMO1, FMO3, GAP43, GDF10, GJB2, GSC, HOXA5, HSD11B2, HSPA6, HSPB3, IFI27, INA, KCNMB1, KIAA0644, KRT14, KRT17, KRT34, LAMC2, IGFL3, LOC92196, MFAP5, MEOX1, MEOX2, MX1, MYBPH, MYH3, MYH11, MYL4, IL32, NPPB, OLR1, PAX2, PITX2, RARRES1, RASD1, RGS1, SMOC1, SMOC2, SNAP25, TAC1, TNFSF7, TNNT2, TRH, TUBB4, UGT2B7, WISP2, ZIC1 and ZIC2.

The cell line Z2 is positive for the markers: BEX1, CCDC3, EGR2, FOXF1, FOXF2, FST, GDF5, HSPB3, IGFBP5, INA, TMEM119, MASP1, MMP1, MSX2, POSTN, PRELP, PRRX2, PTN, SRCRB4D, TFPI2 and TSLP and is negative for the markers: ACTC, AGC1, AKR1C1, ALDH1A1, ANXA8, APCDD1, AQP1, AREG, CFB, BMP4, C3, C6, C7, C20orf103, CD24, CDH3, CLDN11, CNTNAP2, COL21A1, DIO2, DKK2, DLK1, DPT, FGFR3, TMEM100, FMO1, FMO3, GABRB1, GAP43, GDF10, GJB2, GSC, HOXA5, HSD11B2, HSD17B2, HSPA6, ID4, IF127, KCNMB1, KIAA0644, KRT14, KRT17, KRT34, IGFL3, LOC92196, MFAP5, MEOX1, MEOX2, MYBPH, MYH3, MYH11, NLGN4X, NPPB, OGN, OSR2, PAX2, PAX9, PDE1A, PENK, PITX2, PRG4, PROM1, RARRES1, RASD1, RGS1, SMOC1, SMOC2, SNAP25, STMN2, TAC1, RSPO3, TNFSF7, TNNT2, TRH, TUBB4, WISP2, ZIC1 and ZIC2.

The cell line MEL2 is positive for the markers: AKR1C1, AQP1, COL21A1, CRYAB, CXADR, DIO2, TABLE I-continued Exemplary progenitor cell lines and associated gene expression markers at 18-21 doublings of clonal expansion METTL7A, DKK2, DLK1, HSD17B2, HSPB3, MGP, MMP1, MSX2, PENK, PRRX1, PRRX2, S100A4, SERPINA3, SFRP2, SNAP25, SOX11, TFPI2 and THY1 and is negative for the markers: ACTC, ALDH1A1, AREG, CFB, C3, C20orf103, CD24, CDH3, CDH6, CNTNAP2, COL15A1, COMP, COP1, CRLF1, FGFR3, FMO1, FMO3, FOXF2, FST, GABRB1, GAP43, GDF5, GDF10, GJB2, GSC, HOXA5, HSD11B2, HSPA6, ICAM5, KCNMB1, KRT14, KRT17, KRT19, KRT34, MASP1, MEOX1, MEOX2, MYBPH, MYH3, MYH11, TAGLN3, NPAS1, NPPB, OLR1, PAX2, PDE1A, PITX2, PRG4, PTN, PTPRN, RASD1, RELN, RGS1, SMOC1, STMN2, TAC1, TNFSF7, TRH, TUBB4, WISP2, ZIC1 and ZIC2.

The cell line C4ELSR10 is positive for the markers: AKR1C1, ALDH1A1, ANXA8, AREG, CDH6, COP1, DIO2, METTL7A, EGR2, FOXF1, HSD17B2, IGFBP5, KIAA0644, KRT19, KRT34, OLR1, PITX2, S100A4, STMN2 and TFPI2 and is negative for the markers: ACTC, AQP1, C7, C20orf103, CD24, CDH3, CLDN11, CNTNAP2, COMP, CRIP1, CRLF1, DKK2, DLK1, DPT, FGFR3, FMO1, GABRB1, GAP43, GDF10, GJB2, GSC, HSD11B2, HSPA6, HSPB3, ICAM5, ID4, KRT14, KRT17, LAMC2, MFAP5, MASP1, MEOX1, MEOX2, MGP, MMP1, MSX1, MYBPH, MYH3, MYH11, TAGLN3, NPAS1, NPPB, OGN, PAX2, PAX9, PENK, PRELP, PRG4, PRRX1, PRRX2, PTN, RELN, RGS1, SERPINA3, SFRP2, SMOC1, SNAP25, SOX11, TAC1, TNNT2, TUBB4, WISP2, ZIC1 and ZIC2.

The cell line Z3 is positive for the markers: BEX1, CDH6, COL21A1, CXADR, EGR2, FOXF1, FST, HSD17B2, LAMC2, MMP1, MSX1, MSX2, SERPINA3, ZIC1 and ZIC2 and is negative for the markers: ACTC, ALDH1A1, AQP1, ATP8B4, CFB, C3, C7, C20orf103, CDH3, CLDN11, CNTNAP2, COMP, CRIP1, CRLF1, DIO2, METTL7A, DKK2, DLK1, DPT, FGFR3, FMO1, FMO3, GABRB1, GJB2, GSC, HOXA5, HSD11B2, HSPA6, HSPB3, ICAM5, ID4, IF127, IGF2, KCNMB1, KIAA0644, KRT14, KRT17, MFAP5, MASP1, MEOX1, MEOX2, MGP, MX1, MYBPH, MYH3, MYH11, NPAS1, OGN, OLR1, PAX2, PAX9, PDE1A, PRG4, PROM1, PRRX2, PTN, PTPRN, RARRES1, RASD1, RGS1, S100A4, SFRP2, SMOC1, SNAP25, STMN2, TAC1, TNFSF7, TUBB4 and WISP2.

The cell line SK15 is positive for the markers: AREG, BEX1, FOXF1, KRT19, LAMC2, MSX1, PITX2, S100A4, SERPINA3 and THY1 and is negative for the markers: AGC1, ALDH1A1, AQP1, ATP8B4, CFB, C3, C7, C20orf103, CD24, CDH3, CDH6, CLDN11, CNTNAP2, COL15A1, COMP, CRIP1, CRLF1, DLK1, DPT, FMO1, FMO3, GABRB1, GDF10, GJB2, GSC, HOXA5, HSD11B2, HSD17B2, HSPA6, HSPB3, ICAM5, ID4, IGF2, IGFBP5, KCNMB1, KIAA0644, KRT14, KRT17, MFAP5, MASP1, MEOX1, MEOX2, MGP, MSX2, MX1, MYBPH, MYH3, MYH11, OGN, OLR1, PAX2, PAX9, PDE1A, PRG4, PROM1, PRRX2, PTN, RARRES1, RGS1, SFRP2, SMOC1, SNAP25, STMN2, TAC1, TNNT2, TRH, TUBB4, WISP2, ZIC1 and ZIC2.

The cell line W8Rep2a is positive for the markers: AQP1, AREG, BEX1, CDH6, COL21A1, COP1, DIO2, METTL7A, DLK1, FMO1, FMO3, FOXF1, FOXF2, MMP1, MSX1, MSX2, PDE1A, PRRX2, SERPINA3, SNAP25, SOX11, TFPI2 and ZIC2 and is negative for the markers: ALDH1A1, ATP8B4, C3, C7, C20orf103, CD24, CLDN11, CNTNAP2, COMP, CRIP1, CRLF1, CXADR, DKK2, DPT, EGR2, GAP43, GDF10, GJB2, GSC, HOXA5, HSD11B2, HSD17B2, HSPA6, HSPB3, ICAM5, ID4, IF127, KCNMB1, KRT14, KRT17, KRT34, MFAP5, MASP1, MEOX1, MEOX2, MGP, MX1, MYBPH, MYH3, MYH11, NPAS1, NPPB, OLR1, PAX2, PAX9, PITX2, PRG4, PROM1, PRRX1, PTGS2, PTN, PTPRN, RGS1, SFRP2, STMN2, TAC1, THY1, TNNT2, TRH, TUBB4 and ZIC1.

The cell line E55 is positive for the markers: AKR1C1, BEX1, CDH6, COL21A1, DIO2, DKK2, EGR2, GAP43, KRT19, MSX2, PRRX1, S100A4, SOX11, THY1, TNNT2 and ZIC2 and is negative for the markers: ALDH1A1, AQP1, AREG, ATP8B4, C3, C7, C20orf103, CLDN11, CNTNAP2, COMP, CRLF1, CXADR, DLK1, DPT, FMO1, FMO3, FOXF2, GABRB1, GDF10, GJB2, GSC, HOXA5, HSD11B2, HSD17B2, HSPA6, HSPB3, IF127, IGF2, KRT14, KRT34, LAMC2, MFAP5, MASP1, MEOX1, MEOX2, MGP, MYBPH, MYH3, NPAS1, NPPB, OGN, OLR1, PAX2, PAX9, PDE1A, PENK, PITX2, PRG4, PROM1, PRRX2, PTN, PTPRN, RARRES1, RGS1, SFRP2, SMOC1, SNAP25, STMN2, TAC1, TRH, TUBB4, WISP2 and ZIC1.

The cell line T20 is positive for the markers: ACTC, AKR1C1, BEX1, CDH6, COL21A1, CRYAB, DKK2, EGR2, GAP43, LAMC2, MMP1, MSX2, PITX2, SOX11, THY1 and ZIC2 and is negative for the markers: ALDH1A1, AREG, ATP8B4, CFB, C3, C7, C20orf103, CD24, CDH3, CLDN11, CNTNAP2, COMP, CRLF1, METTL7A, DPT, FMO1, FMO3, FOXF2, GDF10, GJB2, GSC, HOXA5, HSD11B2, HSD17B2, HSPA6, HSPB3, ICAM5, IF127, IGF2, KIAA0644, KRT14, MASP1, MEOX2, MGP, MX1, MYBPH, MYH3, TAGLN3, NPAS1, NPPB, OGN, OLR1, PAX2, PDE1A, PRG4, PROM1, PRRX2, PTN, PTPRN, RARRES1, RASD1, RGS1, SFRP2, SMOC1, SNAP25, STMN2, TAC1, TFPI2, TNFSF7, TRH, TUBB4, WISP2 and, ZIC1.

The cell line X4D20.8 is positive for the markers: BEX1, CDH6, CNTNAP2, COL21A1, CRIP1, CRYAB, DIO2, DKK2, GAP43, ID4, LAMC2, MMP1, MSX2, S100A4, SOX11 and THY1 and is negative for the markers: AGC1, ALDH1A1, AREG, ATP8B4, CFB, C3, C7, C20orf103, CDH3, CLDN11, COP1, CRLF1, DLK1, DPT, FMO1, FMO3, GDF10, GJB2, GSC, HOXA5, HSD11B2, HSD17B2, HSPA6, HSPB3, ICAM5, IF127, IGF2, KRT14, KRT17, KRT34, MASP1, MEOX2, MSX1, MX1, MYBPH, MYH3, MYH11, TAGLN3, NPAS1, NPPB, OGN, OLR1, PAX2, PDE1A, PRG4, PROM1, PTN, PTPRN, RARRES1, RGS1, SNAP25, STMN2, TAC1, TNNT2, TRH, TUBB4, WISP2, ZIC1 and ZIC2.

The cell line X4D20.3 is positive for the markers: ACTC, AKR1C1, AQP1, BEX1, CDH6, COL21A1, CRYAB, DKK2, DLK1, GJB2, HSD17B2, KRT17, LAMC2, MYL4, PITX2, S100A4, SOX11, THY1, TNNT2, ZIC1 and ZIC2 and is negative for the markers: AGC1, ALDH1A1, AREG, ATP8B4, CFB, C3, C7, C20orf103, CDH3, CLDN11, CNTNAP2, COMP, COP1, CRLF1, METTL7A, DPT, FGFR3, FMO1, FMO3, FOXF1, GABRB1, GSC, HOXA5, HSD11B2, HSPA6, HSPB3, ICAM5, ID4, IF127, IGF2, IGFBP5, KIAA0644, KRT14, KRT34, MASP1, MEOX2, MGP, MSX2, MX1, MYBPH, MYH3, MYH11, NPAS1, OGN, OLR1, PAX9, PDE1A, PENK, PRG4, PROM1, PRRX2, PTN, RARRES1, RGS1, SFRP2, SNAP25, STMN2, TAC1, TRH, TUBB4 and WISP2.

The cell line E132 is positive for the markers: ACTC, AKR1C1, AQP1, CD24, CDH6, COL21A1, CRYAB, DKK2, KRT19, TAGLN3, RELN, S100A4, SFRP2, SOX11, THY1 and ZIC2 and is negative for the markers: AGC1, ALDH1A1, AREG, ATP8B4, CFB, C3, C7, C20orf103, CLDN11, CNTNAP2, COL15A1, COMP, COP1, CRLF1, DIO2, METTL7A, DLK1, DPT, FMO1, FMO3, FOXF1, FOXF2, FST, GABRB1, GDF10, GJB2, GSC, HOXA5, HSD11B2, HSD17B2, HSPA6, HSPB3, ID4, IF127, IGF2, KCNMB1, KRT14, MFAP5, MASP1, MEOX2, MGP, MYBPH, MYH3, MYH11, NPAS1, NPPB, OGN, OLR1, PDE1A, PRG4, PROM1, PRRX2, PTGS2, PTN, PTPRN, RARRES1, RASD1, RGS1, SERPINA3, SMOC1, SNAP25, STMN2, TAC1, TRH, TUBB4, WISP2 and ZIC1.

TABLE I-continued

Exemplary progenitor cell lines and associated gene expression markers at 18-21 doublings of clonal expansion The cell line M13 is positive for the markers: ACTC, ANXA8, BEX1, CDH6, COL15A1, EGR2, GDF10, GJB2, KRT19, LAMC2, MYL4, TAGLN3, S100A4, SFRP2, SOX11, THY1, ZIC1 and ZIC2 and is negative for the markers: ALDH1A1, AREG, ATP8B4, CFB, C3, C7, C20orf103, CDH3, CLDN11, CNTNAP2, COMP, COP1, CRLF1, DIO2, DLK1, DPT, FGFR3, FMO1, FMO3, FOXF1, GABRB1, GAP43, GSC, HOXA5, HSD11B2, HSD17B2, HSPA6, HSPB3, ICAM5, ID4, IF127, IGF2, KIAA0644, KRT14, MFAP5, MEOX2, MGP, MMP1, MSX2, MYBPH, MYH3, NPAS1, OGN, OLR1, PDE1A, PRELP, PRG4, PROM1, PRRX2, PTN, PTPRN, RARRES1, RASD1, RELN, RGS1, SMOC1, SNAP25, STMN2, TAC1, TRH, TUBB4 and WISP2.

The cell line M10 is positive for the markers: ACTC, BEX1, CDH6, COL21A1, DIO2, DKK2, EGR2, IGFBP5, PRRX1, S100A4, SFRP2, THY1 and ZIC2 and is negative for the markers: AKR1C1, ALDH1A1, AQP1, AREG, ATP8B4, CFB, C3, C7, C20orf103, CD24, CDH3, CLDN11, CNTNAP2, COMP, COP1, CRLF1, CXADR, METTL7A, DPT, FMO1, FMO3, FOXF1, GABRB1, GJB2, GSC, HOXA5, HSD11B2, HSD17B2, HSPA6, HSPB3, ICAM5, IF127, IGF2, KIAA0644, KRT14, MEOX1, MEOX2, MGP, MYBPH, MYH3, MYH11, TAGLN3, NPAS1, OGN, OLR1, PAX2, PAX9, PDE1A, PITX2, PRG4, PROM1, PRRX2, PTN, PTPRN, RELN, RGS1, SERPINA3, SMOC1, SNAP25, STMN2, TAC1, TNFSF7, TNNT2, TRH, TUBB4, WISP2 and ZIC1.

The cell line E109 is positive for the markers: ACTC, AKR1C1, BEX1, CDH6, COL15A1, COL21A1, CRIP1, CRYAB, DIO2, DKK2, GAP43, GDF5, ID4, KRT14, KRT19, KRT34, MFAP5, MEOX2, MGP, MMP1, MYH11, S100A4, TFPI2, THY1 and ZIC1 and is negative for the markers: ALDH1A1, AQP1, AREG, ATP8B4, C3, C7, C20orf103, CD24, CDH3, CLDN11, CNTNAP2, COMP, CRLF1, CXADR, METTL7A, DLK1, DPT, FMO1, FMO3, FOXF1, FOXF2, GDF10, GJB2, GSC, HSD11B2, HSD17B2, HSPA6, ICAM5, IGF2, KIAA0644, MASP1, MEOX1, MYBPH, MYH3, TAGLN3, NPAS1, NPPB, OGN, PAX2, PAX9, PDE1A, PITX2, PRG4, PROM1, PRRX2, PTN, RARRES1, RASD1, RGS1, SFRP2, SMOC1, SNAP25, STMN2, TAC1, TRH, TUBB4 and WISP2.

The cell line E34 is positive for the markers: ACTC, AGC1, AQP1, CDH6, COL15A1, COL21A1, CRYAB, DKK2, GAP43, KRT14, KRT17, KRT19, KRT34, MFAP5, MEOX1, MEOX2, MGP, MYH11, TAGLN3, S100A4, THY1, TNNT2, ZIC1 and ZIC2 and is negative for the markers: ALDH1A1, AREG, ATP8B4, C3, C7, C20orf103, CDH3, CLDN11, CNTNAP2, COMP, COP1, CRLF1, CXADR, DIO2, METTL7A, DPT, FMO1, FMO3, FOXF1, FOXF2, FST, GABRB1, GDF10, GJB2, GSC, HOXA5, HSD11B2, HSPA6, IF127, IGF2, KIAA0644, LAMC2, MASP1, MSX2, MX1, MYBPH, MYH3, NPAS1, OLR1, PAX9, PDE1A, PRG4, PROM1, PRRX2, PTN, RARRES1, RASD1, RGS1, SERPINA3, SFRP2, SMOC1, SNAP25, STMN2, TAC1, TFPI2, TRH, TUBB4 and WISP2.

The cell line E122 is positive for the markers: ACTC, AGC1, AKR1C1, BEX1, CDH6, COL21A1, CRIP1, CRYAB, DIO2, DKK2, GAP43, ID4, KRT19, MFAP5, MYH11, MYL4, OGN, PRRX1, PTGS2, S100A4, SOX11 and THY1 and is negative for the markers: ALDH1A1, AREG, ATP8B4, CFB, C3, C7, C20orf103, CD24, CDH3, CLDN11, CNTNAP2, COL15A1, COP1, CRLF1, METTL7A, DLK1, DPT, FMO1, FMO3, FOXF2, GABRB1, GDF10, GJB2, GSC, HOXA5, HSD11B2, HSD17B2, HSPA6, HSPB3, ICAM5, IF127, IGF2, KIAA0644, KRT14, KRT17, KRT34, LAMC2, MASP1, MEOX1, MEOX2, MYBPH, NPAS1, NPPB, OLR1, PAX2, PAX9, PDE1A, PRG4, PROM1, RARRES1, RASD1, RGS1, SERPINA3, SFRP2, SMOC1, SNAP25, STMN2, TAC1, TUBB4, WISP2 and ZIC2.

The cell line E65 is positive for the markers: ACTC, AKR1C1, AQP1, BEX1, CD24, CDH6, COL21A1, CRYAB, DKK2, GAP43, KRT17, KRT19, KRT34, TAGLN3, RELN, S100A4, SFRP2, SOX11, THY1 and ZIC2 and is negative for the markers: AGC1, ALDH1A1, ATP8B4, CFB, C3, C7, C20orf103, CDH3, CLDN11, CNTNAP2, COMP, COP1, CRIP1, CRLF1, CXADR, METTL7A, DLK1, DPT, FMO1, FMO3, FOXF2, FST, GABRB1, GDF10, GJB2, GSC, HOXA5, HSD11B2, HSD17B2, HSPA6, HSPB3, ICAM5, IF127, IGF2, KIAA0644, KRT14, MFAP5, MASP1, MEOX2, MGP, MYBPH, MYH3, NPAS1, OGN, OLR1, PAX9, PDE1A, PITX2, PRG4, PROM1, PRRX2, PTGS2, PTN, RARRES1, RASD1, RGS1, SMOC1, SNAP25, STMN2, TAC1, TRH, TUBB4, WISP2 and ZIC1.

The cell line E76 is positive for the markers: ACTC, BEX1, COL21A1, CRIP1, CRYAB, DIO2, DKK2, EGR2, GAP43, KRT17, KRT19, MMP1, MSX2, PTGS2, S100A4 and THY1 and is negative for the markers: ALDH1A1, AREG, ATP8B4, CFB, C3, C7, C20orf103, CDH3, CLDN11, CNTNAP2, COP1, CRLF1, METTL7A, DPT, FMO1, FMO3, FOXF1, GABRB1, GDF10, GJB2, GSC, HOXA5, HSD11B2, HSD17B2, HSPA6, ICAM5, IF127, IGF2, KRT14, MEOX2, MGP, MYBPH, MYH3, NPAS1, NPPB, OGN, OLR1, PAX2, PAX9, PDE1A, PENK, PITX2, PRG4, PROM1, PRRX2, PTN, PTPRN, RARRES1, RGS1, SFRP2, SMOC1, SNAP25, STMN2, TAC1, TFPI2, TNNT2, TRH, TUBB4, WISP2 and ZIC1.

The cell line E108 is positive for the markers: ACTC, BEX1, CDH6, COL21A1, CRIP1, CRYAB, DIO2, DKK2, IGFBP5, KRT17, KRT19, MYH11, S100A4, SOX11, THY1 and ZIC2 and is negative for the markers: ALDH1A1, AQP1, AREG, ATP8B4, CFB, C3, C7, C20orf103, CD24, CDH3, CLDN11, CNTNAP2, COMP, COP1, CRLF1, CXADR, METTL7A, DLK1, DPT, FMO1, FMO3, FOXF1, FOXF2, GABRB1, GDF10, GJB2, GSC, HOXA5, HSD11B2, HSD17B2, HSPA6, ICAM5, IF127, IGF2, KRT14, KRT34, MASP1, MEOX1, MEOX2, MGP, MYBPH, MYH3, NPAS1, NPPB, OGN, OLR1, PAX2, PAX9, PRG4, PROM1, PTN, PTPRN, RARRES1, RASD1, RGS1, SERPINA3, SFRP2, SMOC1, SNAP25, STMN2, TAC1, TFPI2, TNNT2, TRH, TUBB4 and WISP2.

The cell line E85 is positive for the markers: ACTC, BEX1, CDH6, COL21A1, CRYAB, DIO2, DKK2, EGR2, FGFR3, ID4, KRT17, KRT19, MFAP5, MGP, MMP1, MYH11, PRELP, S100A4, SOX11, THY1, TNNT2, ZIC1 and ZIC2 and is negative for the markers: ALDH1A1, AQP1, AREG, ATP8B4, CFB, C3, C7, C20orf103, CD24, CDH3, CNTNAP2, COMP, COP1, CRLF1, METTL7A, DPT, FMO1, FMO3, GABRB1, GDF5, GDF10, GJB2, GSC, HOXA5, HSD11B2, HSD17B2, HSPA6, ICAM5, IF127, IGF2, KRT14, MASP1, MEOX1, MEOX2, MYBPH, MYH3, NPAS1, OGN, OLR1, PAX9, PDE1A, PITX2, PRG4, PROM1, PRRX2, PTN, RARRES1, RASD1, RGS1, SFRP2, SMOC1, STMN2, TAC1, TFPI2, TRH, TUBB4 and WISP2.

The cell line M1 1 is positive for the markers: BEX1, CDH6, COL21A1, CRYAB, DKK2, GAP43, ID4, MMP1, MYH11, SOX11, THY1 and ZIC1 and is negative for the markers: AGC1, ALDH1A1, AREG, ATP8B4, C3, C7, C20orf103, CD24, CDH3, CLDN11, CNTNAP2, COMP, COP1, CRLF1, CXADR, METTL7A, DLK1, DPT, FMO1, FMO3, FOXF2, FST, GABRB1, GDF10, GJB2, GSC, HOXA5, HSD11B2, HSD17B2, HSPA6, ICAM5, IGF2, IGFBP5, KCNMB1, KIAA0644, KRT14, MASP1, MEOX1, MEOX2, MSX2, MX1, MYBPH, MYH3, TAGLN3, NPAS1, OLR1, PAX2, PAX9, PDE1A, PENK, PITX2, PRG4, PROM1, PRRX2, PTN, PTPRN, RARRES1, RELN, RGS1, SFRP2, SMOC1, SNAP25, STMN2, TAC1, TFPI2, TNFSF7, TNNT2, TRH, TUBB4, WISP2 and ZIC2.

TABLE I-continued

Exemplary progenitor cell lines and associated gene expression markers at 18-21 doublings of clonal expansion The cell line E8 is positive for the markers: ACTC, BEX1, CDH6, COL21A1, CRIP1, CRYAB, DIO2, DKK2, ID4, KCNMB1, KRT14, KRT17, KRT19, KRT34, MFAP5, MGP, MYH11, PTGS2, S100A4, SOX11 and THY1 and is negative for the markers: ALDH1A1, AREG, ATP8B4, C3, C7, C20orf103, CDH3, CNTNAP2, COMP, COP1, CXADR, METTL7A, DPT, FMO1, FMO3, FOXF1, FOXF2, GABRB1, GDF10, GJB2, GSC, HOXA5, HSD11B2, HSD17B2, HSPA6, HSPB3, ICAM5, IF127, IGF2, IGFBP5, KIAA0644, LAMC2, MASP1, MEOX1, MSX2, MX1, MYBPH, TAGLN3, NPAS1, NPPB, OLR1, PAX2, PAX9, PDE1A, PRELP, PRG4, PROM1, PRRX2, PTN, PTPRN, RARRES1, RASD1, RGS1, SFRP2, SMOC1, SNAP25, STMN2, TAC1, TFPI2, TNFSF7, TRH, WISP2, ZIC1 and ZIC2.

The cell line E80 is positive for the markers: ACTC, BEX1, CDH6, COL21A1, CRYAB, DKK2, ID4, KRT19, MMP1, MYH11, TAGLN3, SOX11 and THY1 and is negative for the markers: ALDH1A1, AQP1, AREG, ATP8B4, CFB, C3, C7, C20orf103, CDH3, CLDN11, CNTNAP2, COMP, CRIP1, CRLF1, METTL7A, DLK1, DPT, FMO1, FMO3, FOXF1, FOXF2, GABRB1, GDF10, GSC, HOXA5, HSD11B2, HSD17B2, HSPA6, ICAM5, IF127, IGF2, KIAA0644, KRT14, KRT34, MASP1, MEOX2, MGP, MYBPH, MYH3, NPAS1, OGN, OLR1, PAX9, PDE1A, PRELP, PRG4, PROM1, PRRX2, PTN, RARRES1, RASD1, RGS1, SERPINA3, SMOC1, SNAP25, STMN2, TAC1, TNNT2, TRH, WISP2, ZIC1 and ZIC2.

The cell line RA.D20.24 is positive for the markers: ACTC, BEX1, CRYAB, CXADR, DKK2, FOXF1, GAP43, HOXA5, IGFBP5, KRT19, LAMC2, MFAP5, MMP1, MSX1, MYL4, PITX2, PTGS2, RELN, THY1 and TNNT2 and is negative for the markers: AGC1, ALDH1A1, AQP1, AREG, ATP8B4, CFB, C7, C20orf103, CDH3, CNTNAP2, COL15A1, COMP, COP1, CRLF1, DLK1, DPT, FGFR3, FMO1, FMO3, FOXF2, GDF10, GJB2, GSC, HSD11B2, HSD17B2, HSPA6, HSPB3, ICAM5, ID4, IF127, IGF2, KCNMB1, KRT14, MASP1, MEOX1, MEOX2, MGP, MSX2, MX1, MYBPH, MYH3, MYH11, NPAS1, OGN, PAX2, PAX9, PDE1A, PRG4, PROM1, PRRX2, PTN, PTPRN, RARRES1, RGS1, SFRP2, SMOC1, SNAP25, STMN2, TAC1, TUBB4, WISP2, ZIC1 and ZIC2.

The cell line RA.D20.6 is positive for the markers: ACTC, CRYAB, CXADR, DKK2, FOXF1, GAP43, HOXA5, IGFBP5, KRT19, LAMC2, MFAP5, MMP1, MSX1, PITX2, PTGS2, SOX11 and THY1 and is negative for the markers: ALDH1A1, ATP8B4, CFB, C3, C7, C20orf103, CDH3, CNTNAP2, COL15A1, COMP, COP1, CRLF1, DIO2, DLK1, DPT, FMO1, FMO3, FOXF2, GDF10, GSC, HSD11B2, HSD17B2, HSPA6, HSPB3, ICAM5, ID4, IGF2, KRT14, MASP1, MEOX1, MEOX2, MGP, MSX2, MX1, MYBPH, MYH3, MYH11, NPAS1, OGN, PAX2, PAX9, PDE1A, PRG4, PROM1, PRRX2, PTN, PTPRN, RARRES1, RGS1, SERPINA3, SFRP2, SMOC1, STMN2, TAC1, TRH, TUBB4, WISP2, ZIC1 and ZIC2.

The cell line RA.SM010 is positive for the markers: ALDH1A1, BEX1, C3, CDH3, COL21A1, CXADR, METTL7A, EGR2, FMO3, FOXF1, HOXA5, KIAA0644, MGP, RARRES1, SOX11 and STMN2 and is negative for the markers: ACTC, AGC1, ANXA8, AQP1, CFB, C7, C20orf103, CD24, CDH6, CNTNAP2, COL15A1, COMP, COP1, CRIP1, CRLF1, DPT, FOXF2, GAP43, GDF10, GSC, HSD11B2, HSD17B2, HSPA6, HSPB3, ICAM5, ID4, IF127, KRT14, KRT17, KRT34, MASP1, MEOX1, MEOX2, MMP1, MSX2, MYBPH, MYH3, MYH11, TAGLN3, NPAS1, NPPB, OGN, PAX2, PAX9, PDE1A, PITX2, PRELP, PRG4, PROM1, PRRX2, PTN, PTPRN, RGS1, S100A4, SERPINA3, SFRP2, SMOC1, TAC1, TFPI2, THY1, TNFSF7, TRH, TUBB4, WISP2, ZIC1 and ZIC2.

The cell line RA.SM014 is positive for the markers: ACTC, BEX1, CD24, CXADR, FOXF1, GDF5, GJB2, HOXA5, IGFBP5, KRT19, LAMC2, MFAP5, MMP1, RELN, SOX11 and STMN2 and is negative for the markers: AGC1, ALDH1A1, AQP1, ATP8B4, CFB, C3, C7, CDH6, CLDN11, CNTNAP2, COL15A1, COL21A1, COMP, COP1, CRIP1, CRLF1, DIO2, DLK1, DPT, FGFR3, FMO1, FMO3, FOXF2, GABRB1, GDF10, GSC, HSD11B2, HSD17B2, HSPA6, HSPB3, ICAM5, ID4, IF127, IGF2, KCNMB1, KRT14, KRT17, KRT34, MASP1, MEOX1, MEOX2, MGP, MSX2, MYBPH, MYH3, MYH11, NPAS1, NPPB, OGN, PAX2, PAX9, PDE1A, PITX2, PRELP, PRG4, PROM1, PRRX1, PRRX2, PTN, PTPRN, RGS1, SERPINA3, SFRP2, SMOC1, TAC1, TNFSF7, TUBB4, WISP2, ZIC1 and ZIC2.

The cell line RA.PEND18 is positive for the markers: C3, CDH3, COL21A1, METTL7A, DLK1, EGR2, FOXF1, GABRB1, HOXA5, IGF2, KIAA0644, KRT19, MSX1, PITX2, PROM1, PTGS2, SNAP25 and SOX11 and is negative for the markers: ACTC, AGC1, ALDH1A1, AQP1, BEX1, CFB, C20orf103, CDH6, CNTNAP2, COL15A1, COMP, CRIP1, CRLF1, CXADR, DPT, FMO1, FOXF2, GAP43, GDF10, GSC, HSD11B2, HSD17B2, HSPA6, HSPB3, ICAM5, ID4, IF127, KCNMB1, KRT14, KRT34, MFAP5, MASP1, MEOX1, MEOX2, MGP, MMP1, MSX2, MYBPH, MYH3, MYH11, TAGLN3, NPAS1, NPPB, PAX2, PAX9, PENK, PRELP, PRG4, PRRX2, PTN, PTPRN, RARRES1, RELN, RGS1, SFRP2, SMOC1, STMN2, TAC1, TNFSF7, TRH, TUBB4, WISP2, ZIC1 and ZIC2.

The cell line RA.PEND10 is positive for the markers: AREG, C3, CDH3, CDH6, COL21A1, METTL7A, DLK1, EGR2, FOXF1, FST, GDF5, HOXA5, IGF2, IGFBP5, KRT19, PDE1A, PITX2, RELN and SOX11 and is negative for the markers: ACTC, AGC1, ALDH1A1, ATP8B4, CFB, C7, C20orf103, CLDN11, CNTNAP2, COL15A1, COMP, CRIP1, CRLF1, CRYAB, DPT, FOXF2, GAP43, GDF10, GSC, HSD11B2, HSD17B2, HSPA6, HSPB3, ICAM5, ID4, IF127, KCNMB1, KRT14, KRT17, KRT34, MASP1, MEOX1, MEOX2, MMP1, MSX2, MYBPH, MYH3, MYH11, TAGLN3, NPAS1, NPPB, OGN, PAX2, PAX9, PRELP, PRG4, PROM1, PRRX1, PRRX2, PTN, PTPRN, RGS1, S100A4, SERPINA3, SFRP2, SMOC1, STMN2, TAC1, THY1, TNFSF7, TRH, TUBB4, WISP2, ZIC1 and ZIC2.

The cell line RA.SKEL21 is positive for the markers: AREG, BEX1, C3, CD24, COL21A1, COP1, METTL7A, FOXF1, KRT19, MSX1, PITX2, SERPINA3, SOX11 and THY1 and is negative for the markers: ACTC, AGC1, ALDH1A1, AQP1, ATP8B4, CFB, C7, C20orf103, CDH6, CLDN11, CNTNAP2, COL15A1, COMP, CRIP1, CRLF1, DKK2, DPT, FGFR3, FMO1, FMO3, FOXF2, GAP43, GDF10, GSC, HSD11B2, HSD17B2, HSPA6, HSPB3, ICAM5, ID4, IF127, KCNMB1, KRT14, KRT17, KRT34, MASP1, MEOX1, MEOX2, MGP, MMP1, MSX2, MX1, MYBPH, MYH3, TAGLN3, NPAS1, NPPB, OGN, OLR1, PAX2, PAX9, PDE1A, PENK, PRELP, PRG4, PRRX2, PTGS2, PTN, PTPRN, RARRES1, RASD1, RELN, RGS1, SFRP2, SMOC1, STMN2, TAC1, TNFSF7, TRH, TUBB4 and ZIC2.

The cell line RA.SKEL18Rep2a is positive for the markers: AREG, C3, CD24, CDH3, COL21A1, METTL7A, DPT, GJB2, SERPINA3, SNAP25 and SOX11 and is negative for the markers: ALDH1A1, ATP8B4, CFB, C7, C20orf103, CDH6, CLDN11, CNTNAP2, COMP, COP1, DIO2, DKK2, DLK1, FGFR3, FMO1, FMO3, GDF10, GSC, HSD11B2, HSD17B2, HSPA6, HSPB3, ICAM5, ID4, IF127, IGF2, KCNMB1, KRT14, KRT17, KRT19, KRT34, MASP1, MEOX1, MEOX2, MGP, MMP1, MSX2, MYBPH, MYH3, MYH11, TAGLN3, NPAS1, NPPB, OGN, OLR1, PAX2, PAX9, PRELP, PRG4, PROM1, PRRX1, PRRX2, PTGS2, PTN, PTPRN, RARRES1, RELN, RGS1, SFRP2, SMOC1, STMN2, TAC1, THY1, TNFSF7, TNNT2, TRH, WISP2, ZIC1 and ZIC2.

TABLE I-continued

Exemplary progenitor cell lines and associated gene expression markers at 18-21 doublings of clonal expansion The cell line C4.4 is positive for the markers: AKR1C1, BEX1, CDH6, COP1, DIO2, METTL7A, DKK2, DPT, EGR2, FOXF1, FST, KIAA0644, MMP1, MSX1, RELN, S100A4, TAC1 and THY1 and is negative for the markers: AGC1, ALDH1A1, ANXA8, AQP1, AREG, ATP8B4, CFB, C3, C7, C20orf103, CD24, CDH3, CLDN11, CNTNAP2, COL21A1, COMP, CRIP1, CRLF1, CXADR, FGFR3, FMO1, GAP43, GDF10, GJB2, GSC, HOXA5, HSD11B2, HSD17B2, HSPA6, HSPB3, ICAM5, ID4, IF127, IGF2, KCNMB1, KRT14, KRT17, KRT19, KRT34, LAMC2, MFAP5, MASP1, MEOX1, MEOX2, MGP, MYBPH, MYH3, MYH11, TAGLN3, NPAS1, NPPB, OGN, PAX2, PAX9, PDE1A, PENK, PITX2, PRG4, PROM1, PTGS2, PTN, PTPRN, RARRES1, RASD1, RGS1, SERPINA3, SFRP2, SMOC1, SNAP25, STMN2, TNFSF7, TNNT2, TRH, TUBB4, ZIC1 and ZIC2.

The cell line W7 is positive for the markers: AREG, C3, COL15A1, COL21A1, COP1, CXADR, DIO2, DLK1, EGR2, FMO1, FOXF1, GDF5, HOXA5, KIAA0644, METTL7A, PITX2, PROM1, S100A4, SERPINA3 and SOX11 and is negative for the markers: AGC1, ALDH1A1, AQP1, ATP8B4, C20orf103, C7, CD24, CDH3, CDH6, CFB, CLDN11, CNTNAP2, COMP, CRIP1, DKK2, DPT, FMO3, GABRB1, GAP43, GDF10, GSC, HSD11B2, HSD17B2, HSPA6, ICAM5, ID4, IF127, KCNMB1, KRT14, KRT17, KRT19, KRT34, MASP1, MEOX1, MEOX2, MGP, MMP1, MYBPH, MYH11, MYH3, NPAS1, NPPB, OGN, PAX2, PAX9, PRG4, PRRX2, PTN, PTPRN, RARRES1, RASD1, RELN, RGS1, SFRP2, SMOC1, STMN2, TAC1, TNFSF7, TRH, TUBB4, ZIC1 and ZIC2.

The cell line X4SKEL20 is positive for the markers: AREG, BEX1, C3, C7, COP1, CXADR, FOXF1, FST, KRT19, METTL7A, MGP, MSX1, PITX2, SERPINA3 and TFPI2 and is negative for the markers: ALDH1A1, AQP1, ATP8B4, C20orf103, CD24, CDH3, CDH6, CFB, CLDN11, CNTNAP2, COL15A1, COMP, DKK2, DLK1, DPT, EGR2, FGFR3, FMO1, FOXF2, GABRB1, GAP43, GDF10, GDF5, GJB2, GSC, HOXA5, HSD11B2, HSD17B2, HSPA6, HSPB3, ICAM5, ID4, IF127, IGF2, IGFBP5, KCNMB1, KRT14, KRT34, MASP1, MEOX1, MEOX2, MFAP5, MMP1, MSX2, MX1, MYBPH, MYH11, MYH3, NPAS1, NPPB, OGN, OLR1, PAX2, PENK, PRG4, PROM1, PRRX1, PRRX2, PTN, PTPRN, RARRES1, RELN, RGS1, SFRP2, SMOC1, SOX11, STMN2, TAC1, TAGLN3, THY1, TNFSF7, TNNT2, TRH, WISP2, ZIC1 and ZIC2.

The cell line C4ELSR6 is positive for the markers: ACTC, BEX1, C7, CDH6, COL21A1, DIO2, METTL7A, DKK2, FOXF1, FOXF2, LAMC2, PITX2, PRRX1, S100A4, SFRP2, SNAP25, SOX11, TAC1 and TFPI2 and is negative for the markers: AGC1, ALDH1A1, AREG, ATP8B4, CFB, C3, C20orf103, CD24, CLDN11, CNTNAP2, COMP, CRIP1, CRLF1, CRYAB, DLK1, DPT, FGFR3, FMO3, GAP43, GDF5, GDF10, GJB2, GSC, HOXA5, HSD11B2, HSD17B2, HSPA6, HSPB3, ICAM5, ID4, IF127, IGF2, KCNMB1, KRT14, KRT17, KRT34, MFAP5, MASP1, MEOX1, MEOX2, MGP, MMP1, MYBPH, MYH3, MYH11, NPAS1, NPPB, PAX2, PAX9, PENK, PRG4, PTN, PTPRN, RARRES1, RASD1, RGS1, SMOC1, STMN2, TNFSF7, TRH, TUBB4, WISP2 and ZIC1.

The cell line J2 is positive for the markers: ACTC, AKR1C1, BEX1, CDH6, COL15A1, COL21A1, DIO2, METTL7A, DKK2, DLK1, FOXF1, KIAA0644, MGP, PDE1A, PRRX1, SFRP2, SNAP25, TNNT2 and ZIC2 and is negative for the markers: AGC1, ALDH1A1, ATP8B4, CFB, C3, C20orf103, CD24, CNTNAP2, COMP, CRIP1, CRLF1, DPT, FGFR3, GABRB1, GDF10, GSC, HOXA5, HSD11B2, HSD17B2, HSPA6, ICAM5, ID4, IF127, KCNMB1, KRT14, KRT17, KRT19, KRT34, LAMC2, MFAP5, MASP1, MEOX1, MMP1, MSX1, MYBPH, MYH3, MYH11, NPAS1, NPPB, OGN, OLR1, PAX2, PAX9, PENK, PROM1, PRRX2, PTN, PTPRN, RARRES1, RGS1, SMOC1, STMN2, TAC1, TNFSF7, TRH and TUBB4.

The cell line F15 is positive for the markers: BEX1, CDH6, COL15A1, COL21A1, DKK2, DLK1, FOXF1, FST, GDF5, KRT19, MGP, MMP1, PRRX1, SERPINA3, SNAP25, SOX11, ZIC1 and ZIC2 and is negative for the markers: ACTC, AGC1, ALDH1A1, AQP1, AREG, ATP8B4, CFB, C3, C7, C20orf103, CD24, CDH3, CNTNAP2, COMP, CRLF1, DIO2, DPT, FGFR3, FMO1, FMO3, FOXF2, GABRB1, GDF10, GJB2, GSC, HOXA5, HSD11B2, HSD17B2, HSPA6, HSPB3, ICAM5, ID4, IF127, IGF2, KCNMB1, KIAA0644, KRT14, KRT17, MASP1, MEOX1, MEOX2, MYBPH, MYH3, MYH11, NPAS1, NPPB, OGN, OLR1, PAX2, PDE1A, PENK, PITX2, PRG4, PROM1, PRRX2, PTN, PTPRN, RGS1, SFRP2, SMOC1, STMN2, TFPI2, TNNT2, TRH and TUBB4.

The cell line X4SKEL4 is positive for the markers: ANXA8, AREG, BEX1, C3, COL21A1, COP1, CXADR, METTL7A, EGR2, FOXF1, FST, KRT19, LAMC2, MYL4, PITX2 and SERPINA3 and is negative for the markers: ALDH1A1, AQP1, ATP8B4, CFB, C7, C20orf103, CD24, CDH3, CDH6, CLDN11, CNTNAP2, COL15A1, COMP, CRLF1, DKK2, DLK1, DPT, FGFR3, FMO3, FOXF2, GABRB1, GAP43, GDF5, GDF10, GJB2, GSC, HOXA5, HSD11B2, HSD17B2, HSPA6, HSPB3, ICAM5, ID4, IF127, IGF2, IGFBP5, KIAA0644, KRT14, KRT17, KRT34, MASP1, MEOX1, MEOX2, MGP, MMP1, MSX2, MX1, MYBPH, MYH3, NPAS1, NPPB, OGN, OLR1, PAX2, PAX9, PDE1A, PENK, PRELP, PRG4, PROM1, PRRX2, PTN, PTPRN, RARRES1, RASD1, RGS1, SFRP2, SMOC1, SOX11, STMN2, TAC1, TNNT2, TRH, TUBB4, WISP2 and ZIC1.

The cell line X4SKEL19 is positive for the markers: AREG, COL21A1, COP1, DIO2, METTL7A, EGR2, FOXF1, FST, KIAA0644, KRT19, MGP, PDE1A, PITX2, SERPINA3 and TFPI2 and is negative for the markers: ACTC, AGC1, ALDH1A1, AQP1, ATP8B4, CFB, C20orf103, CD24, CDH3, CDH6, CLDN11, CNTNAP2, COL15A1, COMP, CRIP1, CRLF1, CXADR, DKK2, DLK1, DPT, FGFR3, FMO1, FOXF2, GABRB1, GAP43, GDF5, GDF10, GJB2, GSC, HOXA5, HSD11B2, HSD17B2, HSPA6, HSPB3, ICAM5, ID4, IF127, IGF2, KCNMB1, KRT14, KRT17, KRT34, MFAP5, MASP1, MEOX1, MEOX2, MMP1, MSX2, MX1, MYBPH, MYH3, MYH11, TAGLN3, NPAS1, NPPB, OGN, OLR1, PAX2, PAX9, PRELP, PRG4, PRRX2, PTN, PTPRN, RELN, SFRP2, SMOC1, SOX11, STMN2, TAC1, THY1, TRH, WISP2, ZIC1 and ZIC2.

The cell line X4SKEL8 is positive for the markers: AREG, BEX1, COL21A1, DIO2, METTL7A, DKK2, EGR2, FMO3, FOXF1, FST, MYL4, PITX2, PTGS2, S100A4 and SERPINA3 and is negative for the markers: ALDH1A1, AQP1, ATP8B4, CFB, C3, C20orf103, CD24, CLDN11, CNTNAP2, COMP, CRIP1, CRLF1, DLK1, DPT, FGFR3, FOXF2, GABRB1, GDF5, GDF10, GJB2, GSC, HOXA5, HSD11B2, HSD17B2, HSPA6, HSPB3, ICAM5, ID4, IF127, IGF2, KRT14, KRT17, KRT34, MFAP5, MASP1, MEOX1, MEOX2, MGP, MMP1, MSX2, MX1, MYBPH, MYH3, MYH11, TAGLN3, NPAS1, NPPB, OGN, OLR1, PAX2, PAX9, PDE1A, PENK, PRG4, PRRX1, PRRX2, PTN, PTPRN, RARRES1, RASD1, RELN, RGS1, SFRP2, SMOC1, STMN2, TAC1, THY1, TNFSF7, TNNT2, TRH, TUBB4, ZIC1 and ZIC2.

The cell line RA.PEND17Bio2a is positive for the markers: AREG, BEX1, CDH6, COL15A1, COL21A1, COP1, METTL7A, DPT, EGR2, FOXF1, FST, GJB2, LAMC2, MSX2, PTGS2, SERPINA3 and SFRP2 and is negative for the markers: ACTC, ALDH1A1, AQP1, ATP8B4, CFB, C20orf103, CD24, CDH3, CNTNAP2, COMP, CRIP1, CXADR, FGFR3, FMO1, GABRB1, GAP43, GDF10, GSC, HOXA5, HSD11B2, HSD17B2,

TABLE I-continued

Exemplary progenitor cell lines and associated gene expression markers at 18-21 doublings of clonal expansion HSPA6, HSPB3, ID4, IF127, IGF2, KCNMB1, KRT14, KRT17, KRT34, MFAP5, MASP1, MEOX1, MEOX2, MGP, MMP1, MX1, MYBPH, MYH3, MYH11, NPAS1, NPPB, OLR1, PAX2, PAX9, PDE1A, PRELP, PRG4, PROM1, PRRX2, PTN, PTPRN, RELN, RGS1, SMOC1, STMN2, TAC1, THY1, TNFSF7, TNNT2, TRH, TUBB4, ZIC1 and ZIC2.

The cell line W9 is positive for the markers: AKR1C1, C7, CDH6, COL21A1, METTL7A, DLK1, EGR2, FOXF1, GDF5, GJB2, HOXA5, IGFBP5, KIAA0644, KRT19, MGP, OGN, PITX2, SERPINA3, SOX11, TFPI2 and ZIC2 and is negative for the markers: AGC1, ALDH1A1, AQP1, CFB, C3, C20orf103, CD24, CDH3, CLDN11, CNTNAP2, COL15A1, COMP, CRIP1, CRLF1, CRYAB, DKK2, FGFR3, FMO1, FMO3, FOXF2, GDF10, GSC, HSD11B2, HSD17B2, HSPA6, HSPB3, ICAM5, ID4, IF127, IGF2, KCNMB1, KRT14, KRT17, KRT34, MFAP5, MASP1, MEOX1, MEOX2, MSX2, MX1, MYBPH, MYH3, MYH11, NPAS1, NPPB, OLR1, PAX2, PAX9, PDE1A, PENK, PRG4, PROM1, PRRX2, PTN, PTPRN, RARRES1, RASD1, RGS1, SFRP2, SNAP25, STMN2, TAC1, THY1, TNFSF7, TNNT2, TRH, TUBB4 and ZIC1.

The cell line MW4 is positive for the markers: AKR1C1, AREG, BEX1, C7, COL15A1, COL21A1, DIO2, METTL7A, DKK2, EGR2, FMO3, FOXF1, FOXF2, PITX2, PRELP, SERPINA3, SFRP2 and TFPI2 and is negative for the markers: ALDH1A1, AQP1, ATP8B4, CFB, C3, C20orf103, CD24, CDH3, CLDN11, CNTNAP2, CRIP1, CXADR, DLK1, GABRB1, GDF5, GDF10, GJB2, GSC, HOXA5, HSD11B2, HSD17B2, HSPA6, HSPB3, ICAM5, ID4, IF127, IGF2, KCNMB1, KRT14, KRT17, KRT19, KRT34, MFAP5, MASP1, MEOX1, MEOX2, MGP, MMP1, MSX1, MX1, MYBPH, MYH3, MYH11, NPAS1, NPPB, OLR1, PAX2, PAX9, PDE1A, PENK, PRG4, PROM1, PRRX1, PTN, PTPRN, RARRES1, RELN, RGS1, SMOC1, STMN2, TAC1, TNNT2, TUBB4, ZIC1 and ZIC2,.

The cell line SK58 is positive for the markers: AKR1C1, AREG, BEX1, C7, COL15A1, COL21A1, METTL7A, EGR2, FMO1, FOXF1, PTGS2, SERPINA3, SFRP2, TAC1 and TFPI2 and is negative for the markers: ACTC, AGC1, ALDH1A1, AQP1, ATP8B4, CFB, C3, C20orf103, CD24, CDH3, CDH6, CLDN11, CNTNAP2, COP1, CRIP1, DIO2, DLK1, DPT, GABRB1, GDF5, GDF10, GSC, HOXA5, HSD11B2, HSD17B2, HSPB3, ID4, IF127, IGF2, KCNMB1, KRT14, KRT17, KRT19, KRT34, MFAP5, MASP1, MEOX1, MEOX2, MMP1, MSX2, MX1, MYBPH, MYH3, MYH11, NPAS1, NPPB, OLR1, PAX2, PAX9, PDE1A, PRG4, PROM1, PRRX2, PTN, PTPRN, RARRES1, RELN, RGS1, SMOC1, STMN2, TNNT2, TRH, TUBB4, ZIC1 and ZIC2,.

The cell line SK25 is positive for the markers: BEX1, COL21A1, METTL7A, FMO1, FOXF1, LAMC2, SERPINA3, SFRP2 and WISP2 and is negative for the markers: ACTC, ALDH1A1, ANXA8, AQP1, ATP8B4, CFB, C3, C20orf103, CD24, CDH3, CLDN11, CNTNAP2, COMP, CRIP1, CRLF1, CXADR, DIO2, DKK2, DPT, EGR2, FGFR3, GABRB1, GAP43, GDF10, GJB2, GSC, HOXA5, HSD11B2, HSD17B2, HSPA6, HSPB3, ICAM5, ID4, IF127, IGF2, KCNMB1, KIAA0644, KRT14, KRT17, KRT34, MFAP5, MASP1, MEOX1, MEOX2, MGP, MMP1, MSX2, MYBPH, MYH3, MYH11, NPAS1, NPPB, OGN, OLR1, PAX2, PAX9, PDE1A, PITX2, PRELP, PRG4, PROM1, PTN, RARRES1, RASD1, RGS1, SMOC1, STMN2, TAC1, TFPI2, TNFSF7, TNNT2, TRH, ZIC1 and ZIC2.

The cell line SK16 is positive for the markers: AREG, BEX1, COL15A1, COL21A1, METTL7A, EGR2, FMO1, FOXF1, LAMC2, MSX1, PITX2, SERPINA3, ZIC1 and ZIC2 and is negative for the markers: AGC1, ALDH1A1, AQP1, ATP8B4, CFB, C3, C20orf103, CD24, CDH3, CLDN11, CNTNAP2, COMP, CRIP1, CXADR, DIO2, DKK2, DPT, FGFR3, GABRB1, GDF10, GSC, HSD11B2, HSD17B2, HSPA6, HSPB3, ID4, IF127, IGF2, KIAA0644, KRT14, KRT17, KRT19, KRT34, MFAP5, MASP1, MEOX1, MEOX2, MGP, MMP1, MSX2, MX1, MYBPH, MYH3, MYH11, TAGLN3, NPAS1, NPPB, OLR1, PAX2, PAX9, PENK, PRELP, PRG4, PROM1, PRRX2, PTN, RARRES1, RELN, RGS1, STMN2, TAC1, TFPI2, THY1, TNFSF7, TNNT2, TRH and TUBB4,.

The cell line EN20 is positive for the markers: BEX1, COL21A1, METTL7A, DLK1, FMO1, FOXF1, FST, GDF5, LAMC2, MGP, PRRX1, S100A4, SERPINA3, SOX11, TFPI2 and WISP2 and is negative for the markers: ALDH1A1, AQP1, ATP8B4, C3, C7, C20orf103, CD24, CDH3, CNTNAP2, COL15A1, COMP, CRIP1, CXADR, DIO2, DKK2, FGFR3, GABRB1, GAP43, GDF10, GSC, HOXA5, HSD11B2, HSD17B2, HSPA6, HSPB3, ICAM5, ID4, IF127, KCNMB1, KRT14, KRT17, KRT34, MFAP5, MASP1, MEOX1, MEOX2, MMP1, MX1, MYBPH, MYH3, MYH11, NPAS1, NPPB, OLR1, PAX2, PDE1A, PITX2, PRELP, PRG4, PROM1, PTN, PTPRN, RASD1, RGS1, SFRP2, SMOC1, SNAP25, STMN2, TAC1, TNFSF7, TNNT2, TRH, TUBB4, ZIC1 and ZIC2,.

The cell line EN43 is positive for the markers: AKR1C1, BEX1, C7, CDH6, COL21A1, DIO2, METTL7A, DLK1, FMO1, FMO3, FOXF1, FOXF2, FST, GDF5, MMP1, MSX1, OGN, PRRX1, S100A4, SERPINA3 and SOX11 and is negative for the markers: ALDH1A1, ANXA8, AQP1, ATP8B4, C3, C20orf103, CD24, CDH3, CLDN11, CNTNAP2, COMP, CRIP1, CRLF1, DKK2, DPT, GABRB1, GAP43, GDF10, GJB2, GSC, HOXA5, HSD11B2, HSD17B2, HSPA6, ID4, IF127, IGF2, KCNMB1, KRT14, KRT17, KRT19, KRT34, MFAP5, MASP1, MEOX1, MEOX2, MGP, MYBPH, MYH3, MYH11, NPAS1, NPPB, OLR1, PAX2, PAX9, PDE1A, PITX2, PRG4, PROM1, PTN, PTPRN, RASD1, RGS1, SFRP2, SMOC1, STMN2, THY1, TNNT2, TRH, TUBB4, ZIC1 and ZIC2.

TABLE II

Culture Conditions

1. Subconfluent Monolayer Culture: Cells are plated and exposed to combinations of the conditions listed in Tables I-IV herein while said cells are in a subconcluent state.
2. Confluent Monolayer Culture: Cells are plated and exposed to combinations of the conditions listed in Tables I-IV herein while said cells are in a confluent monolayer state.
3. Micromass Culture: Cells are plated and exposed to combinations of the conditions listed in Tables I-IV herein while said cells are in a highly dense micromass state as described herein.
4. Subconfluent Mixed Culture: Cells are plated and exposed to combinations of the conditions listed in Tables I-IV herein while said cells are in a subconfluent state and juxtasposed (co-cultured) potentially in physical contact with cells of another differentiated state or another distinguishable cell line of the present invention.

TABLE II-continued

Culture Conditions

5. Subconfluent Transwell Culture: Cells are plated and exposed to combinations of the conditions listed in Tables I-IV herein while said cells are in transwell vessels or tissue cultureware of similar design that allows the physical separation of diverse cell types but allowing a sharing of their media. Such subconfluent transwell culture is where the cell lines of the present invention are subconfluent and share culture media with a cell type of a different differentiated state wherein the cells of a different differentiated state may be themselves in a subconfluent or confluent state.
6. Confluent Mixed Culture: Cells are plated and exposed to combinations of the conditions listed in Tables I-IV herein while said cells are in a confluent state and juxtaposed (co-cultured) potentially in physical contact with cells of another differentiated state or another distinguishable cell line of the present invention.
7. Confluent Transwell Culture: Cells are plated and exposed to combinations of the conditions listed in Tables I-IV herein while said cells are in transwell vessels or tissue cultureware of similar design that allows the physical separation of diverse cell types but allowing a sharing of their media. Such subconfluent transwell culture is where the cell lines of the present invention are confluent and share culture media with a cell type of a different differentiated state wherein the cells of a different differentiated state may be themselves in a subconfluent or confluent state.
8. Micromass Mixed Culture: Cells are plated and exposed to combinations of the conditions listed in Tables I-IV herein while said cells are in a highly dense micromass state as described herein and juxtasposed (co-cultured) potentially in physical contact with cells of another differentiated state or another distinguishable cell line of the present invention.
9. Micromass Transwell Culture: Cells are plated and exposed to combinations of the conditions listed in Tables I-IV herein while said cells are in transwell vessels or tissue cultureware of similar design that allows the physical separation of diverse cell types but allows a sharing of their media while said cells are in a highly dense micromass state as described herein. Such subconfluent transwell culture is where the cell lines of the present invention are confluent and share culture media with a cell type of a different differentiated state wherein the cells of a different differentiated state may be themselves in a subconfluent or confluent state.

Culture Exposed to Cell Extracts of Cells of a Different Differentiated State: Target cells are plated and exposed to combinations of the conditions listed in Tables I-IV herein while said cells are in a subconfluent state and wherein the media for said cells contains extracts of cells of a differing differentiated state and wherein said target cells are exposed to conditions that facilitate the intracellular trafficking of molecules such as described in U.S. patent application Ser. No. 10/910,156 filed on Aug. 2, 2004 and titled "Methods for Altering Cell Fate", and U.S. patent application Ser. No. 10/015,824 filed on Dec. 10, 2001 and titled "Methods for Altering Cell Fate", both incorporated herein by reference in their entirety.

Lengthy table referenced here

US10920191-20210216-T00001

Please refer to the end of the specification for access instructions.

Lengthy table referenced here

US10920191-20210216-T00002

Please refer to the end of the specification for access instructions.

Lengthy table referenced here

US10920191-20210216-T00003

Please refer to the end of the specification for access instructions.

Lengthy table referenced here

US10920191-20210216-T00004

Please refer to the end of the specification for access instructions.

Lengthy table referenced here

US10920191-20210216-T00005

Please refer to the end of the specification for access instructions.

Lengthy table referenced here

US10920191-20210216-T00006

Please refer to the end of the specification for access instructions.

Lengthy table referenced here

US10920191-20210216-T00007

Please refer to the end of the specification for access instructions.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

LENGTHY TABLES

The patent contains a lengthy table section. A copy of the table is available in electronic form from the USPTO web site (https://seqdata.uspto.gov/?pageRequest=docDetail&DocID=US10920191B2). An electronic copy of the table will also be available from the USPTO upon request and payment of the fee set forth in 37 CFR 1.19(b)(3).

What is claimed is:

1. An isolated clonal progenitor cell line expressing EYA4, ADH1A and ADH1B, wherein the clonal progenitor cell line is an in vitro human pluripotent stem cell-derived embryonic cutaneous progenitor cell line and wherein the clonal progenitor cell line is encapsulated in a biomaterial.

2. The isolated clonal progenitor cell line of claim 1, wherein the cell line also expresses FABP4, CD36, PPARG, ANGPT2, EBF2 and DBC1.

3. The isolated clonal progenitor cell line of claim 1, wherein the biomaterial comprises a hydrogel.

4. The isolated clonal progenitor cell line of claim 1, wherein the biomaterial comprises hyaluronic acid.

5. The isolated clonal progenitor cell line of claim 1, wherein the biomaterial is chosen from calcium alginate, agarose, polylactic acid/polyglycolic acid derivatives, and fibrin.

6. A kit comprising the cell line of claim 1.

* * * * *

```
                                SEQUENCE LISTING

<160> NUMBER OF SEQ ID NOS: 92

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
ccgacagcaa cgtggtctt                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
caggttggcc cagatgatg                                                    19

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tgctcagatt gcaaaagtgg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
tatctgggaa acccacgaag                                                   20

<210> SEQ ID NO 5
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 5
cctggtcctg gaagtcacat                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ccatgttgtc cactcaccag                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
atccgtagag agcacggaga                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ggactctcca tgggacaaga                                                 20

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
ggcaatagca ggttcacgta ca                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
cgataacagt cttgccccac tt                                              22

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
```
tggcctgaga cagcatga                                                     18

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
agtgttggga gccagattg                                                    19

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
atccgtagag agcacggaga                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
ggactctcca tgggacaaga                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tacgactaca ccgaccacca                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tcaaggtcga gtgagctgtg                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tccagctaca tctcgcacct                                                   20

<210> SEQ ID NO 18
<211> LENGTH: 20
<212> TYPE: DNA
<213> ORGANISM: Artificial Sequence -continued
<220> FEATURE:
<223> OTHER INFORMATION: Synthetic oligonucleotide

<400> SEQUENCE: 18
cggtccttgc tcaactttct                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ggacttggct cagtctctgg                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tggggatgga gttcttcttg                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
ggcctccaag gagtaagacc                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
aggggtctac atggcaactg                                                    20

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
atttggtcgt ggacgtggt                                                     19

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
tttggctgta agtttattca atgc                                               24

```
<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
ctctcgtcgg tgactgttca                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
ctctcgtcgg tgactgttca                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tctaccccaa tccagcaaac                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gttgggagcc agattgtcat                                                   20

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
cacactggta agtggggcaa gaccg                                             25

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
acgaggtcct cactggtgaa                                                   20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 31
tgagtcctca agcctcctgt                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tggtctgcag cagttgattc                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
acagctgggg acattagtgg                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
gtggaatgca gaggtggttt                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
gctaagggtg aaagggqttc                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
ctccaggatc accttttgga                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ggactctgtc acacccacct                                          20

<210> SEQ ID NO 38
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
agctcggaga tgtcgttgtt                                                   20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
agcatcattc ggctgttacc                                                   20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
ctgaggggtg gaactgtagc                                                   20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
cccatcagca tcctcttcat                                                   20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tgtagatgct cctgccacag                                                   20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
accacgcttc ctatgtgacc                                                   20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
```
tgttgtaact gggtggcaaa                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
tcgagggttt gatggacttc                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
catcttctcc cctcattcca                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
tggcaacaaa atcagcagag                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
gccattgtca acagcagaga                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
cctccaaggc aataggatca                                              20

<210> SEQ ID NO 50
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 50
gctgcgcttg atctcgttc                                               19

<210> SEQ ID NO 51
<211> LENGTH: 20
<212> TYPE: DNA

-continued

```
<213> ORGANISM: Artificial Sequence
<220> FEATURE:
<223> OTHER INFORMATION: Synthetic oligonucleotide

<400> SEQUENCE: 51
tgatctgcag tggctcattc                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
aaaagagccc agctttgtga                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
gtgctaaagg tgccaatggt                                                   20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
accaggttca ccgctgttac                                                   20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
gtgctaaagg tgccaatggt                                                   20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ctcctcgctt tccttcctct                                                   20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
tcccaatctt gccttcattc                                                   20
```

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
gtcatggaac gccactaggt                                               20

<210> SEQ ID NO 59
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 59
tcgaggacag cgaggcc                                                  17

<210> SEQ ID NO 60
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 60
tcgagggtgt agcgtgtaga ga                                            22

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
caaggcacca tctccaggaa                                               20

<210> SEQ ID NO 62
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 62
aaagggtatt tgtggcagca tatt                                          24

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
ttccacaagc acaaacttta cacat                                         25

<210> SEQ ID NO 64
<211> LENGTH: 30
<212> TYPE: DNA
<213> ORGANISM: Artificial Sequence
<220> FEATURE:

<223> OTHER INFORMATION: Synthetic oligonucleotide

<400> SEQUENCE: 64
gtgaaactga gttttgtata acctctcagt					30

<210> SEQ ID NO 65
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 65
accagattga ccatattgat ga					22

<210> SEQ ID NO 66
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 66
ggacagatcc agctcaacc					19

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
aggcaagcaa aggagatgaa					20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
tggtgttctg agaggcacag					20

<210> SEQ ID NO 69
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 69
actgagtcat ttgcagtgtt ttctgcc					27

<210> SEQ ID NO 70
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 70
gtgggctgat cccctccagg t					21

```
<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
tggcactgca ctgggtagga                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
aaggctggga gcccgtcact                                               20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
tgagtcctca agcctcctgt                                               20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
cctctgtctc cttgcaggtc                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
ggccgggaga ccgtgtgttg                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
tggggctcgc ggtccagtaa                                               20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 77
tacgcctgga gagtggggcg                                          20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
tggggctcgc ggtccagtaa                                          20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
tcgtgggtcc cagggtgaa                                           20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
gacctggagg gccctgtgcg                                          20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
tgctgcccca tctgcccaac                                          20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
cctgcaggtc cctgaggccc                                          20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
agggccagga tgtccggcaa                                          20

<210> SEQ ID NO 84
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 84
tctgccacga ggtccagggg                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
cggggcgatg gcacctttgt                                              20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
gatagaggcg gtgggggcca                                              20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
acaatgacgg agtccctgac                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
tctgcatcaa agtcgtcctg                                              20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
gagtcagaga cggaacagcc                                              20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
```

```
agtcccagag actgagccaa                                              20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
gcgcaagtga aggctcgtat                                              20

<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 92
gtttggagga gatgctctgt ttg                                          23
```